US012613234B2

(12) United States Patent
Huang et al.

(10) Patent No.: US 12,613,234 B2
(45) Date of Patent: Apr. 28, 2026

(54) STRUCTURAL-PROFILING OF ANALYTES BY NANOPORE TRAPPING

(71) Applicant: NANJING UNIVERSITY, Nanjing (CN)

(72) Inventors: Shuo Huang, Nanjing (CN); Yao Liu, Nanjing (CN); Yuqin Wang, Nanjing (CN); ShanYu Zhang, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 218 days.

(21) Appl. No.: 18/560,547

(22) PCT Filed: May 12, 2022

(86) PCT No.: PCT/CN2022/092553
§ 371 (c)(1),
(2) Date: Nov. 13, 2023

(87) PCT Pub. No.: WO2022/237883
PCT Pub. Date: Nov. 17, 2022

(65) Prior Publication Data
US 2024/0272137 A1    Aug. 15, 2024

(30) Foreign Application Priority Data

May 13, 2021  (WO) ............... PCT/CN2021/093507
Dec. 3, 2021  (WO) ............... PCT/CN2021/135373

(51) Int. Cl.
G01N 33/487    (2006.01)
G01N 33/00    (2006.01)
G01N 33/04    (2006.01)

(52) U.S. Cl.
CPC ...  G01N 33/48721 (2013.01); G01N 33/0091 (2024.05); G01N 33/04 (2013.01); *G01N 2333/47* (2013.01)

(58) Field of Classification Search
None
See application file for complete search history.

(56) References Cited

FOREIGN PATENT DOCUMENTS

CN      106133513 A    11/2016
WO      2015/126494 A1    8/2015
WO      2015/148567 A1    10/2015

OTHER PUBLICATIONS

E.A. Manrao, et al., "Nucleotide Discrimination with DNA Immobilized in the MspA Nanopore", PLOS One, 6(10): p. e25723, 7 pages, Oct. 2011.*

(Continued)

*Primary Examiner* — J. Christopher Ball
(74) *Attorney, Agent, or Firm* — Duane Morris LLP; Thomas J. Kowalski

(57) ABSTRACT

A method of characterizing an analyte or the interaction between the analyte and an agent in a nanopore system, wherein the nanopore system comprises a protein nanopore disposed in a membrane that separates a first conductive liquid medium from a second conductive liquid medium, wherein the protein nanopore is MspA, MspA homolog or variant thereof, wherein the analyte has an conformation and the analyte with the conformation can be accommodated in the vestibule of the MspA, the MspA homolog or the variant thereof but cannot translocate through the MspA, the MspA homolog or the variant thereof, the method comprising: i) applying an electrical potential difference between the first conductive liquid medium and the second conductive liquid medium to drive the analyte into the nanopore, and optionally contacting the agent with the analyte; ii) measuring an ionic current through the protein nanopore to provide a tested current pattern that contains at least ionic current measured during the analyte is in the vestibule of the MspA, the MspA homolog or the variant thereof; iii) associating the (Continued)

A

*cis:* KCl

*trans:* KCl or CaCl$_2$ tested current pattern with at least one characteristic of the analyte or the interaction between the analyte and an agent.

20 Claims, 96 Drawing Sheets

Specification includes a Sequence Listing.

(56) References Cited

OTHER PUBLICATIONS

Int'l Search Report and Written Opinion issued Aug. 19, 2022 in Int'l Application No. PCT/CN2022/092553.

Garbine Celaya, et al., Label-Free, Multiplexed, Single-Molecule Analysis of Protein-DNA Complexes with Nanopores, American Chemical Society Nano (2017) 11, 5815-5825.

Dong-Hwa Lee, et al., Tertiary RNA Folding-Targeted Drug Screening Strategy Using a Protein Nanopore, Analytical Chemistry (2021) 93, 2811-2819.

Haofu Niu, et al., Rapid Nanopore Assay for Carbapenem-Resistant Klebsiella pneumoniae, Frontiers in Microbiology (Jul. 2019) vol. 10, Article 1672, 1-9.

Ji Wook Shim, et al., Single-molecule detection of folding and unfolding of the G-quadruplex aptamer in a nanopore nanocavity, Nucleic Acids Research (2009) vol. 37, No. 3, 972-982.

Extended European Search Report issued Apr. 7, 2025 in co-pending EP Application No. 22806845.8.

* cited by examiner

L1: low range RNA ladder
L2: yeast tRNA^Phe
L3: yeast tRNA
L4: *E.coli* tRNA

STRUCTURAL-PROFILING OF ANALYTES BY NANOPORE TRAPPING

CROSS-REFERENCE TO RELATED APPLICATIONS

The present application is a § 371 of International Application No. PCT/CN2022/092553 filed May 12, 2022, which published as International Publication No. WO 2022/237883 on Nov. 17, 2022 and which claims priority to International Application No. PCT/CN2021/093507, filed May 13, 2021, and International Application No. PCT/CN2021/135373, filed Dec. 3, 2021, the entire content of each of which is incorporated herein by reference.

SEQUENCE STATEMENT

The instant application contains a Sequence Listing which has been submitted electronically and is hereby incorporated by reference in its entirety. Said ASCII copy, is named Y9516_00005SL.txt and is 2,916 bytes in size.

FIELD OF THE INVENTION

The present invention generally relates to the use of nanopores, especially structural-profiling of molecules, such as biological molecules, e.g., RNAs or proteins, by nanopore trapping.

BACKGROUND OF THE INVENTION

The functional diversity of RNA stems in part from its ability to fold into elaborate tertiary structures that can specifically bind with ligands to regulate cellular activities[1, 2]. Many novel biological roles of RNA have been discovered[3, 4], leading to a growing demand for determination of RNA tertiary structures. Classical structural biology techniques including X-ray crystallography[5] and NMR spectroscopy[6, 7] have contributed most to the RNA tertiary structure determination, preferentially those with small RNA architectures[8]. As a complement, cryo-electron microscopy (cryoEM) plays an increasingly important role in unveiling the structures of larger (>50 kDa) RNA molecules[9, 10]. Emerging techniques such as single-molecule Förster Resonance Energy Transfer (smFRET)[11] and single molecule force spectroscopy[12] have also been applied to probe RNA structure and interaction dynamics at the molecular level. However, high end equipment and laborious efforts in sample preparation are required and the risk of perturbing non-covalent interactions within the RNA structure is also present. As a consequence, direct interrogation of tertiary structures of RNA in its native state remains a challenge.

RNA structures can be probed by solid state nanopores[13-17] and clinical applications such as the quantification of severe acute respiratory syndrome coronavirus 2 were as well demonstrated[14]. However, the thickness of a solid state nanopore prohibits it from producing refined sensing information, limiting its resolution to clearly resolve structurally similar RNA structures. Besides, the geometric reproducibility of a solid state nanopore remains a technical bottleneck, reducing the consistency of sensing when different batches of pores are used. Biological nanopores represent a growing family of channel proteins used for single molecule sensing[18]. Emerging nanopores such as ferric hydroxamate uptake component A (FhuA) or aerolysin are capable of performing sensing of nucleic acids[19], protein-protein interactions[20] or amino acids[21] with a high accuracy and consistency. Previous studies of transfer RNA (tRNA) using biological nanopores were carried out with wild type α-hemolysin (α-HL)[22]. However, chemical ligation with a leading strand is required and the acquired information reflects the difference of unfolding kinetics or the primary sequence rather than the overall tertiary structures of different tRNAs, largely due to a limited size of the pore constriction. To permit passage of large biomolecules, recent efforts have been made to develop new biological nanopores with large constrictions. These pores include Cytolysin A (ClyA)[23], Phi29 connector protein[24], Fragaceatoxin C (FraC)[25], FhuA[20] and Pleurotolysin A (PlyA)/Pleurotolysin B (PlyB)[26], with which dsDNA, proteins or protein-small molecule complexes were thoroughly investigated. However, to the best of our knowledge studies of such complexes with RNA tertiary structures have not yet been carried out. These large pores are also associated with various issues such as short storage time[23], non-uniform pore assembly[27] or spontaneous gating when a large potential is applied[27].

Actions of proteins often involve conformational changes,[101-114] such as side-chain fluctuations, loop dynamics, domain movements or allosteric motions.[105,106] Methods such as Fourier-transform infrared spectroscopy (FTIR),[107] ultrafast two-dimensional infrared spectroscopy (2D IR)[108] and NMR spectroscopy[109] have been widely applied in the analysis of such structural changes. Information obtained by these methods however, only reflects ensemble averaged behaviors of the proteins being investigated and the activities of individual molecules are not resolvable. Single-molecule techniques such as AFM-based single-molecule force spectroscopy (SMFS),[110-112] scanning tunneling microscopy (STM),[113] single molecule Förster resonance energy transfer (smFRET),[114,115] optical tweezers,[116-118] magnetic tweezers,[119-121] thermophoresis traps[122] and electrostatic fluidic traps[123] can directly examine the size, charge, mobility, folding, ligand-binding or allosterism of a single protein. These single-molecule tools have provided a significantly larger amount of information bearing on the intrinsic functional mechanism of a single protein, but are inevitably limited by the requirement for fluorescent labeling or surface immobilization of the protein. Some imaging-based techniques also demonstrate a limited temporal resolution, which may result in overlooking short-lived events of protein conformational changing.

Nanopore techniques, in which a single molecule analyte is directly probed during translocation through a nanopore sensor, have been used to study proteins. Single molecule properties of proteins such as structural folding/unfolding,[124-28] aggregation,[129] size,[130] charge,[131] geometry,[132] dipole moment,[133] enzymatic kinetics[134] or the flexibility[135] can be directly investigated using nanopores. Such techniques require no chemical labeling of the protein and achieve a ~μs temporal resolution.[136] Nanopore sensing of proteins has been carried out with protein-based,[137] solid-state[137] or DNA-based pores.[138] Solid state nanopores have larger pore diameters and the pore size is highly tunable, which is advantageous when probing proteins of large dimensions.[124,130-133,135,136,139-141] However, solid state nanopores generally suffer from a poor reproducibility and additional sources of noise[142], which limits a satisfactory measurement consistency and a further refined sensing resolution.

Protein nanopores offer an atomically accurate structure and a highly refined sensing resolution, but the constrictions of conventional protein nanopores such as FhuA[143], OmpG[144] and α-hemolysin[145] are generally smaller than most protein analytes of interest. Consequently, protein analytes must be unfolded, either electrophoretically or enzymatically to achieve nanopore translocation and thus, probing of a protein in its native form becomes infeasible.[126, 146, 147] Nanopore sensing of folded proteins can however be carried out by conjugating receptor modules to the outer rims of a nanopore, which reports current perturbations caused by analyte-receptor interactions during single channel recordings[143-145,148]. The effort of conjugation between the pore and the receptor is non-trivial and the sensing resolution is limited because the protein of interest is distant from the pore constriction.

Recent research into large protein nanopores such as Cytolysin A (ClyA),[149] Fragaceatoxin C (FraC)[150] and Pleurotolysin AB (PlyAB)[151] has offered an inspiring strategy, in which protein analytes were directly lodged in the large lumen of the pores and direct sensing of protein biomarkers,[152, 153] protein-ligand interactions,[154, 155] conformer exchanges in catalysis,[134] post-translational protein modification[156] was consequently achieved. However, these nanopores were often associated with issues such as difficult spontaneous pore insertion,[139] non-uniform pore assembly,[157] unstable structure[158] and spontaneous gating under a high voltage.[157] Though significant efforts of pore engineering by directed evolution were made to overcome these drawbacks, the consistency and stability of these newly developed pores are still unsatisfactory. A recent report of bottom-up fabrication of a multi-component nanopore sensor to investigate protein analyte is motivating[147] but the related challenge of protein engineering is far out of the reach of most academic labs.

Protein recognition at the molecular level is important in the early diagnosis and treatment of diseases. Generally, proteins can be identified by immunoassays or mass spectrometry (MS). However, intricate pretreatment including purification, denaturation, alkylation, enzymatic digestion, and desalting before MS testing is crucial for the detection of target protein in a background milieu of more abundant.[193-195] As for immunoassays, highly-specific antibodies against the target protein are necessary, which requires expensive and repeated preparations of antibodies targeting various substrates.[196] Besides, neither methods can extract characteristics of a single protein from the ensemble. Single-molecule fluorescent protein fingerprinting could address these limitations,[197] but they also face other problems such as dark reads which are common in single-molecule fluorescence detection.[194] Further, none of these strategies possess a resolution to directly resolve conformational change of a protein. Developing a proteomics method that can recognize different proteins and distinguish different structural states of the same protein caused by the processes such as ligand/drug binding and fusions still remains a challenge in basic research.

A variety of nanopore technologies have been developed for single protein analysis.[198-202] They generally report the advantages of possessing a single molecule resolution and a simple configuration. It may also be carried out in a high throughput and portable manner.[203] The requirement for sample pretreatment is also minimum. In principle, under an external potential, a protein is detected in the form of translocation, during which perturbation to the ionic current passing through the pore is observed. A temporal resolution on the order of microseconds can generally be achieved.[204] Unlike nucleic acids, proteins have diverse charge properties and uneven charge distribution, compact structures and different shapes. A reported strategy involves the use of negatively charged polymers to cap proteins. Such polymers assist the analyte capture and can serve as nanopore-addressable barcodes, simplifying protein identification.[205-208] There have also been many label-free attempts by introducing charged amino acids in the pore lumen to generate EOF. The EOF has a considerable influence on the molecular transport through the nanopore as it has no preference for the charge of the analytes.[209-221] However, charge modifications performed by site-directed mutagenesis may cause severe structural disorder in the nanopore and may lead to a significantly reduced yield of nanopore preparation.[222-223] Moreover, unfavorable electrostatic and steric interactions between the negatively charged protein and the positively charged nanopore inner surface may limit the application of the nanopore in simultaneous sensing of proteins with conflicting charge properties.[219] Simultaneous and high-resolution discrimination of different protein analytes with conflicting charge properties using a nanopore remains a challenge.

SUMMARY OF THE INVENTION

The first aspect of the present invention provides a method of characterizing an analyte in a nanopore system, wherein the nanopore system comprises a protein nanopore disposed in a membrane that separates a first conductive liquid medium from a second conductive liquid medium, wherein the protein nanopore is MspA, MspA homolog or variant thereof, wherein the analyte has an conformation and the analyte with the conformation can be accommodated in the vestibule of the MspA, the MspA homolog or the variant thereof but cannot translocate through the MspA, the MspA homolog or the variant thereof, the method comprising:

i) applying an electrical potential difference between the first conductive liquid medium and the second conductive liquid medium to drive the analyte into the nanopore;

ii) measuring an ionic current through the protein nanopore to provide a tested current pattern that contains at least ionic current measured during the analyte is in the vestibule of the MspA, the MspA homolog or the variant thereof, iii) associating the tested current pattern with at least one characteristic of the analyte.

In some embodiments, the analyte is selected from the group consisting of a nucleic acid, a protein, a polysaccharide, a polymer, an enzyme, and a complex of a nucleic acid, a protein, a peptide, a polysaccharide, a polymer, an enzyme and an agent capable of interacting with them.

In some embodiments, the nucleic acid is selected form the group consisting of a LMW RNA, a nucleic acid duplex, an aptamer, a ribozyme or a nucleic acid with a structure of kissing loop, three-way junction, pseudoknot, kink-turn or G-quadruplex.

In some embodiments, the LMW RNA comprises a siRNA with an overhanged or blunt end, a tRNA, a miRNA and/or a rRNA.

In some embodiments, the nucleic acid duplex has an overhanged or blunt end.

In some embodiments, the nucleic acid duplex is consisted of a miRNA and a nucleic acid probe, and the nucleic acid probe is a RNA, a DNA or a nucleic acid analogue.

In some embodiments, the protein analyte is selected from the group consisting of positively charged, neutral or negatively charged.

In some embodiments, the analyte comprises two or more different analytes and the characterization of these analytes is completed in one measurement.

5

6

In some embodiments, step iii) comprising associating the tested current pattern with at least one characteristic selected from the group consisting of the presence or the absence of the analyte, the identity of the analyte, the sequence of the analyte, the mutations in the analyte, the conformation of the analyte, the local structure of the analyte, the content of the analyte, the overall size of the analyte, the charge of the analyte, and the polarity.

In some embodiments, the analyte is a complex formed by the combination of a target molecule and an assistant molecule.

In some embodiments, step iii) comprises associating the tested current pattern with at least one characteristic of the target molecule.

In some embodiments, the target molecule is miRNA.

In some embodiments, step iii) is performed by comparing the tested current pattern with a reference current pattern or by using a machine learning algorithm.

In some embodiments, the conductive liquid medium on the vestibular side of MspA, the MspA homolog or the variant thereof contains monovalent cation, and the conductive liquid medium on the constriction side of MspA, the MspA homolog or the variant thereof contains divalent cation.

In some embodiments, the monovalent cation is alkali metal ion, preferably selected from $K^+$, $Na^+$ and $Li^+$.

In some embodiments, the divalent cation is alkaline earth metal ion, preferably selected from $Ca^{2+}$, $Mn^{2+}$, $Mg^{2+}$ and $Ba^{2+}$.

The second aspect of the present invention provides a method for characterizing the interaction between an analyte and an agent in a nanopore system, wherein the nanopore system comprises a protein nanopore disposed in a membrane that separates a first conductive liquid medium from a second conductive liquid medium, wherein the protein nanopore is MspA, MspA homolog or variant thereof, wherein the analyte has an conformation and the analyte with the conformation can be accommodated in the vestibule of the MspA, the MspA homolog or the variant thereof but cannot translocate through the MspA, the MspA homolog or the variant thereof, the method comprising:

i) contacting the analyte with the agent, and driving the analyte into the nanopore by an electrical potential difference between the first conductive liquid medium and the second conductive liquid medium;

ii) measuring an ionic current through the protein nanopore to provide a tested current pattern that contains at least ionic current measured during the analyte is in the vestibule of the MspA, the MspA homolog or the variant thereof, iii) associated the current pattern with the interaction between the analyte and the agent.

The second aspect of the present invention also provides a method for characterizing an agent capable of interacting with an analyte in a nanopore system, wherein the nanopore system comprises a protein nanopore disposed in a membrane that separates a first conductive liquid medium from a second conductive liquid medium, wherein the protein nanopore is MspA, MspA homolog or variant thereof, wherein the analyte has an conformation and the analyte with the conformation can be accommodated in the vestibule of the MspA, the MspA homolog or the variant thereof but cannot translocate through the MspA, the MspA homolog or the variant thereof, the method comprising:

i) contacting the analyte with the agent, and driving the analyte into the nanopore by an electrical potential difference between the first conductive liquid medium and the second conductive liquid medium;

ii) measuring an ionic current through the protein nanopore to provide a tested current pattern that contains at least ionic current measured during the analyte is in the vestibule of the MspA, the MspA homolog or the variant thereof, iii) associated the current pattern with the agent.

In step i), there is no restriction on the order of "contacting the analyte with the agent" and "driving the analyte into the nanopore by an electrical potential difference between the first conductive liquid medium and the second conductive liquid medium", each of which can go first. For example, it is possible to contact the analyte with the agent first, and then drive the analyte into the nanopore by an electrical potential difference between the first conductive liquid medium and the second conductive liquid medium. It is also possible to drive the analyte into the nanopore by an electrical potential difference between the first conductive liquid medium and the second conductive liquid medium first, and then contact the analyte with the agent.

In some embodiments, the analyte is selected from the group consisting of a nucleic acid, a protein, a polysaccharide, a polymer and an enzyme.

In some embodiments, the nucleic acid is an aptamer or a ribozyine.

In some embodiments, the analyte can interact with an ion, a small molecule, a ligand, a receptor or a substrate.

In some embodiments, the agent is an ion, a small molecule, a ligand, a receptor or a substrate.

In some embodiments, the agent is a polysaccharide, preferably popidglycan, chitosan or chitin.

In some embodiments, the analyte is lysozyme.

In some embodiments, step iii) is performed by comparing the tested current pattern with a reference current pattern or by using a machine learning algorithm.

In some embodiments, the conductive liquid medium on the vestibular side of MspA, the MspA homolog or the variant thereof contains monovalent cation, and the conductive liquid medium on the constriction side of MspA, the MspA homolog or the variant thereof contains divalent cation.

In some embodiments, the monovalent cation is alkali metal ion, preferably selected from $K^+$, $Na^+$ and $Li^+$.

In some embodiments, the divalent cation is alkaline earth metal ion, preferably selected from $Ca^{2+}$, $Mn^{2+}$, $Mg^{2+}$ and $Ba^{2+}$.

The third aspect of the present invention provides a method for detecting an analyte of interest in a sample in a nanopore system, wherein the nanopore system comprises a protein nanopore disposed in a membrane that separates a first conductive liquid medium from a second conductive liquid medium, wherein the protein nanopore is MspA, the MspA homolog or the variant thereof, wherein the analyte of interest has an conformation and the analyte of interest with the original conformation can be accommodated in the vestibule of MspA, the MspA homolog or the variant thereof but cannot translocate through MspA, the MspA homolog or the variant thereof, the method comprising:

i) adding the sample to the at least one of the first conductive liquid medium from a second conductive liquid medium and applying an electrical potential difference between the first conductive liquid medium and the second conductive liquid medium that is suitable for driving the analyte of interest into the nanopore;

ii) measuring an ionic current through the protein nanopore for a period of time to provide a tested current pattern;

iii) comparing the tested current pattern with a reference current pattern which comprises at least ionic current trace measured during the analyte of interest is in the vestibule of MspA, the MspA homolog or the variant thereof, iv) determining the presence or the absence of the analyte of interest in the sample and/or the content of the analyte of interest in the sample by the comparison of iii).

In step i), there is no restriction on the order of "adding the sample to the at least one of the first conductive liquid medium from a second conductive liquid medium" and "applying an electrical potential difference between the first conductive liquid medium and the second conductive liquid medium that is suitable for driving the analyte of interest into the nanopore", each of which can go first. For example, it is possible to add the sample to the at least one of the first conductive liquid medium from a second conductive liquid medium first, and then apply an electrical potential difference between the first conductive liquid medium and the second conductive liquid medium that is suitable for driving the analyte of interest into the nanopore. It is also possible to apply an electrical potential difference between the first conductive liquid medium and the second conductive liquid medium that is suitable for driving the analyte of interest into the nanopore first, and then add the sample to the at least one of the first conductive liquid medium from a second conductive liquid medium.

In some embodiments, the analyte of interest is selected from the group consisting of a nucleic acid, a protein, a polysaccharide, a polymer and an enzyme.

In some embodiments, the analyte is whey protein.

In some embodiments, the analyte is α-lactalbumin and/or β-lactoglobulin.

In some embodiments, wherein the sample is milk or protein powder.

In some embodiments, the conductive liquid medium on the vestibular side of MspA, the MspA homolog or the variant thereof contains monovalent cation, and the conductive liquid medium on the constriction side of MspA, the MspA homolog or the variant thereof contains divalent cation.

In some embodiments, the monovalent cation is alkali metal ion, preferably selected from $K^+$, $Na^+$ and $Li^+$.

In some embodiments, the divalent cation is alkaline earth metal ion, preferably selected from $Ca^{2+}$, $Mn^{2+}$, $Mg^{2+}$ and $Ba^{2+}$.

Figure 18:
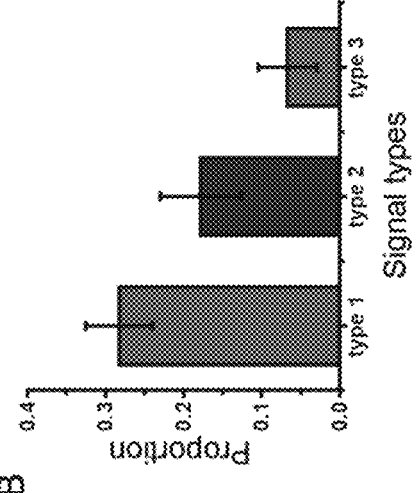
Figure 18:
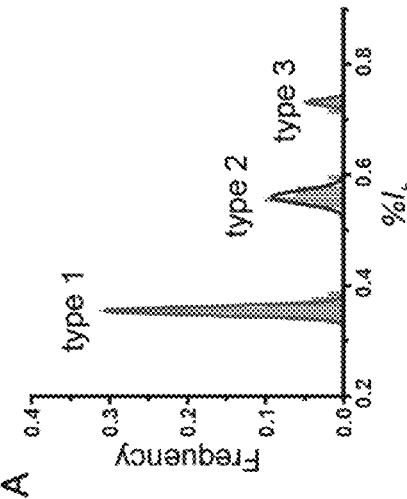

FIG. 18 shows statistics for 5S rRNA sensing events. A. Histogram of % $I_b$ of the three types sensing events. The distributions of each types follow a Gaussian fitting. B. The proportion of the three types sensing events. Type 1 events account for the highest proportion, followed by type 2 and type 3. This suggests that 5S rRNA has a more favored orientation when entering into MspA, which results in the type 1 event. Three independent measurements were performed to form the statistics.

Figure 19:
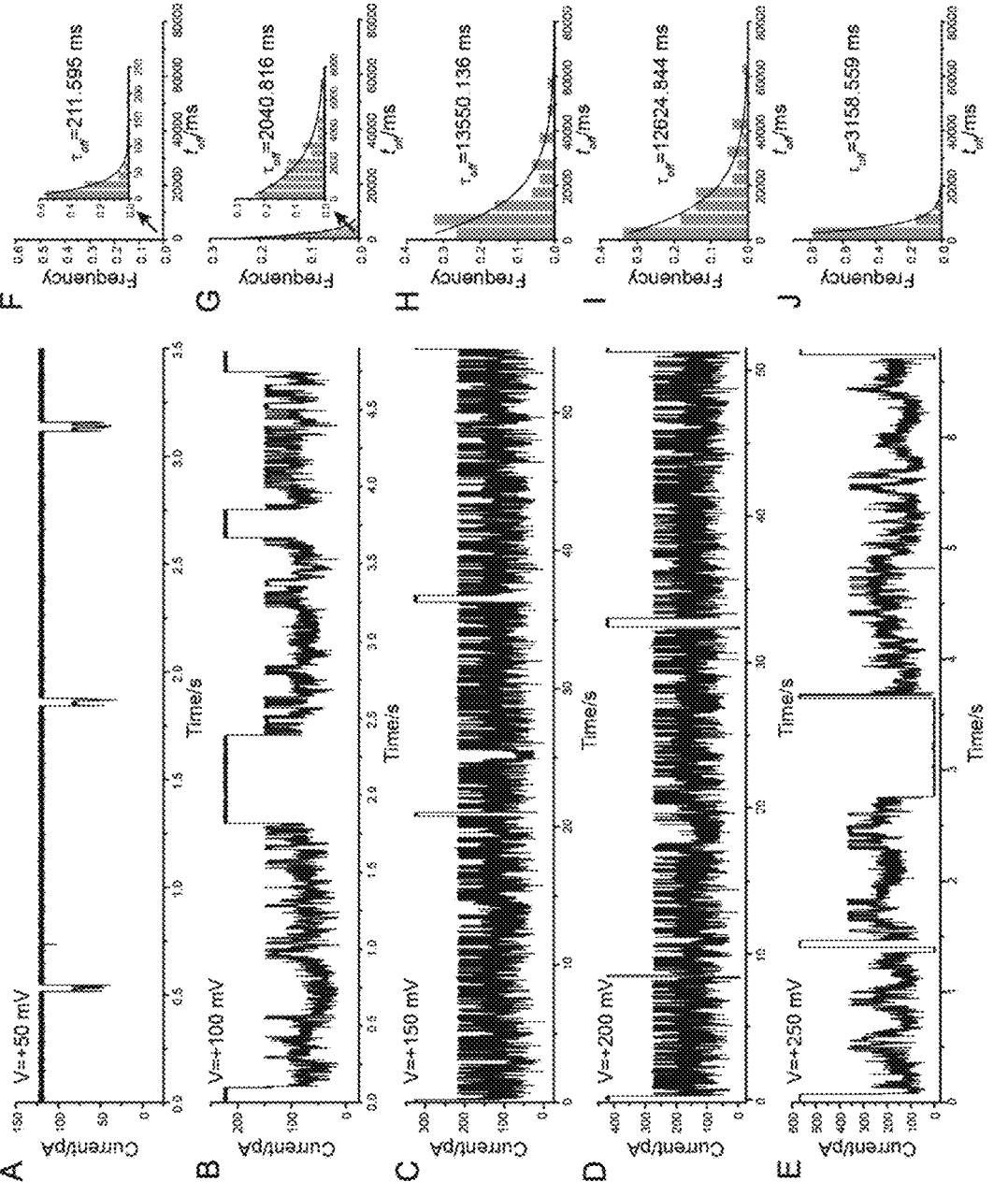

FIG. 19 shows type 1 events of 5S rRNA at different voltages. A-E. Representative type 1 events at +50 mV (A), +100 mV (B), +150 mV (C), +200 mV (D) and +250 mV (E). F-J. Corresponding histograms of ty, at +50 mV (F), +100 mV (G), +150 mV (H), +200 mV (I) and +250 mV (J). $\tau_{off}$ increased when the applied potential was increased from +50 mV to +150 mV. However, $\tau_{off}$ decreased when the potential was further increased from +150 mV to +250 mV. At +250 mV, all events demonstrate significant fluctuations followed with a deep blockage and a spontaneous restoration to the open pore state. These results indicate that successful translocation of 5S rRNA requires overcoming of a high entropic barrier. A high applied potential would promote translocation of 5S rRNA. The fluctuation noises observed likely result from electrophoretic driven unfolding of its overall structure. Thus, the helix I-down conformation is most likely happening when a type 1 event was observed. The type 1 event is less likely from the loop C or loop E-down conformation since a loop structure is much more difficult to be electrophoretically unfolded than the helix. All measurements were carried out as described in Methods. 5S rRNA was added to cis with a final concentration of 10 nM.

Figure 7:
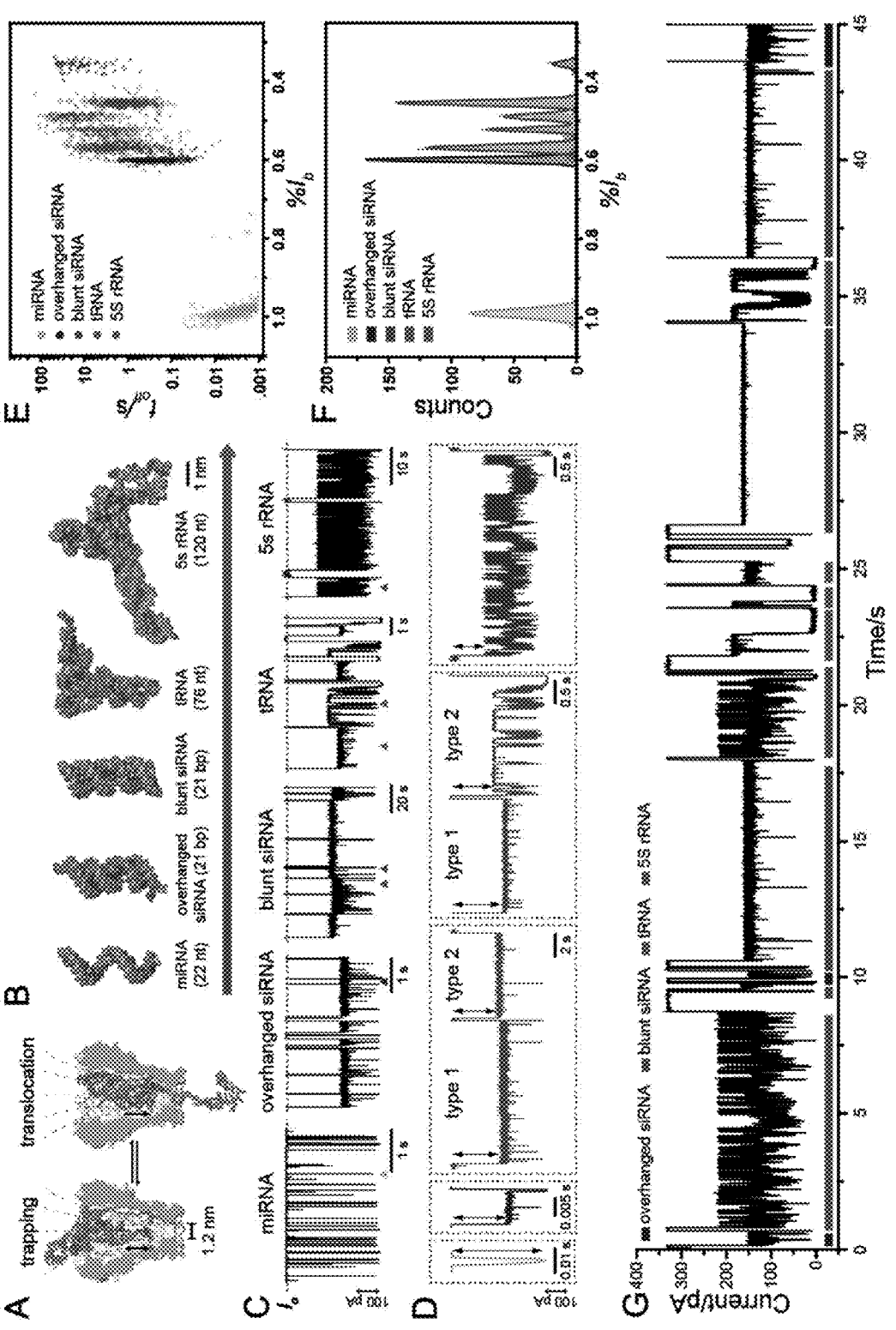
FIG. 7 shows distinguishing between LMW RNA tertiary structures with MspA. A. The scheme of nanopore trapping/translocation using MspA. Left: RNA structural profiling by nanopore trapping. In this case, the RNA is electrophoretically trapped in the pore vestibule, giving rise to the blockade level that is highly dependent on the structure of the analyte. Right: RNA structural profiling by nanopore translocation. In this case, the trapped RNA is electrophoretically unzipped to translocate through the pore, normally causing a much deeper blockade level. Current fluctuations between trapping and translocation reveal the RNA identity. TRNA was employed as an example in this scheme. B. Representative RNA molecules studied by nanopore trapping/translocation using MspA in this manuscript. Five types of non-coding RNAs, including miRNA (single stranded, 22 nt), overhanged siRNA (double stranded, 21 bp), blunt siRNA (double stranded, 21 bp), tRNA (L shaped, 76 nt) and 5S rRNA (Y shaped, 120 nt) were investigated. The measurements were carried out as described in Methods. MiRNA (has-miR-21), overhanged siRNA (SiFoxA1), blunt siRNA (luciferase siRNA) or tRNA (tRNA$^{phe}$) were added to the cis chamber with a final concentration of 200 nM for each analyte. E. coli 5S rRNA was added to cis with a final concentration of 10 nM. C. Representative traces of successive translocations of miRNA, overhanged siRNA, blunt siRNA, tRNA or 5S rRNA through MspA. The open pore current ($I_o$) is marked with dashed lines. D. Zoom-in views of representative translocation events from marked triangles of corresponding traces. Translocations of different types of RNAs result in highly distinguishable events features. MiRNA gives rise to fast spiky events. Overhanged siRNA produces two-step events. Blunt siRNA and tRNA both generate two types of events generates two types of events, termed type 1 and type 2. 5S rRNA gives rise to three types of signals, which the most characteristic type is shown in the figure. The % $I_b$ refers to the first-level blockade amplitude which is defined as marked in D. E. A scatter plot of % $I_b$ versus $t_{off}$ for five RNA samples (the scatter plots from left to right correspond to miRNA, overhanged siRNA, blunt siRNA, tRNA and 5S rRNA, respectively). Events from three types of RNAs are clearly distinguishable. F. The corresponding event histogram of % $I_b$ of different RNA types (from left to right correspond to miRNA, overhanged siRNA, blunt siRNA, tRNA and 5S rRNA, respectively). Black lines are Gaussian fittings to the data. G. A representative trace during simultaneous sensing of siRNA, tRNA and 5S rRNA. Different RNA types (overhanged siRNA: 25 nM; blunt siRNA: 10 nM; tRNA: 400 nM; 5S rRNA: 30 nM) were simultaneously added to cis side. Characteristic events from different RNA types are clearly recognized from the trace, which are marked with blue, green red or purple bars respectively.
Figure 8:
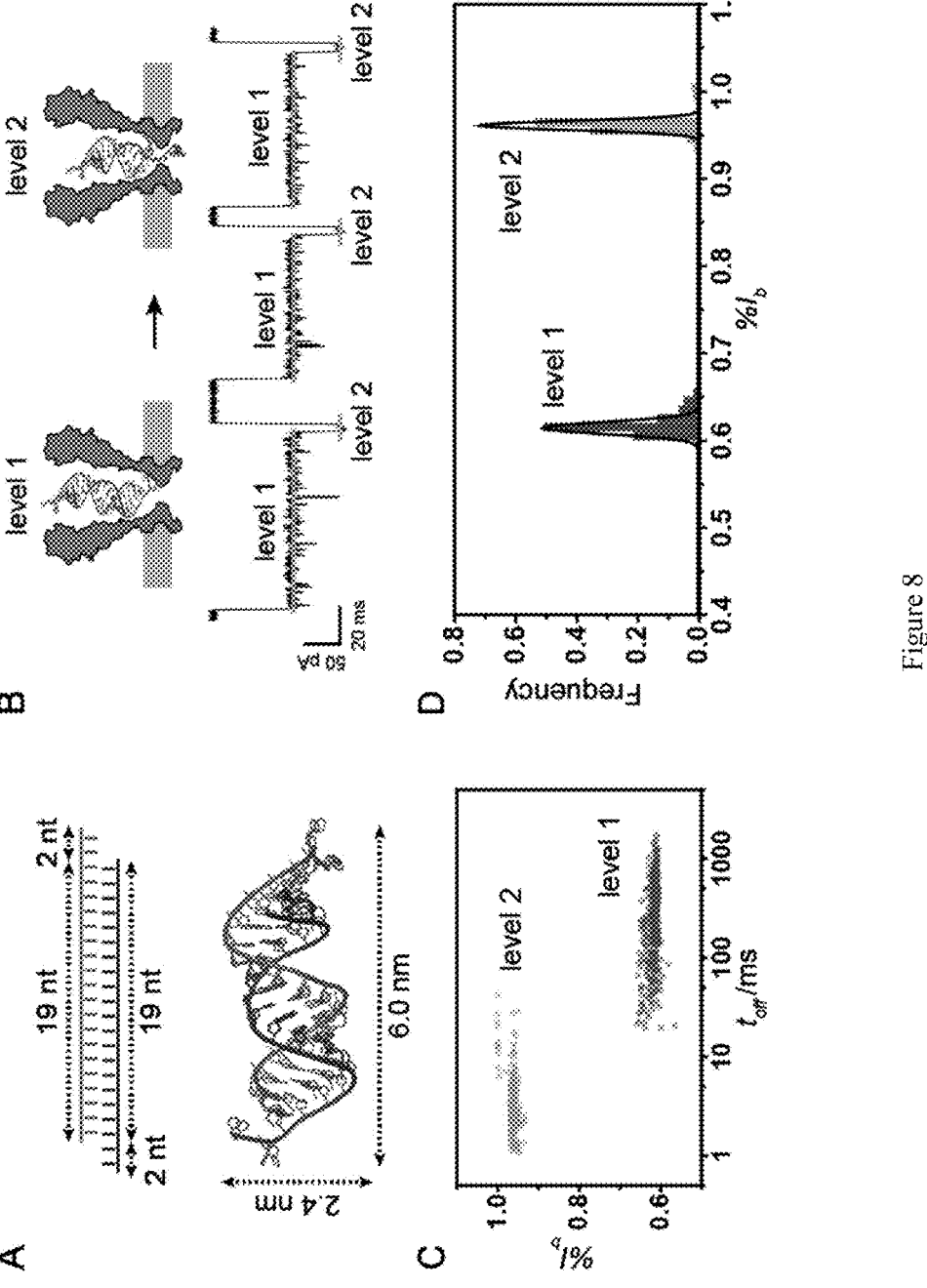
FIG. 8 shows overhanged siRNA translocation events. A. The structure of overhanged siRNA (PDB:IRUP). The secondary structure of overhanged siRNA (top) is composed of a 19-bp double strand and two 2-nt overhangs. They fold into an A-form duplex (bottom). B. Representative overhanged siRNA translocation events (bottom) and a suggested model of translocation (top). The model suggests that overhanged siRNA first partially blocks the pore followed with an electrophoretically driven unzipping of the duplex. The measurement was performed with a +150 mV continuously applied potential. In this condition, the majority of overhanged siRNA translocation events appear as characteristic 2-step shaped events (bottom left), which start with an initial partial blockage (level 1) followed with a further deeper blockage (level 2). Please note that some events may have missing level 1 or level 2. Events with missing level 1 is however extremely rare to observe. Events with missing level 2 are well recognized since the characteristics of level 1 is more significant in the evaluation of the event identity. C. The scatter plot of % $I_b$ versus $t_{off}$. D. The corresponding event histogram of % $I_b$. Nanopore measurements were performed as described in Methods. Hybridized overhanged siFoxA1 (Materials, Table 1) was added in cis with a final concentration of 200 nM.
Figure 20:
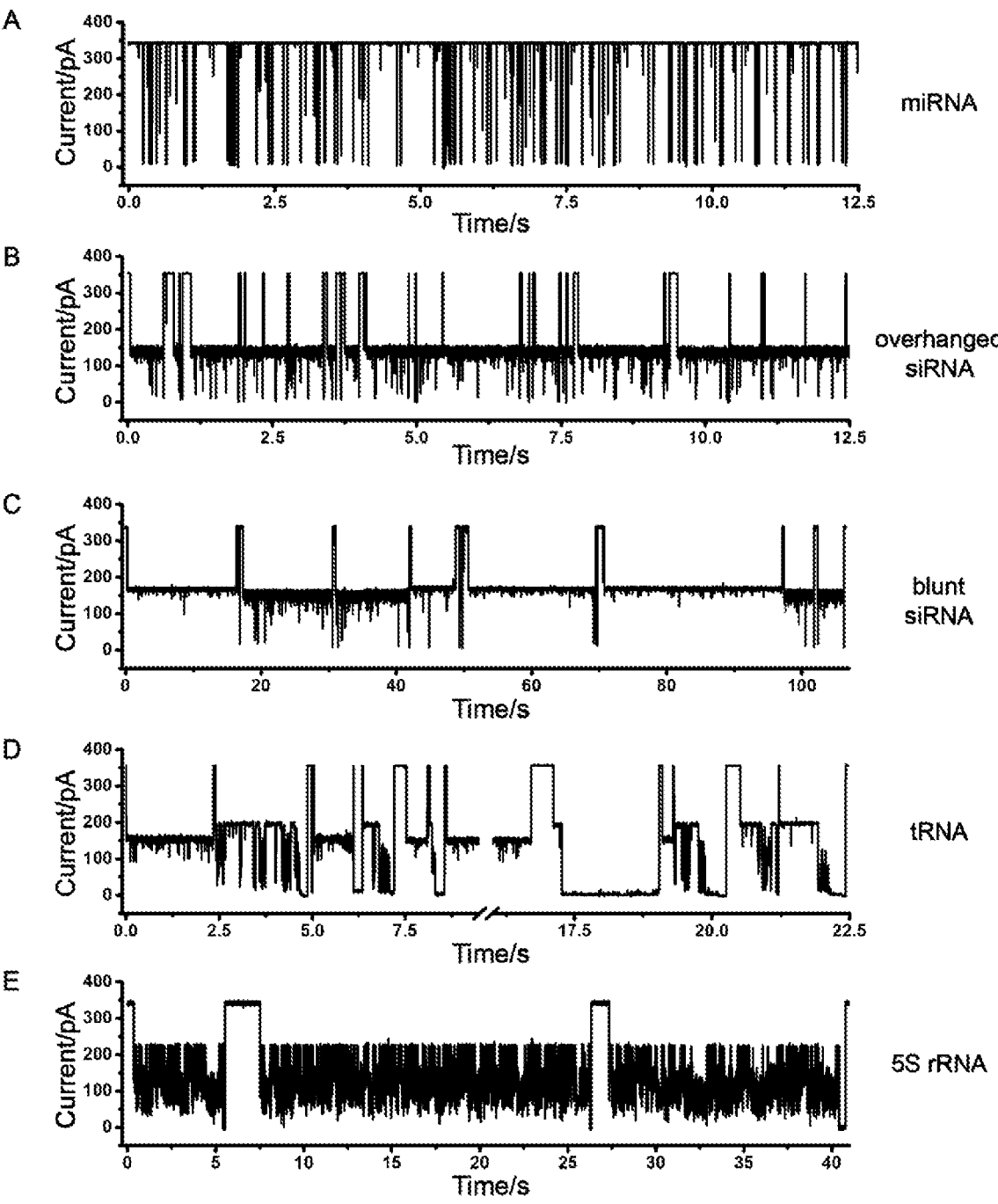

FIG. 20 shows representative traces of RNA translocations. Nanopore measurements were performed as described in Methods. Model analyte of miRNA, siRNA or tRNA was respectively added to cis with a final concentration of 200 nM. 5S rRNA was added to cis with a final concentration of 10 nM. A. A representative trace containing successive miRNA translocation events. Hsa-miR-21 (Table 1) is the sole analyte. Translocation of miRNA appears as fast and deep current blockades. B. A representative trace containing successive overhanged siRNA translocation events. Hybridized siFoxA1 (Table 1) is the sole analyte. Translocation of overhanged siRNA gives rise to characteristic two-step shaped events (FIG. 8). C. A representative trace containing successive blunt siRNA translocation events. Luciferase siRNA serves as the sole analyte. D. A representative trace containing successive tRNA translocation events. Brewer's yeast phenylalanine specific tRNA (Sigma-Aldrich), also termed as tRNA$^{phe}$, serves as the sole analyte. Two types of events with highly distinguishable event characteristics form the majority of all acquired events (FIG. 7B). The current traces from 9.5 s to 16 s has been omitted due to an event with an extremely long residence time. E. A representative trace containing successive 5S rRNA translocation events. *E. coli* 5S rRNA recovered from polyacrylamide gels serves as the sole analyte.

Figure 21:
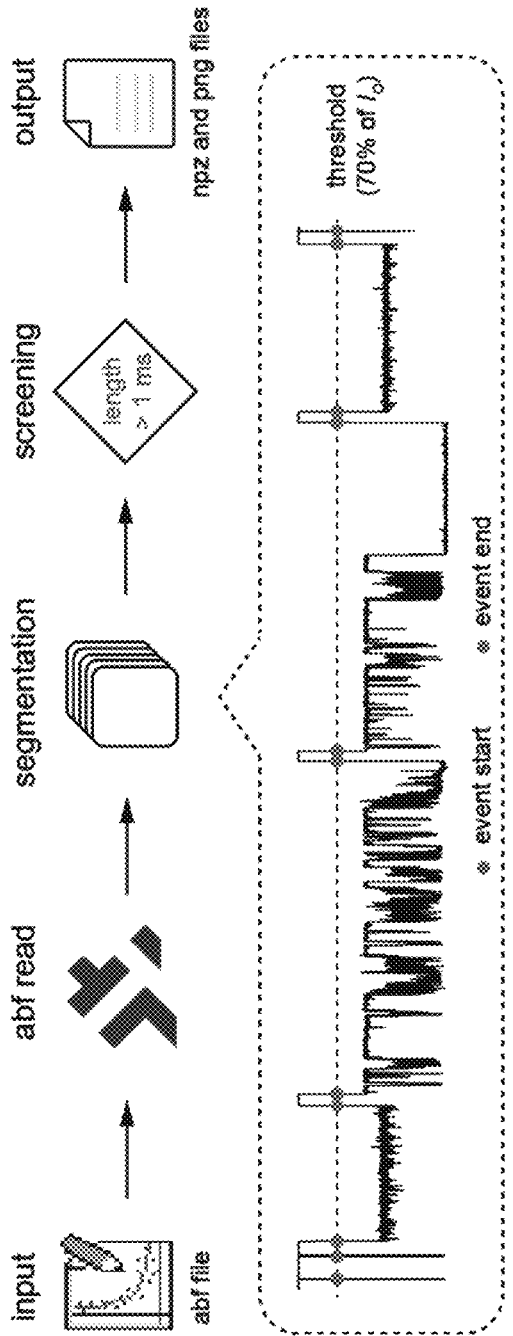

FIG. 21 shows a workflow of event extraction. All single channel recordings results were first recorded in .abf files. All .abf files were first imported into the Python environment by the Neo package. Event segmentation was carried out by a threshold search routine custom programmed by Python. Its principle is demonstrated in the dotted box. The threshold of 70% of 1, was selected because it is much higher than the highest level of all events being studied in this manuscript. No event was missed due to this threshold setting. To perform segmentation, a signal fraction which has a current drop below 70% of % followed with a spontaneous restoration to $I_o$ is recognized as an event. To avoid interference from events caused by transient collision of the analyte to the pore, only events with a dwell time more than 1 ms were saved for downstream analysis. The extracted event data were saved in npz format, each accompanied with a png format figure for an ease of visualization.

Figure 22:
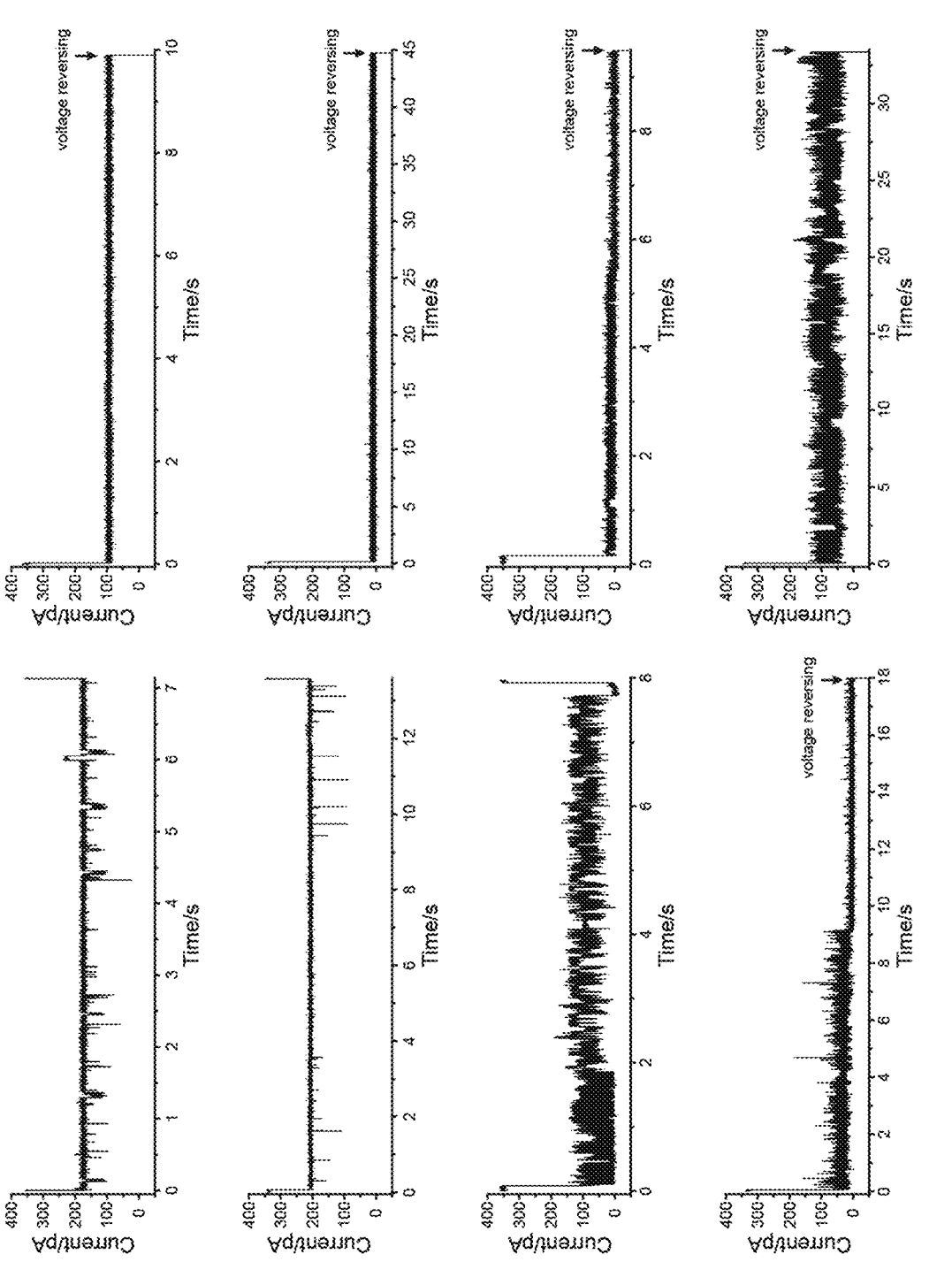

FIG. 22 shows demonstration of "others" events. Nanopore measurements were performed as described in Methods. Events which may result from RNA translocation with an undesired orientation or pore clogging were occasionally observed. Though observable, these events only form a minority of all acquired events and contribute to the type "others" in the machine learning algorithm (FIG. 23A). Please note that a clogged pore can also be manually restored by reversing the applied potential to re-initiate follow-up measurements.

Figure 23:
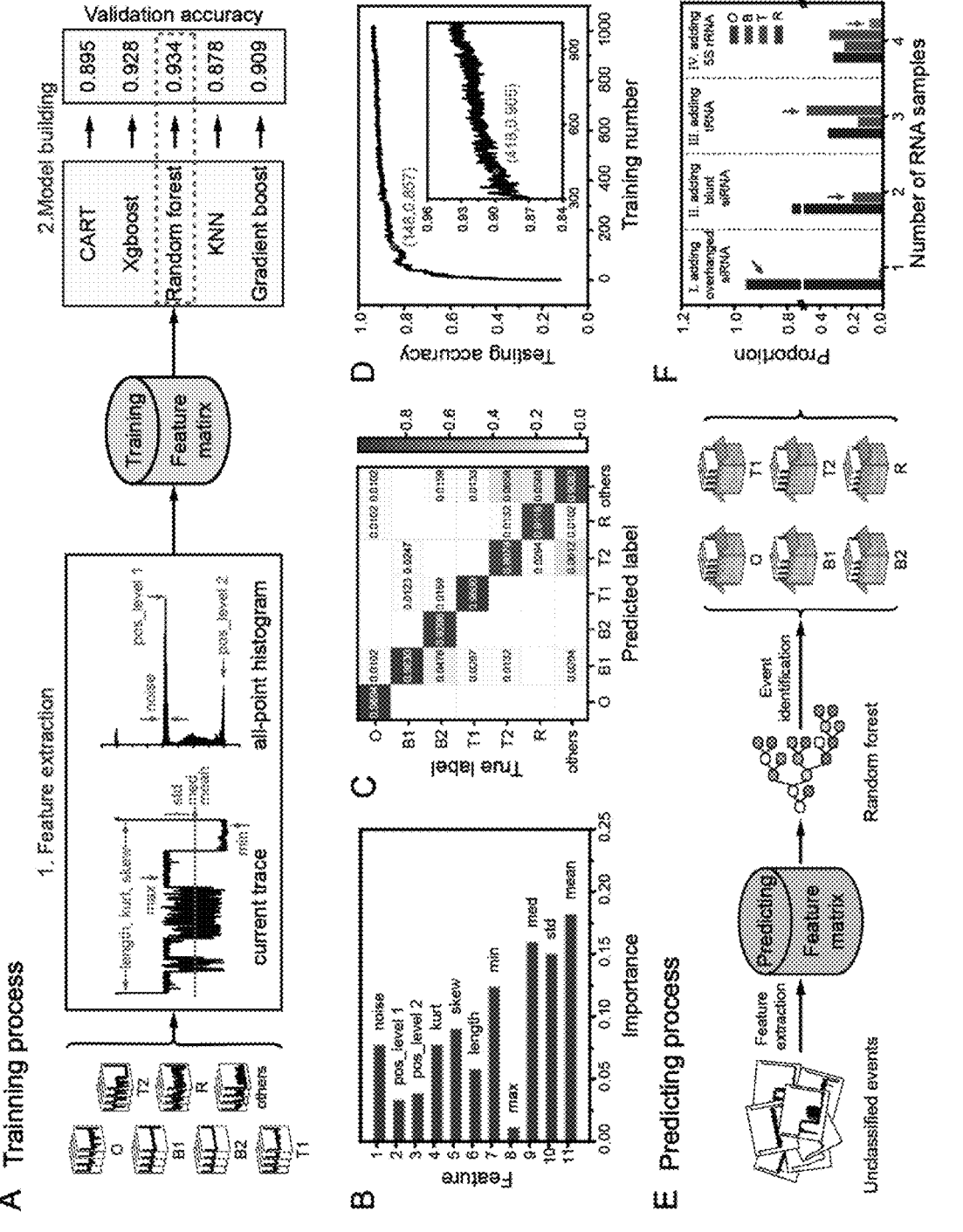

FIG. 23 shows machine learning assisted RNA type identification. A. The flow diagram of the training process. Seven classes of events, including overhanged siRNA (O), blunt siRNA type 1 (B1), blunt siRNA type 2 (B2), tRNA type 1 (T1), tRNA type 2 (T2), 5S rRNA (R) and others were formed as the training dataset. Eleven features were extracted to form a feature matrix. The training dataset was then split to training subset and validation subset, of which the validation subset serves to verify the accuracy of the classifier model. The accuracy was defined as the ratio of events in the validation subset that were correctly identified. Five classifiers were investigated to identify the best performing model, for which the random forest model has demonstrated the highest accuracy, scoring 0.934. B. Feature importance obtained from the Random forest model. All features play a role in RNA event recognition. C. The confusion matrix of RNA classification. Accuracies of testing set were obtained by the Random forest model. The testing set was composed of 98 overhanged siRNA events, 81 blunt siRNA type 1 events, 63 blunt siRNA type 2 events, 75 tRNA type 1 events, 76 tRNA type 2 events, 68 5S rRNA and 98 "others". D. The learning curve with varying sample size of the training set. When the sample of the training set exceeds 148, the accuracy of validation has reached 0.85. When it exceeds 418, the accuracy saturates at ~0.90. E. The flow diagram of the predicting process. The raw current traces of mixed samples were segmented into separate, unclassified events. Event features were extracted and serve as predicting set, which was subsequently recognized and sorted using the Random forest model. F. The proportion of different RNA events determined with the Random forest model. The arrows indicate the proportion of RNA newly added. Four sets of data were recorded when overhanged siRNA, blunt siRNA, tRNA and 5S rRNA were sequentially added to cis.

Figure 24:
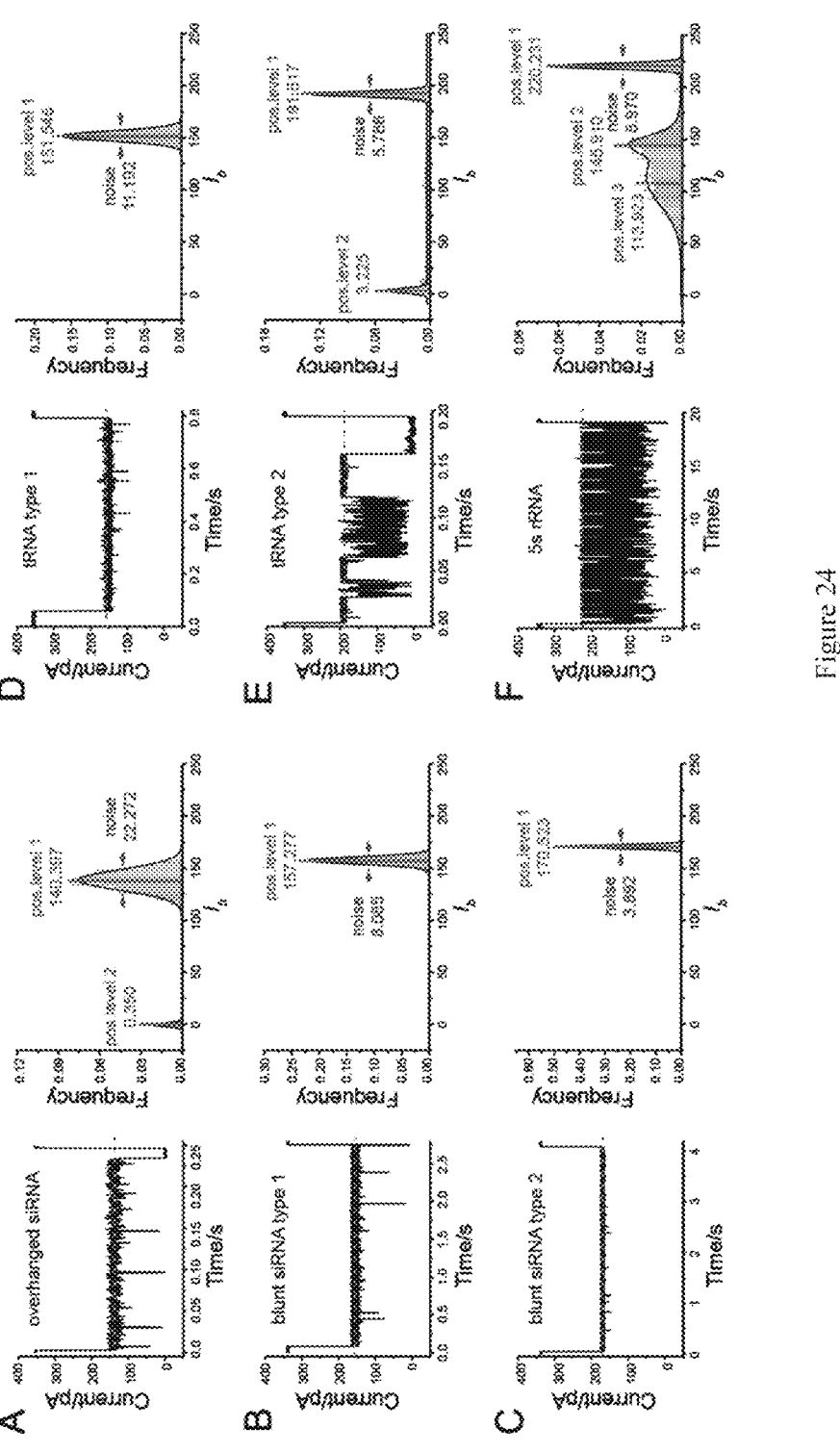

FIG. 24 shows event feature extraction. Multi-peak Gaussian fitting to all point histogram was used to extract event features such as the identity, the position and the noise of the levels from each event. Representative translocation events of overhanged siRNA (siFoxA1) (A), blunt siRNA (luciferase siRNA) type 1(B), blunt siRNA type 2(C), tRNA (tRNA$^{phe}$) type 1 (D), tRNA type 2 (E), *E. coli* 5S rRNA (F) and their corresponding all point histogram were demonstrated. When there is only one recognizable Gaussian peak in the histogram (B, C, D), the identity of the peak is determined as 1. The position and the noise of the peak is determined from the Gaussian fitting results. When more than 2 Gaussian peaks were recognized (B, A, E, F), the peak closer to the open pore current was considered to be peak 1 and the other peak is considered to be peak 2, 3. Position and noise of each peak were respectively determined according to the fitting results. With these extracted event features, different types of RNA translocation events are clearly recognizable.

Figure 25:
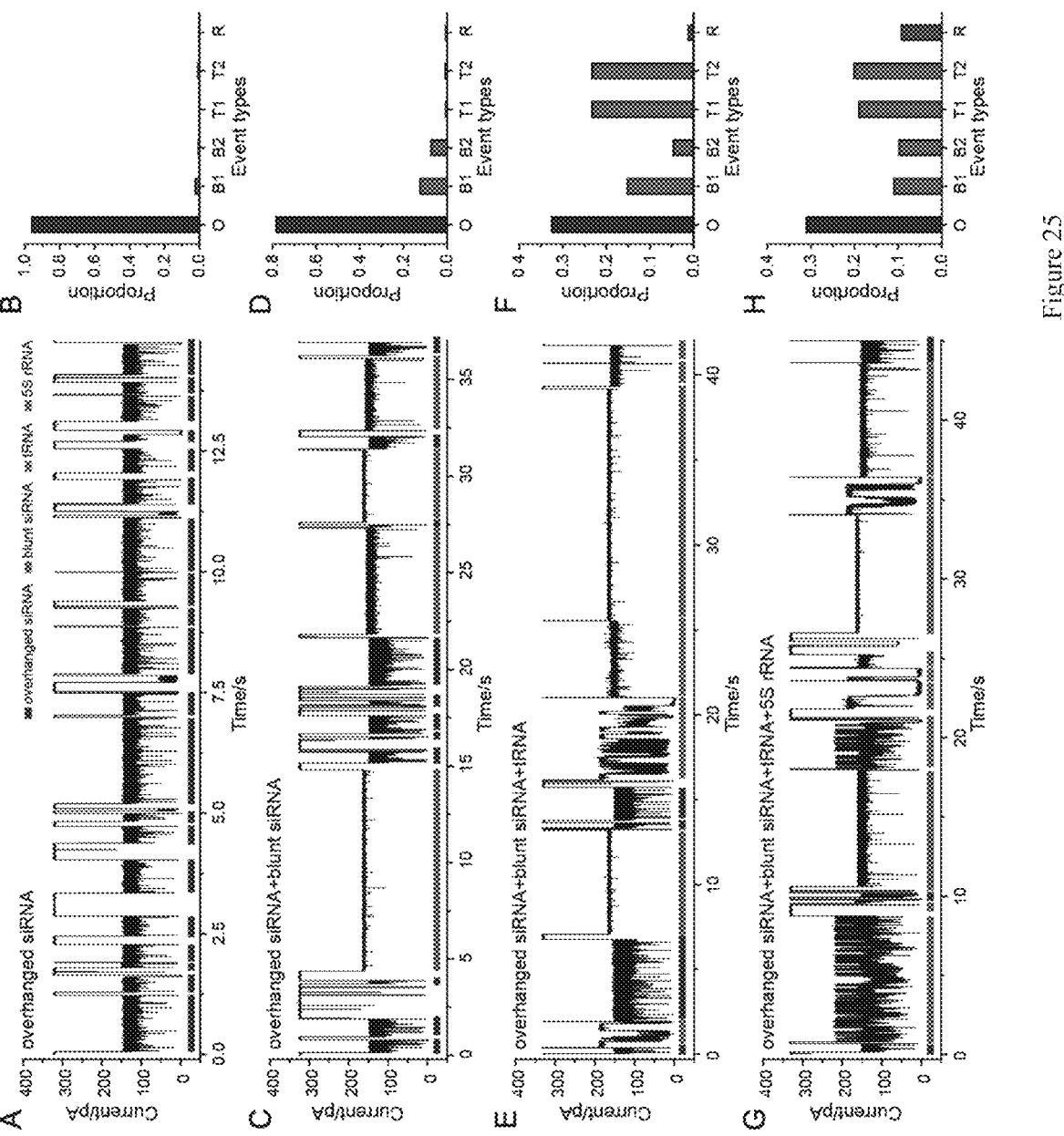

FIG. 25 shows MD analysis of tRNA translocations. A-C. Equilibrated structures of tRNA entering an MspA nanopore. The conformations are respectively termed as stem-down (A), loop-down (B) or arm-down (C). The green sphere marked on each conformation referred to the leading nucleotide, which was used to characterize the position of tRNA in following simulation results. D-E. The z-coordinates of the leading nucleotide as a function of time for the simulations with the stem-down (D), the loop-down (E), and the arm-down (F) conformation. Seven trajectories were shown for each condition. The results show that the stem-down conformation has a higher tendency to translocate through the pore, while the other two conformations cannot reach the pore constriction to initiate a translocation. G. Simulated cumulative ion currents through the pore at the open pore (green), the arm-down (grey), the stem-down (red), the loop-down (blue) and the tRNA translocation (purple) state (the position of the corresponding ion current curve in the figure is from top to bottom). The external electric field was 0.09 V/10 nm, which corresponds to a voltage bias of ~+150 mV. The tRNA does not have obvious movement along the z-axis during the simulation timescale with such a low voltage. The slopes of the cumulative currents represent the ion current values. H. The derived ionic currents for different states of sensing. All values were scaled so that the open pore current reports 1.

Figure 26:
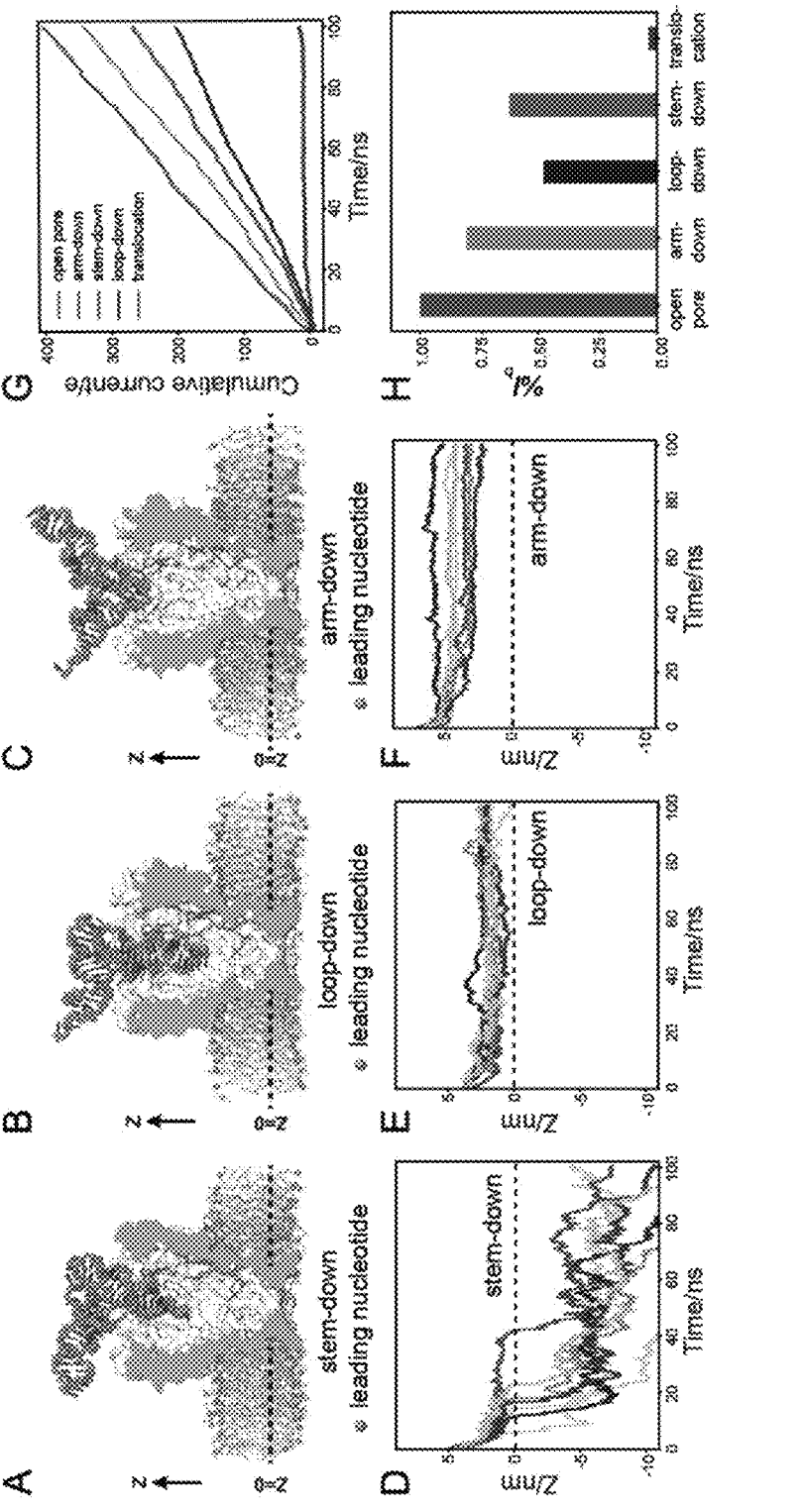

FIG. 26 shows RNA type identification with machine learning algorithms. A. A representative trace in the presence of overhanged siRNA (25 nM). Characteristic events of overhanged siRNA (marked with blue bars) were observed in the majority. B. Corresponding proportion of different RNA events determined with the Random forest model. 95.8% events were identified as characteristic events of overhanged siRNA. C. A representative trace during successive addition of blunt siRNA (10 nM). Except overhanged siRNA events (marked with blue bars), blunt siRNA type 1 and type 2 events (marked with greet bars) were also observed. D. Corresponding proportion of different RNA events determined with the Random forest model. Proportions of blunt siRNA type 1 and type 2 events accounted for 0.12 and 0.08. E. A representative trace during successive addition of tRNA (450 nM). TRNA type 1 and type 2 events (marked with red bars) appeared in the current trace. F. Corresponding proportion of different RNA events determined with the Random forest model. Proportions of tRNA siRNA type 1 and type 2 events accounted for 0.26 and 0.23. F. A representative trace during successive addition of 5S rRNA (30 nM). Fingerprint events from the four types of RNA types are clearly recognized from the trace, which are marked with blue, green red or purple bars respectively. H. Corresponding proportion of different RNA events determined with the Random forest model. After the addition, the Proportion of 5S rRNA events increased from 0 to 0.09. Nanopore measurements were performed as described in Methods. A twenty-minute trace was recorded for each condition.

Figure 27:
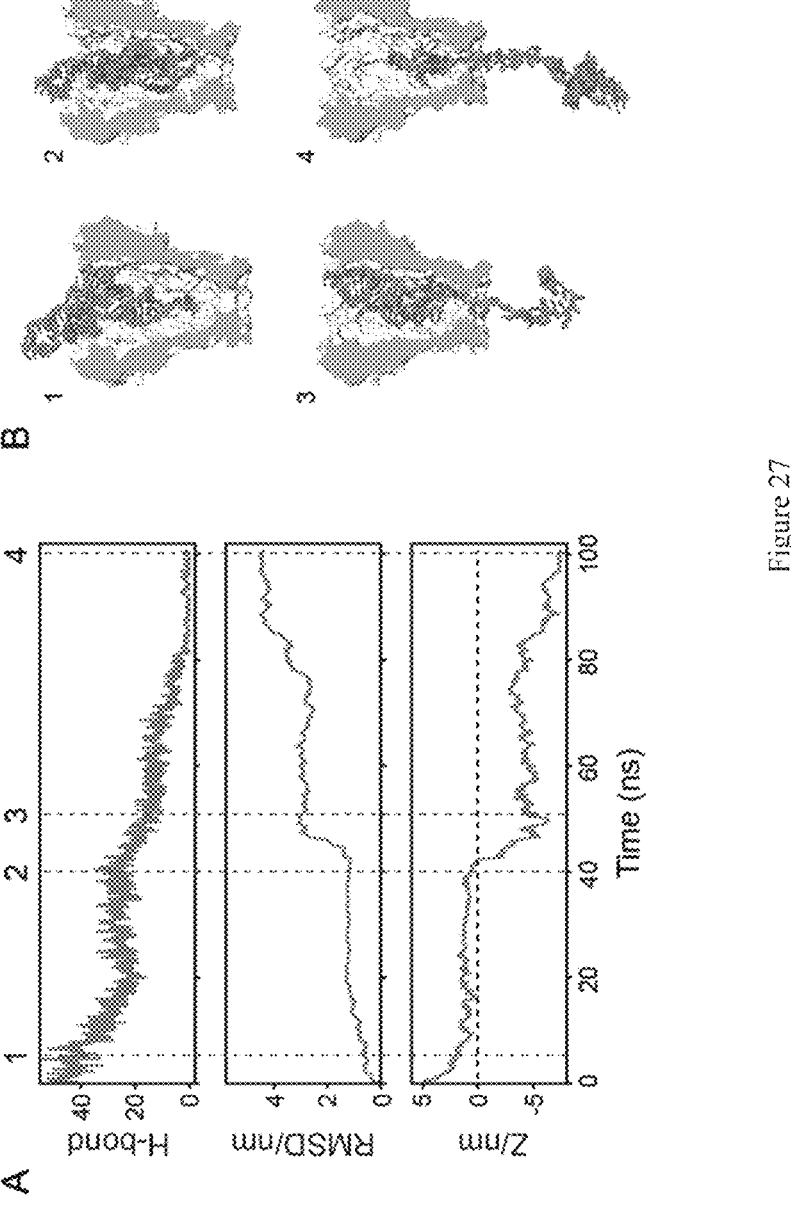

FIG. 27 shows simulated tRNA translocation with the stem-down pose. A. The number of base-pair hydrogen bonds (H-bond), the root mean square deviation (RMSD)

from crystal structure, and the z-coordinate (Z) of the tRNA as a function of time for a representative MD trajectory with the stem-down pose. An external electric field of 4.0 V/10 nm along the Z-axis was applied to drive the tRNA translocation. B. The snapshots of corresponding structures to the four time points labelled in panel A (red dashed lines).

Figure 28:
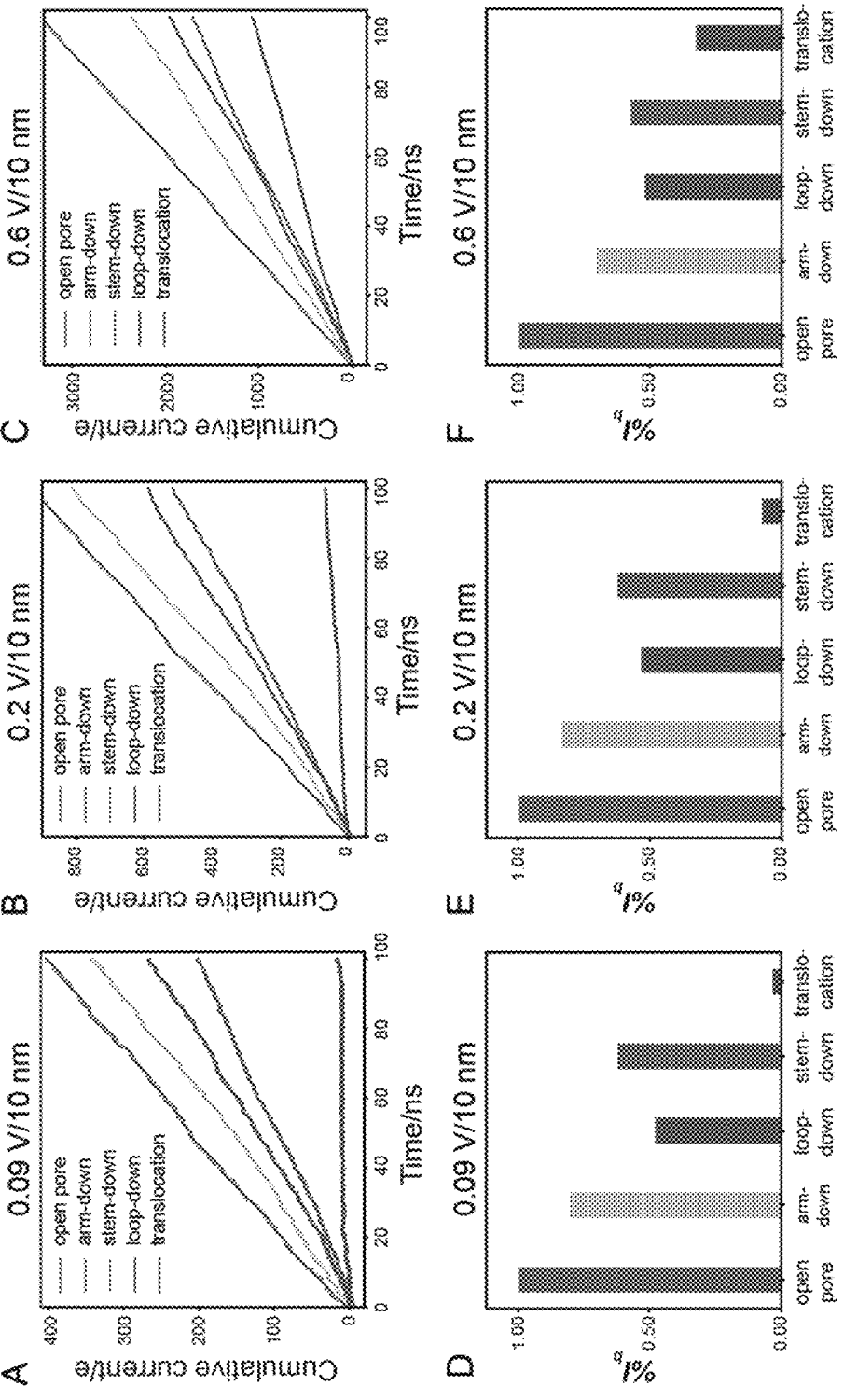

FIG. 28 shows molecular dynamics simulation results. A-C. Cumulative ion currents for the simulations of open pore state (green), the arm-down (gray), the stem-down (red), the loop-down (blue) conformations during the trapping state and when the tRNA was translocating through the pore (purple) under an external electric fields of 0.09 V/10 nm (A), 0.2 V/10 nm (B) and 0.6 V/10 nm (C), respectively (the position of the corresponding ion current curve in each figure from top to bottom). D-F. The relative ionic currents for different tRNA orientations under the external electric fields of 0.09 V/10 nm (D), 0.2 V/10 nm (E) and 0.6 V/10 nm (F), respectively.

Figure 29:
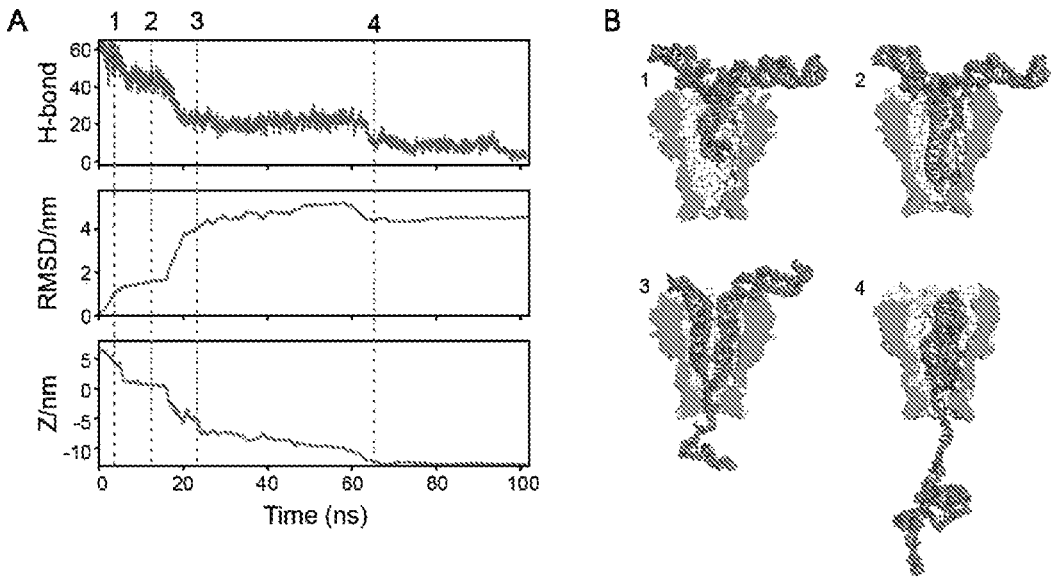

FIG. 29 shows simulated 5S rRNA translocation through MspA. A. The number of base-pair hydrogen bonds (H-bond), the root mean square deviation (RMSD) from crystal structure, and the z-coordinate (Z) of the 5S rRNA as a function of time for a representative MD trajectory with the helix I-down pose. An external electric field of 4.0 V/10 nm along the Z-axis was applied to drive the 5S rRNA translocation. B. The snapshots of corresponding structures to the four time points labelled in panel A (red dashed lines). Translocation of 5srRNA shows similar behavior as that of tRNA. At the initial stage, the 5srRNA has dramatic deformation without disrupting the base-pair hydrogen bonds as shown by the increase of the RMSD and relatively stable values of the number of formed hydron bonds. After reaching the deeper position of MspA, the 5srRNA gets unfolded by unzipping of the helix domain followed by successful translocation of the leading nucleotide through the pore constriction and further unfolding of the entire structure.

Figure 30:
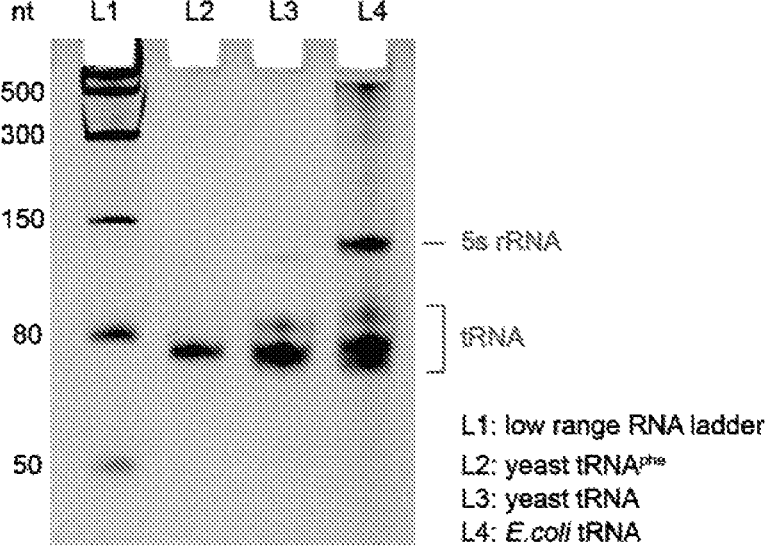

FIG. 30 shows gel electrophoresis of tRNAs from commercial sources. 12% urea-PAGE gel electrophoresis was performed for various tRNA samples from commercial sources, including yeast tRNA$^{phe}$, yeast total tRNA and *E. coli* total tRNA (Sigma-Aldrich). L1: low range RNA ladder; L2: yeast tRNA$^{phe}$; L3: yeast tRNA, L4: *E. coli* tRNA. Gel electrophoresis was continuously run for 60 min with a +180 V applied potential. From the gel results, yeast tRNA$^{phe}$ and yeast tRNA have the desired purity. However, *E. coli* total tRNA contains recognizable contaminations from 5S rRNA (120 nt) and some other RNAs with a higher molecular weight. The identities of these contaminations were determined according to results in the literature[97].

Figure 31:
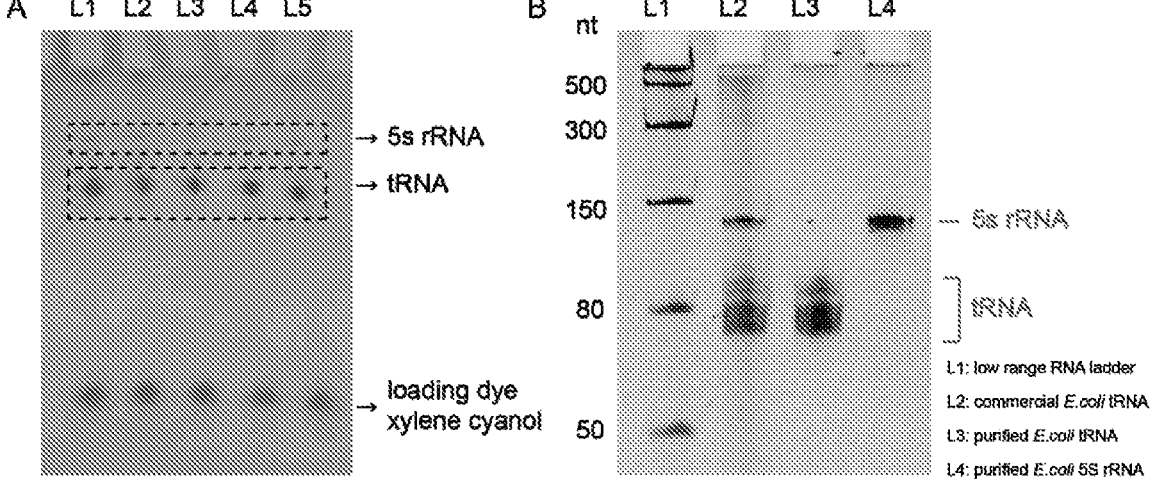

FIG. 31 shows further purification of commercial *E. coli* tRNA. A. *E. coli* total tRNA (Sigma-Aldrich) was loaded onto a 12% urea-PAGE gel. Gel electrophoresis was continuously run for 100 min with a +180 mV applied potential. L1-L5: *E. coli* total tRNA. The gel was visualized with a portable UV lamp (254 nm). Three bands were clearly observable and were respectively recognized as 5S rRNA, tRNA and xylene cyanol, according to the published literature[97]. The region marked with dashed boxes was separately excised. The excised gel fragments were treated with the ZR small-RNA™ PAGE Recovery Kit to recover the RNA (Example 2 Methods). B. Recovered RNA fragments characterized using 12% urea-PAGE gel electrophoresis. Gel electrophoresis was continuously run for 100 min with a +180 mV applied potential. L1: low range RNA ladder; L2: commercial *E. coli* total tRNA; L3: excised *E. coli* tRNA; L4: excised *E. coli* 5S rRNA. The recovered *E. coli* 5S rRNA and tRNA were separated from each other and can be separately studied in downstream nanopore measurements.

Figure 12:
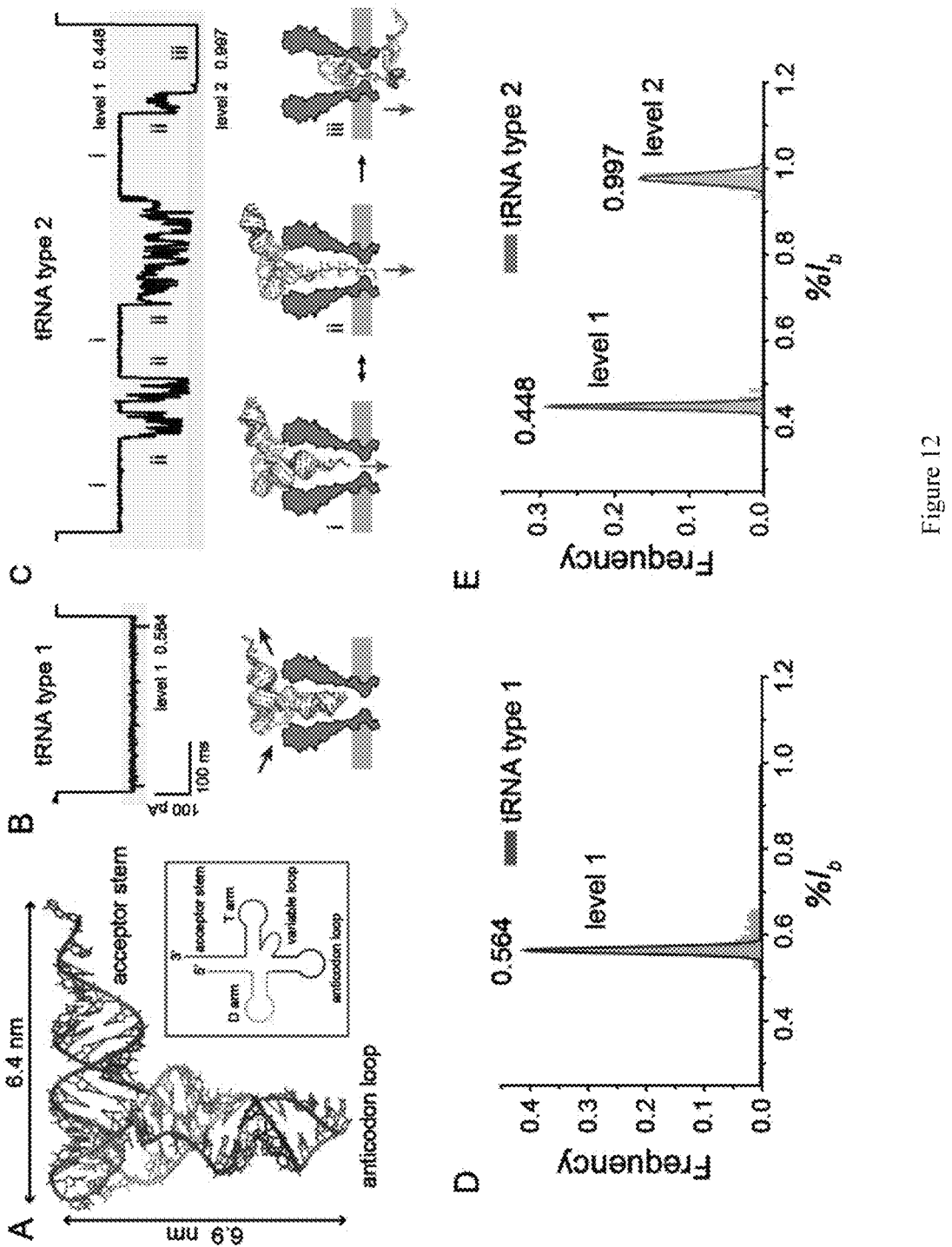
FIG. 12 shows translocation of yeast tRNA$^{phe}$. A. The structure of yeast tRNA$^{phe}$. The secondary structure of yeast tRNA$^{phe}$ (shown in the rectangular box) is composed of four domains, including the acceptor stem (red), the D-arm (orange), the T-arm (green) and the anticodon loop (blue). They fold into an L-shaped tertiary structure, where the anticodon loop and the acceptor stem are located at the two ends of the "L" shape. B. A representative tRNA type 1 event (top) and the diagram of a possible configuration of translocation (bottom). The type 1 event has a single blockage level with a % $I_b$ of about 0.564 (level 1). C. A representative tRNA type 2 event (top) and the diagram of a possible translocation configuration (bottom). The type 2 event has two blockage levels. The % $I_b$ measures about 0.448 (i, level 1). Triggered by the applied electrophoretic force, the overhang of the acceptor stem attempts to enter the pore constriction, producing drastic current fluctuations (ii). tRNA$^{phe}$ is eventually unfolded which gives rise to the second blockage level with a % $I_b$ of about 0.997 (iii, level 2). D. The histogram of % $I_b$ of type 1 events. E. The histogram of % $I_b$ of type 2 events. Nanopore measurements were performed as described in Methods. tRNA$^{phe}$ (Materials, Table 1) was added in cis with a final concentration of 200 nM.
Figure 32:
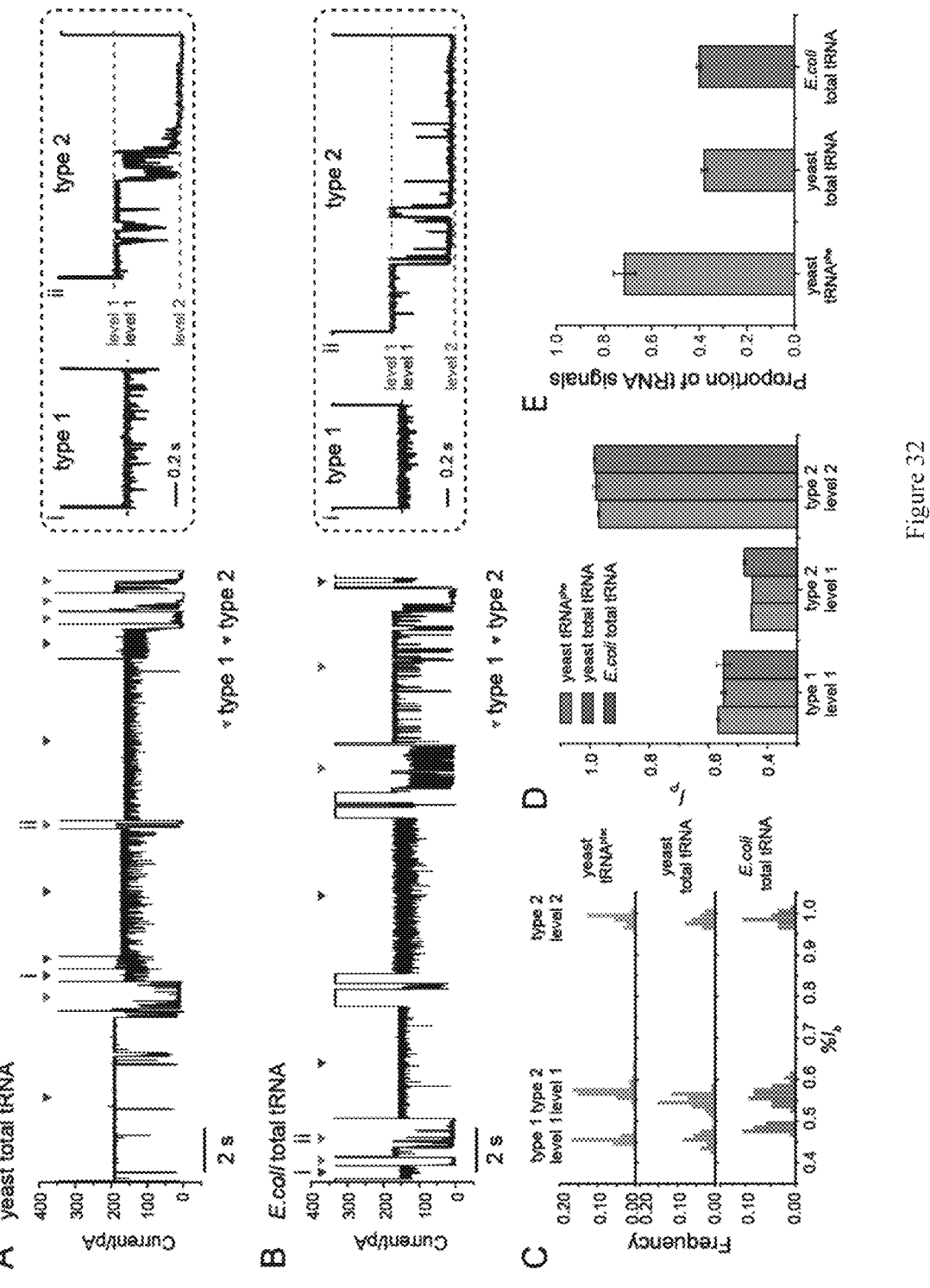

FIG. 32 shows single-molecule sensing of total tRNAs from different species. All measurements were performed as described in Methods. Yeast tRNA was added to cis with a final concentration of 20 ng/μL. *E. coli* tRNA was added to cis with a final concentration of 2 ng/μL. Trace segmentation and event recognition were performed with the custom machine learning algorithm (FIG. 23A). A. A representative trace containing successive yeast tRNA translocation through MspA. Two types of events, termed type 1 (blue triangle) and type 2 (red triangle), were observed, forming the majority of all events that were recorded. Dashed box: Zoomed-in views of representative type 1 and type 2 events, which are respectively marked with i and ii on the trace. The type 1 event has a single blockade level (level 1). The type 2 event contains two blockade levels (level 1 and level 2). B. A representative trace containing successive *E. coli* tRNA translocation through MspA. Two types of events, termed type 1 (blue triangle) and type 2(red triangle) events, were also observed, forming the majority of all events that were recorded. Dashed box: Zoomed-in views of representative type 1 and type 2 events, which are respectively, marked with i and ii on the trace. C. The event histogram of blockade amplitude of type 1 and type 2 events. Please note that the current fluctuations between level 1 and 2 show slight variations between events. This variation of fluctuation is more clearly observed in measurements with total tRNAs than those with tRNA$^{phe}$ (FIG. 12). However, the % $I_b$ of level 1 and 2 of type 2 events are much more conserved. D. Comparison of percentage blockage ($I_p$) of type 1 and type 2 events acquired from different tRNA samples (the three bars in each record represent from left to right yeast tRNA$^{phe}$, yeast total tRNA and *E. coli* total tRNA, respectively). E. The proportion of characteristic tRNA events from different sources of tRNAs. Statistics in C-E were formed from three independent measurements performed for each condition.

Figure 33:
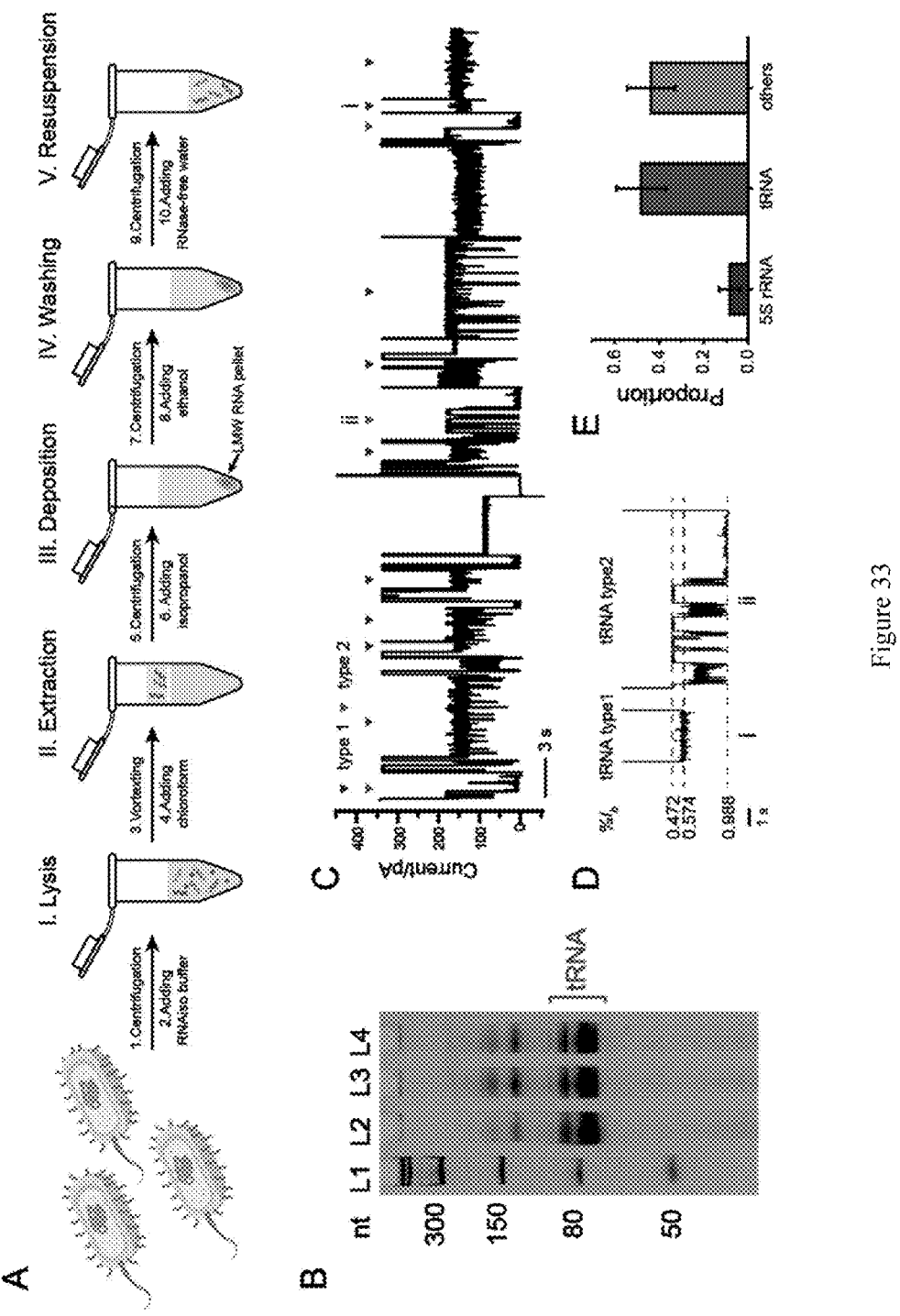

FIG. 33 shows direct identification of tRNA from *E. coli* LMW RNA extracts. A. Isolation of LMW RNA from *E. coli*. (I). *E. coli* pellets were lysed in the RNAiso buffer (Takara). (II). LMW RNA was extracted with chloroform and retained in the supernatant. (III). After centrifugation, the supernatant was collected and added with isopropanol to precipitate all LMW RNA. (IV). The precipitant was collected and washed with 75% ethanol. (V). The LMW RNA was dissolved in ribonuclease (RNase)-free water. B. Denaturing urea polyacrylamide gel electrophoresis (Urea-PAGE) analysis of *E. coli* LMW RNA, extracted as described in A. L1: low range RNA ladder. L2-L4: *E. coli* LMW RNA. The band corresponding to tRNA is marked on the gel. C. A representative trace containing successive translocation of *E. coli* LMW RNA through MspA. Characteristic tRNA type 1 and type 2 events are respectively marked with blue and red triangles. D. Zoomed-in views of representative translocation events in (C), which were marked with i and ii on the trace. E. The proportion of tRNA translocation events. 48% of all acquired events were recognized as either tRNA type 1 or tRNA type 2 events. The measurements in (C-E) were performed as described in Methods. *E. coli* LMW RNA was added to cis with a final concentration of 40 ng/μL. Trace segmentation and event recognition were performed with the custom machine learning algorithm (FIG. 23A).

Figure 34:
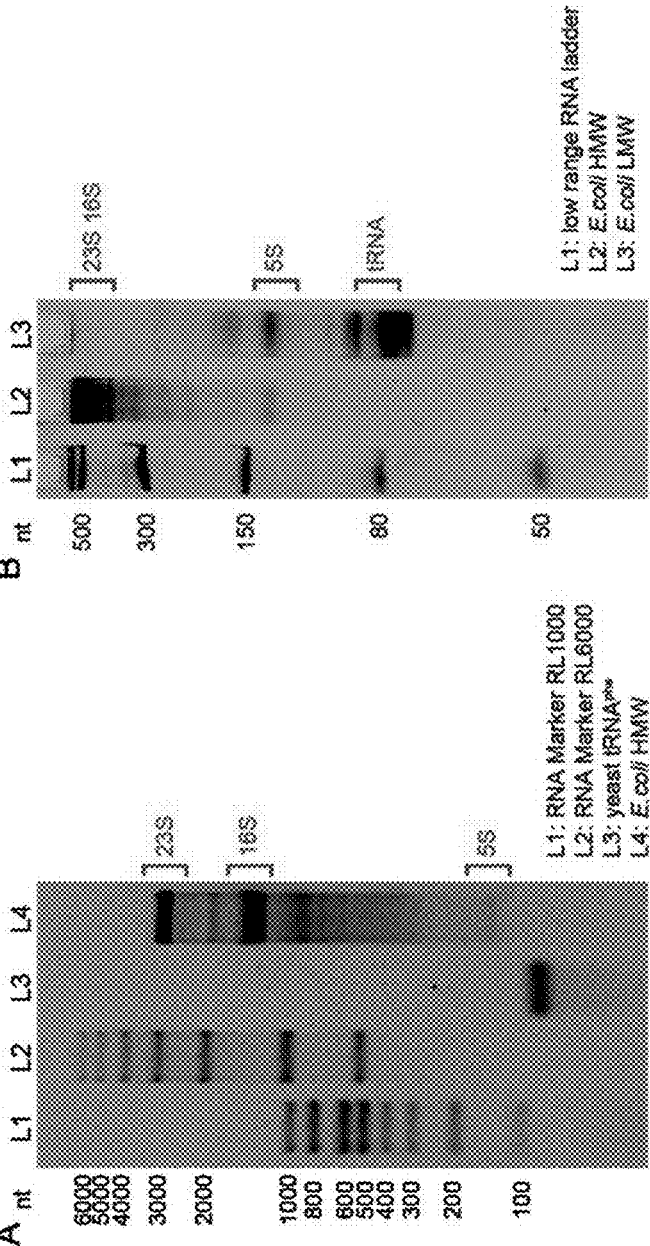

FIG. 34 shows characterization of *E. coli* HMW RNA extraction. *E. coli* HMW RNA was prepared using Mini-BEST Universal RNA Extraction Kit (Takara) which specifically extracts RNA with a molecular weight greater than 200 nucleotides[98]. A. 1% agarose gel electrophoresis characterization of *E. coli* HMW RNA. Gel electrophoresis was continuously run for 35 min at 4° C. with a +180 V applied potential. L1: RNA Marker RL1000; L2: RNA Marker RL6000; L3: brewer's yeast tRNA$^{phe}$ from sigma; L4: *E. coli* RNA extraction. From the gel results, the main fractions of the extracted sample are 23S rRNA (2904 nt) and 16S rRNA (1542 nt)[99]. Traces of tRNAs were not observed. B. 12% urea-PAGE gel electrophoresis characterization of *E. coli* HMW RNA. Gel electrophoresis was continuously run for 100 min with a +180 mV applied potential. L1: low range RNA marker; L2: *E. coli* HMW; L3: *E coli* LMW. 12% urea-PAGE gel electrophoresis was performed to resolve RNAs with a smaller molecular weight[100]. The gel results further confirm that no trace of tRNA were observed from *E. coli* HMW RNA extraction.

Figure 35:
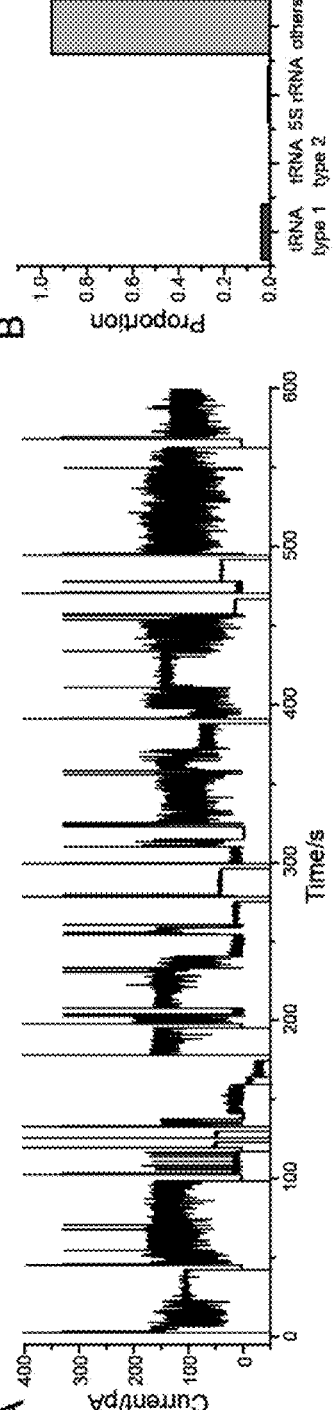

FIG. 35 shows *E. coli* HMW RNA sensing. The measurement was performed as described in Methods. *E. coli* HMW RNA was added to the cis chamber with a final concentration of 50 ng/μL. A. A representative trace of *E. coli* HMW RNA translocation. Most events appear to be extremely long residing. Sometimes HMW RNA may even cause pore clogging. B. The proportion of tRNA and 5S rRNA translocation events. No events were recognized as tRNA type 2 events. Only 3.7% signals were recognized as tRNA type 1 events. The demonstrated results indicate that event characteristics of tRNA type 2 are more reliable in the recognition of tRNA. Events resulted from HMW RNAs can be efficiently excluded by the event characteristics.

Figure 36:
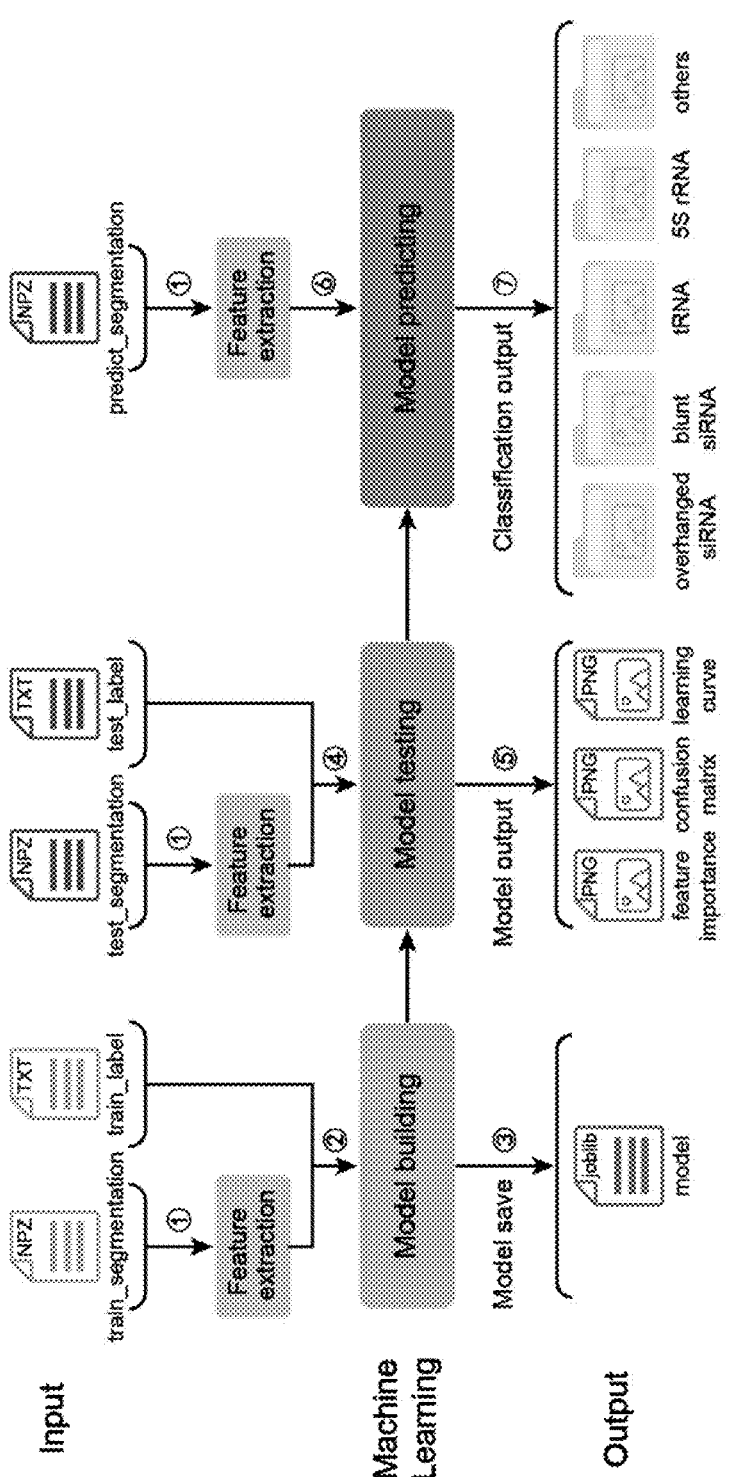

FIG. 36 shows the workflow diagram of RNA-Classification. The machine learning based algorithm RNA-Classification, which was developed and used in this study, has been shared (https://drive.google.com/file/d/17JoqS2JUY-QOY4e5Ib0HE4PsexYtEIKq/view?usp=sharing) for validation and further development. Briefly, the inputs contain five files, including the tables of features, labels of the training set and the testing set, as well as the segmentation data of the predicting dataset. Here, the training set and the testing set are model events of different types RNA but with previously known identities. Four sets of data acquired from nanopore measurements with a sequential addition of overhanged siRNA, blunt siRNA, tRNA and 5S rRNA are provided as demo predicting set. The whole workflow is composed of seven steps as below. Step 1: Feature extraction. Eleven parameters of individual events in the segmentation data of dataset are extracted, forming a feature matrix for each event. Step 2: Model building. The feature matrixes and labels of the training set generated by 10-fold cross validation for building the model and fine-tune the parameter. and the best performing trained model is saved into local. Step 3: Model save: The trained model is saved to local for quick loading next time. Step 4: Model testing: The feature matrixes and labels of the testing set are tested by the trained model and validate the performance of the models. Step 5: Model output. Plots of feature importance, confusion matrix and learning curve of the best performing classifiers are generated. Step 6: Model prediction. The feature table of predicting set are loaded to established machine learning model for event identification. Step 7: Classification output. Five folders with sorted events of overhanged siRNA, blunt siRNA, tRNA, 5S rRNA and others are generated.

Figure 37:
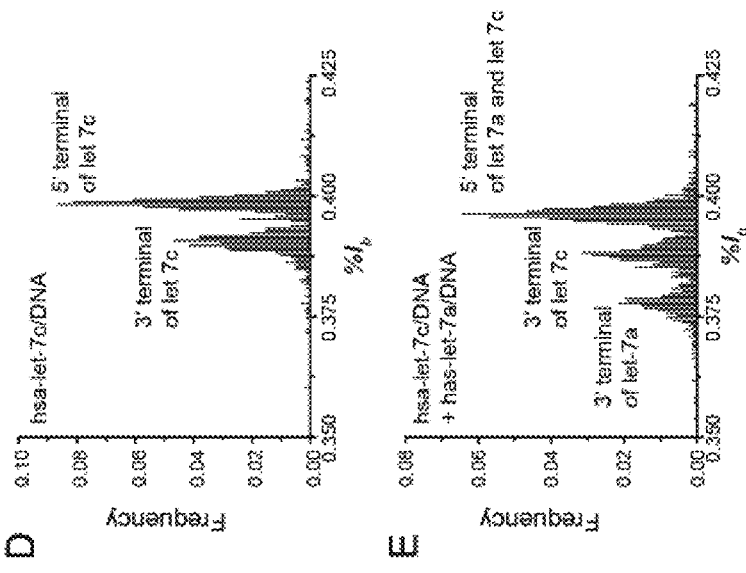
Figure 37:
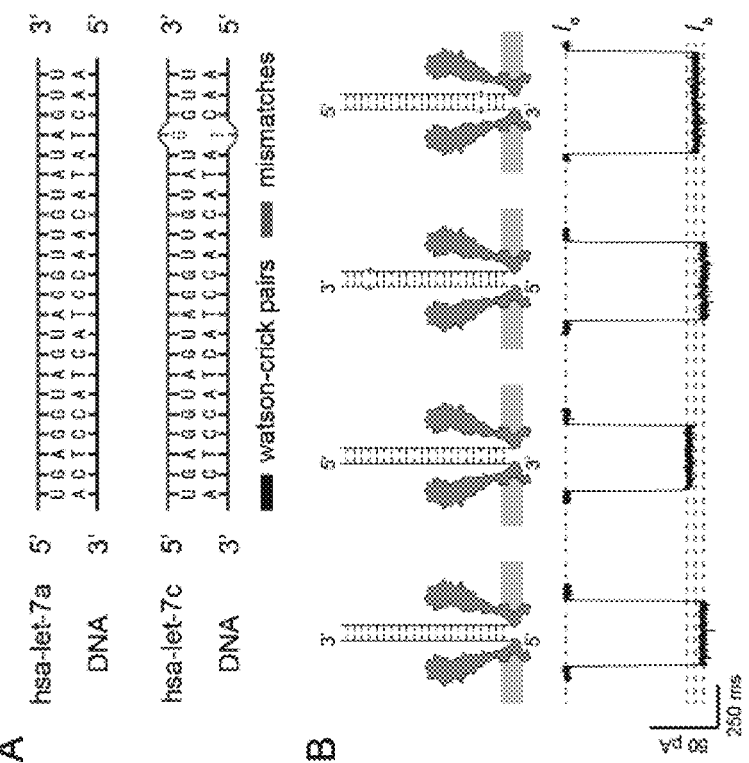

FIG. 37 shows direct discrimination of Let-7 family miRNAs by MspA based nanopore trapping/translocation. Hsa-let-7a and hsa-let 7c, when hybridized with relevant DNA probes, can be directly discriminated by MspA based nanopore trapping/translocation. We consider this as a follow up work upon publishing of this manuscript describing a more general methodology. Please note that MspA is so sensitive to discriminate different orientations of the analyte entering the pore so even for the same double stranded nucleic acids, it normally reports two peaks in the event distribution. However, with differently hybridized miRNAs, say those with a single base mismatch, it is directly discriminated during nanopore trapping.

Figure 38:
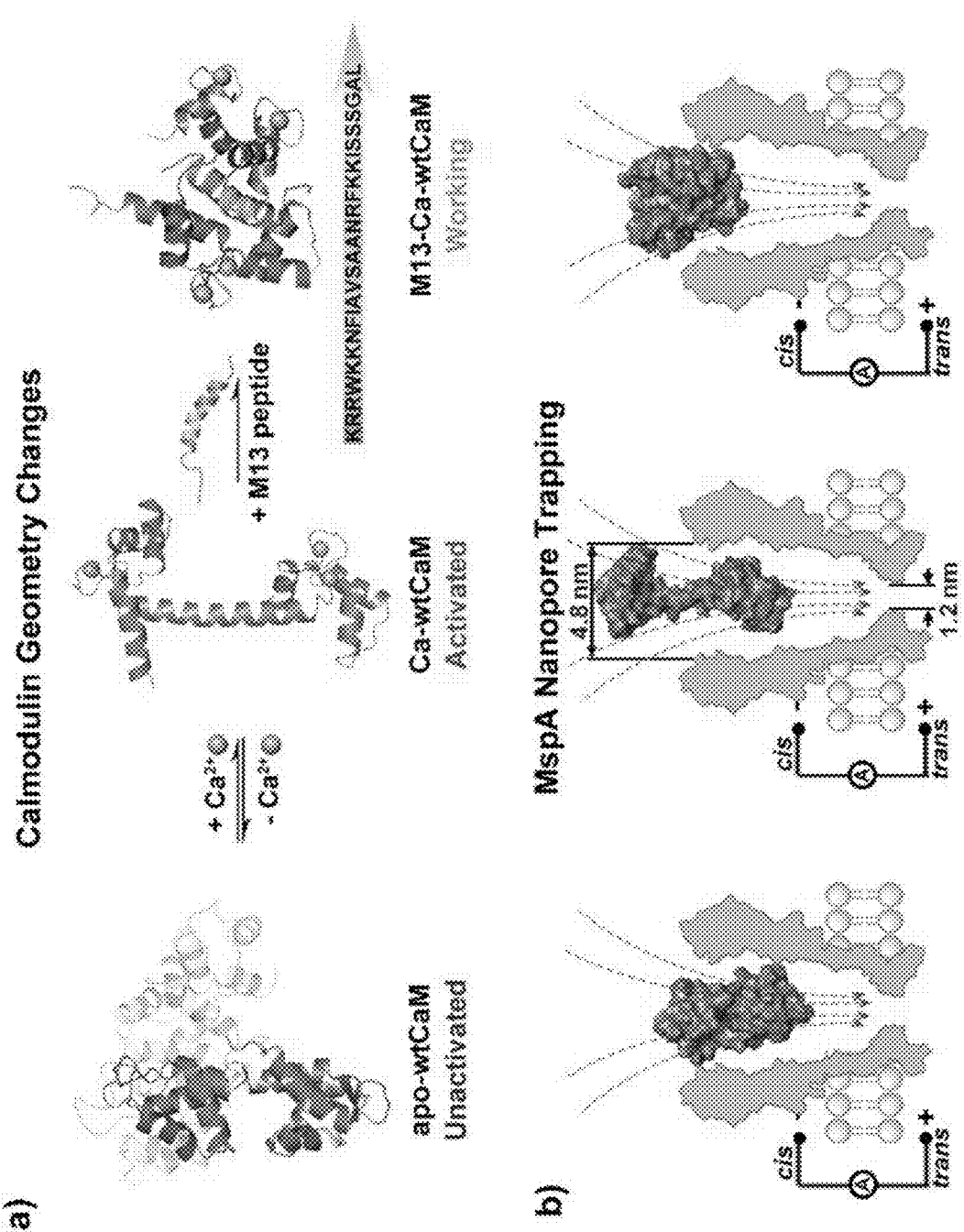

FIG. 38 shows stochastic sensing of allosteric switching of calmodulin (CaM) by an MspA nanopore-trap. (a) Schematic diagram of the allosteric behavior of CaM upon sequential binding with $Ca^{2+}$ and M13 peptide. More detailed mechanisms are summarized in FIG. 39. Upon binding $Ca^{2+}$ (orange spheres), the central α-helix of a CaM is constrained to a structurally rigid activated state, ready to bind an M13 peptide. Upon further binding the M13 peptide, the structure collapses (the working state). The annotation apo-wtCaM, Ca-wtCaM or M13-Ca-wtCaM respectively demonstrate the state when a wtCaM is not bound by any ligand, but is bound with $Ca^{2+}$ ions or with an M13 peptide. The crystal structures of apo-wtCaM, Ca-wtCaM and M13-Ca-wtCaM were generated using structure files from the Protein Data Bank (PDB). PDB IDs: 1CFC (apo-wtCaM), 1CLL (Ca-wtCaM) and 2BBN (M13-Ca-wtCaM) respectively. Structures of apo-wtCaM demonstrate a highly flexible state, generating possible variant structures (the transparent structural diagram). The aforementioned allosteric transitions result in dramatic structural changes in a CaM, detectable by a suitable nanopore sensor. (b) Cross-sectional views of MspA (yellow) with a CaM (purple) trapped in its vestibule. The trapped CaM could be in the form of an apo-wtCaM (left), a Ca-wtCaM (middle) or a M13-Ca-wtCaM (right). The conical vestibule of an MspA, measuring 4.8 nm in diameter, can easily accommodate CaM in either form. The narrower pore constriction, measuring 1.2 nm in diameter, prohibits CaM from translocation. However, when accommodated by the conically shaped pore vestibule, different forms of CaM demonstrate highly distinguishable trapping states. Here, the demonstrated states were predicted by molecular dynamics (MD) simulations equilibrated for more than 100 ns (Example 5 Methods 5, FIG. 48).

Figure 39:
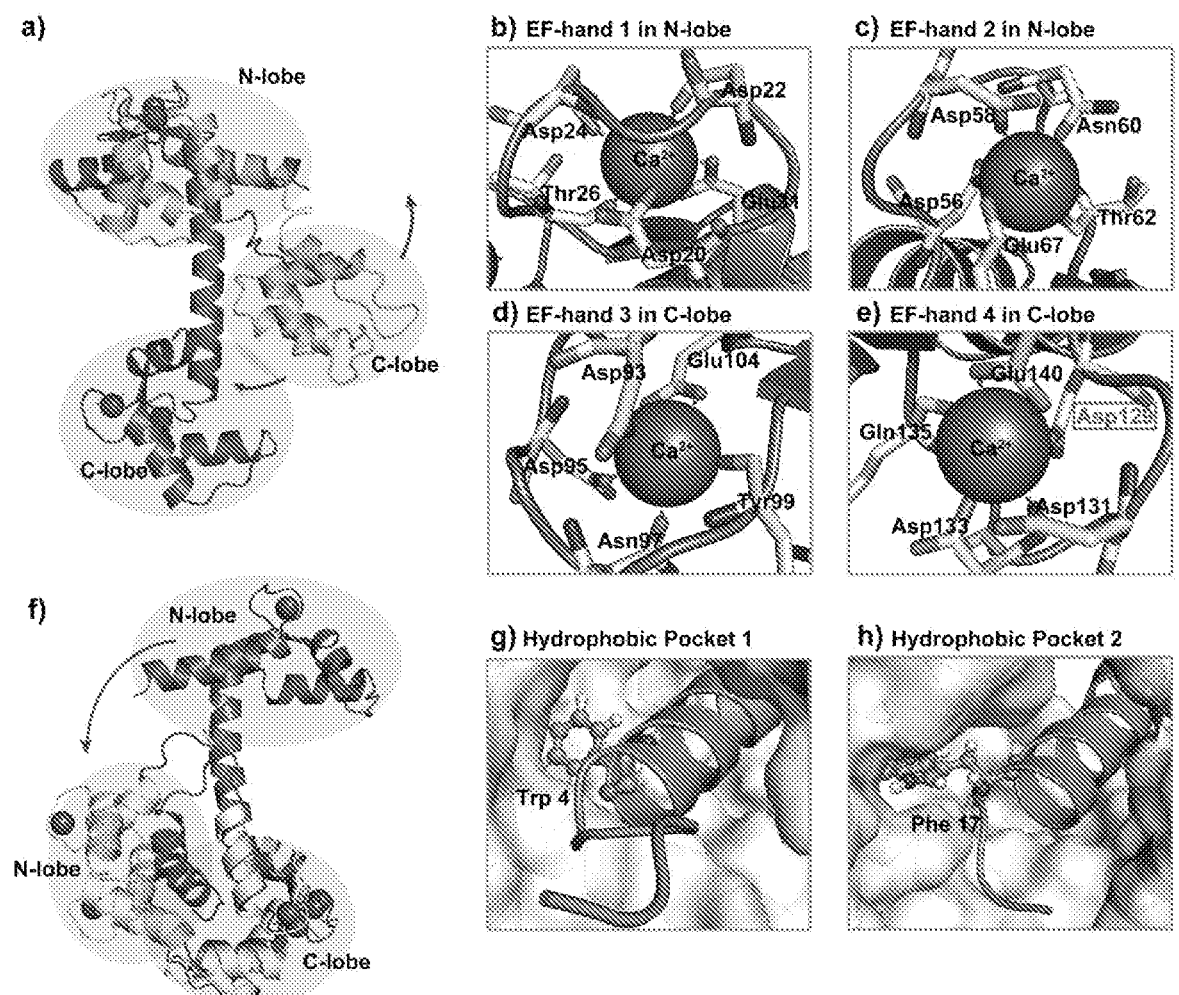

FIG. 39 shows conformations of the allosteric protein wtCaM. Results here are crystal structures of wtCaM conformers before and after allosteric transitions. All structures presented were derived from PDB files 1CFC (apo-wtCaM), 1CLL (Ca-wtCaM) and 2BBN (M13-Ca-wtCaM), reported in the early 1990s[190,191]. CaM consists of two similar domains (N-lobe and C-lobe), each containing two $Ca^{2+}$-binding sites (EF-hands). To compare structural differences between different wtCaM conformers, either the N-lobe (amino acids 1-70) or the C-lobe (amino acids 90-146) of CaM conformers were aligned by PyMOL. The resulting alignment diagrams are respectively presented in a and f. (a) The N-lobe alignment diagram of apo-wtCaM (yellow) and Ca-wtCaM (green). Without $Ca^{2+}$ binding, the N- and the C-lobe of wtCaM are connected by a highly flexible linker (residues 77-80, red). 9 Upon $Ca^{2+}$ binding, this highly flexible linker is recombined (red) with the adjacent α-helix, forming an overall dumbbell-shaped structure of Ca-wt-CaM. (b-e) A detailed demonstration of the EF-hands, in which $Ca^{2+}$ is coordinated by relevant amino acid residues of CaM. The disease-related mutation (D129G) is one of the key amino acids in the structural domain of EF-hand 4 (e) for $Ca^{2+}$ binding. (f) The C-lobe alignment diagram of Ca-wtCaM (green) and the M13 peptide (orange) bound Ca-wtCaM (M13-Ca-wtCaM, light gray). Upon binding an M13 peptide, the major conformational change of a CawtCaM involves the re-dissolution of the central helix into two helices connected by a long flexible loop, thereby enabling a significant structural collapse (marked by the gray arrow) so that the N- and C-lobe come together to grip an M13 peptide (orange colored).[10] This complex is stabilized mainly by numerous hydrophobic interactions, especially the extensive contacts between the two bulky hydrophobic residues Trp4 (g) and Phe17 (h) of the M13 peptide and Ca-wtCaM at the deep hydrophobic pockets on both domains of CaM.

Figure 40:
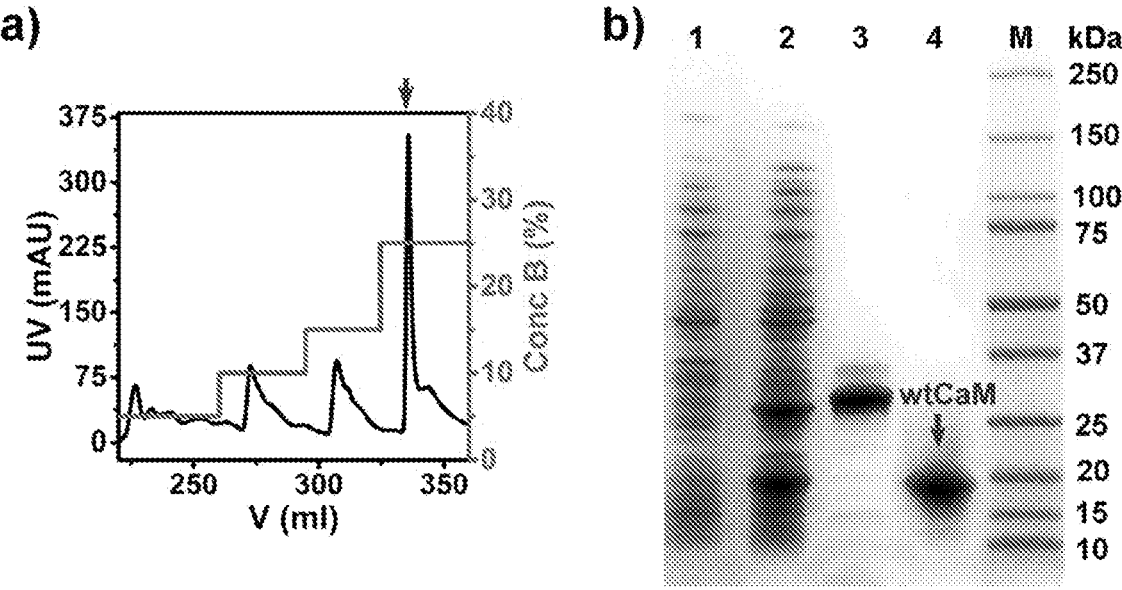

FIG. 40 shows purification and characterization of wtCaM. Preparation of wtCaM is detailed in Example 5 Methods 1. The expressed wtCaM was purified by anion exchange chromatography and characterized by gel electrophoresis. (a) The UV absorbance spectrum during anion exchange chromatography. The lysate containing wtCaM was applied to the column. The column was eluted by different ratios of buffer B1 (Conc B) in the elution buffer and different elution peaks were reported. wtCaM is a typical acidic protein and the peak corresponding to the eluent containing wtCaM was expected to appear later, when a higher Conc B was applied. The peak marked with a blue arrow was expected to contain the desired wtCaM. (b) Gel electrophoresis results. Lane M: precision plus protein standards; Lane 1: Bacterial lysates containing wtCaM plasmid without IPTG induction; Lane 2: Bacterial lysates containing wtCaM plasmid with IPTG induction; Lane 3: The fraction collected from the anion exchange column immediately after lysate loading; Lane 4: The eluents correspond to the peak marked with a blue arrow in (a). The band in lane 4, which is marked with a blue arrow, was recognized as an overexpressed protein when comparing results in lane 1 with those in lane 2. The migration distance of this band is between 15 kDa and 20 kDa, consistent with that of wtCaM (16.8 kDa), further confirming that this band corresponds to the desired wtCaM. The corresponding eluent was directly used in all downstream nanopore measurements without any further purifications.

Figure 41:
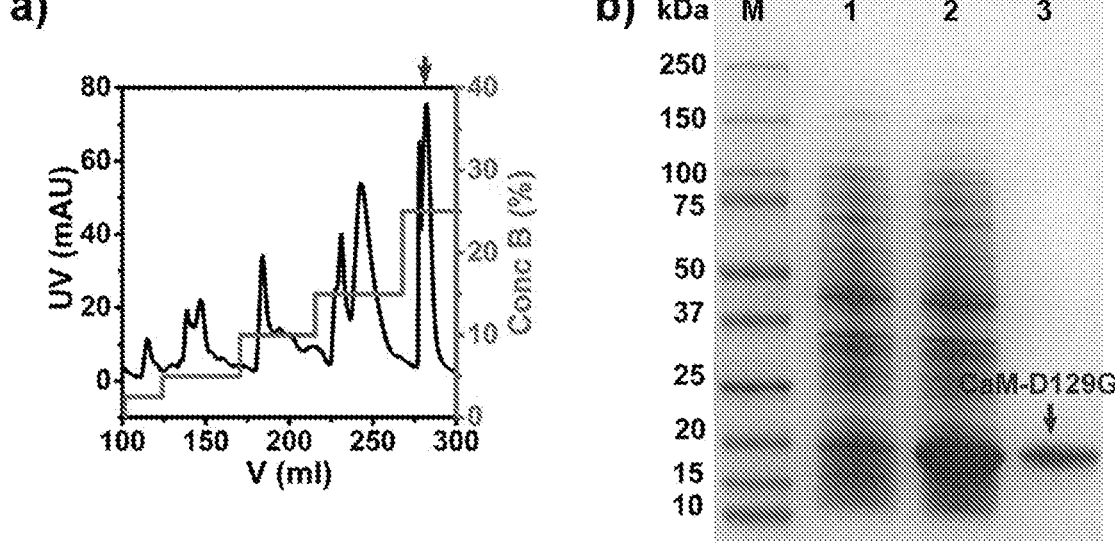

FIG. 41 shows purification and characterization of CaM-D129G. Preparation of CaM-D129G is detailed in Example 5 Methods 1. The expressed CaM-D129G was purified by anion exchange chromatography and characterized by gel electrophoresis. (a) The UV absorbance spectrum during anion exchange chromatography. The lysate containing CaM-D129G was applied to the column. The column was eluted by different ratios of buffer B1 (Conc B) in the elution buffer and different elution peaks are reported. According to results of wtCaM purification (FIG. 40*a*), the peak corresponding to the eluent containing CaM-D129G was expected to appear later during column elution. The peak marked with a blue arrow was expected to contain the desired CaM-D129G. (b) Gel electrophoresis results. Lane M: precision plus protein standards; Lane 1: Bacterial lysates containing CaM-D129G plasmid without IPTG induction; Lane 2: Bacterial lysates containing CaM-D129G plasmid with IPTG induction; Lane 3: The eluent corresponding to the peak marked with a blue arrow in (a). The band in lane 3, which is marked with a blue arrow, was recognized as an overexpressed protein when comparing results in lane 1 with those in lane 2. It has a migration distance between 15 kDa and 20 kDa, consistent with that of CaM-D129G (16.8 kDa), further confirming that this band corresponds to the desired CaM-D129G. The corresponding eluent was used in all downstream nanopore measurements without any further purifications.

Figure 42:
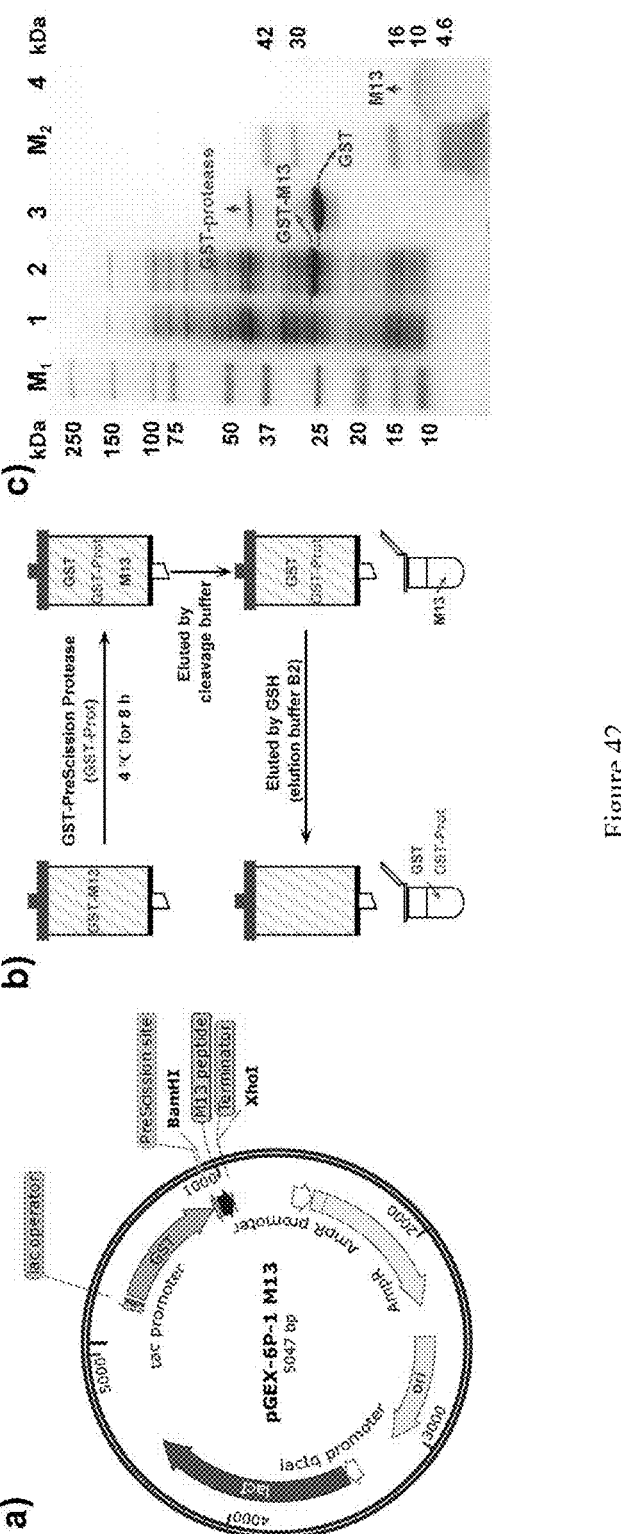

FIG. 42 shows preparation of M13 peptide. Preparation of the M13 peptide is detailed in Example 5 Methods 2. (a) The construction of the plasmid coding for the GST-M13 fusion protein. The gene coding for the fusion protein was cloned into the pGEX-6P-1 plasmid. The gene coding for the M13 peptide (with a terminator at the end of the sequence, blue) was inserted between the recognition sequence of BamH I and Xho I, immediately after the PreScission site (pink). The PreScission site of the expressed protein is cleavable when treated by corresponding protease. (b) A schematic diagram of M13 separation. The expressed fusion protein GST-M13 was first applied to a GSTrap™ column. The column was further applied with the PreScission Protease (GST-Prot) which also has a GST-tag on its N-terminal. After 8 h of incubation at 4° C., the M13 was completely separated from the GST-M13 fusion protein and was eluted by the cleavage buffer and collected. The GST moiety and the PreScission Protease however remained on the column. Regeneration of the column was performed by elution with the glutathione (GSH) containing solution (elution buffer B2) and the eluted GST and GST-Prot were discarded. (c) Gel electrophoresis results. Lane $M_1$: precision plus protein standards; Lane $M_2$: pre-stained low range protein marker; Lane 1-2: Bacterial lysates containing GST-M13 plasmid induced without or with IPTG; Lane 3: the eluted GST moiety of the fusion protein and the GST-PreScission Protease; Lane 4: the eluted M13 peptide (3.2 kDa). The excessive band in lane 2 in reference to results in lane 1 represents the overexpressed GST-M13. The lower band in lane 3 (violet marked) reports a slightly lower position on the gel, when compared with the band corresponding to GST-M13 (green marked). This is expected since the GST (26 kDa) has a lower molecular weight than GST-M13. The upper band in lane 3 (brown marked) was recognized as the GST-protease (46 kDa). The M13 peptide, as characterized in lane 4, was directly used in all downstream nanopore measurements without any further purifications.

Figure 43:
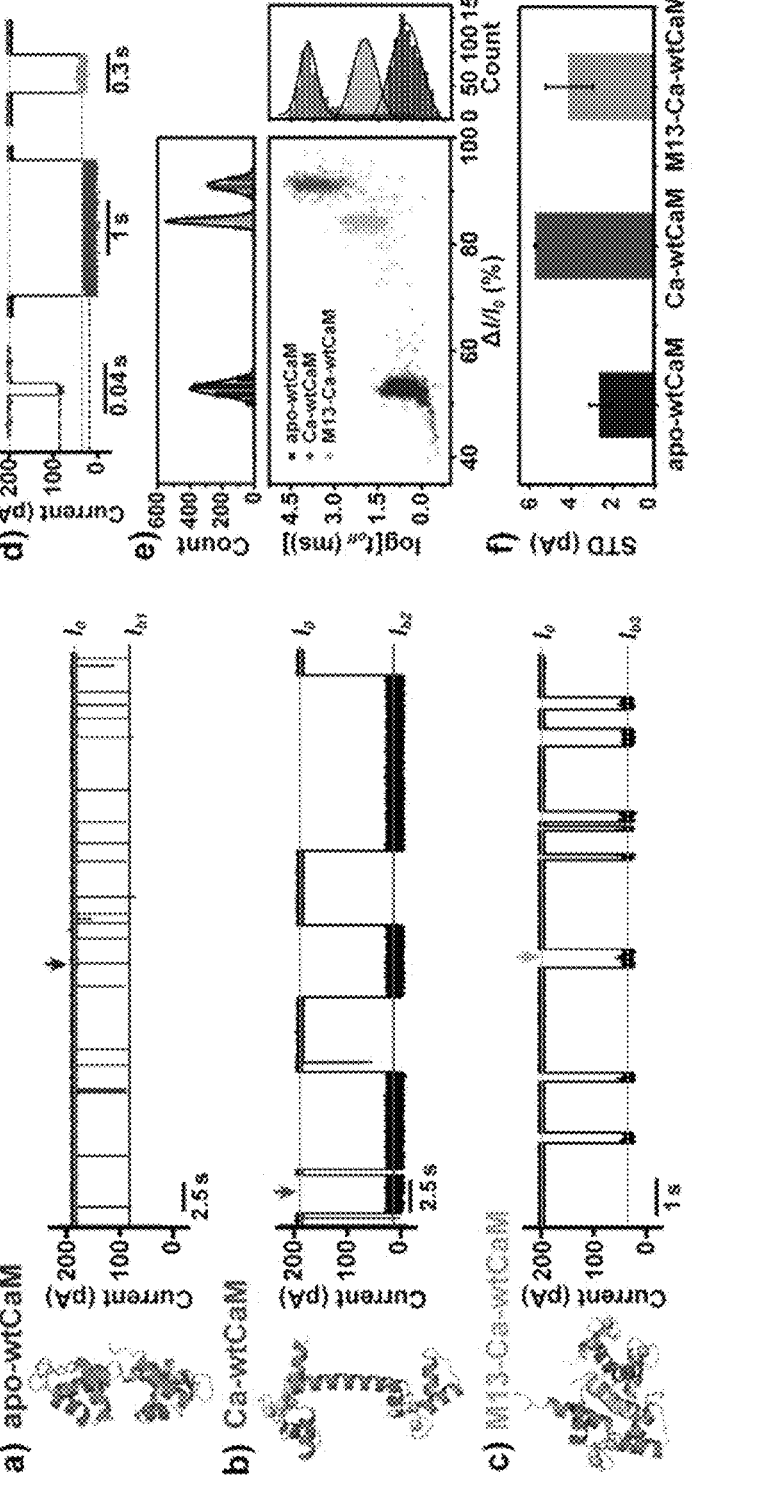

FIG. 43 shows single molecule characteristics of apo-wtCaM, Ca-wtCaM and M13-Ca-wtCaM trapping. (a-c) Representative traces containing events caused by apo-wtCaM (a), Ca-wtCaM (b) or M13-Ca-wtCaM (c) trapping. Corresponding structural diagrams of different states of a CaM are at the left of each trace. For ease of visualization, the CaM, the $Ca^{2+}$ and the M13 peptide respectively, are colored purple, orange and rainbow, respectively. The demonstrated traces were acquired with an MspA (Example 5 Methods 4). wtCaM was added to cis with a 0.6 μM final concentration. The final concentration of $Ca^{2+}$/the M13 peptide in cis were 0 mM/0 μM (a), 4 mM/0 μM (b) and 4 mM/0.8 μM (c). $i_c$ is the open pore level. $I_{b1}$, $I_{b2}$ or $I_{b3}$ respectively denote the blockage levels caused by apo-wtCaM, Ca-wtCaM or M13-Ca-wtCaM trapping. (d) Representative events of apo-wtCaM (left), Ca-wtCaM (middle) or M13-Ca-wtCaM (right) trapping. The events were taken from traces in a-c, as marked by corresponding arrows. For ease of demonstration, the blockage levels of apo-wtCaM, Ca-wtCaM and M13-Ca-wtCaM are correspondingly color coded. The event types are highly discriminable from each other in the dwell time, the blockage depth and the blockage level fluctuations. (e) A scatter plot of log event dwell time ($t_{off}$) vs. percentage blockage ($\Delta I/I_0$). Corresponding histograms of $t_{off}$ and $\Delta I/I_0$ were plotted to the right and the top of the scatter plot. (f) Standard deviation values (STD) of the blockage events resulted from apo-wtCaM, Ca-wtCaM or M13-Ca-wtCaM trapping. Trapping of Ca-wtCaM reports events with the largest level fluctuations. Trapping by apo-wtCaM reports the least noisy events.

Figure 44:
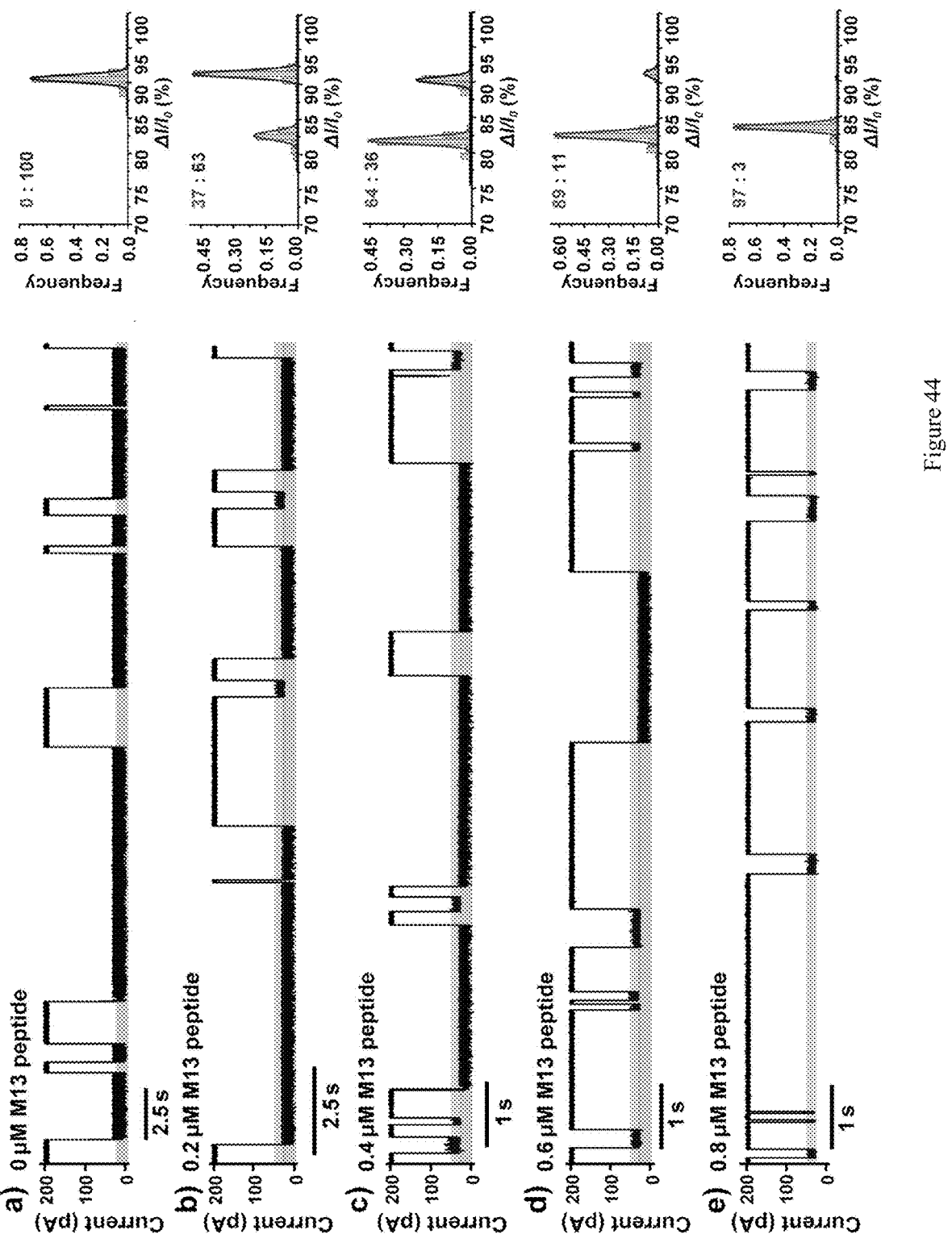

FIG. 44 shows event type conversion from Ca-wtCaM to M13-Ca-wtCaM. Single channel recordings were performed as described in Example 5 Methods 1 with an M2 MspA. Apo-wtCaM was added to cis with a 0.6 μM final concentration along with 4 mM $Ca^{2+}$. The M13 peptide was added to cis with a 0-0.8 μM final concentration, as marked on top of each trace. (a-e) Left: representative traces showing the generation of events caused by trapping of M13-bound Ca-wtCaM. The blue (lower) and red (higher) background respectively represent the blockage depth of events induced by Ca-wtCaM or M13-Ca-wtCaM trapping. Right: the corresponding $\Delta I/I_0$ histogram. The numbers at the top left corner respectively represent the ratio of the blockage events caused by M13-Ca-wtCaM (red numbers, left) or Ca-wtCaM (blue numbers, right) trapping. The peaks were Gaussian fitted. The mean value of $\Delta I/I_0$ ($\overline{\Delta I/I_0}$) was derived from the fitting results. According to above results, trapping events caused by Ca-wtCaM and M13-Ca-wtCaM are highly distinguishable, respectively showing a $\overline{\Delta I/I_0}$ of 93.0% or 83.9%.

Figure 45:
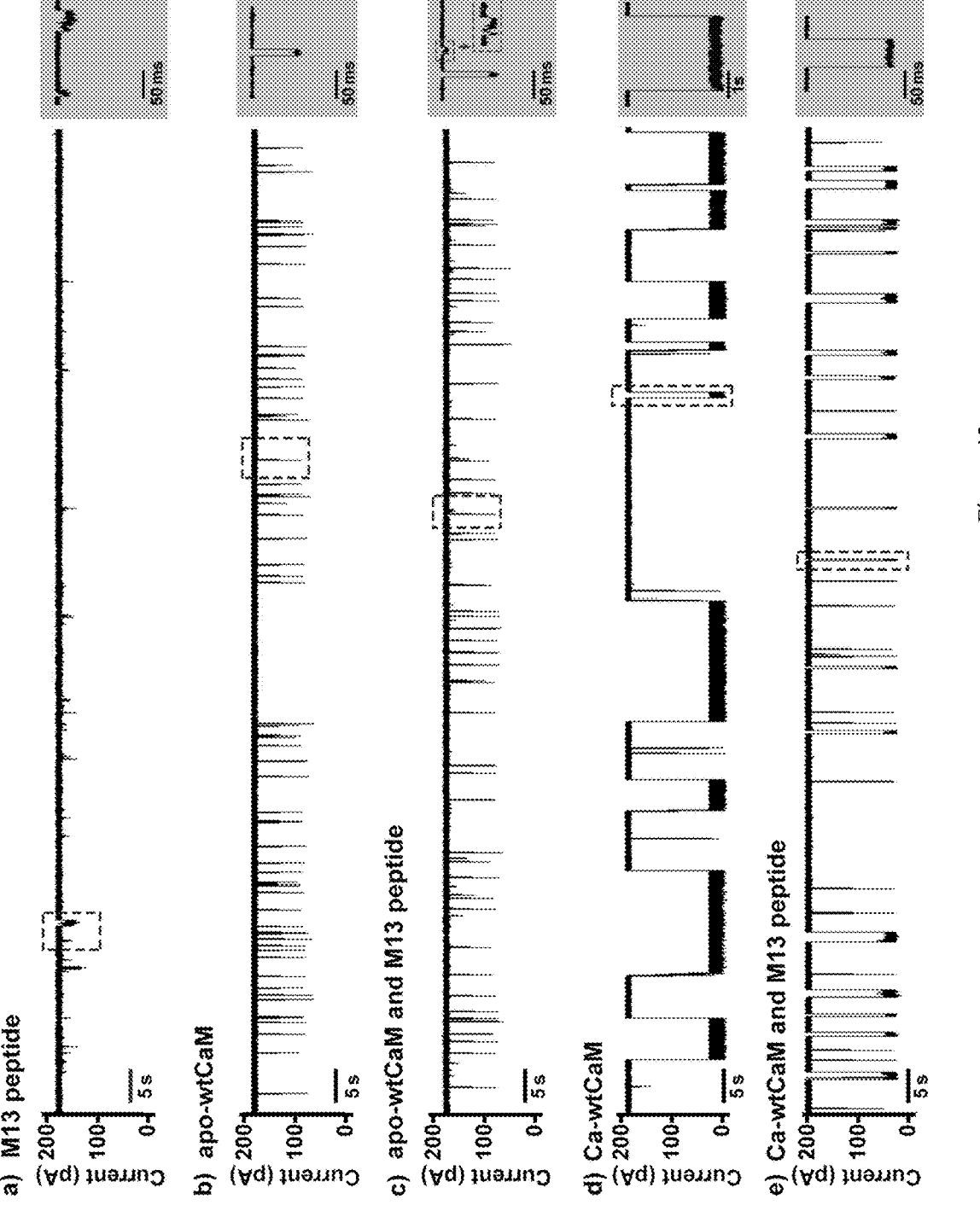

FIG. 45 shows M13 peptide control experiments. Representative traces showing blockage events of (a) M13 (0.8 μM), (b) apo-wtCaM (0.6 μM), (c) apo-wtCaM (0.6 μM) and M13 (0.8 μM), (d) Ca-wtCaM (0.6 μM), (e) Ca-wtCaM (0.6 μM) and M13 (0.8 μM). All demonstrated results were performed with an M2 MspA. All concentrations reported are the final concentration of the analyte being added to cis. Representative events, as marked by blue dashed rectangles on each trace, were placed to the right of each trace as a zoomed-in demonstration. Specifically, M13 could report events when sensed by a nanopore. Based on the molecular size, the event is likely as the result of nanopore translocation instead of nanopore trapping and reports a barely detectable amplitude. Without the addition of $Ca^{2+}$ events caused by apo-wtCaM and M13 peptide were respectively reported (c), indicating that the apo-wtCaM and M13 peptide were not bound together. However, with the addition of $Ca^{2+}$, a new type of event, caused by the bound form between apo-wtCaM and M13 peptide were consistently reported, confirming that the formation of the bound complex requires the presence of $Ca^{2+}$.

Figure 46:
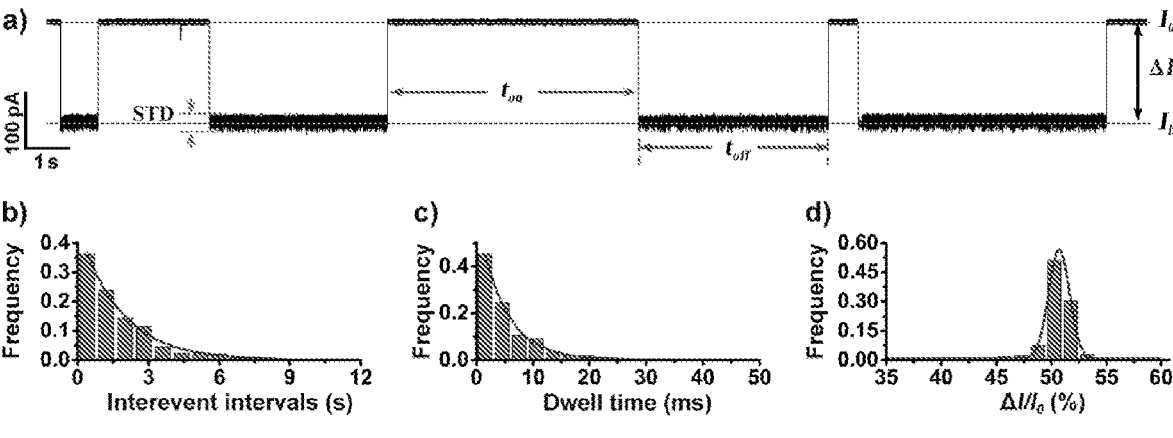

FIG. 46 shows definition of event parameters. (a) A representative electrophysiology trace containing the events of analyte trapping. For a demonstrative purpose, Ca-wtCaM was treated as the model analyte. $r_n$ is the open pore current and $I_b$ is the residual current caused by analyte trapping. ii is derived from $\Delta I=I_a-I_b$. $\Delta I/I_0$ is defined as the blockage ratio. $t_{off}$ represents the dwell time of an event. $t_{on}$ represents the inter-event interval. STD is the standard deviation value of the blockage level. (b-c) The histogram plots of $\tau_{off}$ (b) and $t_{off}$ (c) acquired from a continuously recorded trace. The histogram plots were respectively fit to a single exponential curve, according to the equation $y=\alpha*\exp(-x/\tau)$, from which the mean inter-event interval ($t_{on}$) (b) and the mean event dwell time ($\tau_{off}$) (c) were respectively derived. (d) The histogram plot of $\Delta I/I_0$, acquired from a continuously recorded trace. The peak in the histogram was Gaussian fitted. The center of the fitting results represents the mean value of $\Delta I/I_0$ ($\overline{\Delta I/I_0}$). If not otherwise stated, all results in this manuscript were described by event parameters defined above.

Figure 47:
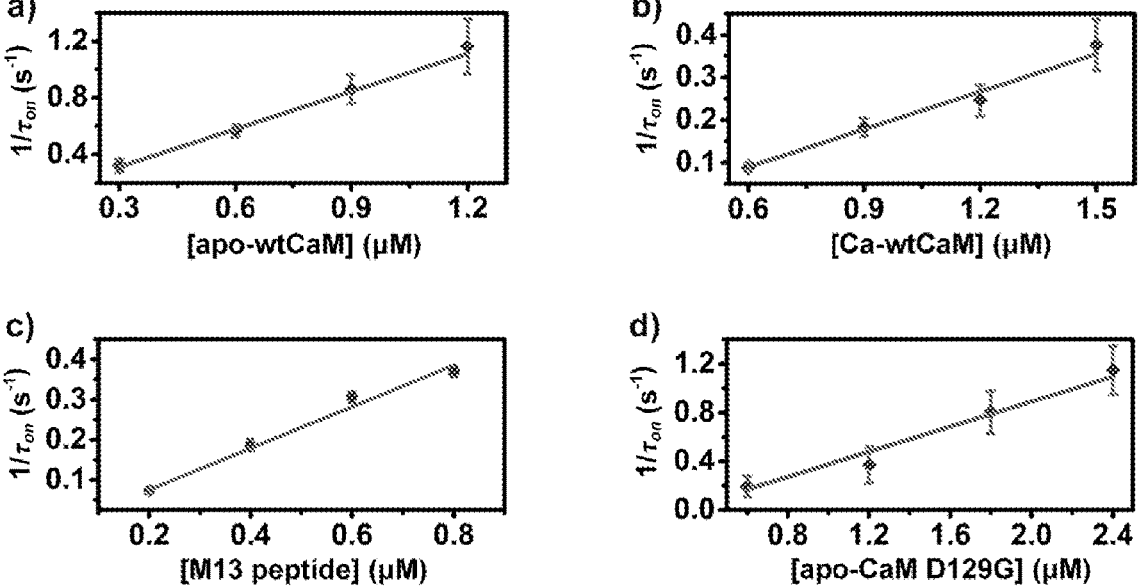

FIG. 47 shows capture frequency ($k_{on}$) of the protein analytes. The capture frequency ($k_{on}$), as defined by the equation $1/\tau_{on}=k_{on}\cdot c$, serves to evaluate the ability of nanopore trapping when different analytes were applied. The reciprocal of the inter-event intervals ($1/\tau_{on}$) of apo-wtCaM (a), Ca-wtCaM (b), M13-Ca-wtCaM (c) and apo-CaM-D129G (d) were plotted against the final concentration of the analyte. Generally, $1/\tau_{on}$ values are positively correlated with the concentration of the added analytes, further confirming that the blocking events were generated by the analytes being added. All results were linear fitted and the mean capture frequency ($\overline{k_{on}}$) was derived as the slope of the fitting results. Error bars in (a-d) represent standard deviations (SD) between independent measurements (N=3). All results discussed above are detailed in Table 7.

Figure 48:
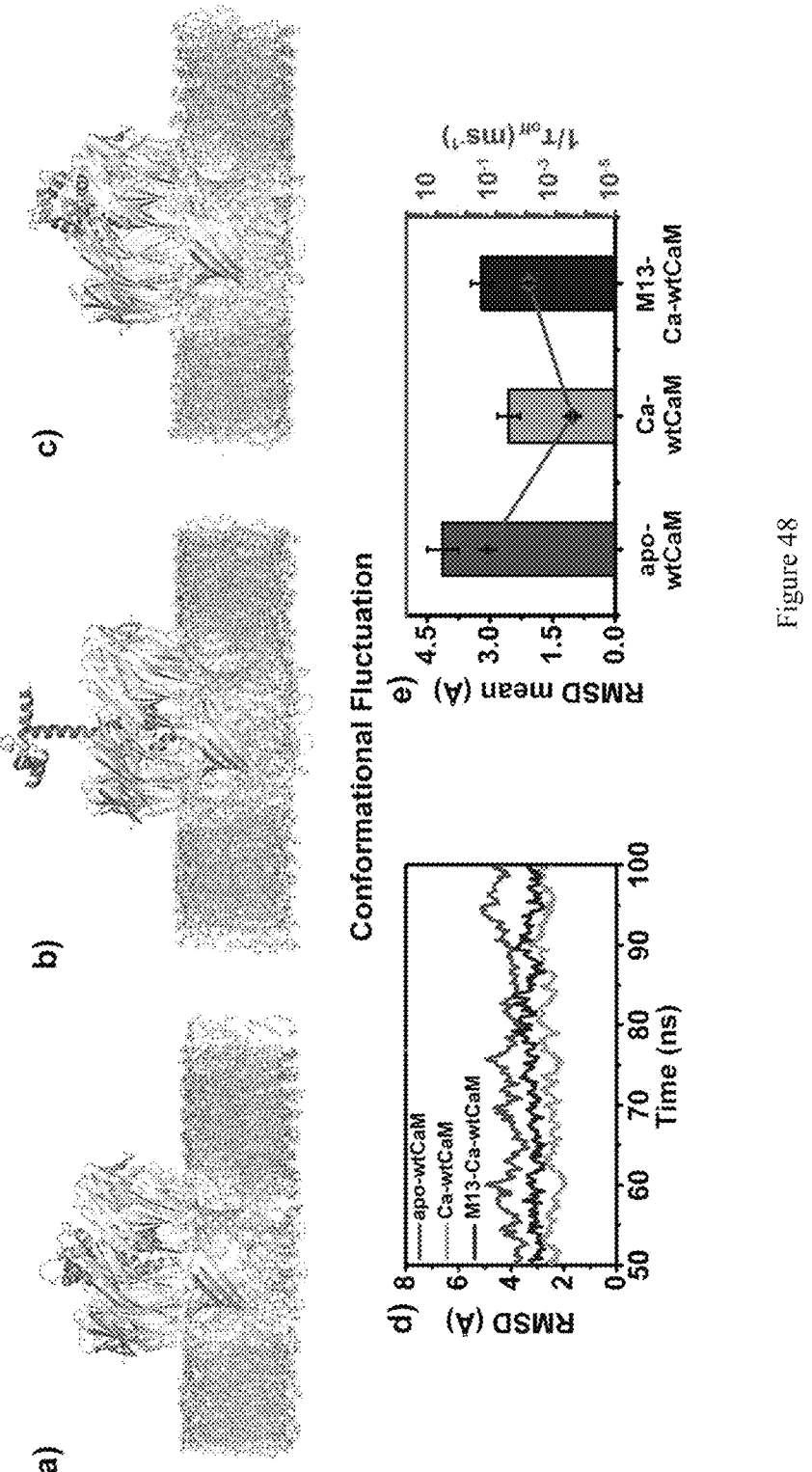

FIG. 48 shows molecular dynamics (MD) simulations of wtCaM conformers. Molecular dynamics simulations were set up as described in Example 5 Methods 5. The equilibrated MD structures of apo-wtCaM (a), Ca-wtCaM (b), M13-Ca-wtCaM (c) and MspAwere respectively demonstrated. The simulated trajectories of 100 ns were shown in Movie S5-S7. (d) The root-mean-square deviation (RMSD) changes of apo-wtCaM (olive, highest), Ca-wtCaM (orange, lowest) and M13-Ca-wtCaM (blue, middle) after being trapped. The RMSD values demonstrate conformational fluctuations of all three wtCaM conformers when lodged in an MspA nanopore-trap. The results indicate that all three conformers were stably trapped within a range of 1.5 Å. (e) Analysis of the correlativity between the mean values of RMSD (the histogram) and the reciprocals of the mean event duration times ($\overline{\tau_{off}}$) (the red line chart). The mean values of RMSD were derived from results of 50 ns simulations as demonstrated in d. The averaged RMSD of apo-wtCaM, Ca-wtCaM and M13-Ca-wtCaM were 4.1±0.4 Å, 2.5±0.3 Å and 3.2±0.3 Å which were highly correlated with the values of $1/\overline{\tau_{off}}$ from the electrophysiological measurements (0.20±0.012 ms$^{-1}$, (2.8±0.46)*10$^{-4}$ ms$^{-1}$ and (7.8±0.96)*10$^{-3}$ ms$^{-1}$). The above comparison may indicate that conformational fluctuations of three conformers may have a strong influence of the escape capacities of the analyte when trapped by an MspA nanopore-trap.

Figure 49:
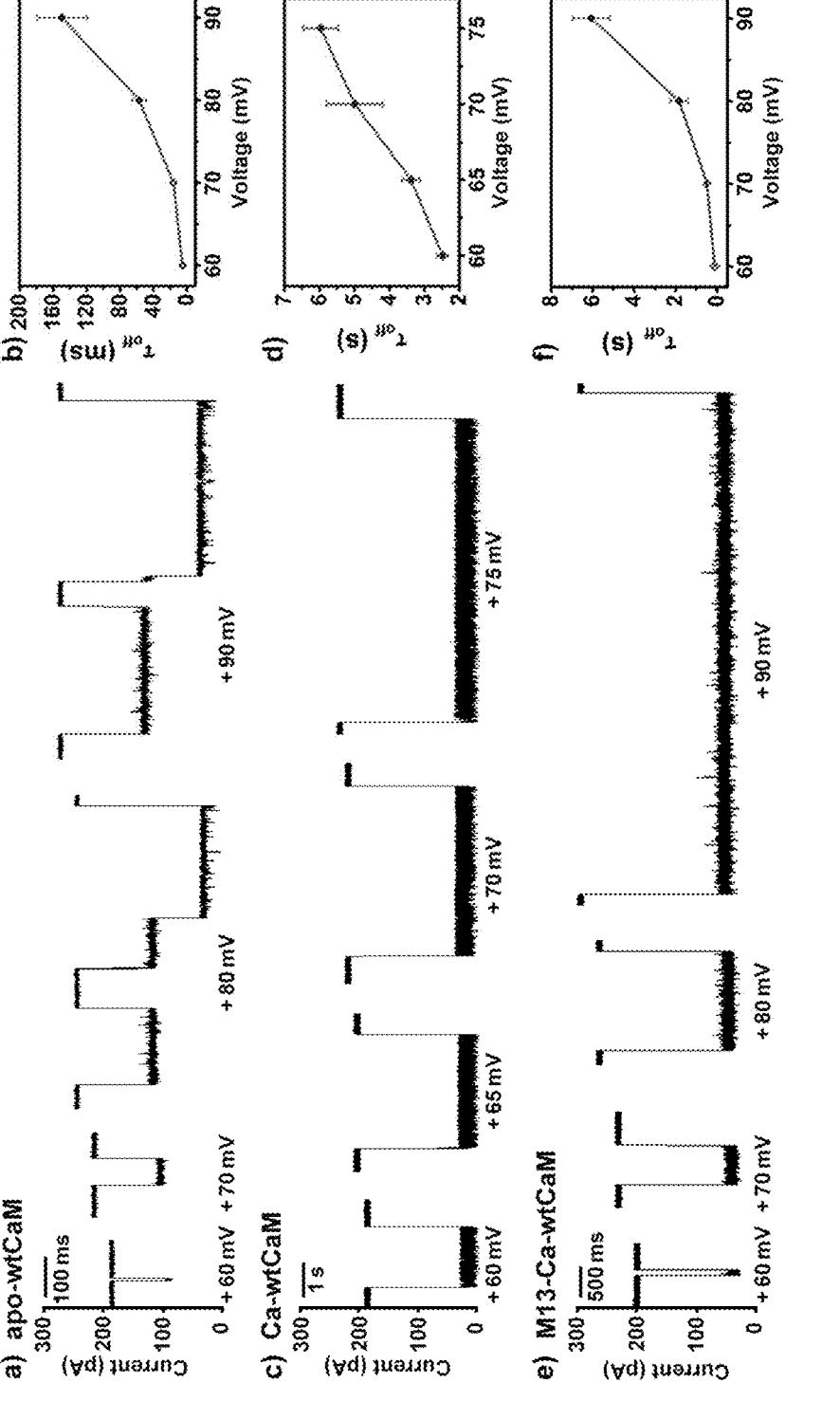

FIG. 49 shows trapping of wtCaM at different voltages. All measurements were carried out with M2 MspA (Example 5 Methods 4). Representative trapping events of apo-wtCaM (a), Ca-wtCaM (c) and M13-Ca-wtCaM (e) were demonstrated when measured with an applied potential of +60 mV, +70 mV, +80 mV or +90 mV. The mean event dwell time ($\tau_{off}$) of apo-wtCaM (b), Ca-wtCaM (d) and M13-Ca-wtCaM (f) when measured at different applied potentials are summarized. Generally, the event dwell time is extended at a higher applied potential, indicating that a wtCaM, in either form (apo-wtCaM, Ca-wtCaM or M13-Ca-wtCaM), will not translocate through the pore. (a) Representative events of apo-wtCaM at different applied potentials. Specifically, when the applied voltage is above +80 mV, a further secondary blockage type was occasionally observed, indicating that a stronger electrophoretic force may mechanically stretch apo-wtCaM so that it can reach deeper to the pore constriction. (b) $\tau_{off}$ of the corresponding trapping events in (a). The dwell time of the two-step blocking events generated under the voltage higher than +80 mV was defined as the total duration of both steps. (c) Representative trapping events of Ca-wtCaM at different applied potentials. (d) $\tau_{off}$ of the corresponding trapping events in (b). (e) Representative trapping events of M13-bound Ca-wtCaM at different applied potentials. (f) $\tau_{off}$ of the corresponding trapping events in (e). Error bars in (b), (d) or (f) represent standard deviations between independent measurements (N=3). The final concentrations of the analytes in cis were (a) 0.6 μM apo-wtCaM, (c) 0.6 μM apo-wtCaM and 4 mM Ca$^{2+}$, (e) 0.6 μM apo-wtCaM, 4 mM Ca$^{2+}$ and 1.0 μM M13 peptide. All results discussed above are detailed in Table 8.

Figure 50:
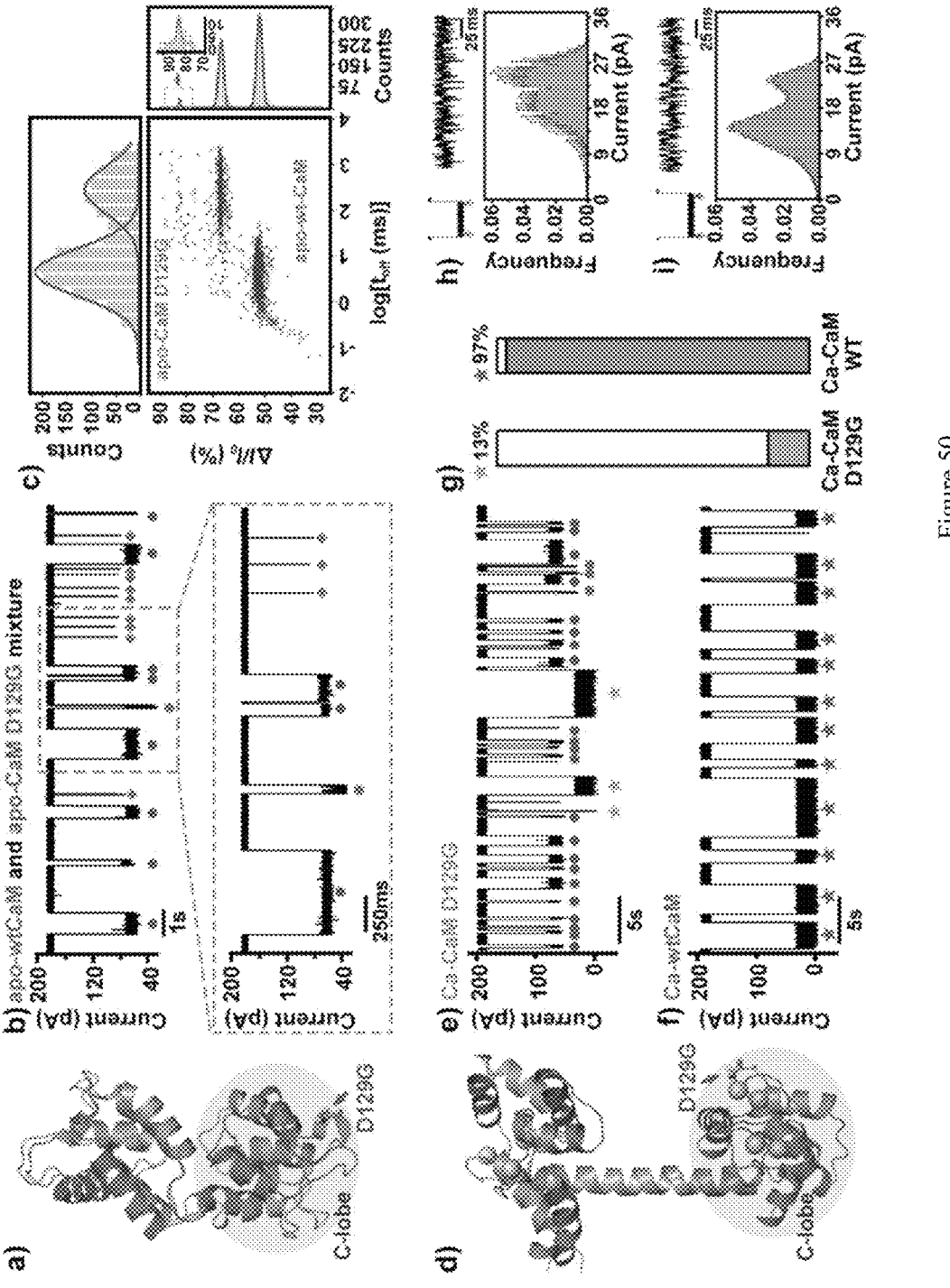
Figure 51:
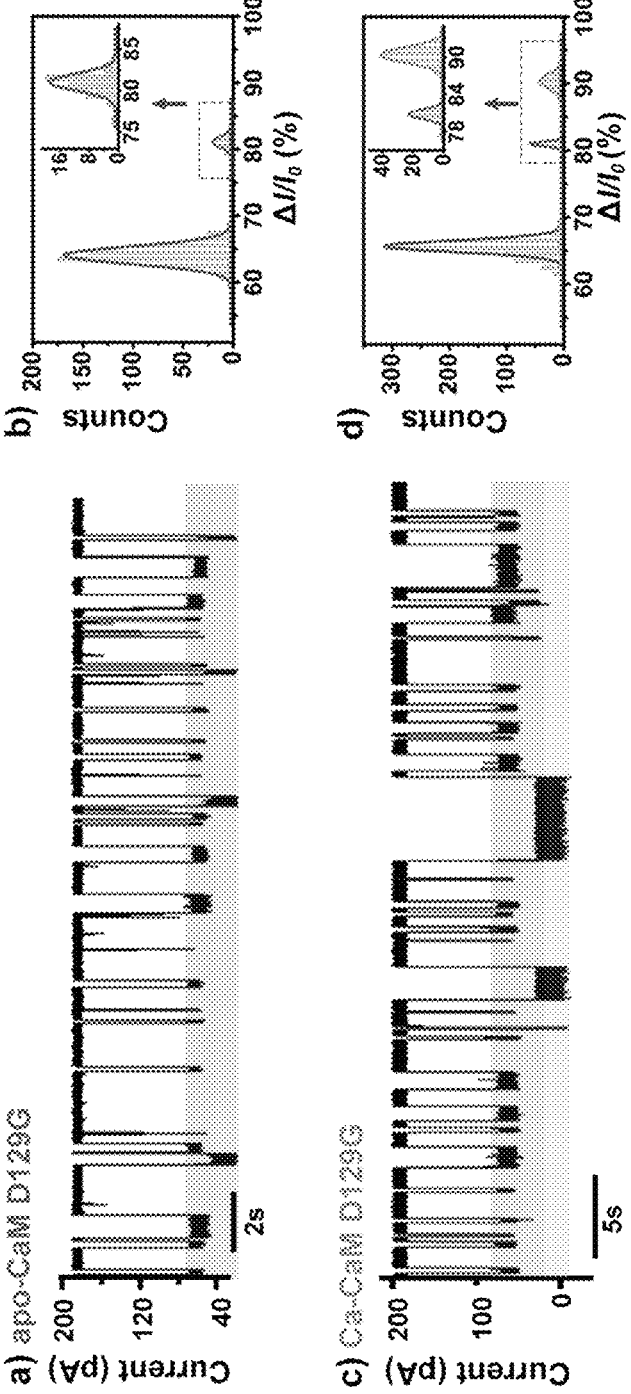

FIG. 50 shows single molecule properties of CaM-D129G. (a) The alignment diagram of wtCaM (purple, apo-wtCaM) and its D129G mutant (red, apo-CaM D129G) lacking any Ca$^{2+}$ binding. The Gly (129) of apo-CaM D129G was highlighted with bold sticks and a significant structural difference was observed in the C-lobe. (b) Stochastic sensing of apo-wtCaM and apo-CaM-D129G (0.6 μM in cis for each analyte). Purple diamonds mark the events of apo-wtCaM. Red or green circles respectively mark two event types of apo-CaM-D129G (FIG. 51). A segment of the trace (gray dashed frame) is enlarged to demonstrate differences between event types. (c) The scatter plot of $\Delta I/I_0$ vs. log($t_{off}$) for events from apo-wtCaM and apo-CaM-D129G. All events are from a 30 min continuously recorded trace as demonstrated in b. Corresponding histogram plots of $\Delta I/I_0$ and log($t_{off}$) are placed to the top and the right margin of the scatter plot. Events caused by trapping of apo-wtCaM or apo-CaM D129G are clearly discriminated in the scatter plot, as color marked by corresponding labels and fitting results. Specifically, the green fitting results correspond to a minor population of events caused by apo-CaM D129G trapping, as also marked with green circles in b. (d) The alignment diagram of the Ca$^{2+}$ bound structure of CaM-D129G (orange) and the wtCaM (purple). The Gly 129 was highlighted with bold sticks. A pathological conformation with complete separation of EF-hands domain within the C-lobe was observed. (e) A representative trace acquired with CaM-D129G in the presence of Ca$^{2+}$. The measurement was performed with 4 mM Ca$^{2+}$ and 0.6 μM apo-CaM-D129G added to cis. Anew type of event, as marked by orange stars and observable only when Ca$^{2+}$ were added, is demonstrated in the trace. (f) A representative trace containing events of Ca-wtCaM. Apo-wtCaM and Ca$^{2+}$ were added to cis with a final concentration of 0.6 μM and 4 mM. (g) The 100% stacked column to count the yield of Ca-CaM D129G (orange) and Ca-wtCaM (purple). The results are from 30 min continuously recorded traces measured with either wtCaM or CaM D129G, as respectively demonstrated in e and f. Events of Ca-CaM D129G (orange stars in e) accounts for only 13% of the total number of events (n=1333) and events of Ca-wtCaM (purple stars in (f)) account for 97% of the total number of events (n=552). (h, i) Discrimination of event features. Events of Ca-wtCaM and the major event of Ca-CaM D129G show a similar blockage depth however still discriminable according to their level fluctuations. Representative events and a zoomed in demonstration of event level fluctuations are demonstrated respectively on the top left and the top right corner of the plots. All-point histogram plots of the blockage levels sections extracted from the blocking events (between the colored arrows). The bin size was set at 0.6 pA. Error bars in the histogram represent the standard deviation values between different events (n=15, FIG. 52 and FIG. 54). All above results were from measurements were carried out as described in Example 5 Methods 4 with MspA. The protein structures were generated from MD simulations based on its crystal structure files. The initial structures of CaM-D129G were acquired from the mutation module of PyMOL.

FIG. 51 shows stochastic sensing of apo-CaM D129G and Ca-CaM D129G. All measurements were performed with M2 MspA, as described in Example 5 Methods 4. The buffer applied was 1.5 M KCl and 10 mM HEPES (pH=7.0) in both cis and trans chamber. The applied potential was +60 mV. (a) A representative trace containing apo-CaM D129G trapping events. Apo-CaM-D129G was added to cis with a final concentration of 0.6 μM. Two types of events, respectively reaching a blockage depth as marked by the red (higher) and green (lower) background, were observed. The majority of events report a blockage depth of ~69 pA, as marked by the red background. (b) The histogram of $\Delta I/I_0$ for apo-CaM-D129G trapping. (c) A representative trace containing Ca-CaM D129G trapping events. The measurements were performed following that demonstrated in (a). $Ca^{2+}$ was further added to cis with a final concentration of 4 mM. In addition to events observed in (a), a new event type reaching a blockage depth of ~20 pA, as marked by the orange (lowest) background, was consistently observed. This new event type represents events from Ca-CaM-D129G, the calcium-bound form of CaM-D129G. (d) The corresponding histogram of $\Delta I/I_0$ for Ca-CaM-D129G trapping. The histograms in the gray dashed frame in (b) and (d) were enlarged and displayed in the upper right corner. All peaks in (b) and (d) were respectively Gaussian fitted and colored correspondingly.

Figure 52:
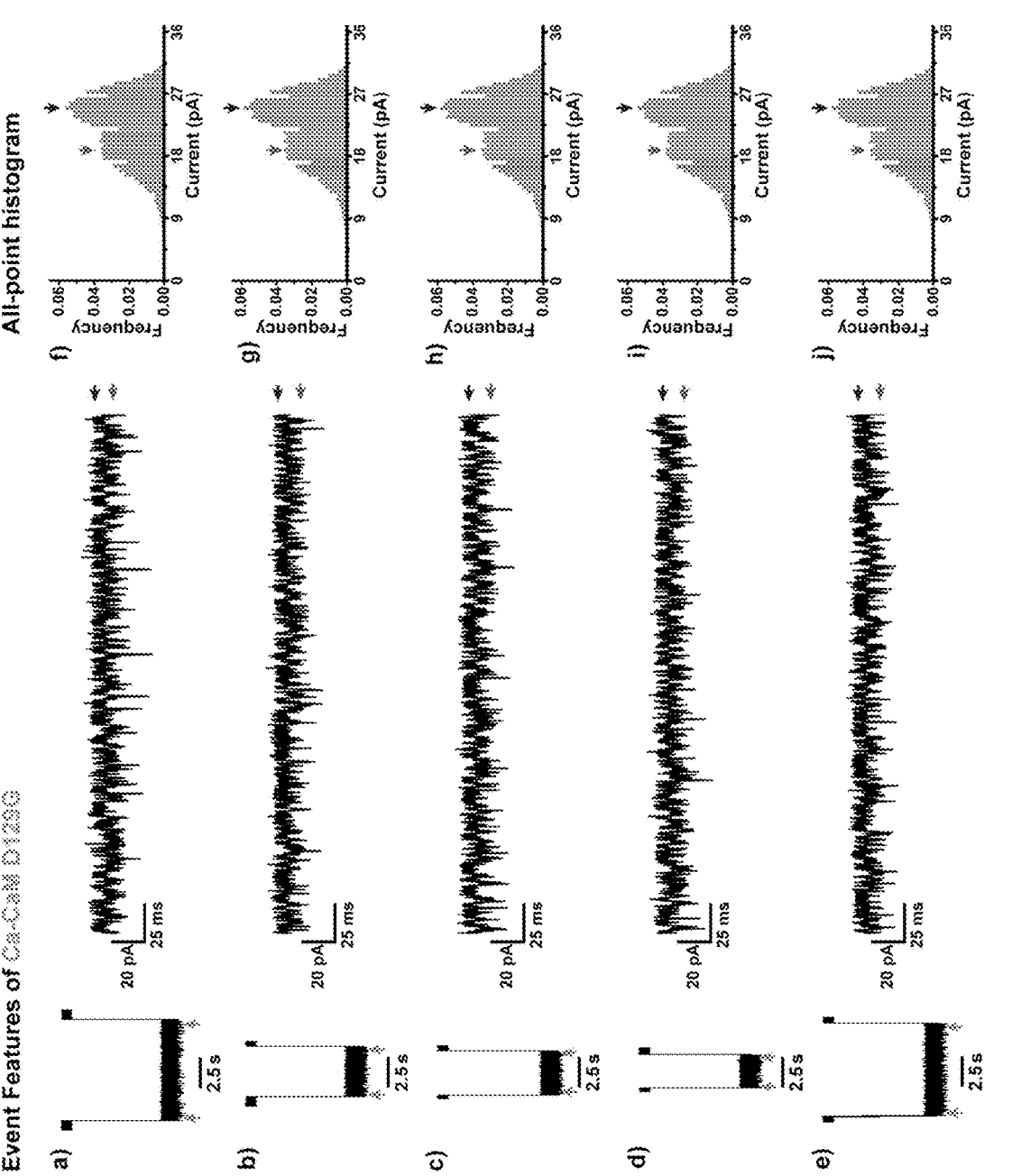

FIG. 52 shows event features of Ca-CaM D129G. All measurements were performed as described in FIG. 50. Trapping events of Ca-CaM D129G were extracted to analyze their event features. The blockage sections, which are the sections between orange arrows in (a-e), were further analyzed by all-point histograms (FIG. 50h) which were generated from 1-second trace sections stochastically extracted from the blockage sections demonstrated in (a-e). The zoomed-in demonstrations of the blockage sections were placed to the right of the representative events. (f-j) The corresponding all-point histograms of the section demonstrated in (a-e). The bin size was set at 0.6 pA. The green (lower) and blue (upper) arrows marked on the trace (a-e) respectively indicate two highly consistent features of the events, which contributed to the peaks in all-point histograms, as marked by green (left) and blue (right) arrows in (f-j).

Figure 53:
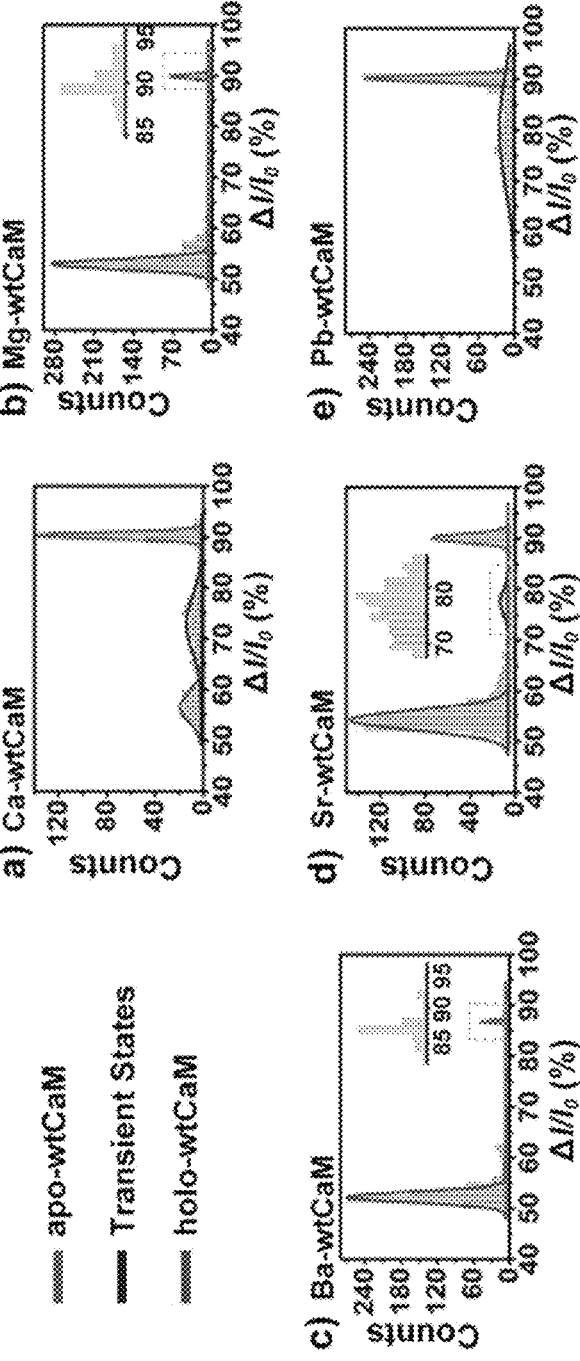

FIG. 53 shows wtCaM in the presence of different divalent ions. (a-e) The histograms of $\Delta I/I_0$ from trapping events of $Ca^{2+}$ (a), $Mg^{2+}$ (b), $Ba^{2+}$ (c), $Sr^{2+}$ (d) or $Pb^{2+}$ (e) bound wtCaM. All events were from 30 min continuously recorded traces as demonstrated in FIGS. 55a-55e. Gaussian fitting was performed for peaks in the histogram. The histograms in the gray dashed frame (b-d) were enlarged and presented. The peaks overlaid with green fitting curves (left) correspond to events of apo-wtCa. Peaks overlaid with blue fitting curves (middle) correspond to events of the transient states in which the EF-hand domains were not fully occupied with divalent ions. The peaks overlaid with red fitting curves (right) were from events of wtCaM when all four EF-hand domains were filled with corresponding ions. All fitting results are detailed in Table 9.

Figure 54:
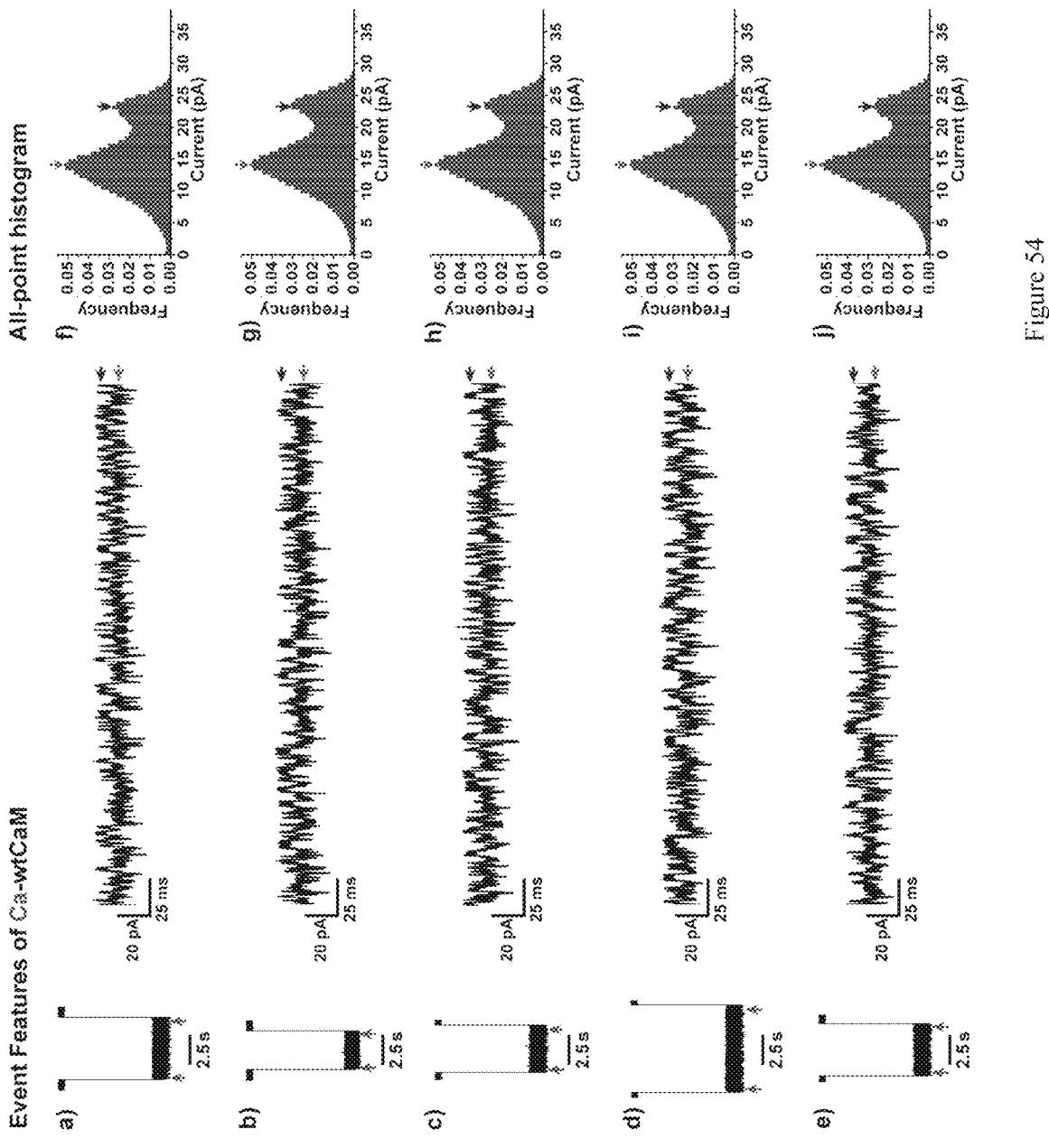
Figure 55:
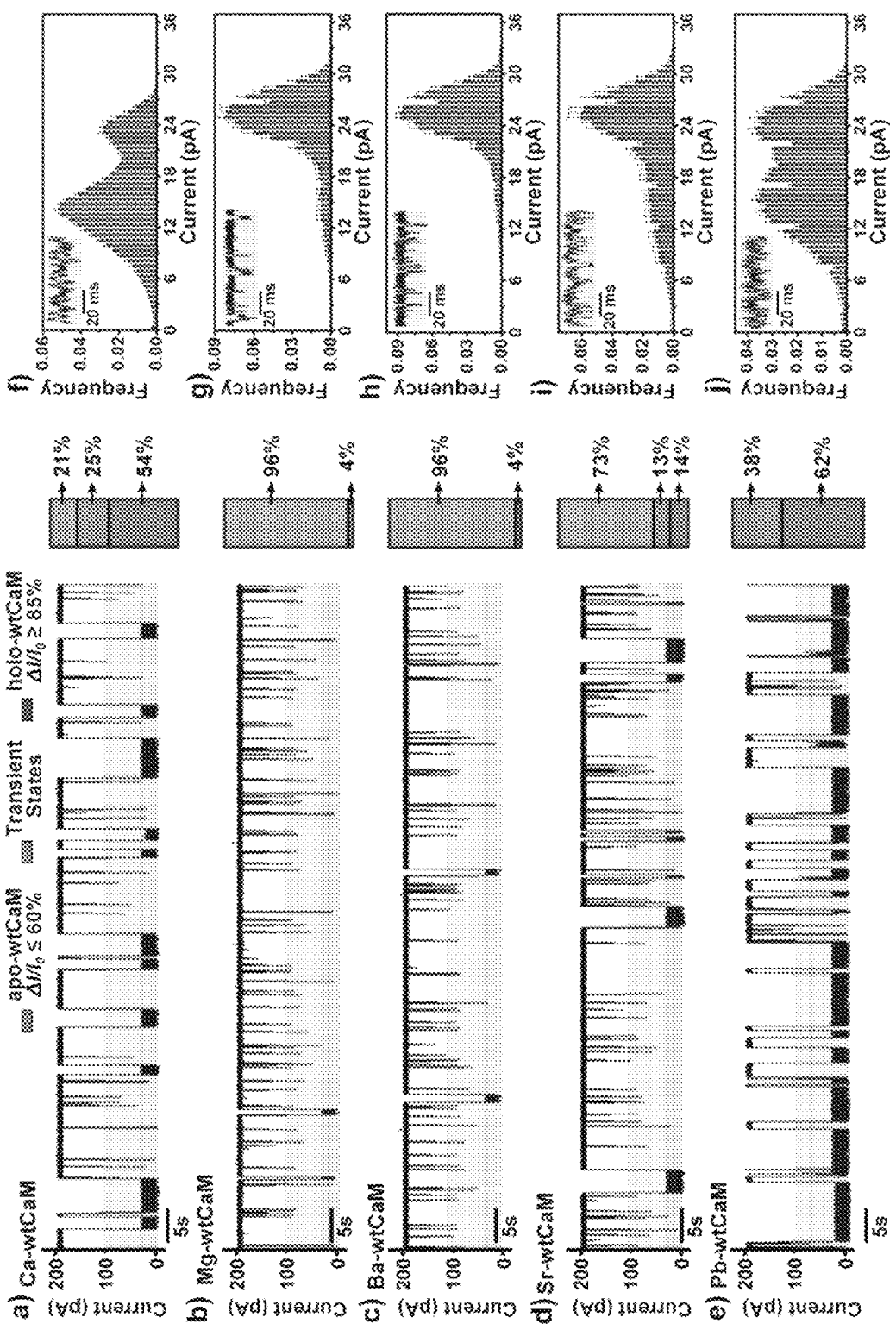

FIG. 54 shows event features of Ca-wtCaM. The measurements were performed with M2 MspA, as described in FIG. 55. Trapping events were extracted to analyze event features. The blockage sections, which are the sections between orange arrows in (a-e), were further analyzed by all-point histograms (FIG. 50i and FIG. 55f). The zoomed-in demonstrations of the blockage sections were placed to the right of the representative events. (f-j) The corresponding all-point histograms of the section demonstrated in (a-e). All-point histograms were generated from 1-second trace sections stochastically extracted from the blockage sections demonstrated in (a-e). The bin size was set at 0.6 pA. The green (lower) and blue (upper) arrows marked on the trace (a-e) respectively indicate two highly consistent features of the events, which contributed to the peaks in all-point histograms, as marked by green (left) and blue (right) arrows in (f-j).

FIG. 55 shows nanopore trapping of wtCaM in the presence of different divalent ions. (a-e) Left: Representative traces containing trapping events of wtCaM (0.6 μM) in the presence of $Ca^{2+}$ (a), $Mg^{2+}$ (b), $Ba^{2+}$ (c), $Sr^{2+}$ (d) or $Pb^{2+}$ (e). To be quantitatively comparable, the final concentration of each type of divalent ions in cis was set identically at 2 mM. Right: the 100% stacked column of events caused by different states of CaM. The different coordination states were recognized by the blockage depth of each event, as marked in the green, blue and red backgrounds (from top to bottom) on the trace. In the 100% stacked column, the red (lowest) column corresponds to events of wtCaM when all four EF-hand domains are filled with ions (holo-wtCaM). The green column (highest, absent in e) corresponds to events of apo-wtCaM. The blue column (middle, absent in b and c) corresponds to events from wtCaM when the EF-hand domains are partially filled with ions (transient states). The proportion of holo-wtCaM (red) is applied to evaluate the binding capacity of divalent ions with wtCaM. (f-j) All-point histograms of the blockage levels from holo-wtCaM events, as demonstrated in a-e. The bin size was set at 0.6 pA. Trapping events of holo-wtCaM caused by binding of different divalent ions share a similar blockage depth. However, their holo-wtCaM events are highly discriminable when bound with $Ca^{2+}$ (f), $Mg^{2+}$ (g), $Ba^{2+}$ (h), $Sr^{2+}$ (i) or $Pb^{2+}$ (j). The enlargements of the trace corresponding to the different divalent ions were shown on the upper left of the histograms. Error bars in (f-j) represent the standard deviations between independent events (n=15, FIG. 54-59). All measurements demonstrated above were carried out as described in Example 5 Methods 4 with MspA.

Figure 56:
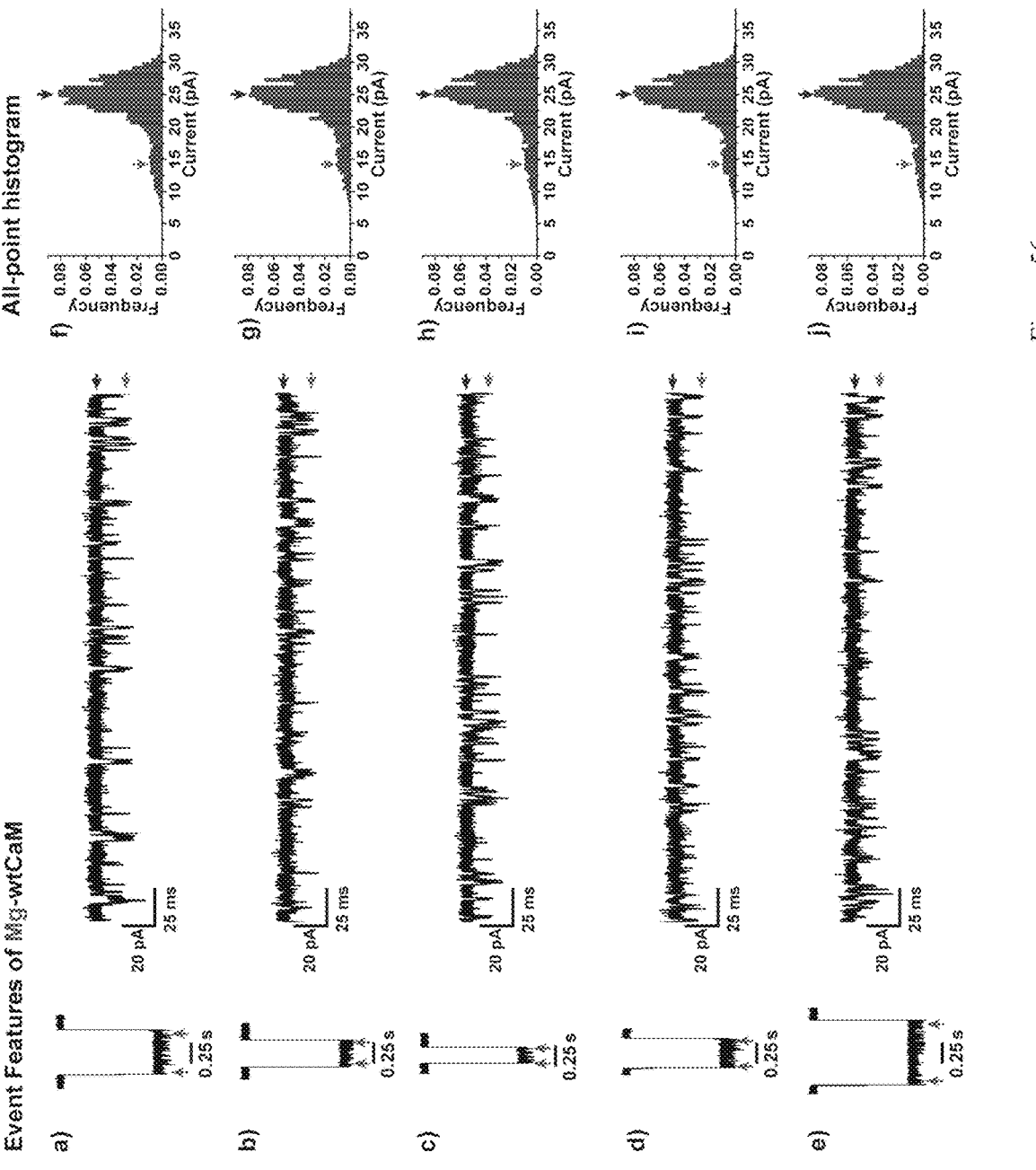

FIG. 56 shows event features of Mg-wtCaM. The measurements were performed with M2 MspA, as described in FIG. 55. Trapping events were extracted to analyze event features. The blockage sections, which are the sections between orange arrows in (a-e), were further analyzed by all-point histograms (FIG. 55g). The zoomed-in demonstrations of the blockage sections were presented to the right of the representative events. (f-j) The corresponding all-point histograms of the section demonstrated in (a-e). All-point histograms were generated from 0.2-second trace sections stochastically extracted from the blockage sections demonstrated in (a-e). The bin size was set at 0.6 pA. The green (lower) and blue (upper) arrows marked on the trace (a-e) respectively indicate two highly consistent features of the events, which contributed to the peaks in all-point histograms, as marked by green (left) and blue (right) arrows in (f-j).

Figure 57:
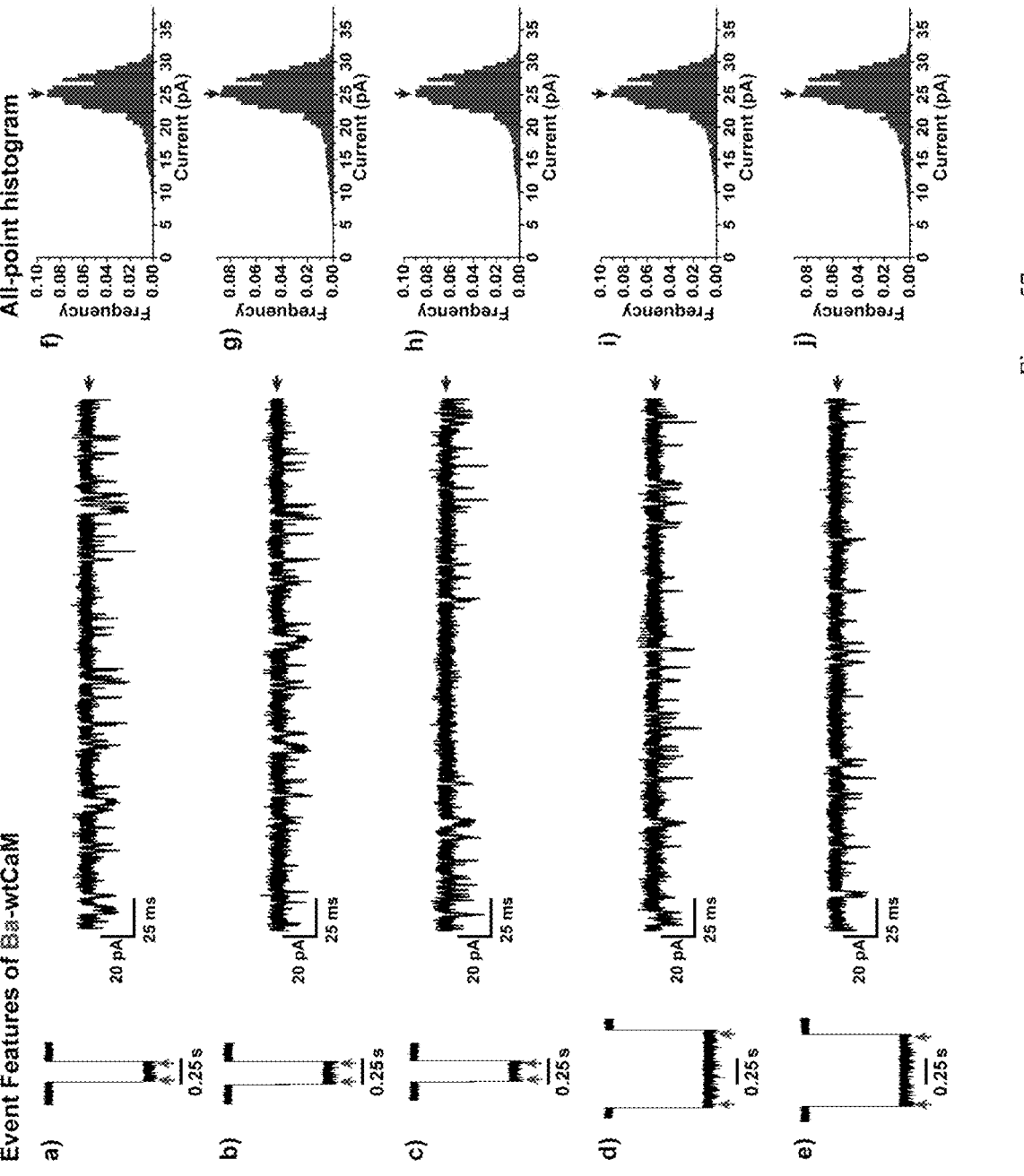

FIG. 57 shows event features of Ba-wtCaM. The measurements were performed with M2 MspA, as described in FIG. 55. Trapping events were extracted to analyze event features. The blockage sections, which are the sections between orange arrows in (a-e), were further analyzed by all-point histograms (FIG. 55h). The zoomed-in demonstrations of the blockage sections were presented to the right of the representative events. (f-j) The corresponding all-point histograms of the section demonstrated in (a-e). All-point histograms were generated from 0.2-second trace sections stochastically extracted from the blockage sections demonstrated in (a-e). The bin size was set at 0.6 pA. The blue arrows marked on the trace (a-e) indicate the highly consistent features of the events, which contributed to the peak in all-point histograms, as marked by blue arrows in (f-j).

Figure 58:
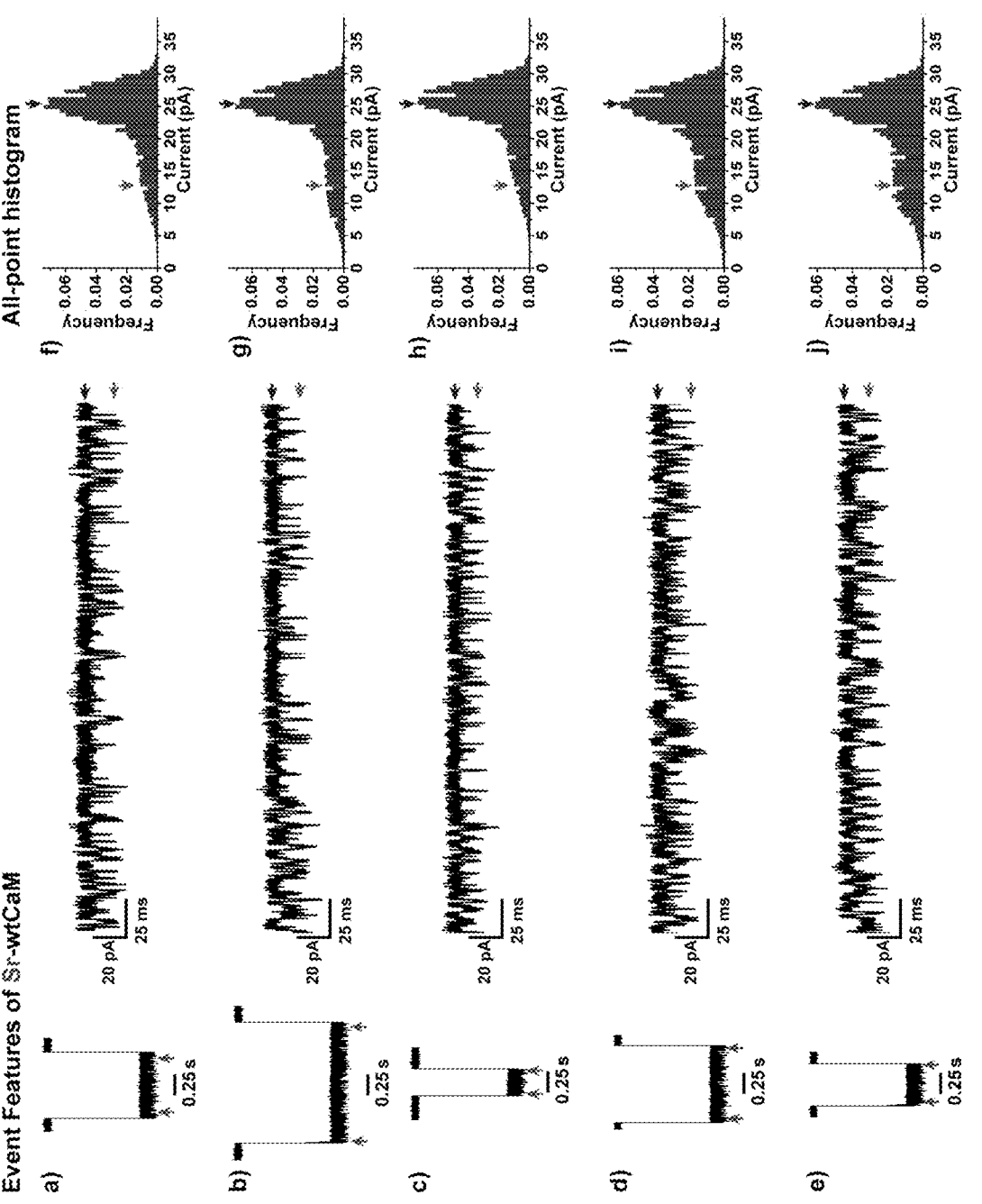

FIG. 58 shows event features of Sr-wtCaM. The measurements were performed with M2 MspA, as described in FIG. 55. Trapping events were extracted to analyze event features. The blockage sections, which are the sections between orange arrows in (a-e), were further analyzed by all-point histograms (FIG. 55i). The zoomed-in demonstrations of the blockage sections were presented to the right of the representative events. (f-j) The corresponding all-point histograms of the section demonstrated in (a-e). All-point histograms were generated from 0.2-second trace sections stochastically extracted from the blockage sections demonstrated in (a-e). The bin size was set at 0.6 pA. The green (lower) and blue (upper) arrows marked on the trace (a-e) respectively indicate two highly consistent features of the events, which contributed to the peaks in all-point histograms, as marked by green (left) and blue (right) arrows in (f-j).

Figure 59:
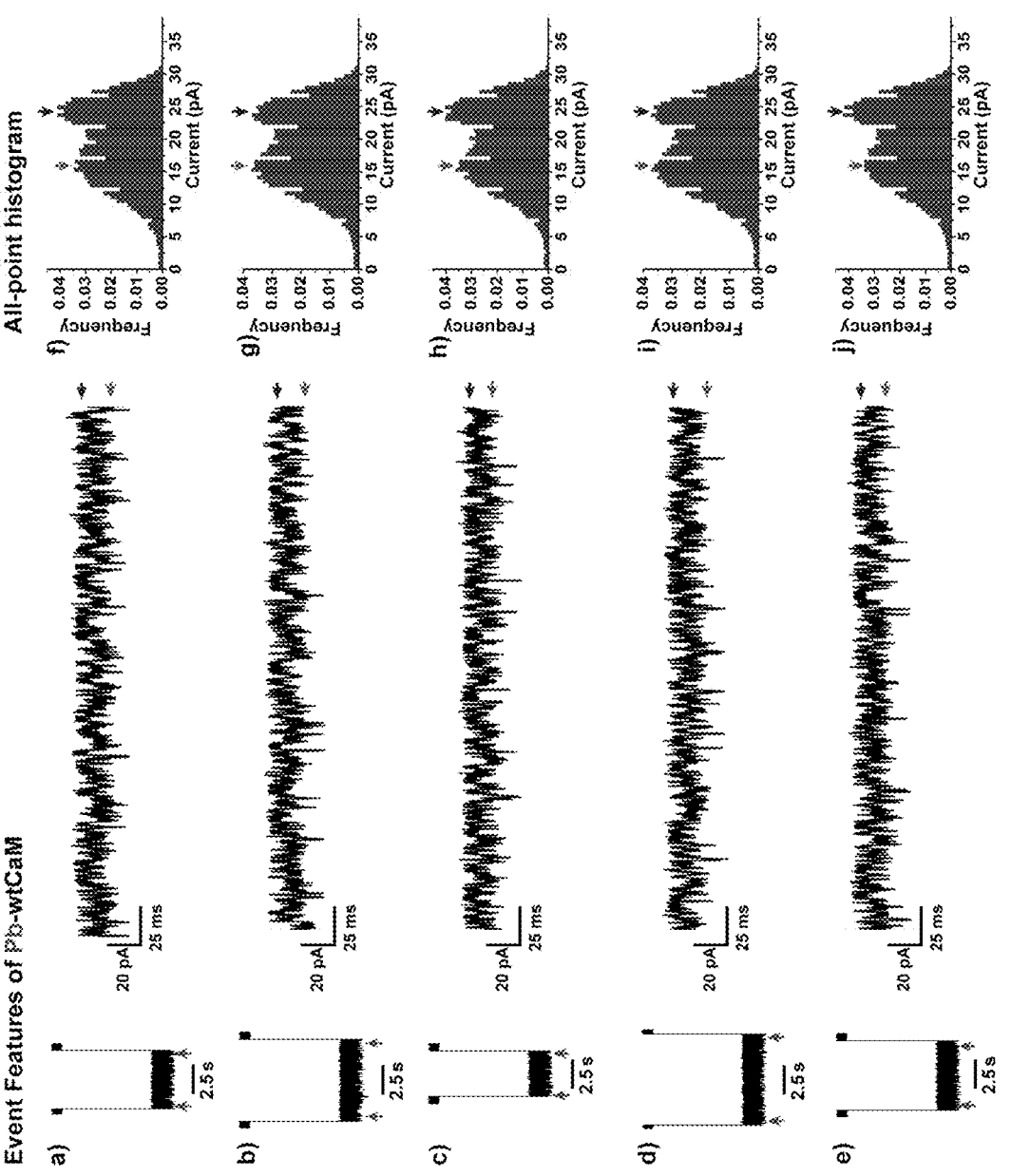

FIG. 59 shows event features of Pb-wtCaM. The measurements were performed with M2 MspA, as described in FIG. 55. Trapping events were extracted to analyze event features. The blockage sections, which are the sections between orange arrows in (a-e), were further analyzed by all-point histograms (FIG. 55j). The zoomed-in demonstrations of the blockage sections are presented to the right of the representative events. (f-j) The corresponding all-point histograms of the section demonstrated in (a-e). All-point histograms are generated from 1-second trace sections stochastically extracted from the blockage sections demonstrated in (a-e). The bin size was set at 0.6 pA. The green (lower) and blue (upper) arrows marked on the trace (a-e) respectively indicate two highly consistent features of the events, which contributed to the peaks in all-point histograms, as marked by green (left) and blue (right) arrows in (f-j).

Figure 60:
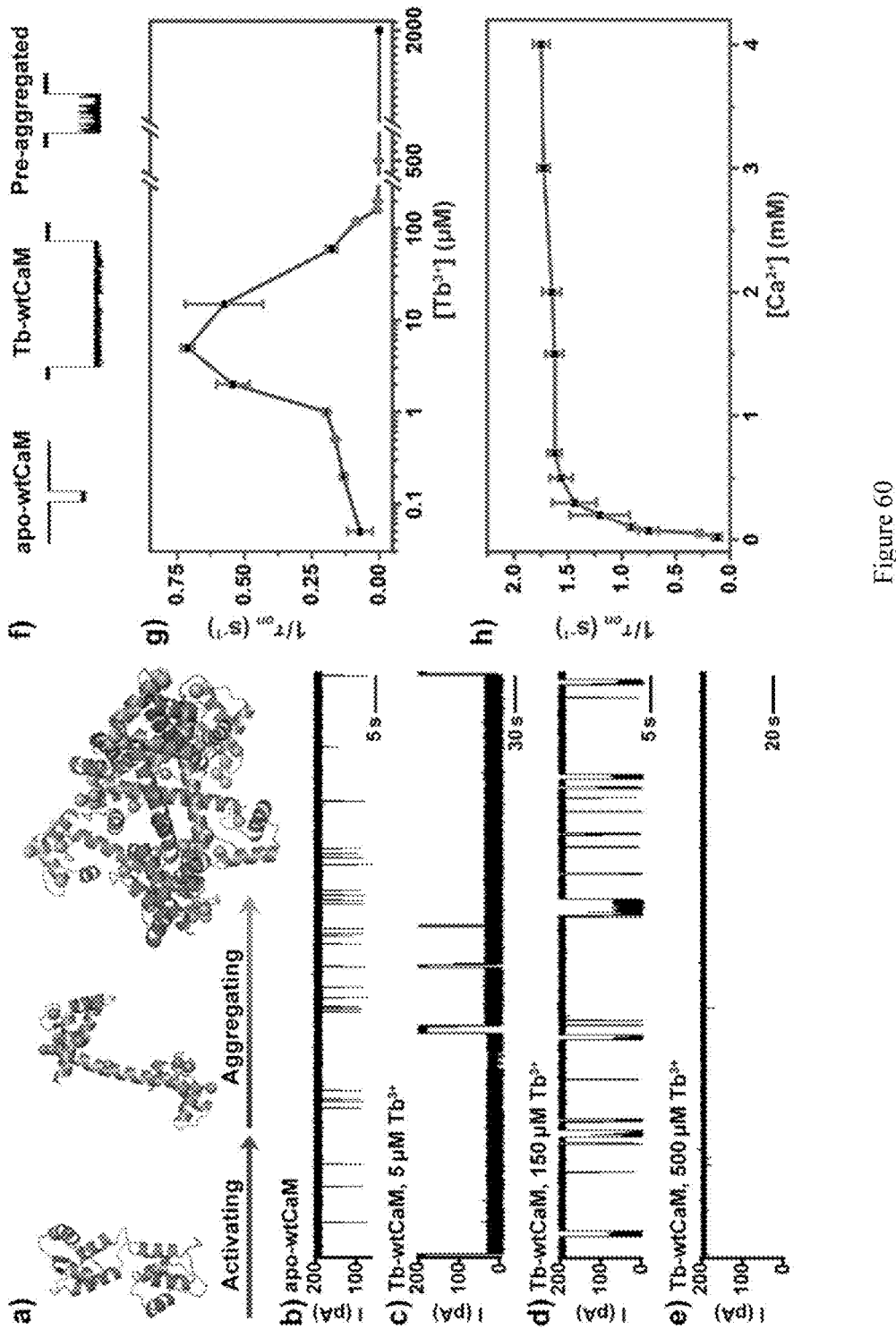
Figure 61:
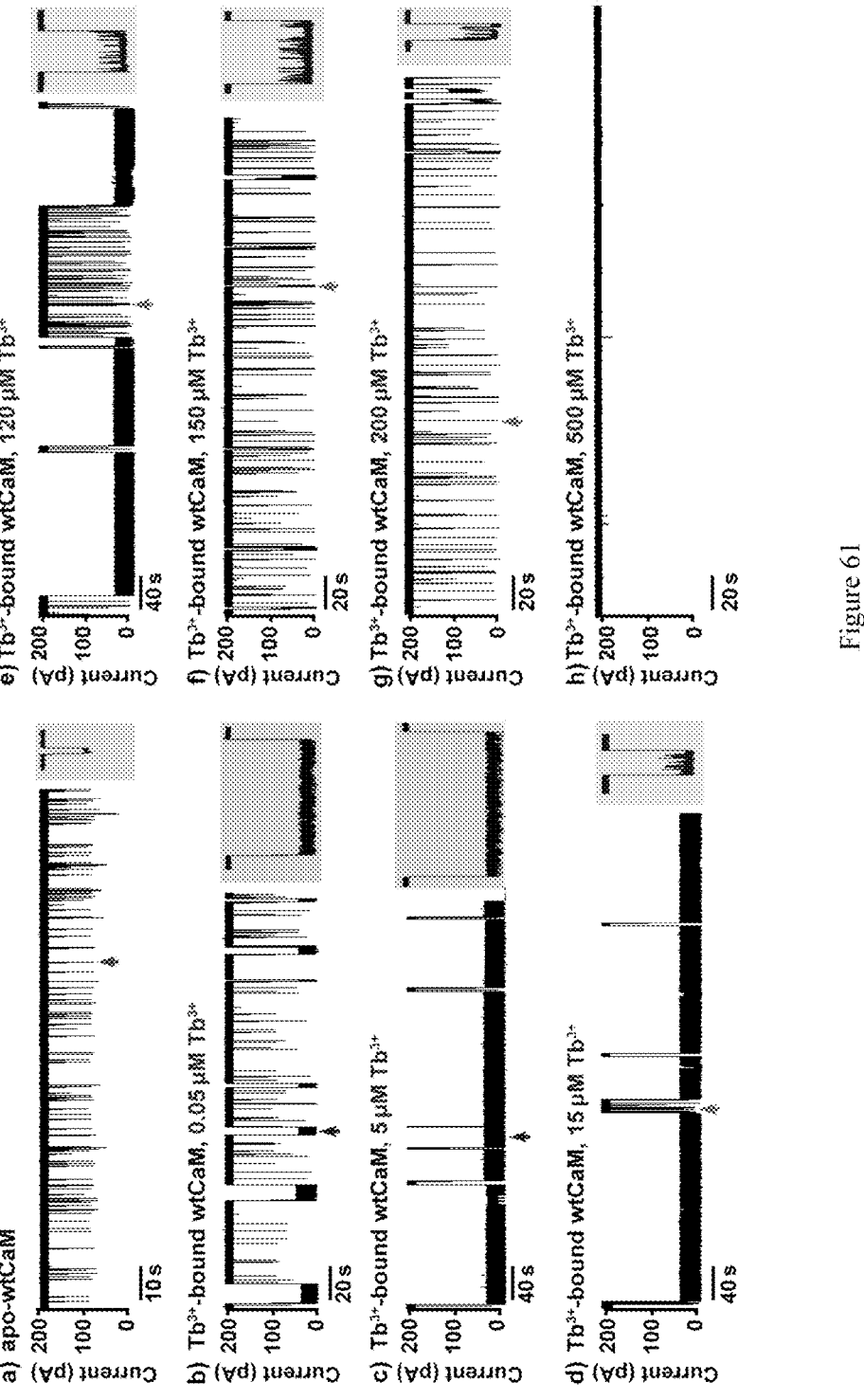

FIG. 60 shows $Tb^{3+}$-induced activation and aggregation of wtCaM. (a) A scheme of CaM aggregation caused by binding of $Tb^{3+}$ (dark gray spheres). A low concentration of $Tb^{3+}$ activates allosterism of wtCaM while a high concentration of $Tb^{3+}$ induces CaM aggregation. (b-e) Representative traces showing state changing of CaM when the final concentration of $Tb^{3+}$ in cis was sequentially titrated to 0 μM (b), 5 μM (c), 150 μM (d) and 500 μM (e). Gradual changing of the event types was consequently observed, caused by allosterism of wtCaM induced by different concentrations of $Tb^{3+}$. With 5 μM of $Tb^{3+}$, events of deep blockage with high level fluctuations were observed, resulted from trapping of Tb-wtCaM. Addition of $Tb^{3+}$ to 150 μM generates a new type of event which is much shorter residing and has a different event feature. Further addition of $Tb^{3+}$ to 500 μM results in complete disappearance of events. (f) Representative allosteric states of wtCaM when detected by nanopore trapping. Specifically, events of Tb-wtCaM or the pre-aggregated state were observed when $Tb^{3+}$ was in the low concentration (0.05-120 μM) or the high concentration (15-200 μM) regime (FIG. 61). The pre-aggregated state appears short resident with positive going spikes on top of the blockage level, highly discriminable from the Tb-wtCaM state. (g-h) Plots of 1 of trapping events induced by $Tb^{3+}$ (g) or $Ca^{2+}$ (h) bound wtCaM versus the concentration of $Tb^{3+}$ or $Ca^{2+}$ in cis. Aggregation of wtCaM caused by addition of $Tb^{3+}$ was not observed with $Ca^{2+}$. The final concentration of wtCaM in cis was 0.3 μM. All above demonstrated results were acquired during measurements as described in Example 5 Methods 4 using MspA.

FIG. 61 shows allosteric transition of wtCaM induced by $Tb^{3+}$. To show more details of gradual structural changes of wtCaM caused by $Tb^{3+}$ binding, representative traces measured with different concentration of $Tb^{3+}$ were demonstrated. All measurements were performed as described in FIG. 60. The final concentration of $Tb^{3+}$ in the cis compartment was 0 μM (a), 0.05 μM (b), 5 μM (c), 15 μM (d), 120 μM (e), 150 μM (f), 200 μM (g) or 500 μM (h) as marked on the top of each traces. The final concentration of apo-wtCaM was 0.3 μM. The traces on the colored background were zoomed-in demonstrations of representative events marked by arrows on the trace. The colors of the backgrounds and the arrows correspond to the representative events of wtCaM when it was in the apo-wtCaM (red), Tb-wtCaM (purple) or pre-aggregated states (green). When 500 μM $Tb^{3+}$ was added, wtCaM was aggregated and no consequent events were observed anymore. The concentrations of 0.05 μM, μM and 500 μM were the critical concentration of $Tb^{3+}$ when the structure of wtCaM started a transition.

Figure 62:
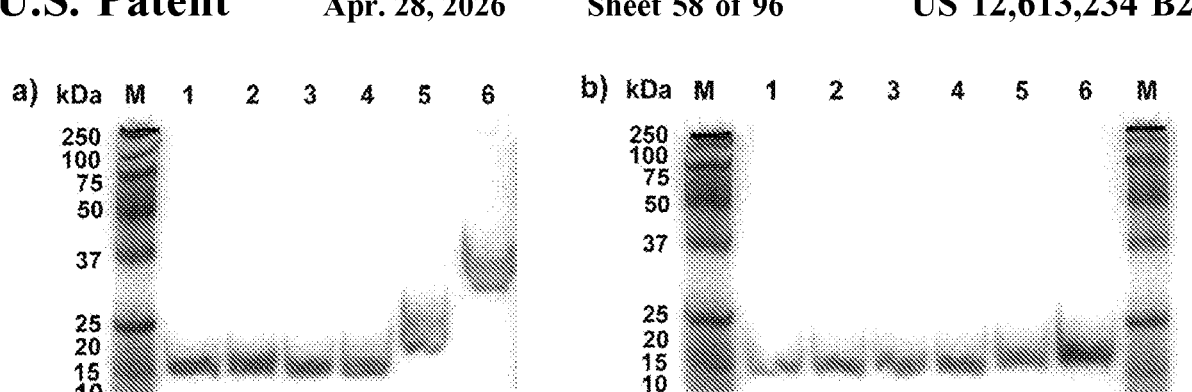

FIG. 62 shows state changing of wtCaM induced by $Tb^{3+}$ or $Ca^{2+}$. State changing in ensembles were characterized by gel electrophoresis. Experimentally, apo-wtCaM was mixed with different concentrations of $Tb^{3+}$ or $Ca^{2+}$ in the electrophysiological testing buffer (1.5 M KCl and 10 mM HEPES, pH=7.0) for 5 min before being loaded to the gel. The final concentrations of $Tb^{3+}$, $Ca^{2+}$ and apo-wtCaM were selected according to results in FIGS. 60g and 60h and were proportionally increased by 25 times to obtain clear electrophoresis results. (a) 15% Native-PAGE characterization of $Tb^{3+}$-induced activation and aggregation process of wtCaM (7.5 μM). Lane 1: apo-wtCaM; Lane 2-6: wtCaM mixed with 5 μM, 25 μM, 1.5 mM, 12.5 mM or 25 mM $Tb^{3+}$. When [$Tb^{3+}$] was increased to 12.5 mM (Lane 5), the electrophoretic migration of Tb-wtCaM was significantly changed, indicating that aggregation has started to occur. (b) Native-PAGE characterization of $Ca^{2+}$-induced activation process of wtCaM (7.5 μM). Lane 1: apo-wtCaM; Lane 2-6: wtCaM mixed with 50 μM, 125 μM, 1.5 mM, 2.5 mM, 25 mM, 50 mM $Ca^{2+}$. A slight decrease in electrophoretic migration distance were observed in Lane 4 and Lane 5, which may be caused by the formation of dumbbell-shaped structures when bound with $Ca^{2+}$. All results were consistent with the electrophysiological experiment in FIG. 60 with the exception of Lane 4 in (a). In the presence of 1.5 mM $Tb^{3+}$ (equivalent to 60 μM in FIG. 60g), the electrophoretic migration of $Tb^{3+}$-bound wtCaM was the same as that of apo-wtCaM, but the current blocking states were significantly different. It possibly indicates that the single-molecule methods demonstrated in this paper can resolve pre-aggregated state of $Tb^{3+}$-bound wtCaM that is however not distinguishable in-ensemble.

Figure 63:
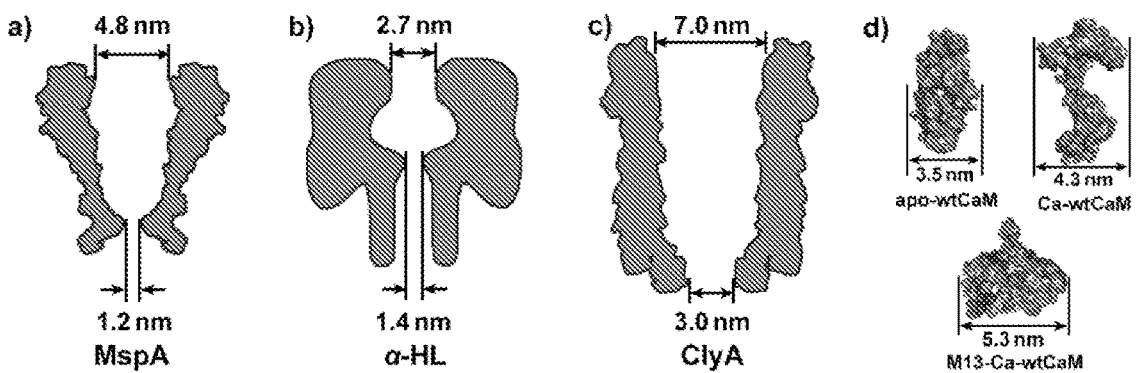

FIG. 63 shows geometric comparison between different nanopores and CaM conformers. Geometries of different nanopores and CaM conformers are presented simultaneously. (a) MspA (PDB ID: 1UUN), (b) α-HL (PDB ID: 7AHL), (c) ClyA (PDB ID: 2WCD), (d) the CaM conformers including the apo-wtCaM (PDB: 1CFC), the Ca-wtCaM (PDB: 1CLL) and the M13-Ca-wtCaM (PDB: 2BBN). The large lumen of MspA or ClyA is ideal when applied as a nanopore trap, but the narrow opening and the restricted lumen size of α-HL is limited when large protein analytes are to be probed.

Figure 64:
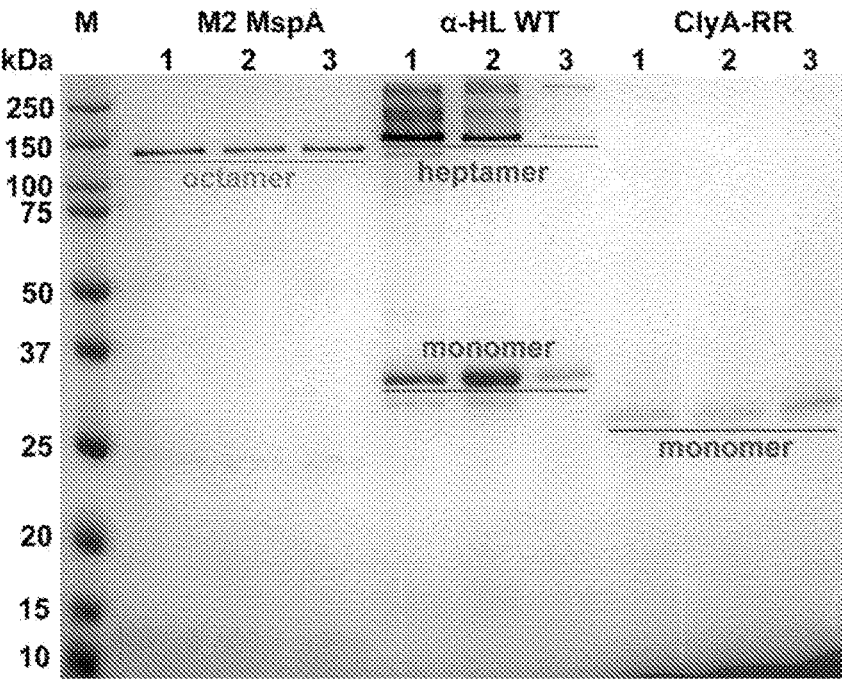

FIG. 64 shows stability comparison between different nanopores. 4-20% SDS-PAGE gel electrophoresis was performed to compare the structural stability of nanopores. For all three types of nanopores (MspA, α-HL WT and ClyA-RR), the freshly prepared nanopores (Lane 1) were compared with nanopores after thermal treatment at 85° C. for 15 min (Lane 2) or stored at −20° C. for 3 months (Lane 3). The colored lines on the gel results respectively mark nanopores in different forms of oligomerizations. Among all nanopores being characterized, MspA has presented the best stability against thermal treatment or long-term storage. Its oligomerization state stays unchanged which provides a great consistency of the measurements. WT α-HL showed depolymerization into monomers after thermal treatment or long-term storage. Aggregation of WT α-HL was also observed as bands of higher molecular weights. ClyA-RR was complete depolymerized under the condition of SDS-PAGE, indicating that its structure assembly is the weakest among nanopores being tested. As reported[192] and observed by us, assembled ClyA and its mutants can only be stored for a short period of time, meaning that a time-consuming preparation of ClyA has to be performed repetitively.

Figure 65:
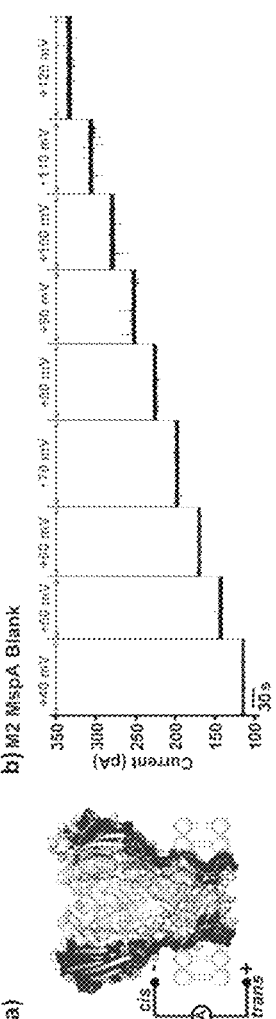

FIG. 65 shows results from a vacant MspA nanopore. The measurement was performed with M2 MspA (Example 5 Methods 4). The applied voltage was ramped up from +40 mV and +120 mV to evaluate the stability of MspA. Specific sections when different potentials were applied are indicated by the green arrows and corresponding labels. (a) The schematic diagram of a vacant MspA nanopore-trap. (b) Current traces of a vacant MspA nanopore when a voltage gradient was applied. MspA remained stable during a continuous 18 min-measurement. No spontaneous gating was observed.

Figure 66:
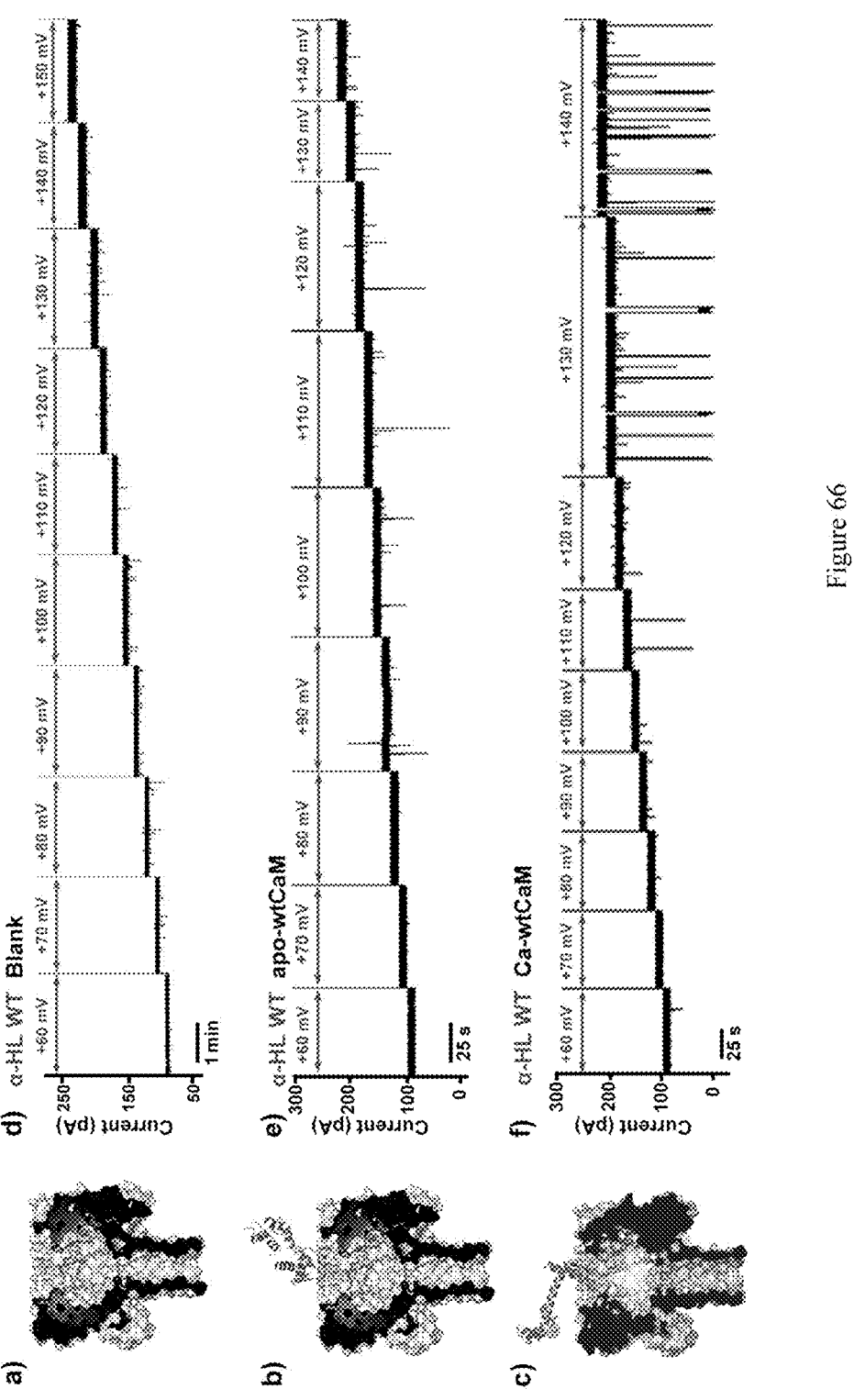

FIG. 66 shows WT α-HL applied as a nanopore-trap. All measurements were performed as described in Example 5 Methods 4 but WT α-HL instead of M2 MspA was applied as the nanopore trap. (a) The schematic diagram of a vacant α-HL nanopore-trap. (b, c) The schematic diagram of an α-HL nanopore-trap when apo-wtCaM (b) or Ca-wtCaM (c) was applied as the analyte. The structures of α-HL and wtCaM were generated by the PDB file 1CFC (apo-wtCaM), 1CLL (Ca-wtCaM) and 7AHL (α-HL). Docking of the trapped analyte was performed by PyMOL. The narrow vestibule of α-HL is geometrically limited to trap either apo-wtCaM or Ca-wtCaM based on a visual inspection. (d) Current traces of a vacant α-HL nanopore when a voltage gradient from +60 mV to +150 mV was applied. No spontaneous gating was observed during the 30 min measurement. (e, f) Representative traces of α-HL nanopore trapping performed when apo-wtCaM (e) or Ca-wtCaM (f) was applied as the analyte. The applied voltage was ramped between +60 mV and +140 mV. Specific sections when different potentials were applied were clearly indicated by the green arrows and corresponding labels. Apo-wtCaM or Ca-wtCaM was separately added to cis with a final concentration of 0.9 μM in different sets of measurements. No blocking events from apo-wtCaM were observed even if a +140 mV potential was applied. Trapping events of Ca-wtCaM were observed when a capture potential of more than +130 mV was applied. The above demonstrations clearly approved that a WT α-HL is a stable nanopore sensor, which stays open without gating during time-extended measurements. However, the small vestibule of α-HL is not compatible with large protein such as an apo-wtCaM. Ca-wtCaM, which is more narrowly structured, can reach deep in the vestibule of α-HL, producing detectable trapping events. However, a large potential has to be applied to observe the phenomenon, indicating the presence of an entropic barrier which prohibits a large analyte to be trapped. On the contrary, trapping of Apo-wtCaM or Ca-wtCaM can be easily achieved by an M2 MspA (FIG. 67), confirming that the wide opening of MspA is advantageous when applied as a nanopore trap.

Figure 67:
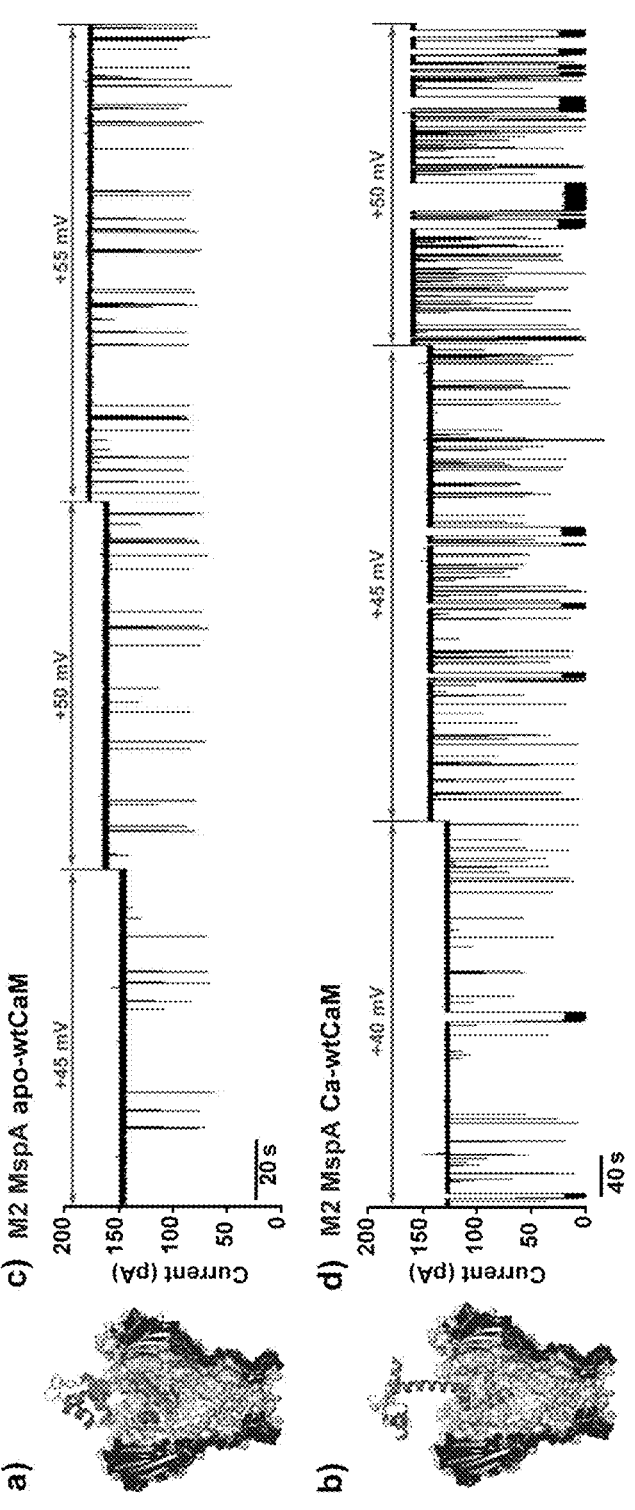

FIG. 67 shows the minimal capture potentials of MspA. All measurements were performed with M2 MspA (Example 5 Methods 4). Different potentials were applied to probe the minimal capture potential required to observe the trapping events. (a-b) The schematic diagram of an MspA nanopore-trap when an apo-wtCaM (a) or a Ca-wtCaM (b) was trapped. The structures of MspA and wtCaM were generated according to the PDB file 1CFC (apo-wtCaM), 1CLL (Ca-wtCaM) and 1UUN (MspA). Docking of the trapped analyte was performed by PyMOL. (c-d) Representative traces of MspA nanopore trapping performed when apo-wtCaM (c) or Ca-wtCaM (d) respectively was applied as the analyte. Experimentally, apo-wtCaM or Ca-wtCaM was separately added to cis with a final concentration of 0.9 μM, in independent measurements. The sections when different potentials were applied were marked with green arrows and corresponding labels. The above results indicate that MspA is a suitable nanopore trap sensor to detect CaM. Acknowledging its conical structure, a minimal capture potential of +40 mV or +45 mV is needed to detect trapping of apo-wtCaM Ca-wtCaM.

Figure 68:
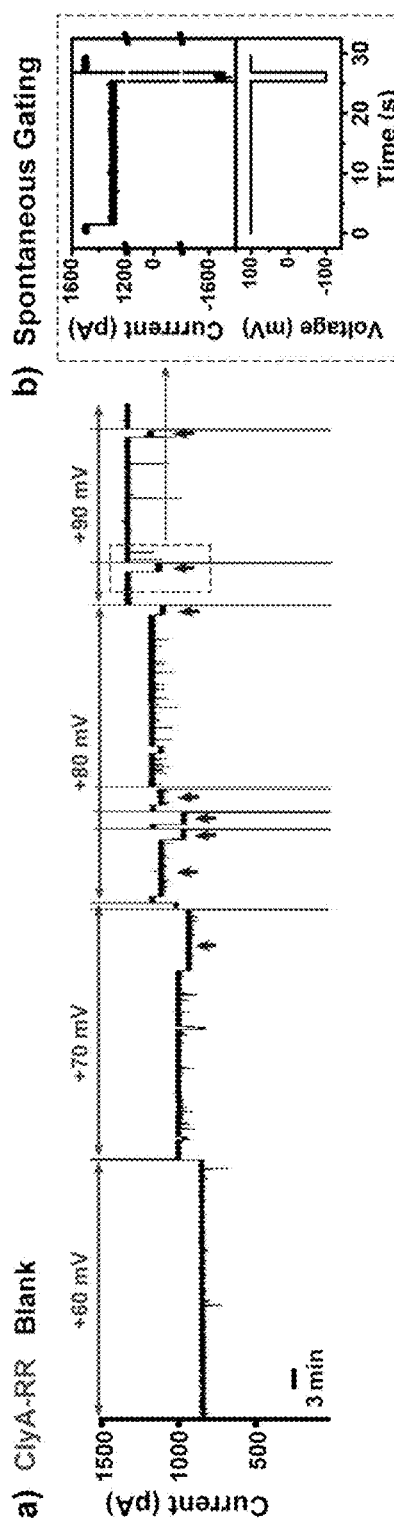

FIG. 68 shows representative traces of a vacant ClyA-RR nanopore. The measurement was performed as described in Example 5 Methods 4. A ClyA mutant (ClyA-RR) was applied as the nanopore trap instead. (a) A representative trace measured by a ClyA-RR without the addition of any analyte. Spontaneous gating events of ClyA-RR, as indicated by the blue arrows, were frequently observed when a potential of +70 mV or higher was applied. Spontaneous gating of ClyA and its mutants at a high applied voltage has also been previously reported.[192] (b) A representative gating event. It is a zoomed-in demonstration of the gating event marked by a red dashed rectangle in a. Though pore gating (marked with the blue arrow) could be restored by voltage reversal, frequent appearance of pore gating would significantly interfere the measurements when a high potential has to be applied.

Figure 69:
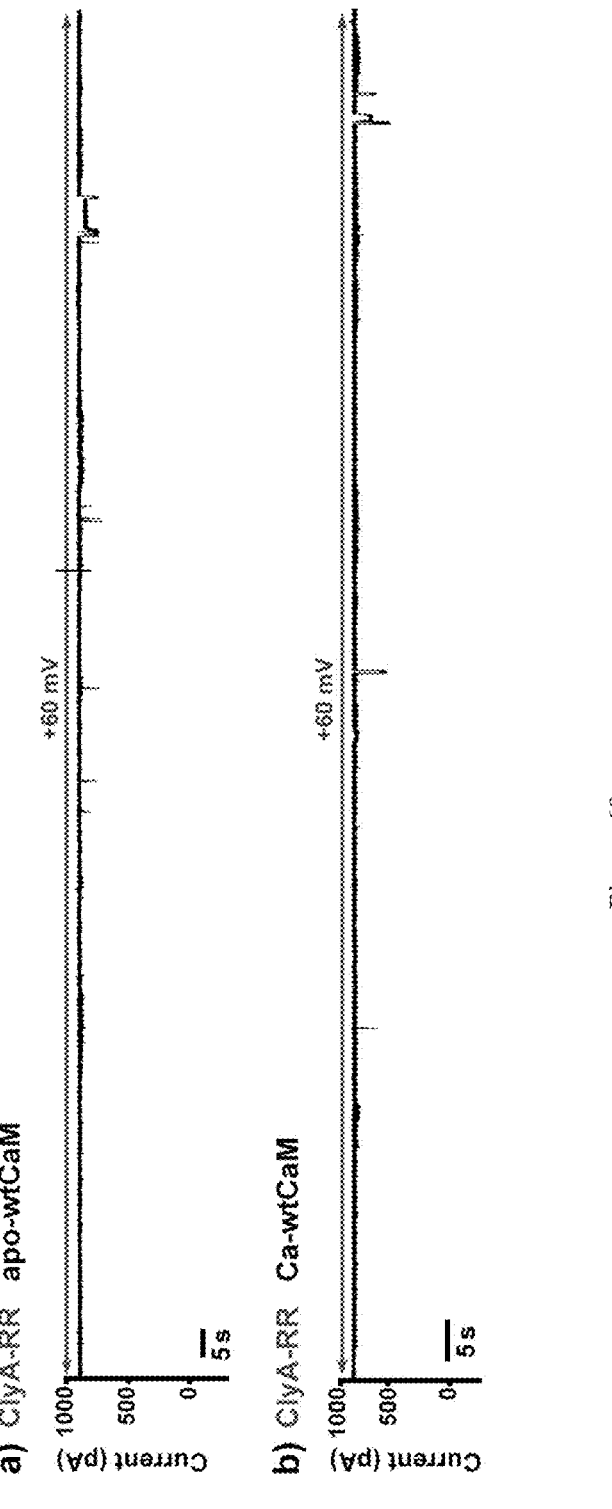

FIG. 69 shows the application of ClyA as a nanopore-trap. All measurements were performed as described in Example 5 Methods 4 with a ClyA-RR. (a-b) Representative traces when apo-wtCaM (a) or Ca-wtCaM (b) was applied as the analyte. Apo-wtCaM or Ca-wtCaM was added to cis with a 0.9 μM final concentration. To eliminate interferences of spontaneous gating, the applied potential was set to +60 mV potential according to results in FIG. 68. However, no trapping events of Apo-wtCaM or Ca-wtCaM were observed, indicating that ClyA-RR is not efficiently trapping wtCaM.

Figure 70:
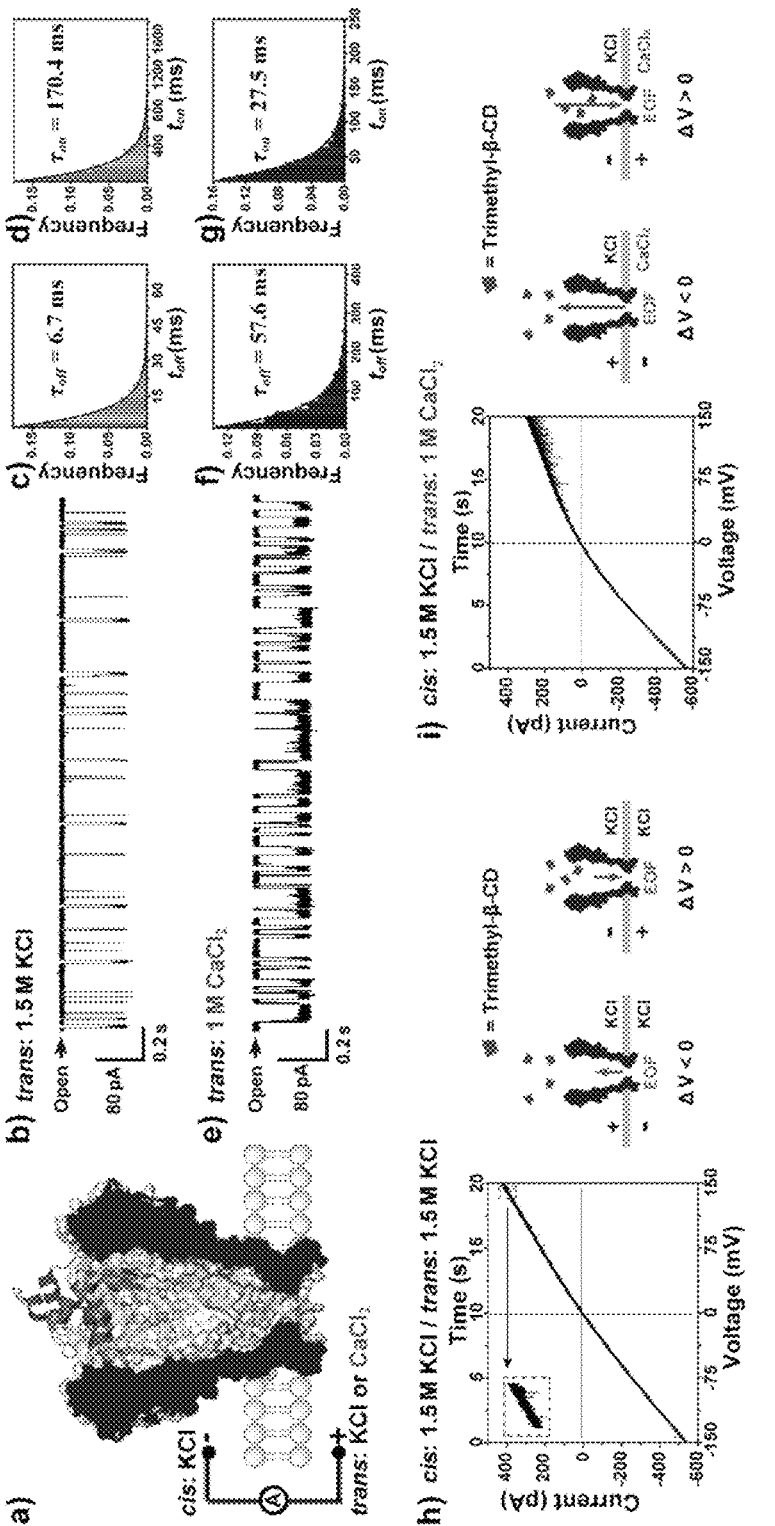

FIG. 70 shows optimized MspA nanopore-trap in the presence of calcium flux. (a) A schematic diagram of stochastic sensing of protein analytes by MspA. Lysozyme was here as a representative protein. The docking diagram of MspA and lysozyme was generated by PyMOL manually according to the structure files from protein data bank. PDB IDs: 1UUN (MspA) and 1DPX (lysozyme). A single MspA is inserted in a lipid membrane separating the cis and the trans chambers. The cis chamber was filled with 1.5 M KCl buffer and the trans chamber with a 1.5 M KCl or a 1 M CaCl$_2$ buffer, pH=7.0. Lysozyme was added to cis with a final concentration of 0.42 μM. A transmembrane potential of +100 mV was continuously applied. (b) Representative traces containing events caused by lysozyme trapping. The measurement was performed with a 1.5 M KCl buffer in both cis and trans. The blue arrow marked the open-pore current. (c-d) Histograms of event dwell time ($t_{off}$) (c) and interevent interval ($t_{on}$) (d) from a 20 min continuously recorded trace as demonstrated in b. (e) A continuous trace containing optimized trapping events of lysozyme when the buffer in trans was changed from 1.5 M KCl to 1 M CaCl$_2$. The blue arrow marked the open-pore current. (f-g) Histograms of event dwell time ($\tau_{off}$) (f) and interevent interval ($t_{on}$) (g) from a 15 min continuously recorded trace as demonstrated in e. Events with a dwell time <1 ms were ignored during the statistics in c and d, for f and g, the ignored duration was set to 2 ms. The mean event dwell time ($\tau_{off}$) and the mean interevent interval ($\tau_{on}$) were all derived from exponential fittings according to the equation y=α*exp (−x/r). In the presence of calcium flux, the trapping events of lysozyme appeared more frequently and the escape time of lysozyme was significantly prolonged. (h-i) Experimental evidence of electroosmotic flow (EOF) through the MspA nanopore-trap. Left: current-voltage (I-V) curves through MspA in 1.5 M KCl/1.5 M KCl buffer (h) or in 1.5 M KCl/1 M CaCl$_2$ buffer (i) with the presence of trimethyl-β-CD added from the cis of the membrane. In each case the voltage was ramped between −150 mV and +150 mV in 20 s. The neutral trimethyl-β-CD in cis could be trapped by the nanopore trap under a positive potential, which provided a basis for determining the direction of EOF. Right: schematics of recording the configuration under a positive or negative potential. The direction of EOF is marked in a green arrow.

Figure 71:
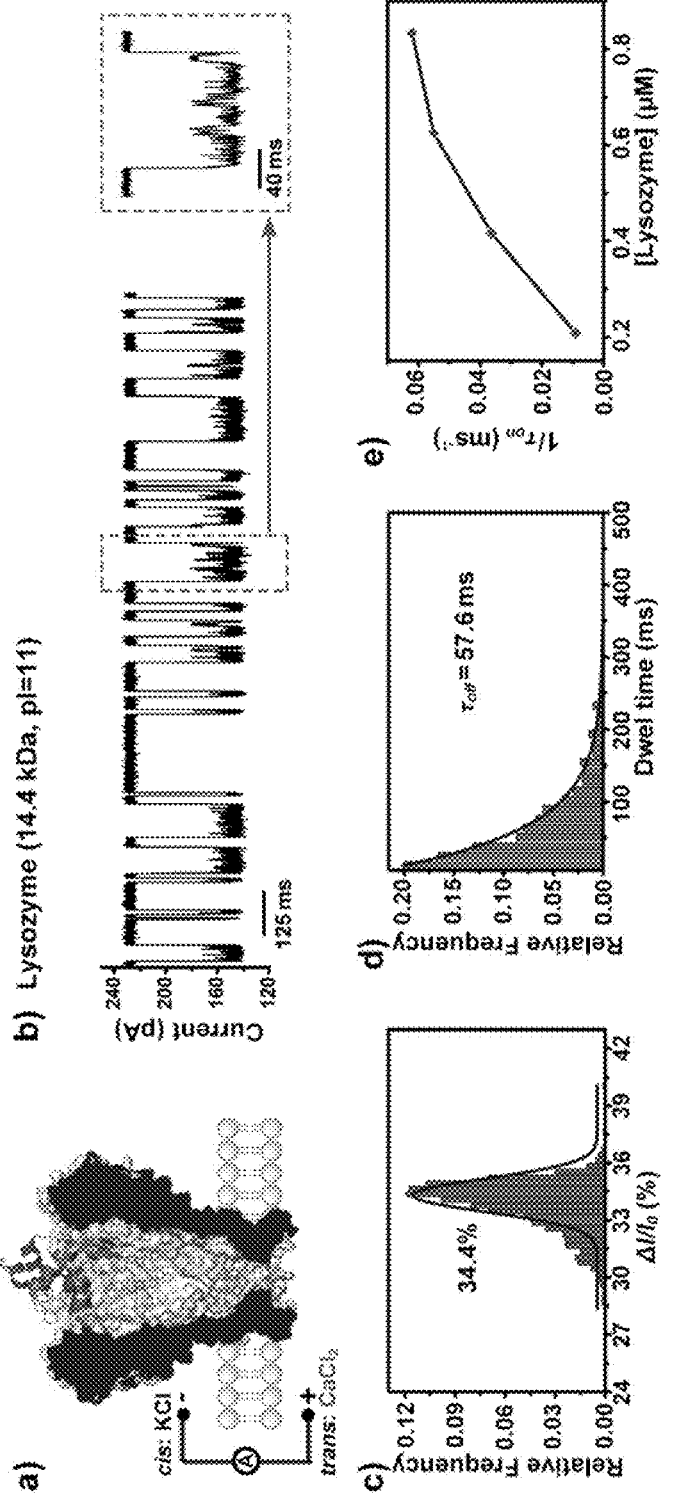

FIG. 71 shows single molecule characteristics of lysozyme trapping. (a) A schematic diagram of stochastic sensing of lysozyme (blue), a typical basic protein by MspA. The docking diagram of MspA and lysozyme was generated by PyMOL manually according to the structure files from protein data bank. PDB IDs: 1UUN (MspA) and 1DPX (lysozyme). The buffers in cis/trans chambers were 1.5 M KCl/1 M CaCl$_2$ (pH=7.0) respectively. Lysozyme was added to the cis chamber. A transmembrane potential of +100 mV was continuously applied. (b) Representative trace showing the blocking events caused by lysozyme trapping. The final concentration of lysozyme was 0.42 μM. Atypical event (gray dashed frame) was enlarged on the right to demonstrate event type. (c) Histograms of percentage blockage (mu&) corresponding to a 15 min continuously recorded trace as demonstrated in b. The mean value of $\Delta I/I_0$ ($\overline{\Delta I/I_0}$) was derived from the Gaussian fitting results. (d) The histogram plots of $t_{off}$ acquired from a 15 min continuously recorded trace as demonstrated in b. The histogram plots were fit with a single exponential curve, from which the mean event dwell time ($\tau_{off}$) was derived. Events with a dwell time <2 ms were ignored during the statistics. (e) Plot of the reciprocals of the mean inter-event intervals ($\tau_{on}$) for lysozyme trapping events versus the final concentrations of lysozyme in cis. The trapping events appeared more frequently as the final concentration of lysozyme increased.

Figure 72:
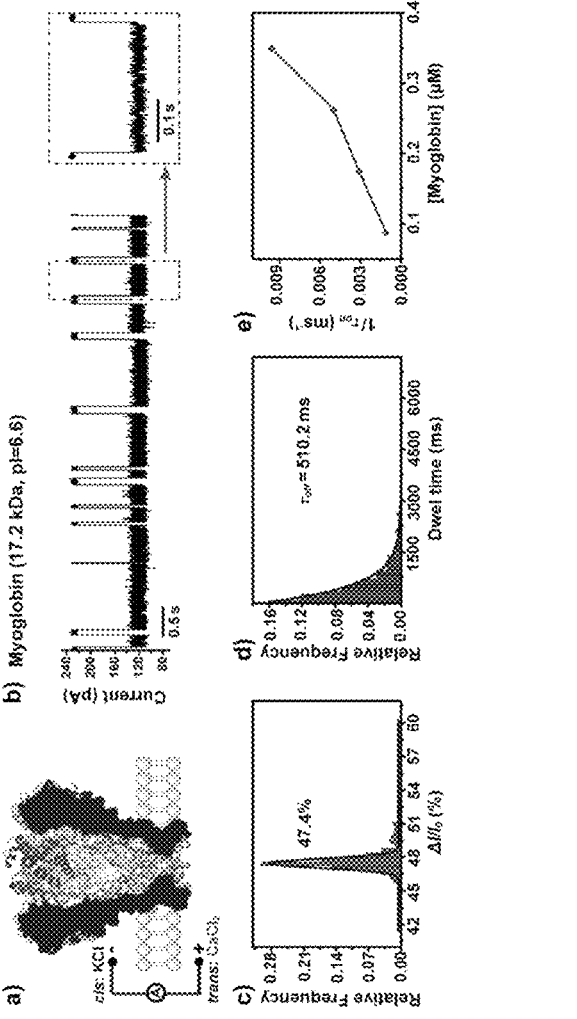

FIG. 72 shows single molecule characteristics of myoglobin trapping. (a) A schematic diagram of stochastic sensing of myoglobin (red), a typical neutral protein by MspA. The docking diagram of MspA and myoglobin was generated by PyMOL manually according to the structure files from protein data bank. PDB IDs: 1UUN (MspA) and 1WLA (myoglobin). The buffers in cis/trans chambers were 1.5 M KCl/1 M CaCl$_2$ (pH=7.0) respectively. Myoglobin was added to the cis chamber. A transmembrane potential of +100 mV was continuously applied. (b) Representative trace showing the blocking events caused by myoglobin trapping. The final concentration of myoglobin was 0.35 μM. A typical event (gray dashed frame) was enlarged on the right to demonstrate event type. (c) Histograms of percentage $\Delta I/I_0$ corresponding to a 25 min continuously recorded trace as demonstrated in b. The mean value of $\Delta I/I_0$ ($\overline{\Delta I/I_0}$) was derived from the Gaussian fitting results. (d) The histogram plots of $t_{off}$ acquired from a 25 min continuously recorded trace as demonstrated in b. The histogram plots were fit with a single exponential curve, from which the $\tau_{off}$ was derived. Events with a dwell time <2 ms were ignored during the statistics. (e) Plot of the reciprocals of $\tau_{on}$ for myoglobin trapping events versus the final concentrations of myoglobin in cis. The trapping events appeared more frequently as the final concentration of myoglobin increased.

Figure 73:
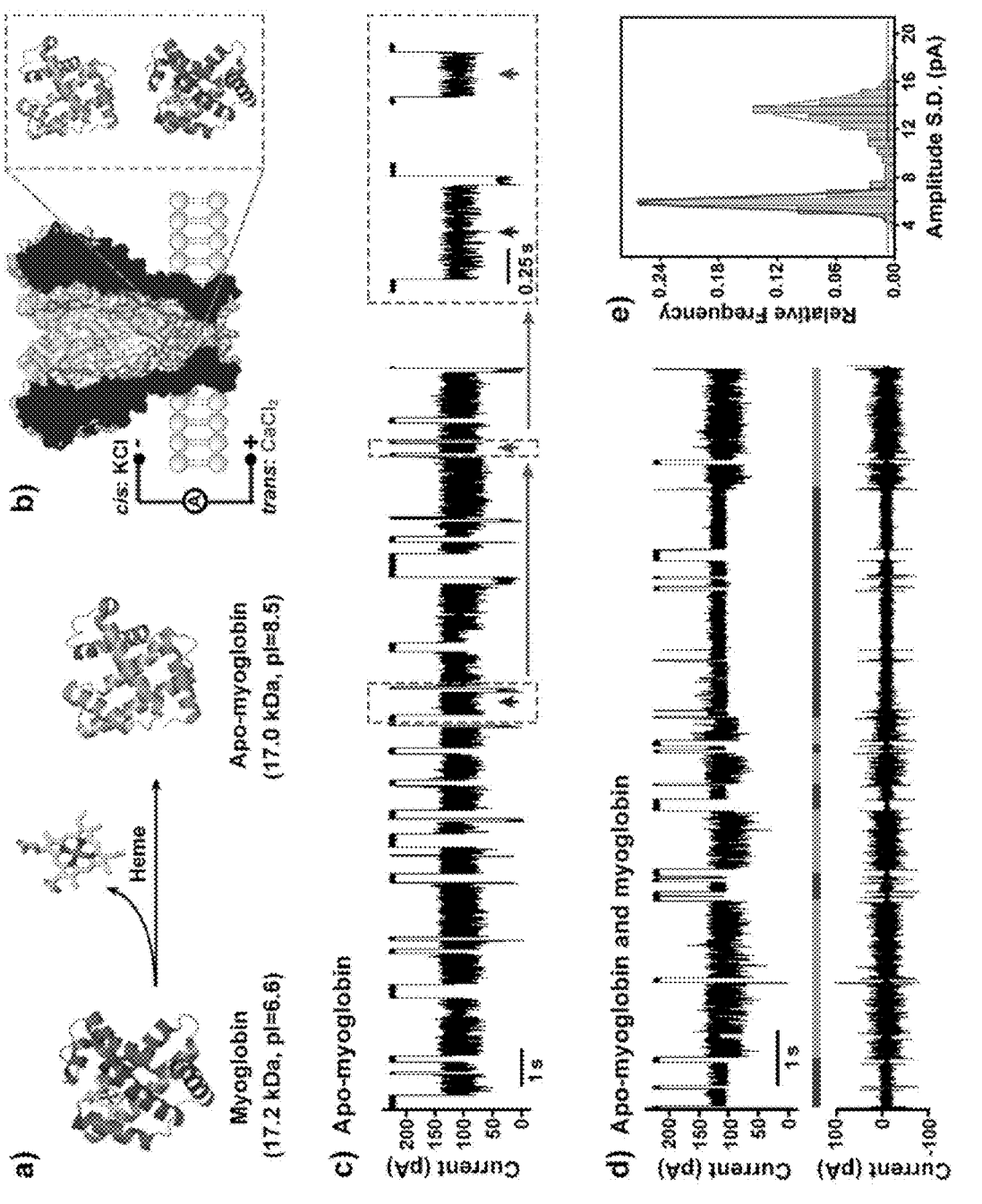

FIG. 73 shows distinguishing of the apo-myoglobin and myoglobin with MspA nanopore-trap. (a) A schematic diagram of the structure of heme-free myoglobin (apo-myoglobin, golden) after heme extraction from myoglobin (red). The structure of heme-free myoglobin was generated by PyMOL manually based on the PDB file of myoglobin (1WLA). (b) Schematic representations of the structures of apo-myoglobin (golden), myoglobin (red) and MspA nanopore-trap (gray). The measurements were carried out in the buffers of 1.5 M KCl/1 M CaCl$_2$ (pH=7.0) under a continuously transmembrane potential of +100 mV (c) Representative trace showing the blocking events caused by apo-myoglobin trapping. apo-myoglobin was added to cis chamber with a final concentration of 0.42 μM. Two typical events (marked with colored arrows in gray dashed frame) were enlarged on the right to demonstrate the two event types, which are both different from the blocking events of myoglobin in FIG. 50b. (d) Simultaneous sensing of myoglobin and apo-myoglobin, the final concentrations were 0.35 μM and 0.12 μM, respectively. Top: a representative trace during simultaneous sensing. Bottom: the corresponding current trace after filtered with a 50 Hz high-pass Bessel filter (8-pole) by Clampfit. Events from myoglobin and apo-myoglobin could be clearly recognized from the trace according to the fluctuation range of current, which are marked with red or golden bars respectively. (e) Histograms of standard deviation of blocking current (Amplitude S.D.) corresponding to a 30 min continuously recorded trace as demonstrated in d. Events with a dwell time <3 ms were ignored during the statistics. The mean value of Amplitude S.D. was derived from the Gaussian fitting results, the Amplitude S.D. of apo-myoglobin is 13.5 pA, which is significantly larger than myoglobin (5.9 pA).

Figure 74:
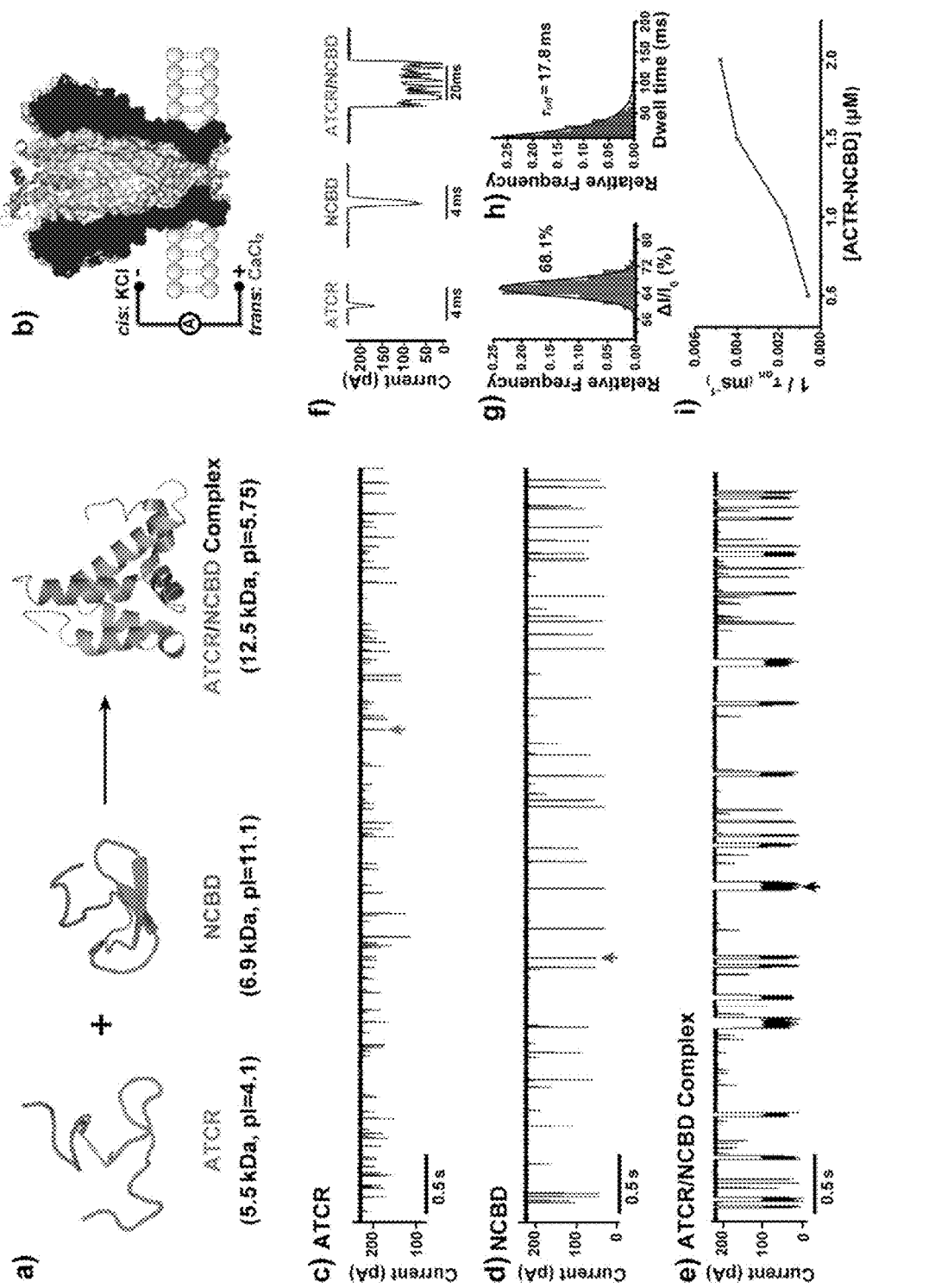

FIG. 74 shows single molecule characteristics of ATCR/NCBD complex trapping. (a) Schematic representations of the p160 steroid receptor coactivator (ACTR, orange) and the nuclear coactivator binding domain of CREB-binding protein (NCBD, green) before association and the well-folded binary complex between the two intrinsically unstructured protein domains (IUP). The structure of the fully unfolded ATCR and the molten globule state NCBD were conceptually displayed here, and the structure of ATCR/NCBD complex was from the PDB file 1KBH. (b) A schematic diagram of stochastic sensing of ATCR/NCBD complex (orange and green) by MspA. The docking diagram of MspA and myoglobin was generated by PyMOL manually. The buffers in cis/trans chambers were 1.5 M KCl/1 M CaCl$_2$ (pH=7.0) respectively. ATCR, NCBD or the complex were added to the cis chamber and a transmembrane potential of +100 mV was continuously applied during the measurement. (c-e) Representative traces containing events caused by ATCR (c), NCBD (d) or ATCR/NCBD complex (e) trapping. Both the two intrinsically unstructured protein domains ATCR and NCBD with opposite electrical properties could separately block the MspA nanopore-trap with fast translocation or escape speed in the presence of calcium flux. A new type of signal was generated in e when the two IUP were mixed in equal proportions, which represented the generation of negatively charged ATCR/NCBD complex. The final concentration of ATCR, NCBD and ATCR/NCBD were the same (1 μM) during the measurements. (f) Representative events of ATCR (left), NCBD (middle) or ATCR/NCBD complex (right) trapping. The events were taken from traces in c-e, as marked by corresponding arrows. (g-h) Histograms of $\Delta I/I_0$ (g) and $\tau_{off}$(h) corresponding to a 30 min continuously recorded trace from ATCR/NCBD complex trapping as demonstrated in e. The mean value of $\Delta I/I_0$ ( $\overline{\Delta I/I_0}$) was derived from the Gaussian fitting results. $\tau_{off}$ was derived from corresponding exponential fittings to the histogram. Events with a dwell time <2 ms were ignored during the statistics. (i) Plot of the reciprocals of the $\tau_{on}$ for ATCR/NCBD complex trapping events versus the final concentrations of ATCR/NCBD complex in cis. The trapping events appeared more frequently as the final concentration of ATCR/NCBD complex increased.

Figure 75:
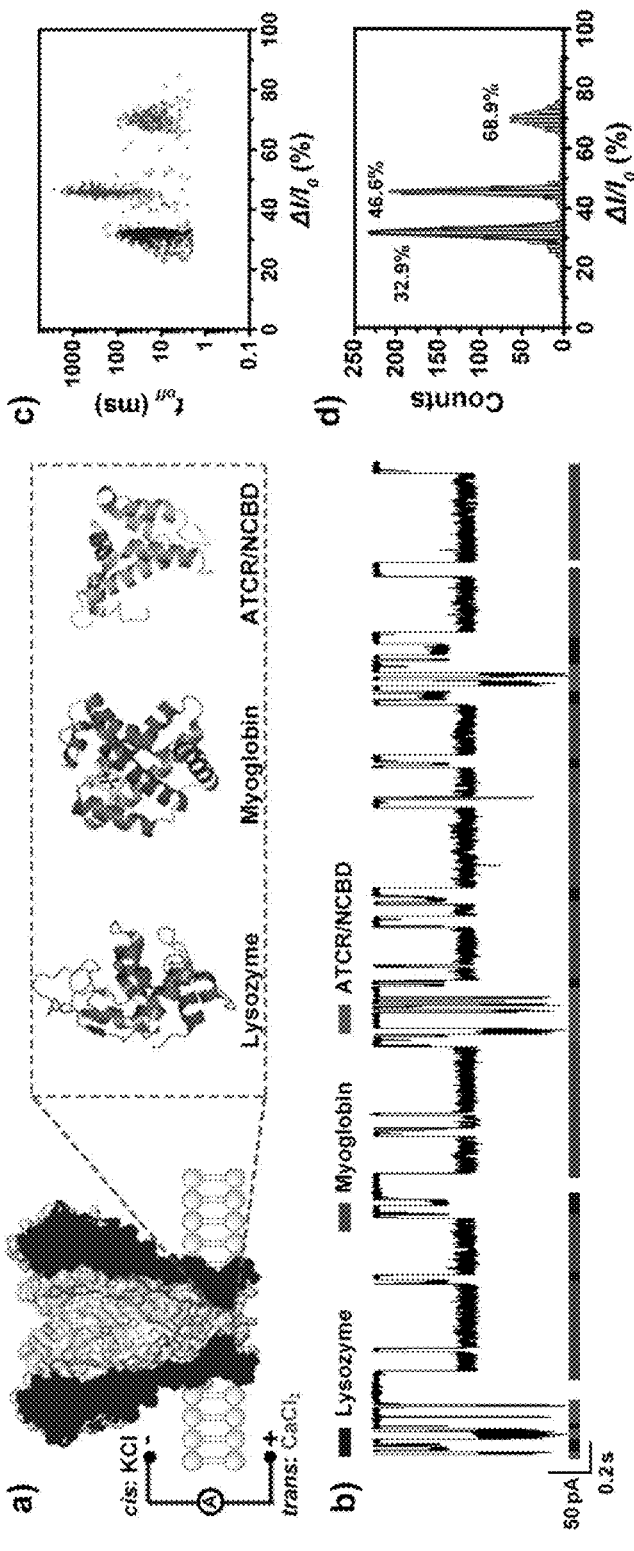

FIG. 75 shows distinguishing of the protein analytes with MspA nanopore-trap. The measurements were carried out in the buffers of 1.5 M KCl/1 M $CaCl_2$ (pH=7.0) under a continuously transmembrane potential of +100 mV. Lysozyme, myoglobin or ATCR/NCBD complex were added to the cis chamber with a final concentration of 0.42 μM, 0.7 μM and 2 μM respectively. (a) Schematic representations of the structures of the three typical protein analytes with different charge at pH 7. (b) A representative trace during simultaneous sensing of lysozyme, myoglobin and ATCR/NCBD complex. Events from different protein analytes could be clearly recognized from the trace, which are marked with blue, green or red bars respectively. (c) A scatter plot of event dwell time ($t_{off}$) vs. percentage blockage ($\Delta I/I_0$) corresponding to a 30 min continuously recorded trace of the simultaneous sensing (n=1178), with an ignored duration <2 ms. Events from three protein are clearly distinguishable. (d) Corresponding histograms of $\Delta I/I_0$ of the trapping events of lysozyme (32.9%), myoglobin (46.6%) and ATCR/NCBD complex (68.9%). The mean value of $\Delta I/I_0$ ($\overline{\Delta I/I_0}$) was derived from the Gaussian fitting results.

Figure 76:
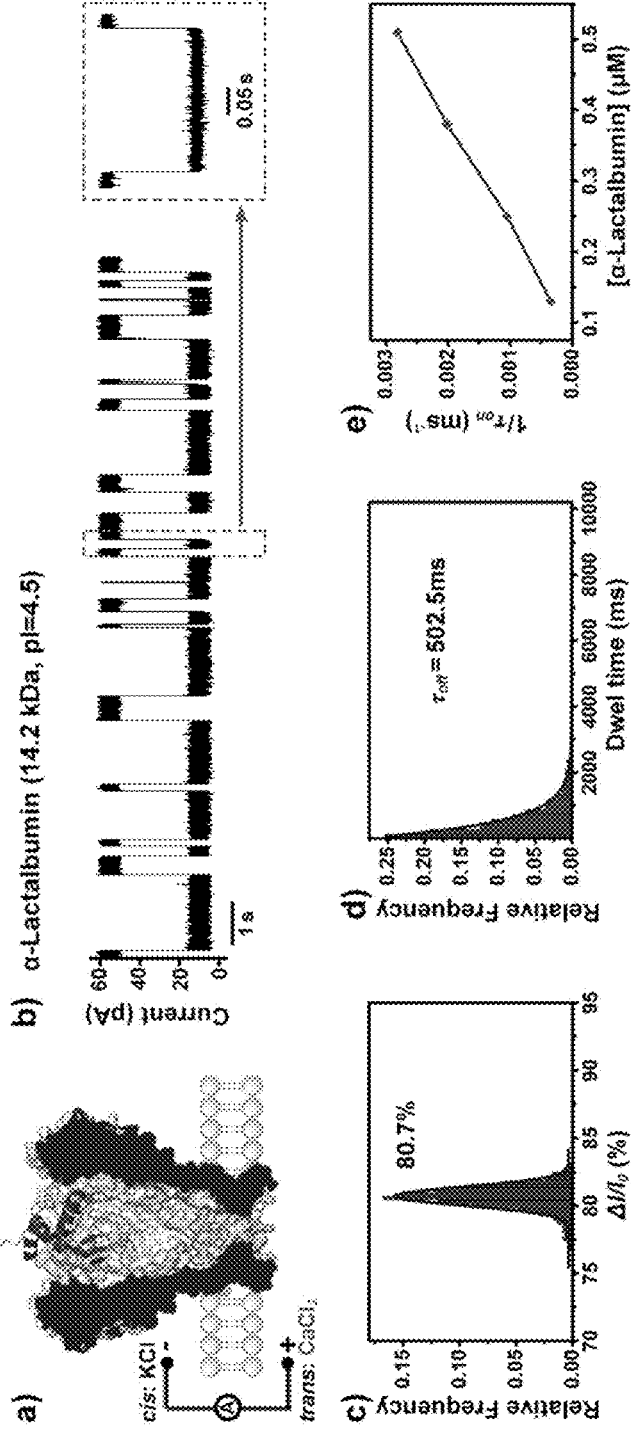

FIG. 76 shows single molecule characteristics of α-lactalbumin trapping. (a) A schematic diagram of stochastic sensing of α-lactalbumin (purple), a typical acidic protein by MspA. The docking diagram of MspA and α-lactalbumin was generated by PyMOL manually according to the structure files from protein data bank. PDB IDs: 1UUN (MspA) and 1F6S (α-lactalbumin). The buffers in cis/trans chambers were 1.5 M KCl/1 M $CaCl_2$ (pH=7.0) respectively. α-Lactalbumin was added to the cis chamber. A transmembrane potential of +20 mV was continuously applied. (b) Representative trace showing the blocking events caused by α-lactalbumin trapping. The final concentration of α-lactalbumin was 0.38 μM. Atypical event (gray dashed frame) was enlarged on the right to demonstrate event type. (c) Histograms of percentage blockage ($\Delta I/I_0$) corresponding to a 15 min continuously recorded trace as demonstrated in b. The mean value of $\Delta I/I_0$ ($\overline{\Delta I/I_0}$) was derived from the Gaussian fitting results. (d) The histogram plots of $t_{off}$ acquired from a 20 min continuously recorded trace as demonstrated in b. The histogram plots were fit with a single exponential curve, from which the mean event dwell time ($\tau_{off}$) was derived. Events with a dwell time <2 ms were ignored during the statistics. (e) Plot of the reciprocals of the mean inter-event intervals ($\tau_{on}$) for α-lactalbumin trapping events versus the final concentrations of α-lactalbumin in cis. The trapping events appeared more frequently as the final concentration of α-lactalbumin increased.

Figure 77:
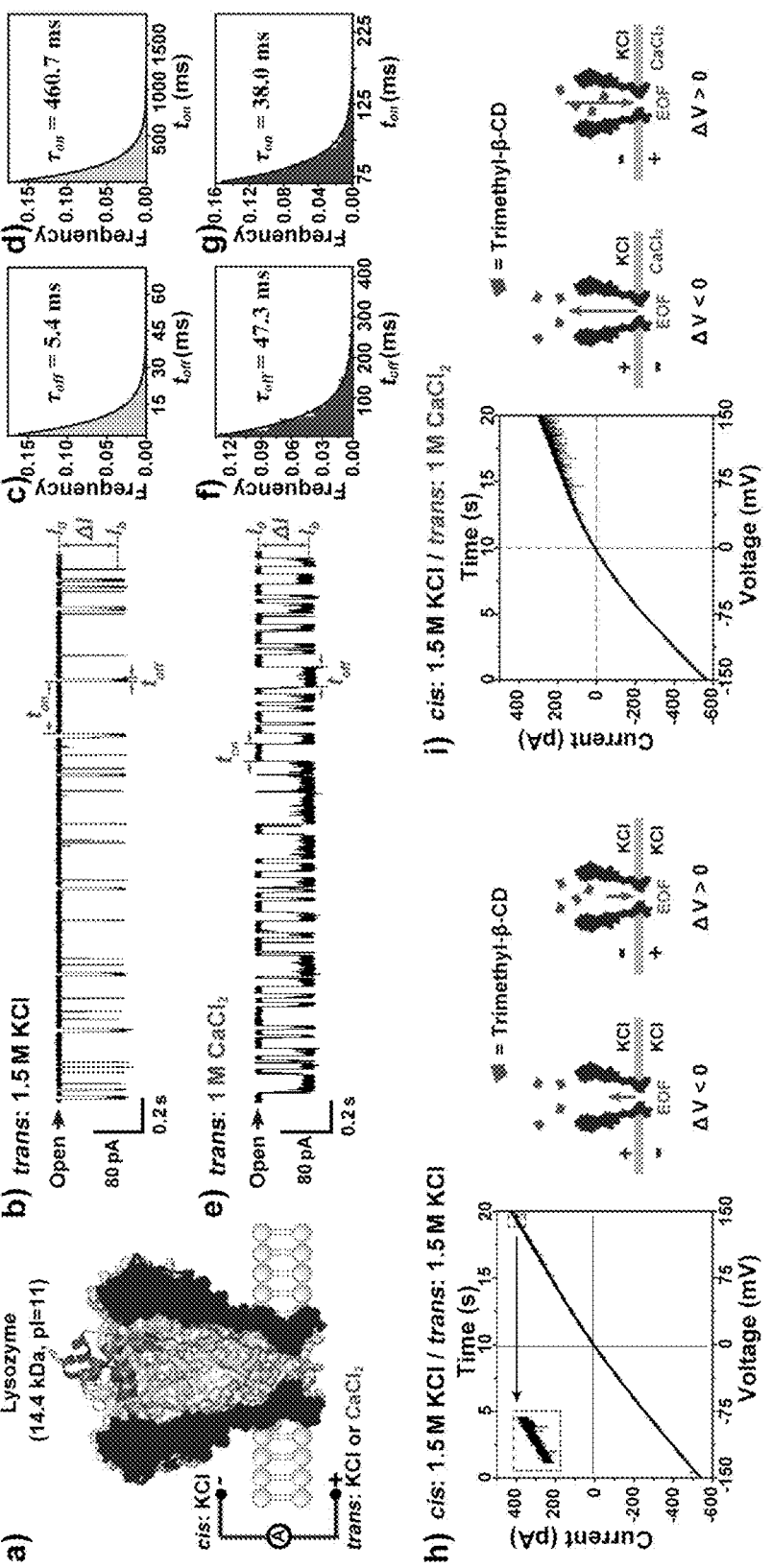

FIG. 77 shows MspA nanopore-trap in the presence of a calcium flux. (a) The schematic diagram of stochastic sensing of protein by MspA. Lysozyme was applied as a representative analyte. The diagram of MspA (black) and lysozyme (blue) was generated by PyMOL according to crystal structures from the Protein Data Bank (PDB). PDB IDs: 1UUN (MspA) and 1DPX (lysozyme). Briefly, a single MspA is inserted in the lipid membrane separating the cis and the trans chambers. The cis chamber was filled with 1.5 M KCl buffer and the trans chamber with 1.5 M KCl or a 1.0 M $CaCl_2$ buffer, pH=7.0. Lysozyme was added to cis with a final concentration of 0.42 μM. A transmembrane potential of +100 mV was applied continuously. (b) A representative trace containing nanopore events caused by lysozyme trapping. The measurement was performed with a 1.5 M KCl buffer in both cis and trans. The open pore current ($I_0$), residual current ($I_b$), dwell time ($t_{off}$) and inter-event duration ($t_{on}$) are respectively marked on the trace. $\Delta I$ is derived from $\Delta I = I_0 - I_b$. (c-d) Histograms of $t_{off}$ (c) and $t_{on}$ (d) from results acquired from a 20 min continuously recorded trace (n=503 events), as demonstrated in b. The ignored duration was set to 1 ms to preclude events caused by transient collision of the analyte with the pore. (e) A representative trace containing events of lysozyme trapping when the buffer in trans was 1.0 M $CaCl_2$. (f-g) Histograms of $t_{off}$ (f) and $t_{on}$ (g) from results acquired from a 15 min continuously recorded trace (n=2066 events) as demonstrated in (e). The mean event dwell time ($\tau_{off}$) and the mean interevent interval ($\tau_{on}$) were derived from exponential fitting results according to the equation $y=\alpha^*\exp(-x/\tau)$ respecively. $\overline{\tau_{off}}$ and $\overline{\tau_{on}}$ were derived from results of three independent measurements (N=3). All detailed fitting results were listed in Table 11. Generally, in the presence of a calcium flux, the trapping events of lysozyme appear more frequently and the event dwell time of lysozyme trapping is significantly extended. (h-i) Experimental evidence of electroosmotic flow (EOF) generation in MspA using an electrically neutral analyte. Left: the current-voltage (I-V) curve acquired with MspA with a 1.5 M KCl/1.5 M KCl buffer (h) or with a 1.5 M KCl/1.0 M $CaCl_2$ buffer (i). Trimethyl-β-CD was added to cis. The voltage was increased from −150 mV to +150 mV. The neutral analyte trimethyl-β-CD in cis could be detected when a positive potential is applied, especially in the presence of $CaCl_2$ in trans, confirming that a larger EOF is generated when an asymmetric buffer environment is applied. The capture frequency increases when the voltage is increased, which suggests that the direction of the EOF is from cis to trans at positive voltages. Right: the schematics of the measurement configuration. The direction of the EOF is marked with a green arrow.

Figure 78:
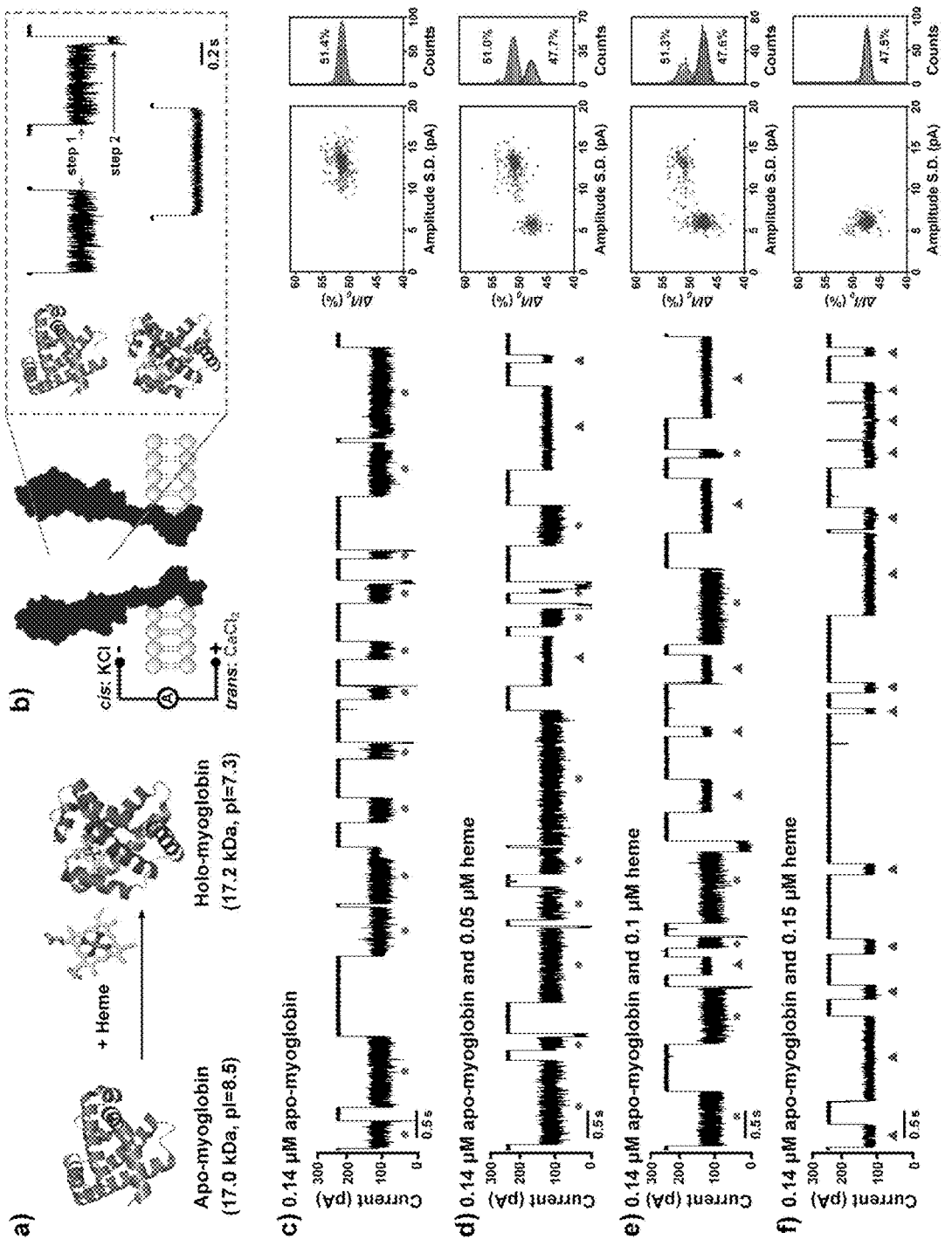

FIG. 78 shows discrimination of apo-myoglobin from holo-myoglobin with MspA nanopore trapping. (a) The schematic diagram of the structures of the heme-free myoglobin (apo-myoglobin, purple) and the heme-bound myoglobin (holo-myoglobin, red). The structure of apo-myoglobin was generated by PyMOL based on the crystal structure of holo-myoglobin (PDB ID: 1WLA). (b) The schematic diagram of apo-myoglobin (purple) or holo-myoglobin (red) trapping. Representative blocking events were demonstrated to the right of the corresponding analyte. The measurements were carried out with the buffer combination of 1.5 M KCl/1.0 M $CaCl_2$ (pH=7.0) and a continuously applied transmembrane potential of +100 mV. The green and blue arrows mark the blocking step 1 and 2 of apo-myoglobin, respectively. (c-f) Left: representative traces showing state changing of apo-myoglobin when the final concentration of heme in cis was sequentially titrated to 0 μM (c), 0.05 μM (d), 0.10 μM (e) and 0.15 μM (f), as marked on top of each trace. Right: the corresponding event scatter plots of the standard deviations of blocking current (Amplitude S.D.) versus the percentage blockage ($\Delta I/I_0$). Each scatter plot was generated from results of 20 min continuously recorded traces (n=376 (c), 382 (d), 497 (e) and 334 (f)). Corresponding histogram plots of $\Delta I/I_0$ are placed to the right of each scatter plot. Gradual changing of the event types was observed, caused by structural changes of apo-myoglobin induced by heme binding. With 0.05 μM of heme (d), events without significant level fluctuations were observed (marked by red triangles). According to the sensing results of myoglobin or heme (FIGS. 86 and 87), it can be concluded that this new type of blocking events results from trapping of holo-myoglobin. Events caused by trapping of apo-myoglobin or holo-myoglobin are highly distinguishable in the scatter plot and the histogram plots of $\Delta I/I_0$, as color marked in each plot. Further addition of heme to 0.15 µM resulted in complete conversion of event types from apo-myoglobin to holo-myoglobin (f).

Figure 79:
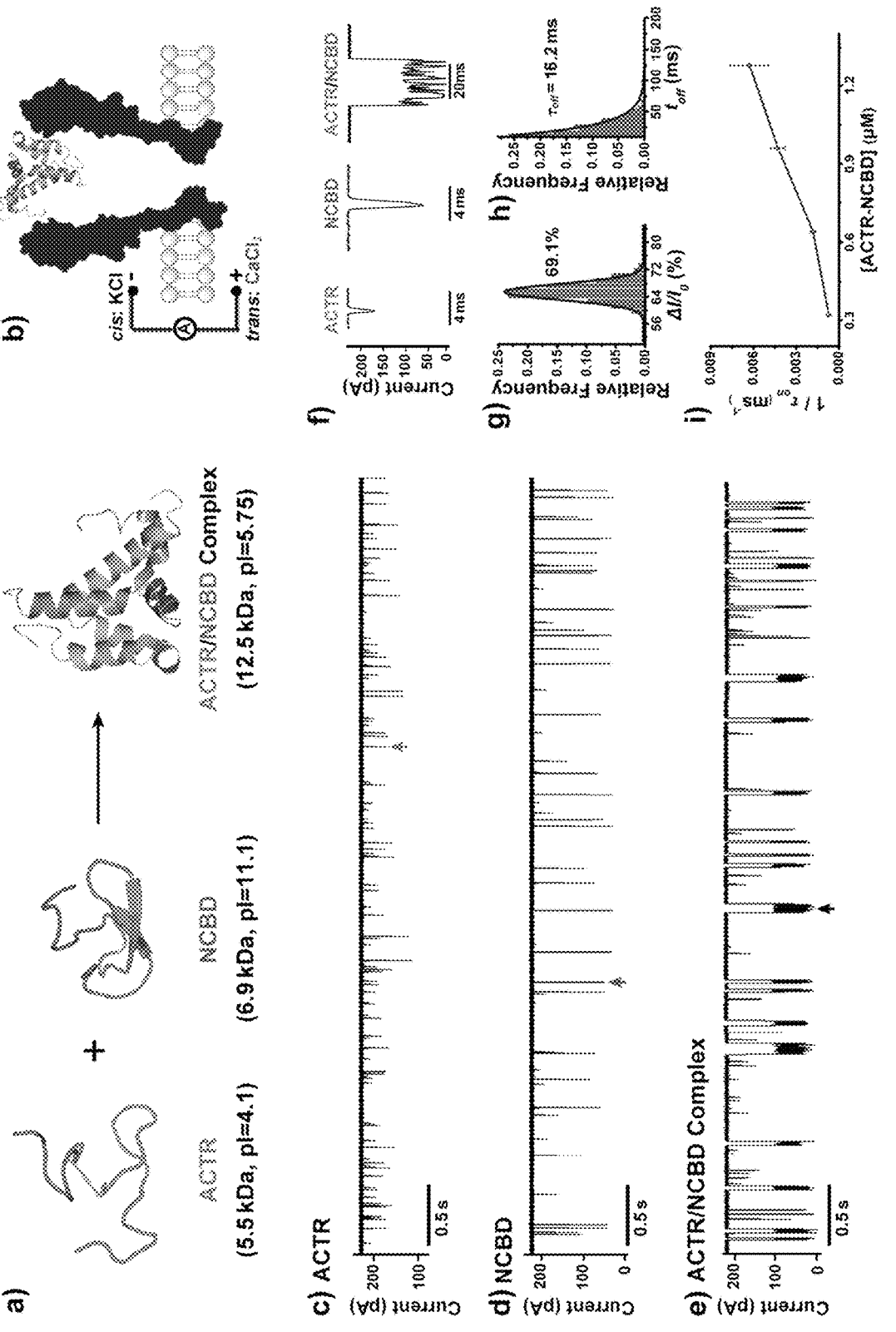

FIG. 79 shows single molecule characteristics of ACTR/NCBD complex trapping. (a) The schematic diagram of ACTR (orange), NCBD (green) and the well-folded binary complex (ACTR/NCBD complex, orange and green) formed by these two intrinsically unstructured protein domains (IUP). The structure of the fully unfolded ACTR and the molten globule state NCBD are demonstrated. The structure of ACTR/NCBD complex is from the crystal structure (PDB ID: 1KBH). (b) The schematic diagram of stochastic sensing of ACTR/NCBD complex (orange and green) by MspA trapping. The diagram of MspA and myoglobin was generated by PyMOL. The buffers in cis/trans chambers were 1.5 M KCl/1.0 M $CaCl_2$ (pH=7.0) respectively. ACTR, NCBD or the complex were added to the cis chamber and a transmembrane potential of +100 mV was applied continuously during the measurement. (c-e) Representative traces containing events caused by ACTR (c), NCBD (d) or ACTR/NCBD complex (e) trapping. Both intrinsically unstructured protein domains ACTR or NCBD could be trapped independently by MspA, resulting in short residing events. (e) When both IUPs were mixed in an equal molar ratio, a new type of event was generated, resulted from the generation of negatively charged ACTR/NCBD complex. The final concentrations of ACTR, NCBD and ACTR/NCBD were 1.28 µM during the measurements. (f) Representative events of ACTR (left), NCBD (middle) or ACTR/NCBD complex (right) trapping. The events were taken from traces in c-e, as marked by arrows on the corresponding traces. (g-h) Histograms of $\Delta I/I_0$ (g) and $t_{off}$ (h). The histogram data were derived from corresponding 30 min continuously recorded traces (n=769 events), as demonstrated in e. The mean value of $\Delta I/I_0$ ($\overline{\Delta I/I_0}$) was derived from the corresponding Gaussian fitting results. $\tau_{off}$—was derived from corresponding exponential fittings to the histogram. Events with a dwell time <1 ms were ignored in the statistics. All detailed fitting results from the independent measurements (N=3) are listed in Table 11 and Table 12. (i) Plot of the reciprocal of the $\tau_{on}$ for ACTR/NCBD complex trapping events versus the final concentration of ACTR/NCBD complex in cis. The trapping events appear more frequently as the final concentration of ACTR/NCBD complex is increased. Error bars represent standard deviations (SD) between independent measurements (N=3) and the results are listed in Table 13.

Figure 80:
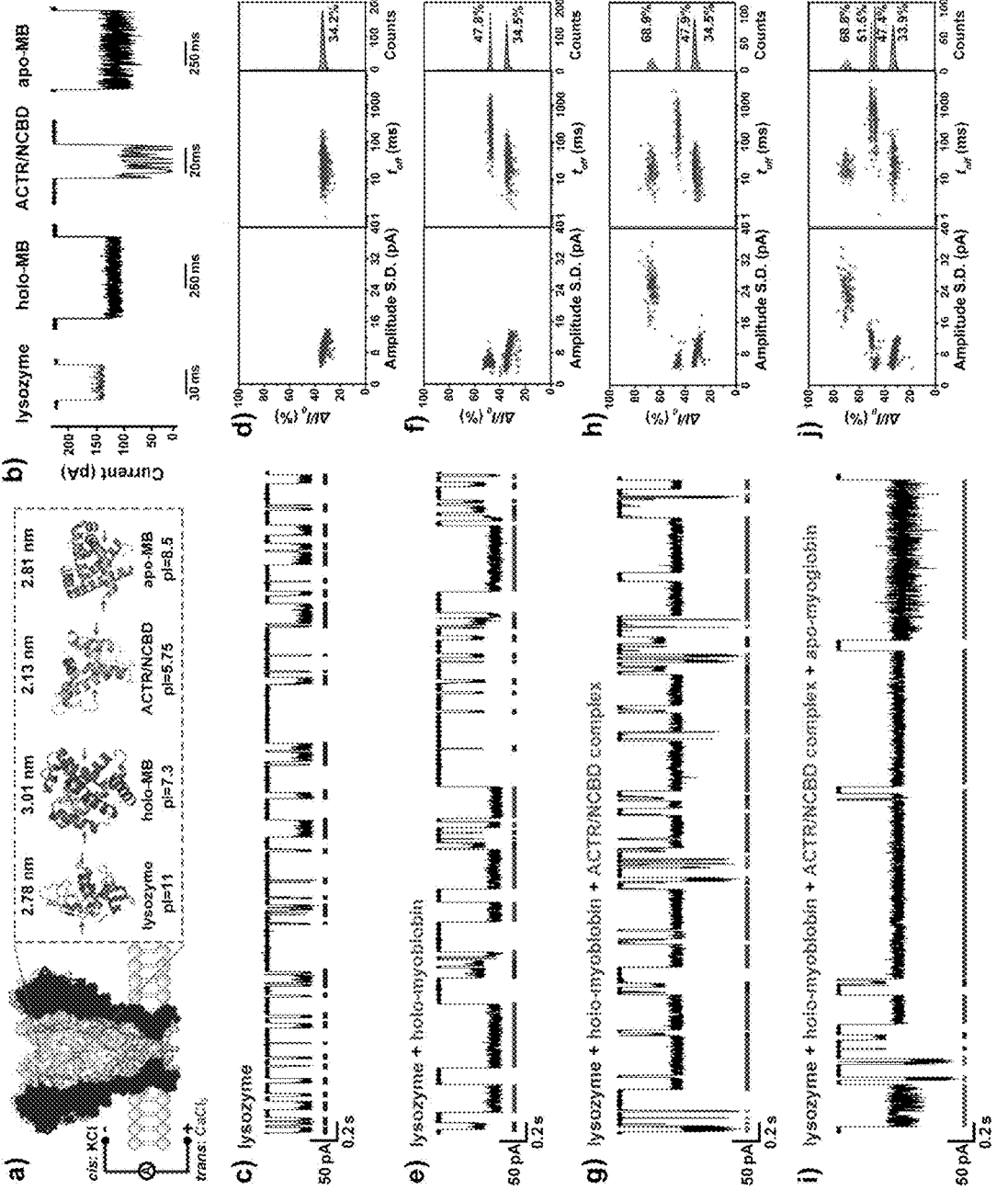

FIG. 80 shows simultaneous sensing of four protein analytes with different pI values in a mixture. The measurements were carried out with the buffer combination of 1.5 M KCl/1.0 M $CaCl_2$ (pH=7.0) and a continuously applied transmembrane potential of +100 mV. (a) The schematic diagram of the structures of four representative protein analytes with different pI values. The size of each protein type is also marked. (b) Representative events of lysozyme, holo-myoglobin, ACTR/NCBD complex or apo-myoglobin trapping. The events were taken from independent measurements as demonstrated in FIGS. 77-79. (c, e, g, i) Representative traces acquired when lysozyme, holo-myoglobin, ACTR/NCBD complex and apo-myoglobin were sequentially added to cis with a final concentration of 0.16, 0.35, 1.28 and 0.18 µM, respectively. The corresponding nanopore events were marked with blue (lysozyme), red (holo-myoglobin), green (ACTR/NCBD complex) and purple (apo-myoglobin) bars below each corresponding trace. Events from different protein analytes could be clearly distinguished from each other. (d, f, h, j) Left: A scatter plot of percentage blockage ($\Delta I/I_0$) versus event dwell time ($t_{off}$) generated by events from a 30 min continuously recorded trace for each condition (d, n=511; f, n=575; h, n=573; j, n=542), respectively corresponding to that of c, e, g, i. Center: scatter plots of the percentage blockage ($\Delta I/I_0$) versus the standard deviation of blocking current (Amplitude S.D.). Right: the corresponding histogram of $\Delta I/I_0$ of the trapping events of lysozyme (blue, 34.2% in d), 34.5% in f), 34.5% in h), 33.9% in j)), holo-myoglobin (red, 47.8% in f), 47.9% in h), 47.4% in j)), ACTR/NCBD complex (green, 68.9% in h), 68.8% in j)) and apo-myoglobin (purple, 51.5% in j)). The mean value of $\Delta I/I_0$ ($\overline{\Delta I/I_0}$) in d, f, h, j, as marked on each fitted peak, was derived from the corresponding Gaussian fitting results.

Figure 81:
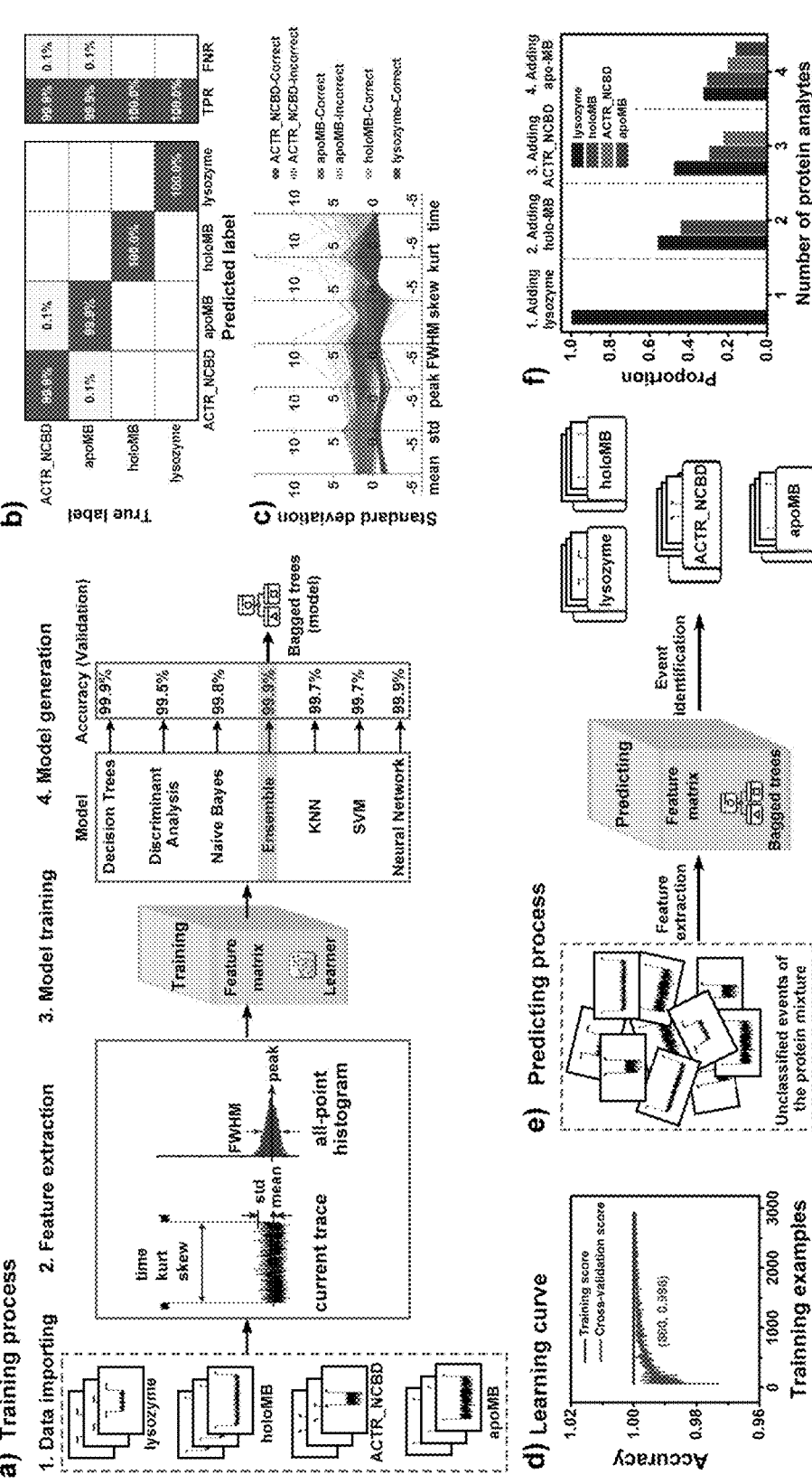

FIG. 81 shows machine learning assisted simultaneous structural profiling of proteins. (a) The flow diagram of the training process. The blocking events of lysozyme (n=785), holo-myoglobin (holoMB, n=763), ACTR/NCBD complex (ACTR_NABD, n=673) and apo-myoglobin (apoMB, n=701) were collected to form the training dataset. Seven event features were extracted from the current blockades to form a feature matrix. The Classification Learner toolbox of MATLAB was used to train models of supervised machine learning for classification. A set of classifiers including decision trees, discriminant analysis, support vector machines (SVM), K nearest neighbors (KNN), naive Bayes, ensemble, and neural network classifiers were evaluated. The validation accuracies were evaluated by 10-fold cross-validation. The bagged trees model is one of the optimum models. (b) The confusion matrix plot of protein classification using a trained bagged trees model. True positive rate (TPR) and false negative rate (FNR) were also demonstrated to the right. (c) The parallel coordinate plots. The correctly classified points were marked as solid lines while the misclassified points were marked as dashed lines. All features play a role in event classification. (d) The learning curve with varying sample sizes of the training dataset. When the samples in the training dataset exceed 860, the accuracy of validation reaches 0.998, the validation accuracy and the training set resubstitution accuracy were hardly changed. The learning curve shows the mean accuracy of four independent tests. (e) The flow diagram of the predicting process. The unclassified blocking events were extracted from raw current traces when different protein analytes were measured in a mixture. The trained bagged trees model was applied to perform predictions. (f) The proportion of different protein events determined with the bagged trees model. All events were acquired similarly to that described in FIG. 80. Each time a new protein analyte was added, the prediction results would report the appearance of the corresponding protein type.

Figure 82:
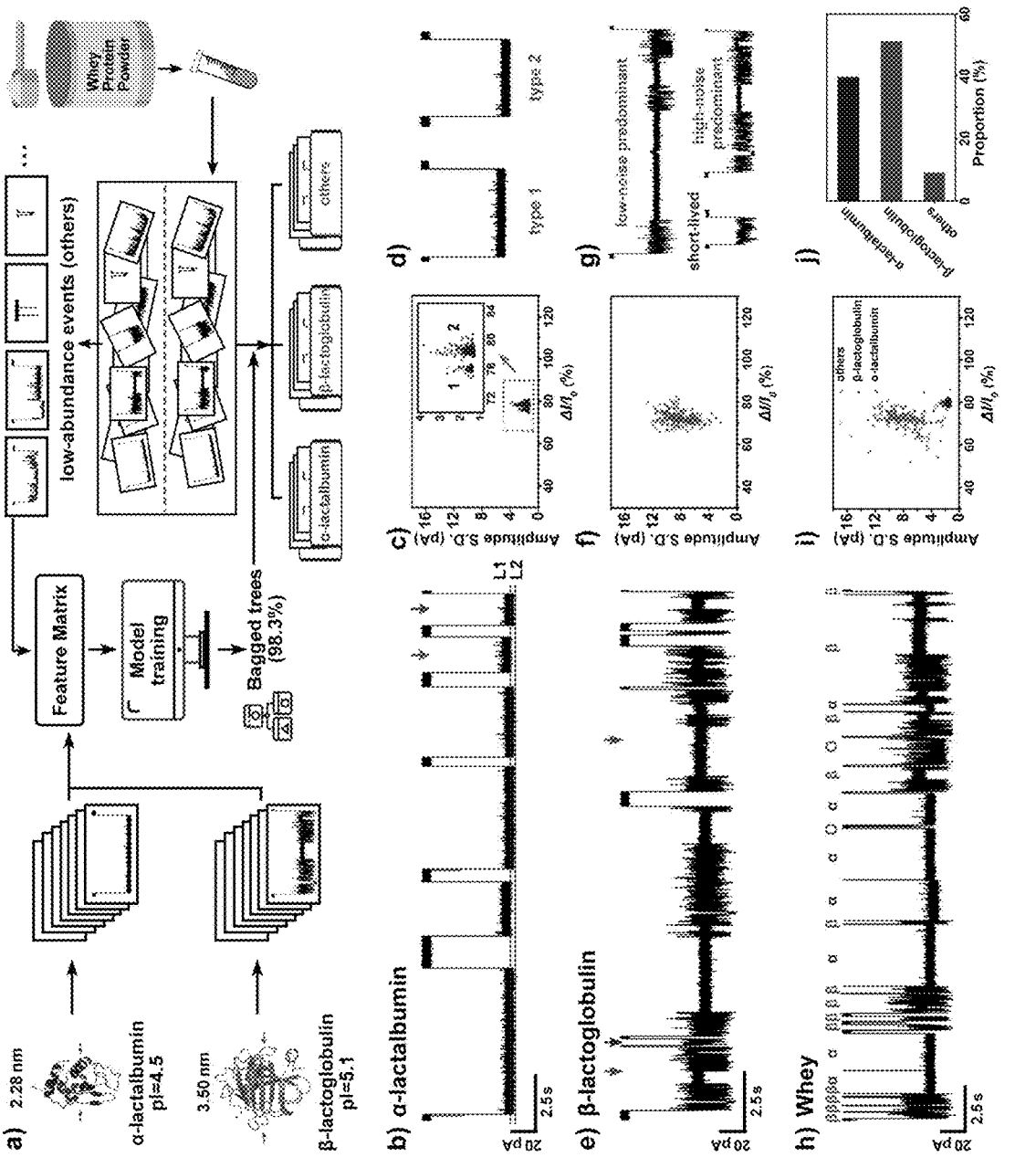

FIG. 82 shows machine learning assists the identification of α-lactalbumin and β-lactoglobulin in commercial whey protein powder. (a) The flow diagram of the training and predicting process. Whey protein powder was formulated into a solution and was added to cis with a final concentration of 25 µg/ml. 1000 nanopore events were collected, from which 109 events were recognized as "others" as they were abnormal nanopore events from low content ingredients. The blocking events of α-lactalbumin standards (PDB ID: 1F6S, n=301 events), β-lactoglobulin standards (PDB ID:

3BLG, n=253 events) and "others" events (n=109 events) were collected respectively as the training dataset. The bagging tree model in Classification Learner toolbox of MATLAB has the highest verification accuracy (98.3%) and the lowest cost (11) which was used for the identification of α-lactalbumin and β-lactoglobulin blocking events in predicting sample. Parameter settings and predicted results of other models were listed in FIG. 100. (b-d) Representative traces acquired when α-lactalbumin was added to cis with a final concentration of 0.21 μM (b) and the corresponding scatter plot of percentage blockage ($\Delta I/I_0$) vs. the standard deviation of blocking current (Amplitude S.D.) generated by events from a 40 min continuously recorded trace (c, n=644). The two types representative blocking events of α-lactalbumin as marked by brown and purple arrows in b were zoomed in demonstrated in d. (e-g) Representative traces acquired when β-lactoglobulin was in cis with a final concentration of 0.21 μM (e) and the corresponding scatter plot of percentage blockage ($\Delta I/I_0$) vs. the standard deviation of blocking current (Amplitude S.D.) generated by events from a 30 min continuously recorded trace (f, n=253). The two types representative blocking events of β-lacto-globulin as marked by red, pink and wine arrows in e were zoomed in demonstrated in g. (h) Representative traces of whey protein. (i-j) The scatter plot (i) and proportion (j) of whey protein translocation events (blue: α-lactalbumin. red: β-lactoglobulin. green: others, n=333) determined with the bagged trees model. 51.4% of all acquired events were recognized as β-lactoglobulin events and 39.6% were recognized as α-lactalbumin events.

Figure 83:
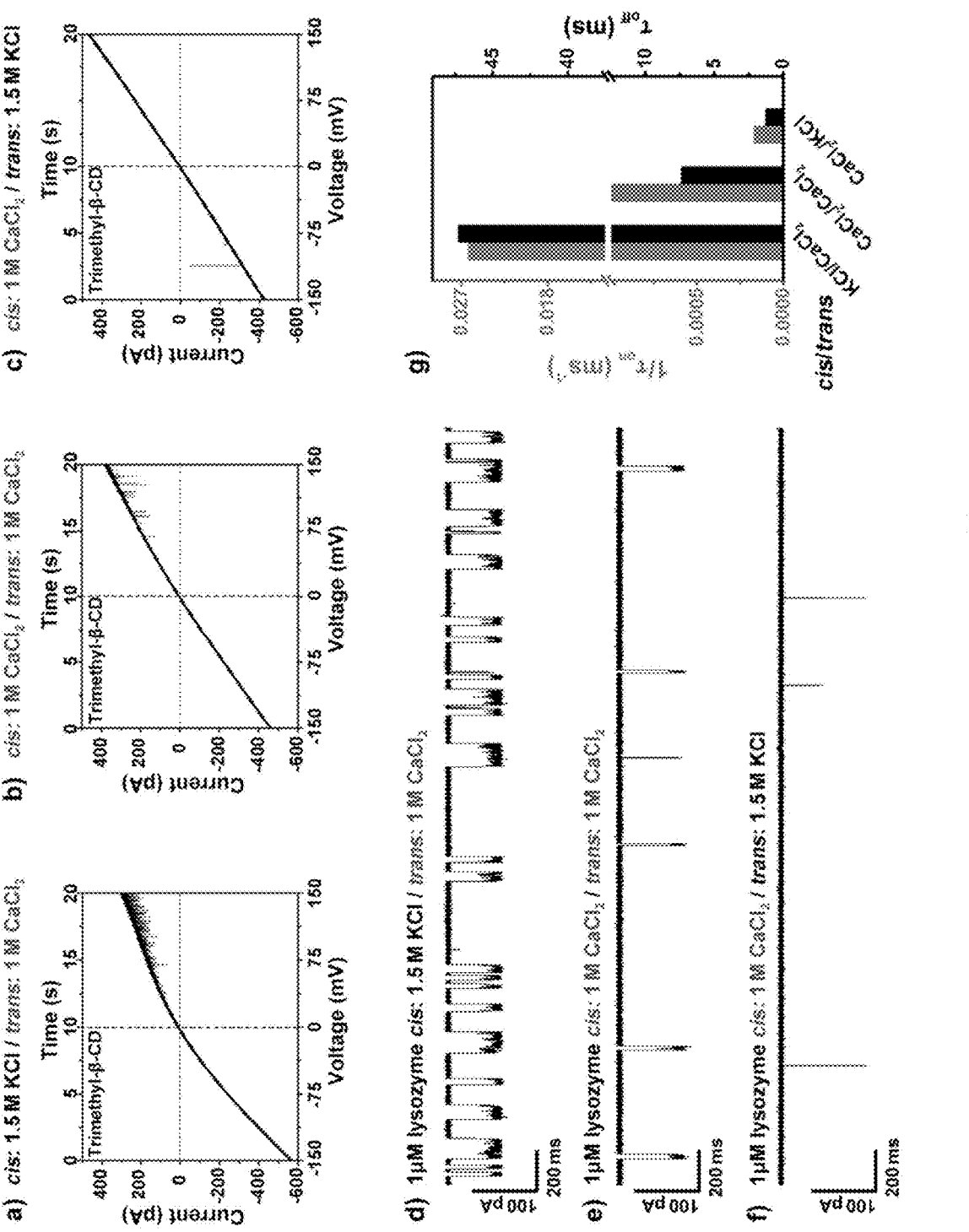

FIG. 83 shows EOF in MspA with varied buffer combinations. (a-c) comparison of the current-voltage (I-V) curve acquired with MspA when the buffer combination in cis/trans chambers was 1.5 M KCl/1.0 M CaCl₂ (a), 1.0 M CaCl₂/1.0 M CaCl₂ (b) or 1.5 M KCl/1.0 M CaCl₂ (c). Trimethyl-β-CD was added to cis as an electrically neutral analyte to reflect the direction and strength of EOF. When $\Delta V > 0$, trimethyl-β-CD could be captured by MspA in the measuring environment of KCl/CaCl₂ or CaCl₂/CaCl₂ buffer combination. The best capture efficiency was observed with the buffer combination of KCl/CaCl₂. (d-f) Representative traces of lysozyme sensing performed with a buffer combination of 1.5 M KCl/1.0 M CaCl₂ (d), 1.0 M CaCl₂/1.0 M CaCl₂ (e) or 1.5 M KCl/1.0 M CaCl₂ (f). Lysozyme was added to cis with a final concentration of 0.42 μM. A transmembrane potential of +100 mV was continually applied. Clearly, the buffer combination of 1.5 M KCl/1.0 M CaCl₂) demonstrates the highest rate of event appearance. (g) $I/\tau_{on}$ and $\tau_{off}$ of lysozyme trapping events acquired with different electrolyte combinations. With the buffer combination of 1.5 M KCl/1.0 M CaCl₂, the best capture efficiency and the most sufficient blocking duration were observed for lysozyme.

Figure 84:
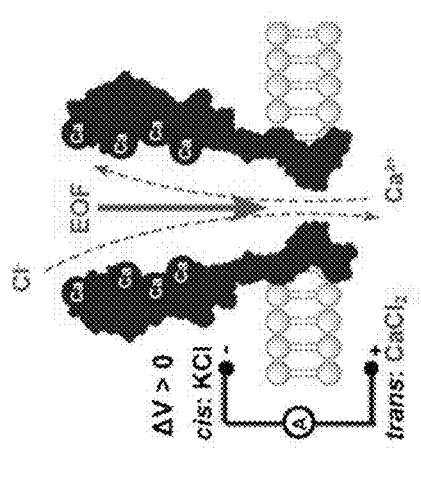
Figure 84:
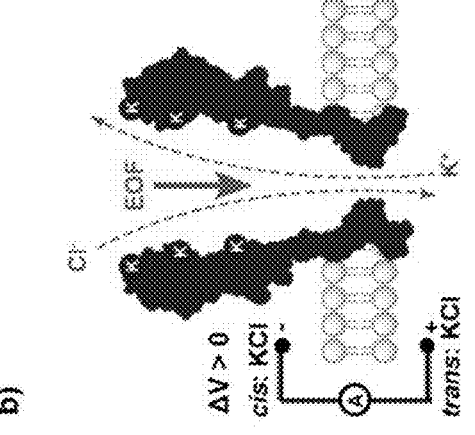
Figure 84:
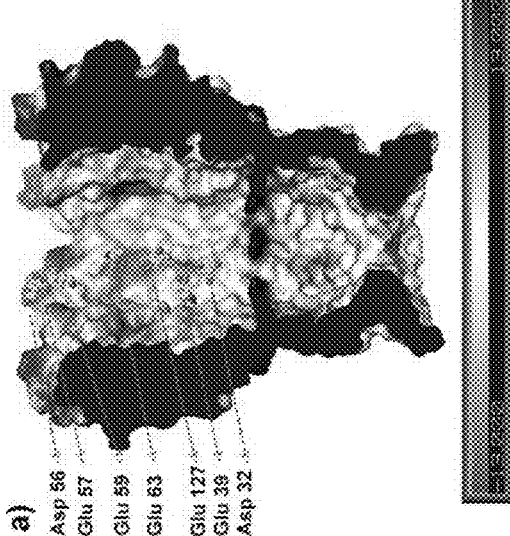

FIG. 84 shows EOF enhancement in MspA lumen. (a) The charge distribution within the pore lumen of an octameric M2 MspA. The structure of the M2 MspA nanopore was adapted from the Protein Data Bank (PDB) (1UUN) by the mutation module of PyMOL software (R96A, D93N, D91N, D90N, D118R, D134R and E139K). The vacuum electrostatics of M2 MspA were generated by the APBS module of PyMOL. The structure of MspA is presented in the surface mode and colored according to the calculated vacuum electrostatics results (red for negative regions and blue for positive regions). The typical acidic amino acids (D32, E39, D56, E57, E59, E63, E127) in the lumen which have potential electrostatic interactions with cations of testing buffer were displayed in the sphere-and-stick mode. (b)

Schematics of positive charge accumulation and EOF enhancement of MspA. Left: the schematic diagram of the measurement configuration in a 1.5 M KCl/1.5 M KCl buffer combination when a positive potential is applied. Right: schematic diagram of the measurement configuration in a 1.5 M KCl/1.0 M CaCl₂ buffer combination when a positive potential is applied. The direction of EOF was marked by a green arrow and the length of the arrow qualitatively represents the relative strength of EOF. With the buffer combination of 1.5 M KCl/1 M CaCl₂, strong coordination interactions between divalent cation ions and MspA leads to enriched positive charges on the inner surface of the pore lumen, which further enhances the EOF.

Figure 85:
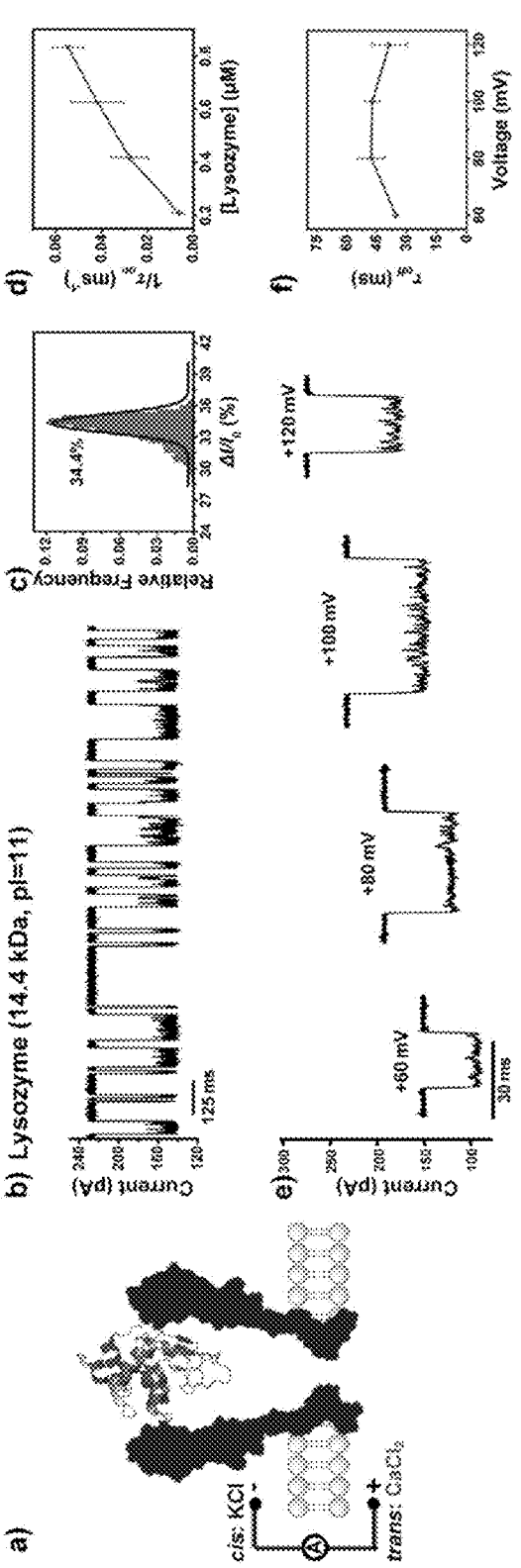

FIG. 85 shows single molecule characteristics of lysozyme trapping. All measurements were carried out as described in Example 8 Methods 1. The buffers in cis/trans chambers are 1.5 M KCl/1.0 M CaCl₂ (pH=7.0) respectively. A transmembrane potential of +100 mV is continuously applied. (a) The schematic diagram of stochastic sensing of lysozyme (blue), a typical basic protein. The diagram was generated by PyMOL according to the PDB files. PDB IDs: 1UUN (MspA) and 1DPX (lysozyme). Lysozyme is added to the cis chamber. (b) A representative trace containing nanopore events caused by lysozyme trapping. The final concentration of lysozyme is 0.42 μM. (c) The histogram of percentage blockage ($\Delta I/I_0$) corresponding to a 15 min continuously recorded trace as demonstrated in b. The mean value of $\Delta I/I_0$ ($\overline{\Delta I/I_0}$) is derived from the Gaussian fitting results. (d) The plot of the reciprocals of the mean inter-event intervals ($1/\tau_{on}$) for lysozyme trapping events versus the final concentrations of lysozyme in cis. The trapping events appear more frequently as the final concentration of lysozyme is increased. (e) Representative trapping events of lysozyme when measured with an applied voltage of +60 mV, +80 mV, +100 mV or +120 mV. (f) The plot of $\tau_{off}$ versus the applied voltage corresponding to the trapping events in (e). Error bars in d and f represent standard deviations between independent measurements (N=3). Detailed results are listed in Table 14. At a varying applied voltage, the mean event dwell time is first extended and then shortened as the voltage is continuously increased. This phenomenon might result from a competition between the electrophoretic force (EPF) and the electroosmotic flow (EOF) on the positive charged lysozyme (pI=11).

Figure 86:
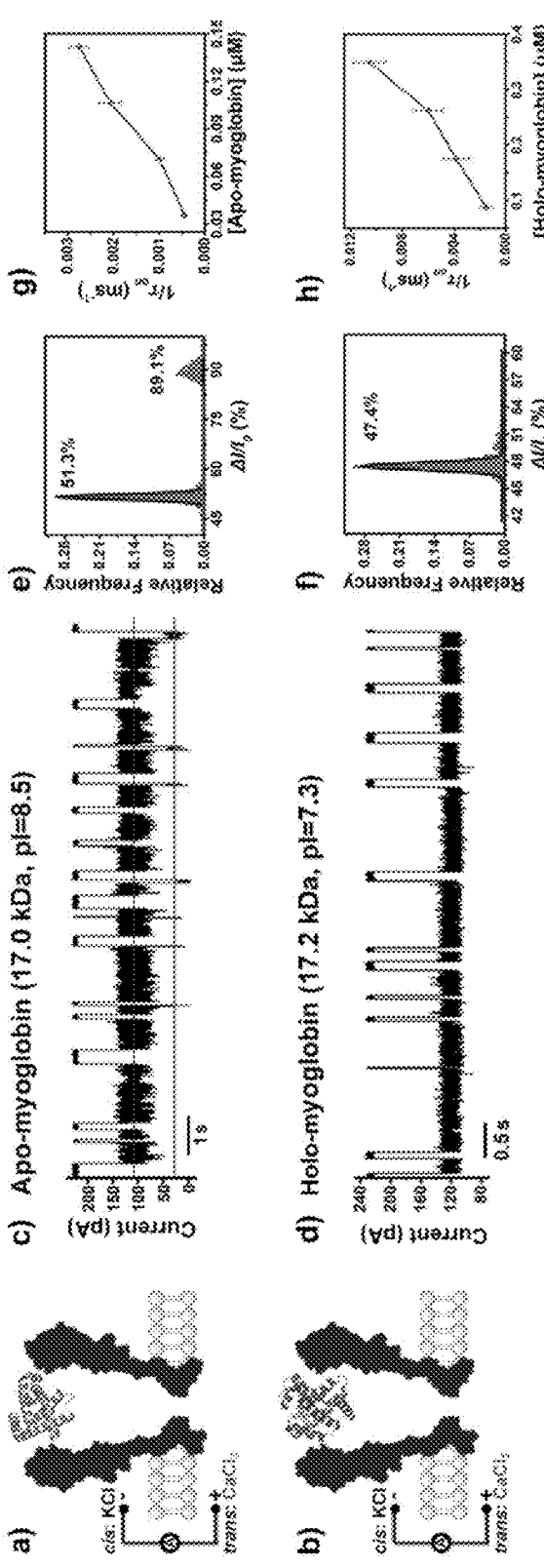

FIG. 86 shows single molecule characteristics of apo-myoglobin or holo-myoglobin trapping. All measurements were carried out as described in Example 8 Methods 1. The buffers in cis/trans chambers are 1.5 M KCl/1.0 M CaCl₂ (pH=7.0). A transmembrane potential of +100 mV was continuously applied. (a, b) Schematic diagrams of stochastic sensing of apo-myoglobin (a, purple) and holo-myoglobin (b, red), two neutrally charged proteins. The structural diagram of MspA and myoglobin was generated by PyMOL according to the PDB files. PDB IDs: 1UUN (MspA) and 1WLA (holo-myoglobin and apo-myoglobin). The holo-myoglobin was measured with an identical condition as described in FIG. 2*d-f.* Holo-myoglobin or apo-myoglobin was added to the cis chamber. (c, d) Representative traces containing nanopore events caused by apo-myoglobin (c) or holo-myoglobin (d) trapping. The final concentrations of holo-myoglobin and apo-myoglobin are 0.26 μM and 0.14 μM, respectively. The blue and green lines on top of the trace respectively mark two residual current levels, corresponding to two blocking steps. Step 2 (green line) may be related to a stretched state of apo-myoglobin so that deeper position of the pore is reached. The feature of step1 (blue line) was regarded as the identification feature of apo-myoglobin for all subsequent analysis. (e, f) Histograms of percentage blockage ($\Delta I/I_0$) corresponding to a 20 min continuously recorded trace as demonstrated in c and d. The mean value of $\Delta I/I_0$ ($\overline{\Delta I/I_0}$) is derived from the Gaussian fitting results of three independent measurements (N=3). For apo-myoglobin, the values are 51.3±0.2% and 89.1±0.3%; for holo-myoglobin, the value is 47.4±0.2%. All fitting results were detailed in Table 12. (g, h) Plot of the reciprocals of the mean inter-event intervals ($1/\tau_{on}$) for apo-myoglobin (g) or holo-myoglobin (h) events versus the final concentrations of the analytes in cis. Error bars in g and h represent standard deviations between independent measurements (N=3). Relevant results are detailed in Table 13. Generally, the trapping events appear more frequently as the final concentration of protein analytes is increased.

Figure 87:
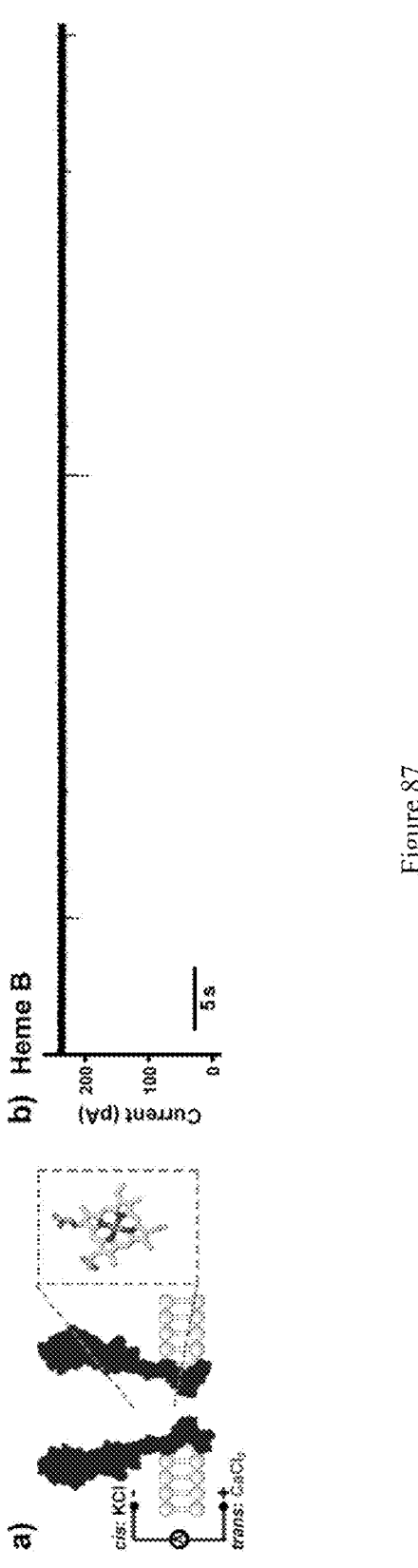

FIG. 87 shows measurement with Heme as the sole analyte. (a) The schematic diagram of the measurement configuration. The measurement was carried out as described in Example 8 Methods 1. The buffers in cis/trans chambers are 1.5 M KCl/1.0 M CaCl$_2$) (pH=7.0) respectively. A transmembrane potential of +100 mV was continuously applied. Heme is shown in the dashed box. (b) A representative trace when heme was added to cis with a final concentration of 0.2 μM. No nanopore events were observed, confirming that Heme alone would not produce any events.

Figure 88:
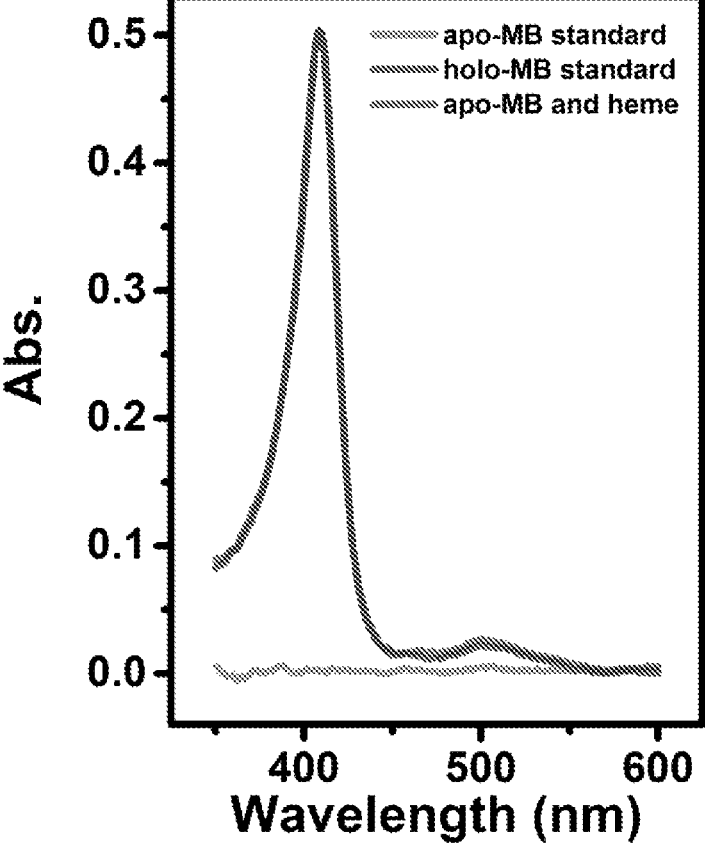

FIG. 88 shows the UV-Vis absorption spectrum of apo-myoglobin-heme complex (blue), apo-myoglobin (orange) and holo-myoglobin standards (red). The protein concentration in all groups was set at 6 μM. Apo-myoglobin/heme complex was obtained by pre-mixing apo-myoglobin and heme in a molar ratio of 14:15 (unified with electrophysiological experiments in FIG. 79) for 10 minutes and then purified using a 3 kDa cut-off ultrafiltration tube. All solution spectrums were recorded in a 1.5 M KCl buffer (1.5 M KCl, 10 mM HEPES, pH 7.0) at room temperature. Compared with apo-myoglobin, the absorption at 410 nm of apo-MB/heme is significantly higher, which confirms the production of holo-myoglobin. At the same concentration, the absorbance of the apo-myoglobin-heme complex and the holo-myoglobin standard is the same, which confirms that apo-myoglobin and holo-myoglobin have an efficient conversion, close to 100%.

Figure 89:
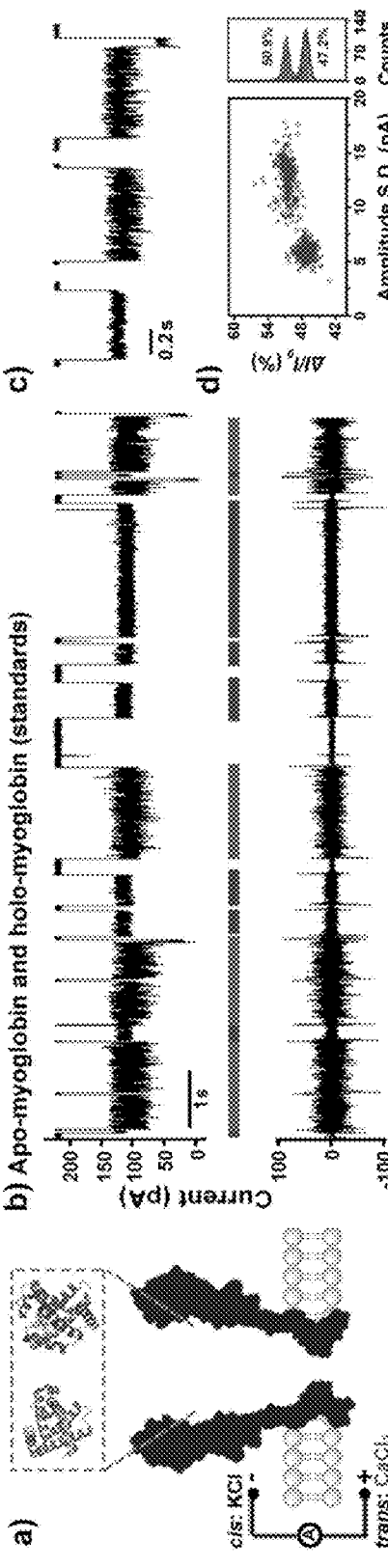

FIG. 89 shows simultaneous sensing of apo-myoglobin and holo-myoglobin with MspA. All measurements were carried out as described in Example 8 Methods 1. The measurements were carried out in the buffers of 1.5 M KCl/1.0 M CaCl$_2$ (pH=7.0) when a transmembrane potential of +100 mV was continuously applied. (a) The schematic diagram of MspA trapping of apo-myoglobin (purple) or holo-myoglobin (red). (b) Simultaneous sensing of apo-myoglobin and holo-myoglobin. The final concentrations for each analyte are 0.18 μM and 0.35 μM, respectively. Top: a representative trace during simultaneous sensing of apo-myoglobin or holo-myoglobin. Bottom: the corresponding trace when digitally filtered with a 50 Hz high-pass Bessel filter (8-pole). Events of holo-myoglobin and apo-myoglobin could be clearly distinguished from each other according to a remarkable difference of high frequency fluctuations, which are marked with red and purple bars, respectively. (c) A zoomed-in view of three representative events of holo-myoglobin (left) and apo-myoglobin (middle and right), as also demonstrated in b. The event placed to the right is a representative 2 step event as demonstrated in FIG. 78b. (d) A scatter plot of standard deviations of the blocking current (Amplitude S.D.) versus the percentage blockage ($\Delta I/I_0$) generated from events from a 20 min continuously recorded trace as demonstrated in b (n=857). The corresponding histogram plots of $\Delta I/I_0$ are placed to the top and to the right margin of the scatter plot (50.9% for apo-myoglobin, 47.5% for holo-myoglobin).

Figure 90:
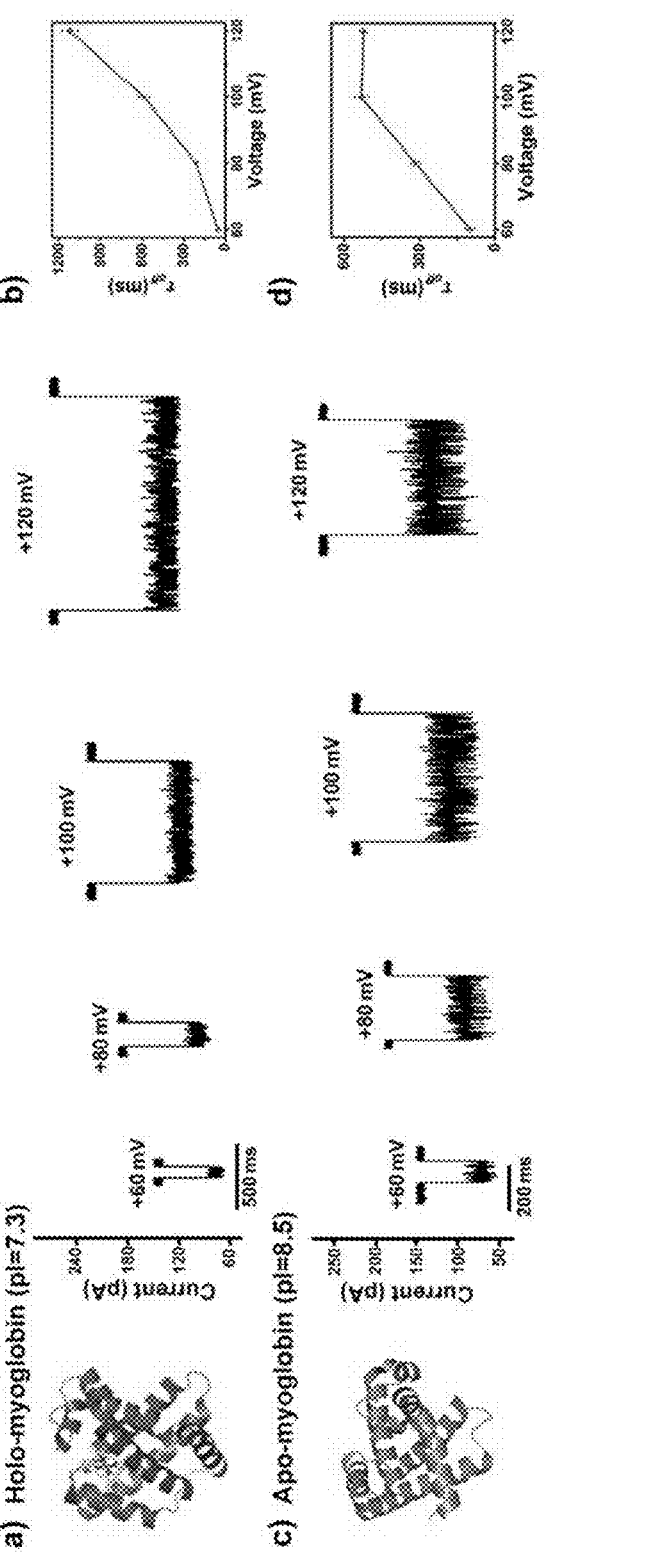

FIG. 90 shows trapping holo-myoglobin or apo-myoglobin at different voltages. All measurements were carried out as described in Example 8 Methods 1 with a buffer combination of 1.5 M KCl (cis)/1.0 M CaCl$_2$ (trans), pH=7.0. Holo-myoglobin or apo-myoglobin was added to the cis chamber. (a) Left: The schematic diagram of the structure of holo-myoglobin (PDB ID: 1WLA). Right: representative trapping events of holo-myoglobin when measured with an applied voltage of +60 mV, +80 mV, +100 mV or +120 mV. The final concentration of holo-myoglobin is 0.26 μM. (b) The plot of $\tau_{off}$ versus the applied voltage. Error bars in b represent standard deviations between independent measurements (N=3). The results are also detailed in Table 14. Generally, the event dwell time is extended at a higher applied potential, indicating that as the voltage increases, the combined effect of EPF and EOF for holo-myoglobin increases in the test solution (pH=7). (c) Left: The schematic diagram of the structure of apo-myoglobin (PDB ID: 1WLA with the removal of heme). Right: representative trapping events of apo-myoglobin when measured with an applied voltage of +60, +80, +100 or +120 mV. The final concentration of apo-myoglobin was 0.14 μM. (d) The plot of $\tau_{off}$ versus the applied voltage. Error bars in d represent standard deviations derived from three independent measurements (N=3). Detailed results are listed in Table 14. The duration of the blocking event is first extended and then shortened as the voltage increases. The competition between the electrophoretic force (EPF) and the electroosmotic flow (EOF) on the relatively positively charged apo-myoglobin (pI=8.5) may change as the applied voltage is increased from +100 mV to 120 mV A similar phenomenon of $\tau_{off}$ versus the applied voltage was observed with Lysozyme (pI=11) (FIG. 85).

Figure 91:
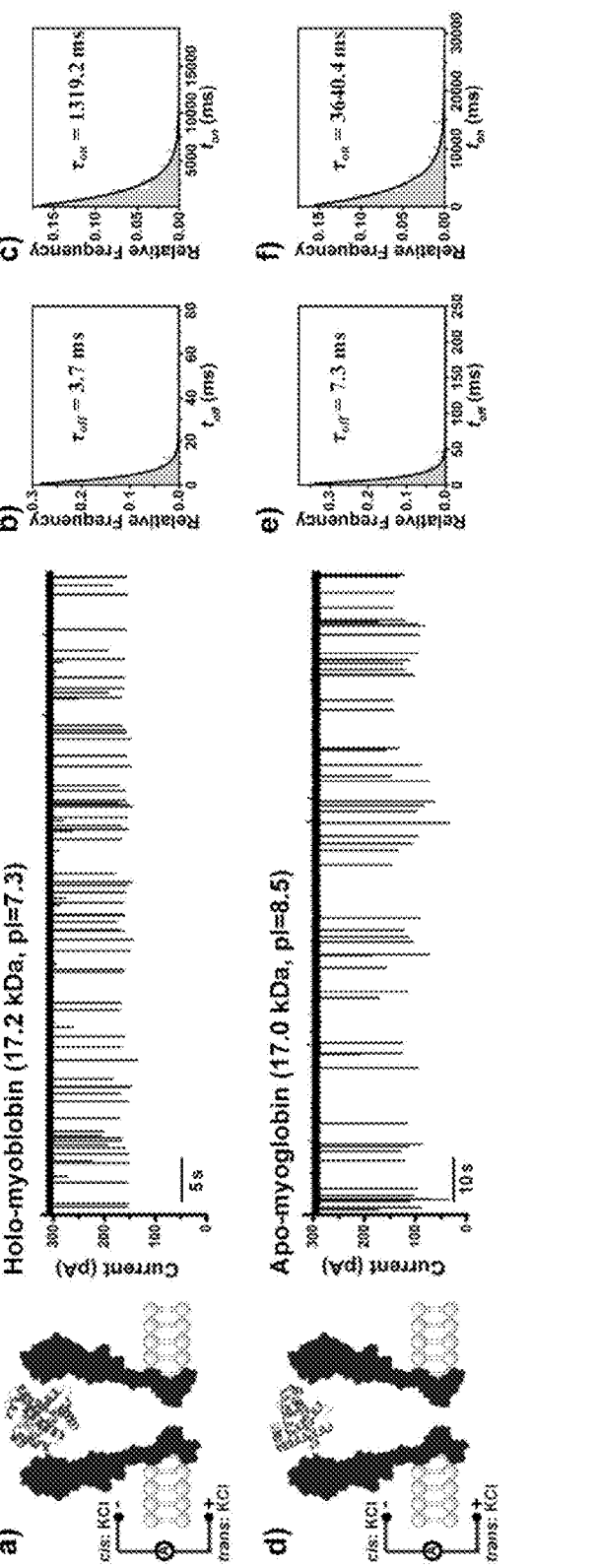

FIG. 91 shows trapping of holo- or apo-myoglobin in a symmetrical KCl buffer. All measurements were carried out as described in Example Methods 1. Specifically, both the cis and the trans chamber were filled with a 1.5 M KCl buffer, pH=7.0. The protein analytes were respectively added to cis. A transmembrane potential of +100 mV was continuously applied. (a) Left: The schematic diagram of stochastic sensing of holo-myoglobin by MspA. PDB IDs: 1UUN (MspA) and 1WLA (holo-myoglobin). Right: A representative trace containing events caused by holo-myoglobin trapping. The final concentration of holo-myoglobin was 0.26 μM. (b-c) Histograms of $t_{off}$ (b) and $t_{on}$ (c). Results of $t_{off}$ and $t_{on}$ were respectively derived from a 20 min continuously recorded trace as demonstrated in a. (d) Left: the schematic diagram of stochastic sensing of apo-myoglobin by MspA. PDB IDs: 1UUN (MspA) and 1WLA (apo-myoglobin, with the removal of heme). Right: a representative trace containing events caused by apo-myoglobin trapping. The final concentration of apo-myoglobin was 0.14 μM. (e-f) Histograms of $t_{off}$ (e) and $t_{on}$ (f). Results of $t_{off}$ and $t_{on}$ were respectively derived from a 30 min continuously recorded trace as demonstrated in d. Events with a dwell time of <1 ms were ignored during the statistics in b, c, e and f. The mean event dwell time ($\tau_{off}$) and the mean interevent interval ($\tau_{on}$) were all derived from exponential fitting results according to the equation $y=a*\exp(-x/\tau)$, $\overline{\tau_{off}}$ and $\overline{\tau_{on}}$ were derived from three independent measurements (N=3). Detailed fitting results are listed in Table 11. Compared with corresponding results acquired in an asymmetric electrolyte testing environment, the capture efficiencies of protein analytes were significantly reduced and the event dwell times were significantly shortened. This further proves that the combination of monovalent and divalent ions has improved the performance of MspA nanopore trapping.

Figure 92:
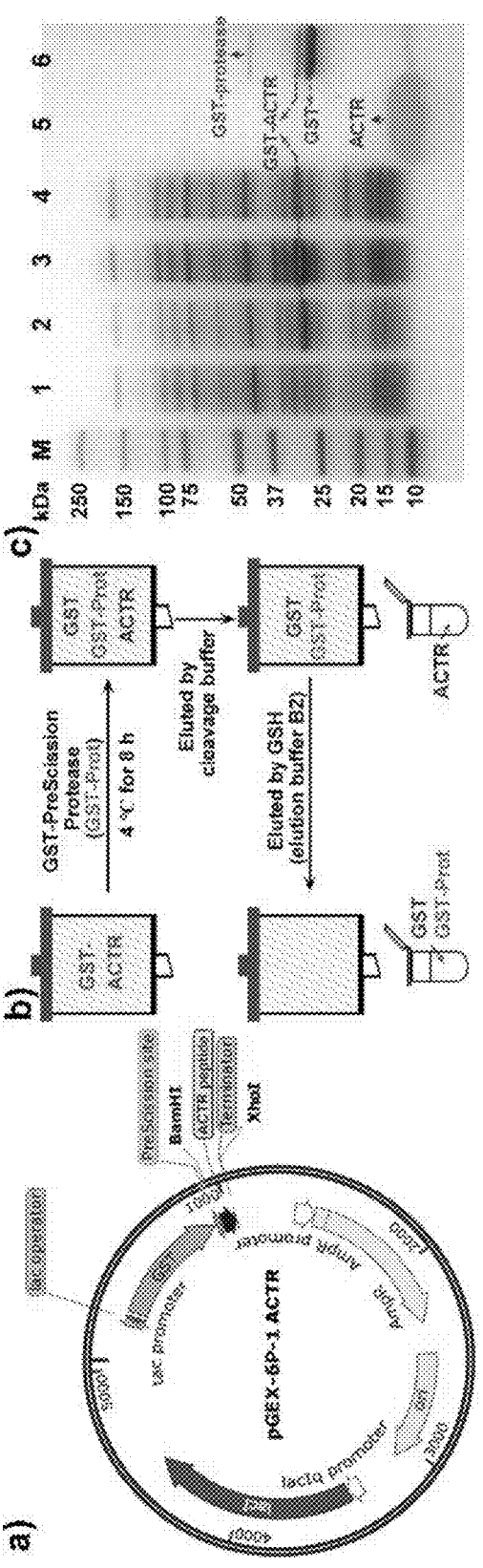

FIG. 92 shows preparation of the ACTR peptide. The preparation of ACTR peptide is detailed in Example 8 Methods 3. (a) The construction of the plasmid coding for the GST-ACTR fusion protein. The gene coding for the fusion protein was cloned into a pGEX-6P-1 plasmid. The gene coding for the ACTR peptide (with a terminator at the end of the sequence, blue) was inserted between the recognition sequence of BamH I and Xho I, immediately after the PreScission site (pink). The PreScission site of the expressed protein is cleavable when treated by corresponding protease. (b) The schematic diagram of ACTR separation. The expressed fusion protein GST-ACTR was first applied to a GSTrap™ column. The column was further applied with the PreScission Protease (GST-Prot) which also has a GST-tag on its N-terminal. After 8 h of incubation at 4° C., the ACTR was completely separated from the GST-ACTR fusion protein and was eluted by the cleavage buffer and collected. The GST moiety and the PreScission Protease however remained on the column. Regeneration of the column was performed by elution with the glutathione (GSH) containing solution (elution buffer B2). The eluted GST and GST-Prot were discarded. (c) Gel electrophoresis results. Lane M: precision plus protein standards; Lane 1-2: The bacterial lysates containing GST-ACTR plasmid without or with IPTG induction. The excessive band in lane 2 in reference to results in lane 1 represents the overexpressed GST-ACTR; Lane 3: the supernatant of the bacteria lysate; Lane 4: the eluent after washing by the extraction buffer A2 (PBS); Lane 5: the eluted ACTR peptide (5.5 kDa); Lane 6: the eluted GST moiety of the fusion protein and the GST-PreScission Protease. The lower band in lane 6 (violet marked) reports a slightly lower position on the gel when compared with the band corresponding to GST-ACTR (marked green). This is expected since GST (26 kDa) has a lower molecular weight than GST-ACTR. The upper band in lane 6 (marked brown) was recognized as the GST-protease (46 kDa). The ACTR peptide, as characterized in lane 5, was directly used in all downstream measurements without any further purifications.

Figure 93:
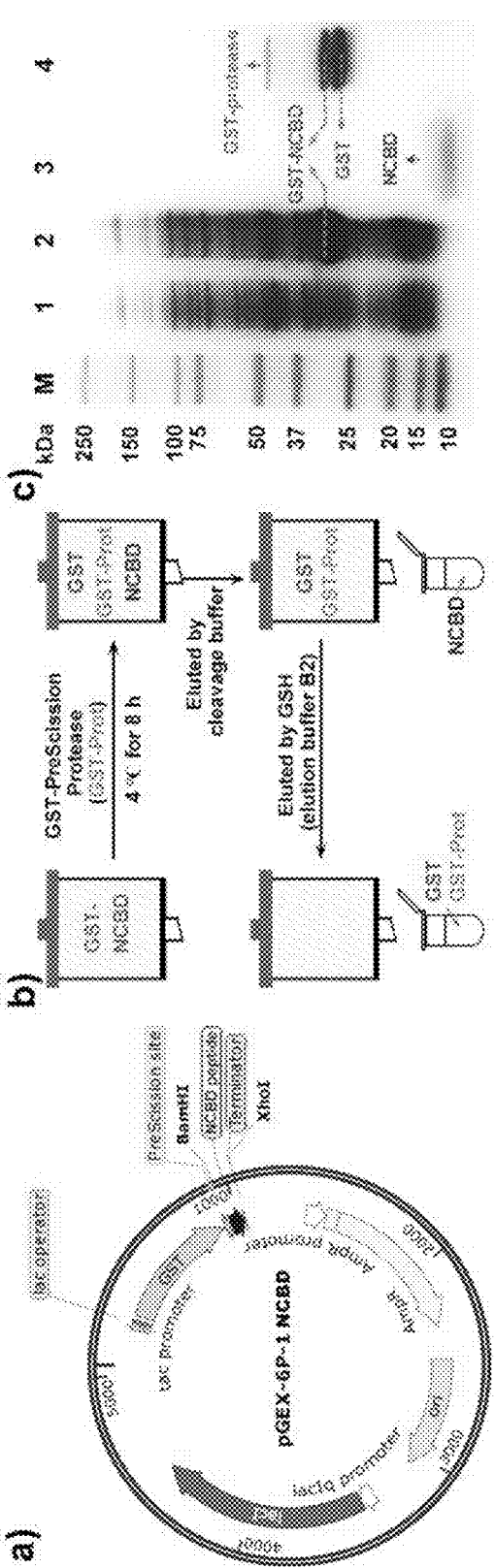

FIG. 93 shows preparation of the NCBD peptide. The preparation of the NCBD peptide is detailed in Example 8 Methods 3. (a) The construction of the plasmid coding for the GST-NCBD fusion protein. The gene coding for the fusion protein was cloned into a pGEX-6P-1 plasmid. The gene coding for the NCBD peptide (with a blue terminator at the end of the sequence) was inserted between the recognition sequence of BamH I and Xho I, immediately after the pink PreScission site. The PreScission site of the expressed protein is cleavable when treated by corresponding protease. (b) The schematic diagram of NCBD separation. The expressed fusion protein GST-NCBD was first applied to a GSTrap™ column. The column was further applied with the PreScission Protease (GST-Prot) which also has a GST-tag on its N-terminal. After 8 h of incubation at 4° C., the NCBD was completely separated from the GST-NCBD fusion protein and was eluted by the cleavage buffer and collected. The GST moiety and the PreScission Protease however remain on the column. Regeneration of the column is performed by elution with the glutathione (GSH) containing solution (elution buffer B2). The eluted GST and GST-Prot were discarded. (c) Gel electrophoresis results. Lane M: precision plus protein standards; Lane 1-2: Bacterial lysates containing GST-NCBD plasmid without or with IPTG induction. The excessive band in lane 2 in reference to results in lane 1 represents the overexpressed GST-NCBD; Lane 3: the eluted NCBD peptide (6.9 kDa); Lane 4: the eluted GST moiety of the fusion protein and the GST-PreScission Protease. The lower band in lane 4 (marked violet) reports a slightly lower position on the gel, when compared with the band corresponding to GST-NCBD (marked green). This is expected since GST (26 kDa) has a lower molecular weight than GST-NCBD. The upper band in lane 4 (marked brown) was recognized as the GST-protease (46 kDa). The NCBD peptide, as characterized in lane 3, was directly used in all downstream measurements without any further purifications.

Figure 94:
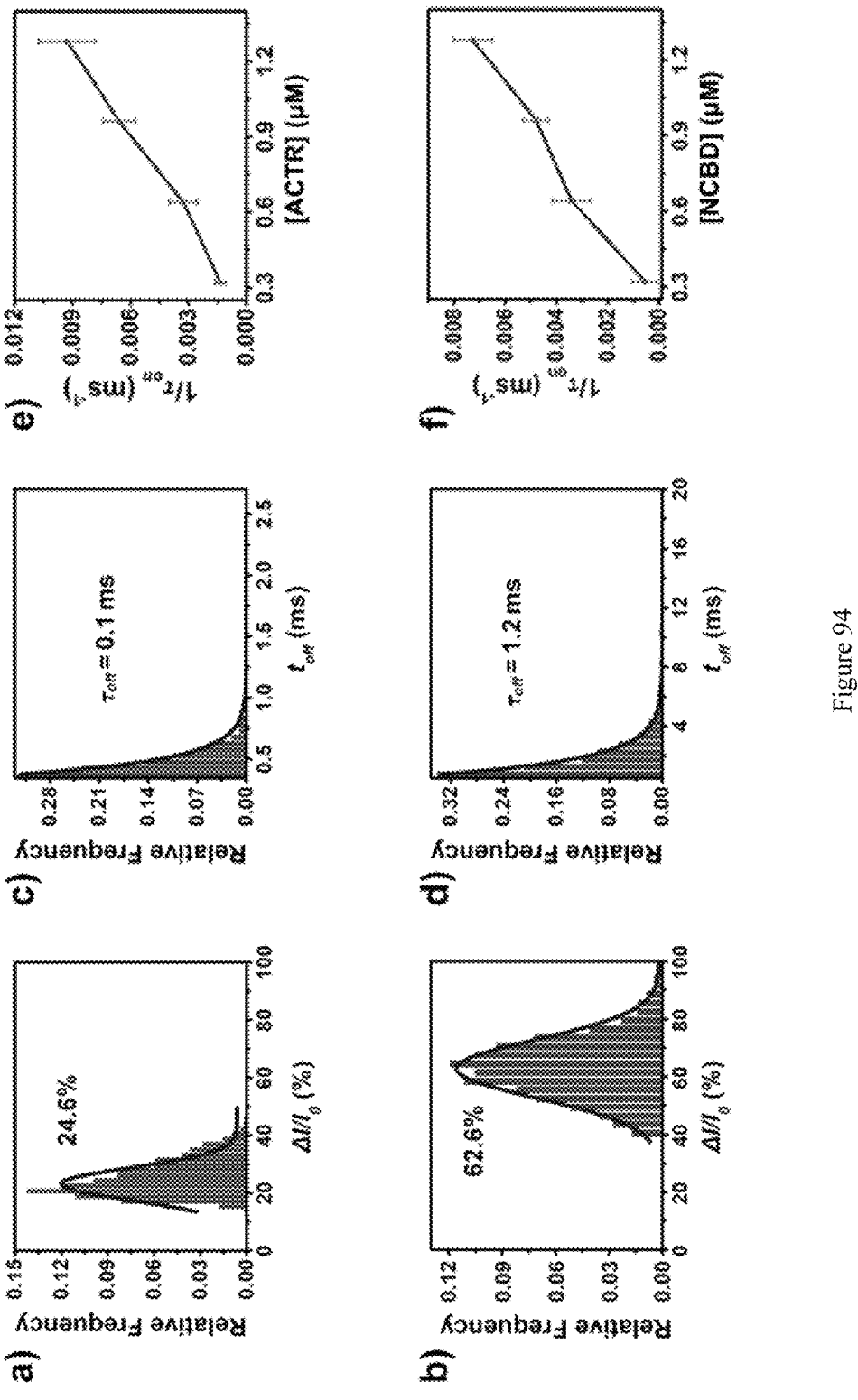

FIG. 94 shows single molecule characteristics of ACTR or NCBD peptide. All measurements were carried out as described in Example 8 Methods 1. A buffer combination of 1.5 M KCl (cis)/1.0 M CaCl$_2$ (trans), pH=7.0 was applied. Both the unstructured ACTR and NCBD could separately block the MspA nanopore-trap in the presence of a calcium flux. (a, b) Histograms of $\Delta I/I_0$ resulted from events from 20 min continuously recorded traces acquired with (a) ACTR or (b) NCBD, as respectively demonstrated in FIGS. 79c and 79d. The mean values of $\Delta I/I_0$ ($\overline{\Delta I/I_0}$), in a and b were derived from corresponding Gaussian fitting results. (c, d) Histograms of t$_{off}$ resulted from events from 20 min continuously recorded traces acquired with ACTR (c) or NCBD (d), as demonstrated in FIGS. 3c and 3d respectively. $\tau_{off}$ was derived from the corresponding exponential fitting results of the histogram. Events with a dwell time of <0.5 ms were ignored during the statistics. All fitting results from independent measurements (N=3) are detailed in Table 11 and Table 12. (e, f) Plot of the reciprocals of the mean inter-event intervals (1/$\tau_{on}$) of trapping events versus the final concentrations of ACTR (e) or NCBD (f) in cis. Error bars in e and f represent standard deviations derived from results of three independent measurements (N=3). Detailed results are listed in Table 13. Generally, the trapping events appear more frequently as the final concentration of the peptides is increased.

Figure 95:
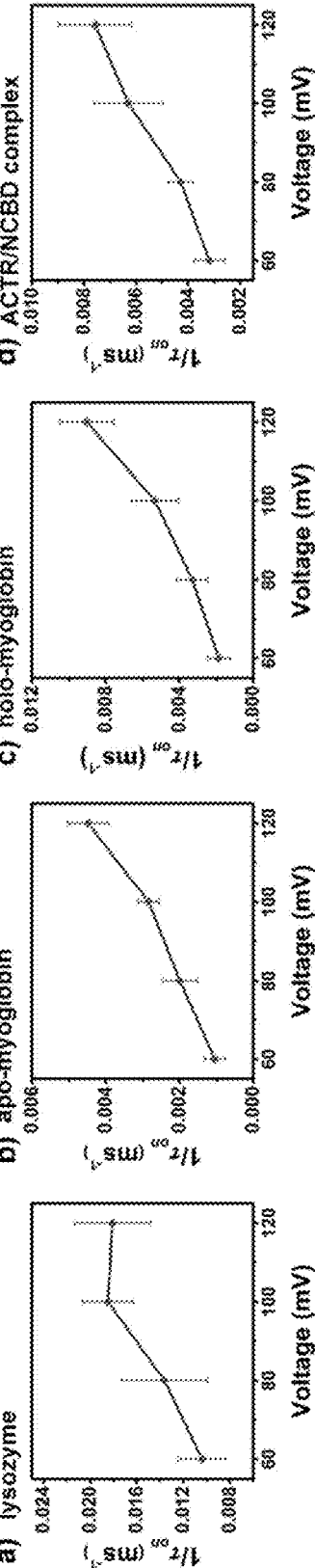

FIG. 95 shows correlation between the capture frequency and the applied voltage. All measurements were carried out as described in Example 8 Methods 1. The buffers in cis/trans chambers were 1.5 M KCl/1.0 M CaCl$_2$ (pH=7.0) respectively. The protein analytes were respectively added to the cis chamber. The final concentration of lysozyme, apo-myoglobin, holo-myoglobin or ACTR/NCBD complex are 0.42, 0.26, 0.14 and 1.28 μM, respectively. (a-d) Plot of 1/$\tau_{on}$ versus the applied voltage (+60 mV, +80 mV, +100 mV or +120 mV) respectively corresponding to the measurement of lysozyme (a), apo-myoglobin (b), holo-myoglobin (c) or ACTR/NCBD complex (d). Error bars in a-d represent standard deviations between independent measurements (N=3). The results are also detailed in Table 14. Generally, the reciprocal of inter-event duration time in b-d is extended at a higher applied potential. This indicates that as the applied voltage is increased, the capture frequencies of apo-/holo-myoglobin and ACTR/NCBD complex increase. For lysozyme, the value of 1/$\tau_{on}$ is first increased and then slightly decreased as the voltage is continuously increased. It may be due to the positive charges of lysozyme in the test solution (pH=7).

Figure 96:
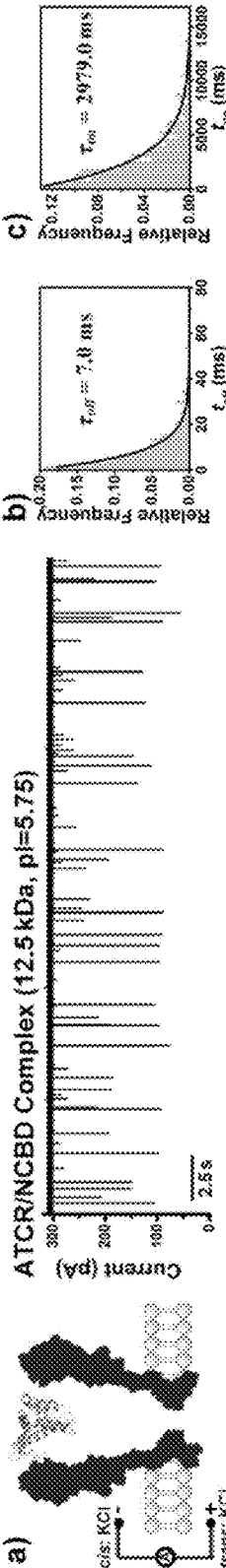

FIG. 96 shows trapping of ACTR/NCBD complex in symmetrical KCl electrolyte. All measurements were carried out as described in Example 8 Methods 1. Specifically, both the cis chamber and the trans chamber were filled with 1.5 M KCl buffer, pH=7.0. ACTR and NCBD were 1:1 premixed for 5 min and added to cis. A transmembrane potential of +100 mV was continuously applied. (a) Left: The schematic diagram of stochastic sensing of ACTR/NCBD complex by MspA. PDB IDs: 1UUN (MspA) and 1KBH (ACTR/NCBD complex). Right: a representative trace containing events caused by ACTR/NCBD complex trapping. The final concentration of ACTR/NCBD complex is 1.28 μM. (b-c) Histograms of $t_{off}$ (b) and $t_{on}$ (c) from a 20 min continuously recorded trace as demonstrated in a. Events with a dwell time <1 ms were ignored during the statistics in b and c. The mean event dwell time ($\tau_{off}$) and the mean interevent interval ($\tau_{on}$) are all derived from exponential fitting results according to the equation y=a*exp(−x/τ). $\overline{\tau_{off}}$ and $\overline{\tau_{on}}$ are derived from three independent measurements (N=3). All detailed fitting results are listed in Table 11. Compared with the corresponding results in an asymmetric electrolyte, the capture efficiency of protein analytes is significantly reduced and the dwell time is also systematically shortened. This further proves that the combination of monovalent and divalent ions improves the performance of MspA nanopore trapping.

Figure 97:
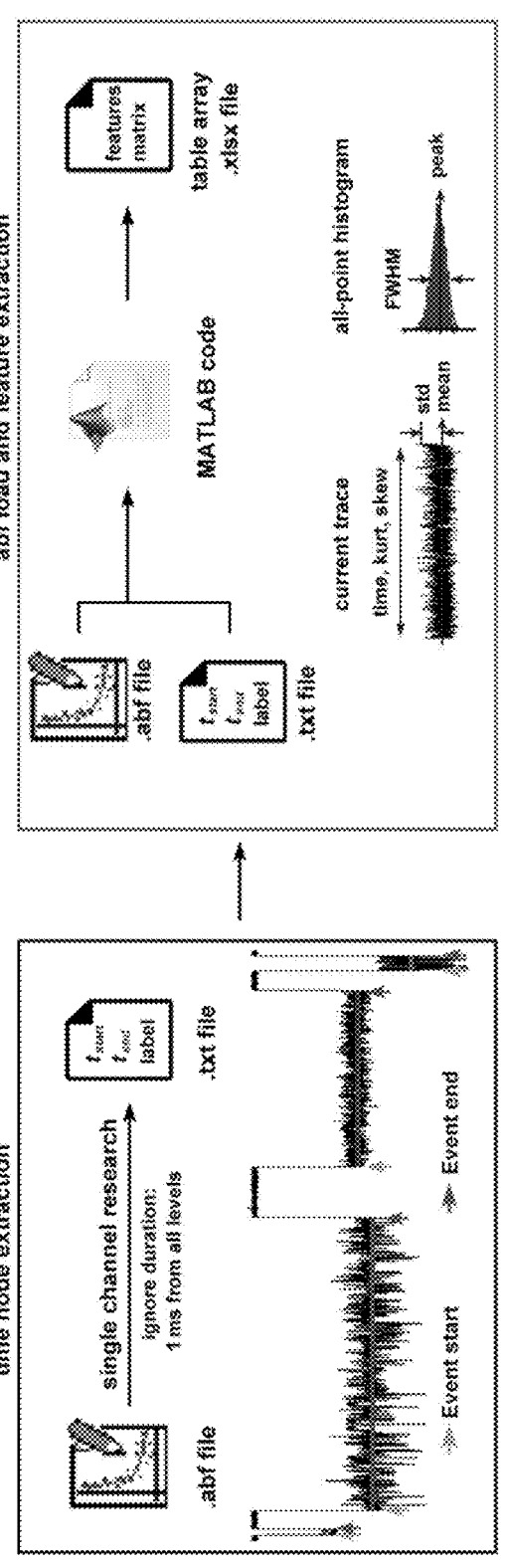

FIG. 97 shows a workflow of event feature extraction. All nanopore sensing events are first automatically detected with the "single channel research" function in Clampfit 10.7. The event start-time ($t_{start}$) and the event end-time ($t_{end}$) of each event are recorded as time stamps for each event in a txt file. The ignored duration is set to 1 ms to preclude events caused by transient collision of the analyte to the pore. The Axon abf file and txt file are imported into MATLAB to extract the features of blocking current (Example 8 Methods 1). Seven event features including mean value (mean), kurtosis (kurt), skewness (skew), dwell time (time), central value of distribution (peak) and noise (FWHM) are extracted using MATLAB to form a feature matrix. The feature matrix was exported as a xlsx file and is applied to perform machine learning using MATLAB.

Figure 98:
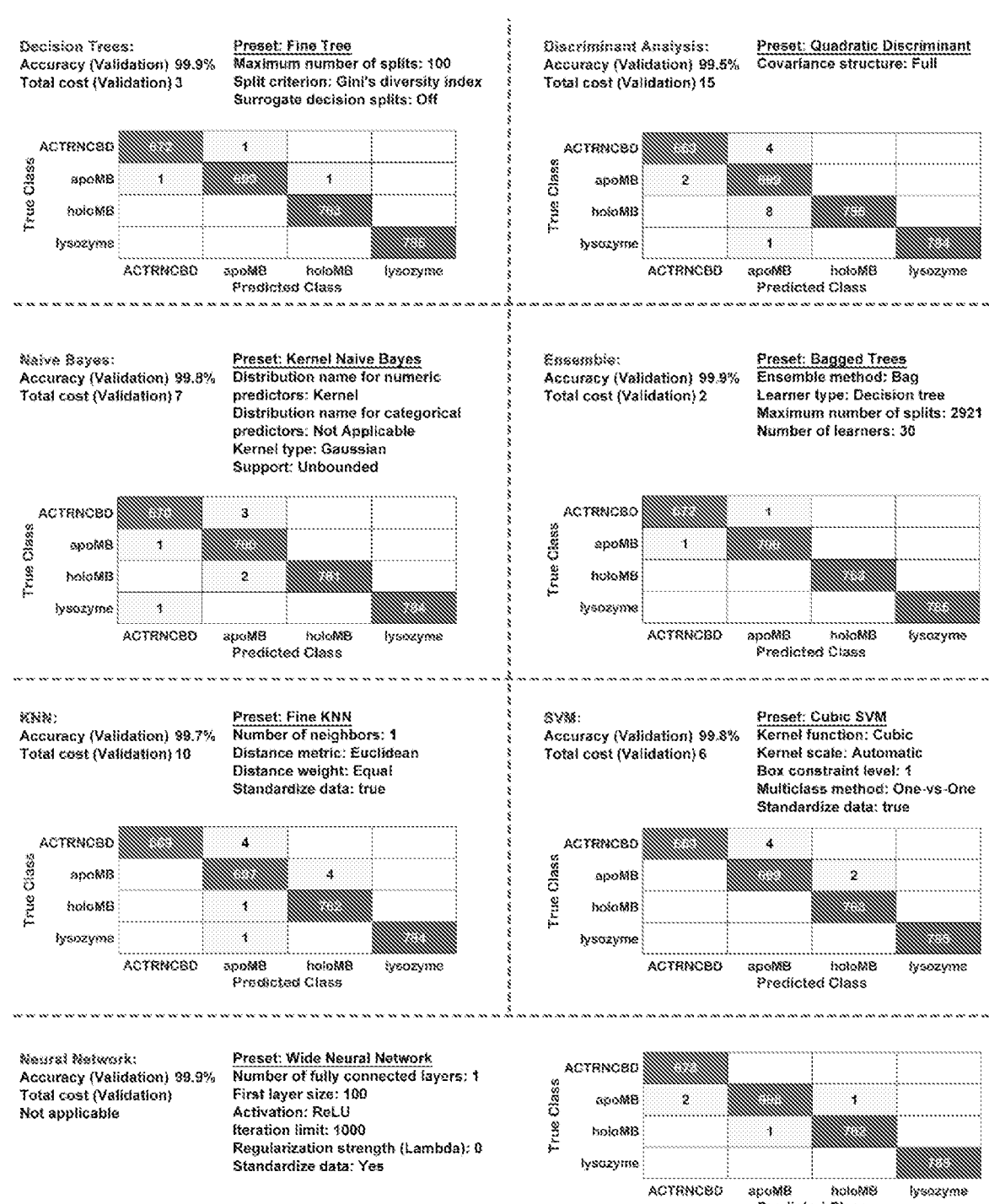

FIG. 98 shows information of different models. The parameter settings with the best verification accuracy and lowest cost of each model are demonstrated. The corresponding verification confusion matrix are also summarized. All models were trained using the Classification Learner toolbox in MATLAB with the training dataset containing the feature matrix of lysozyme, apo-myoglobin, holo-myoglobin and ACTR/NCBD complex trapping events. The accuracies were derived from the 10-fold cross-validation results.

Figure 99:
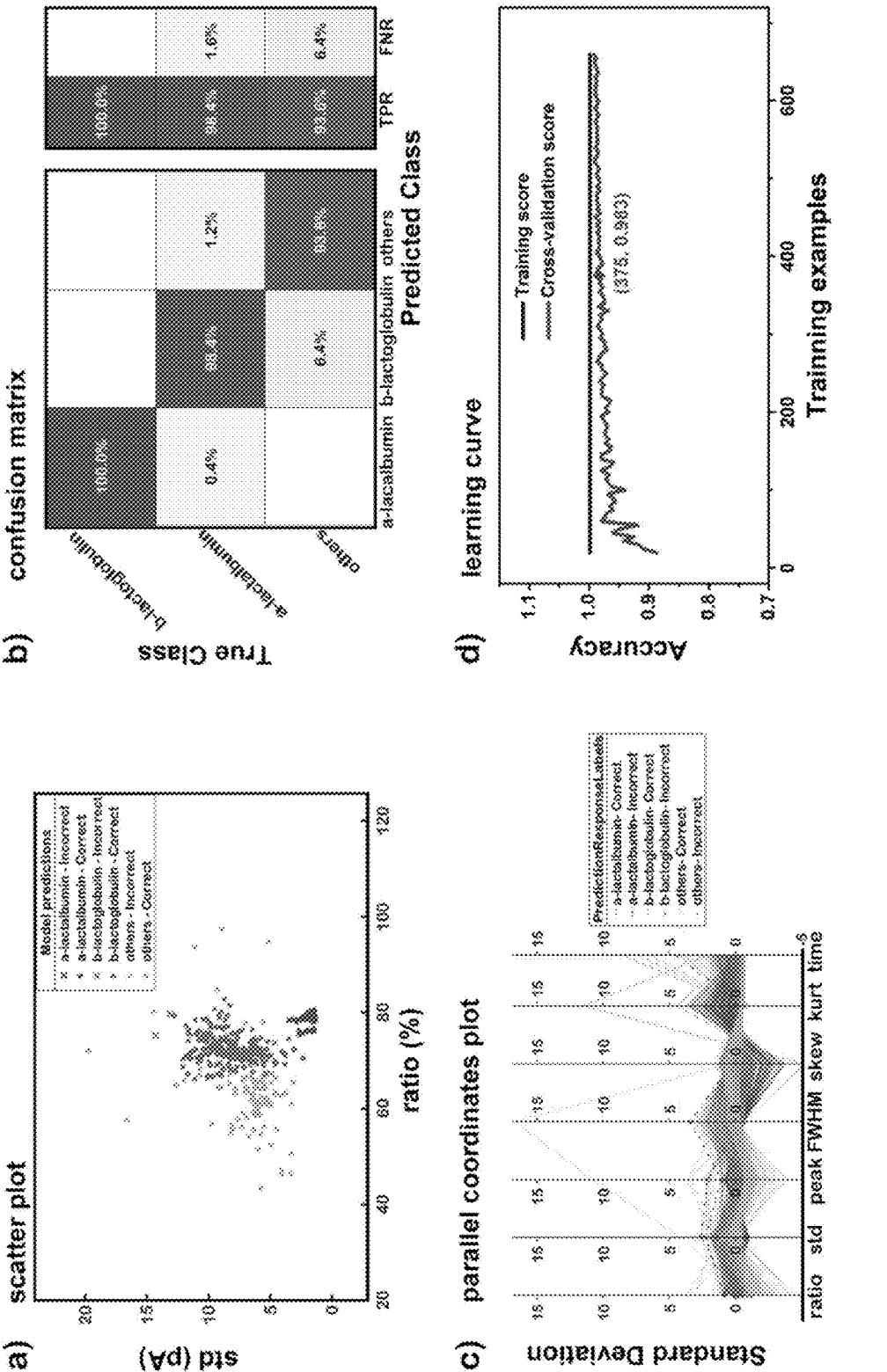

FIG. 99 shows machine learning analysis of whey protein. The bagged tree model was applied. (a) The scatter plot of the training dataset. (b) The confusion matrix of protein classification using a trained bagged trees model. True positive rate (TPR) and false negative rate (FNR) were demonstrated to the right. (c) The parallel coordinate plots of the bagged trees model. The correctly classified points were marked as solid lines while the misclassified points were marked as dashed lines. All features play a role in event classification. (d) The learning curve with varying sample sizes of the training dataset. It shows the mean accuracy of four independent tests. When the samples in the training dataset exceed 375, the validation accuracy and the training set resubstitution accuracy were hardly changed, which proved that the classification model trained with more than 375 training samples demonstrates no overfitting.

Figure 100:
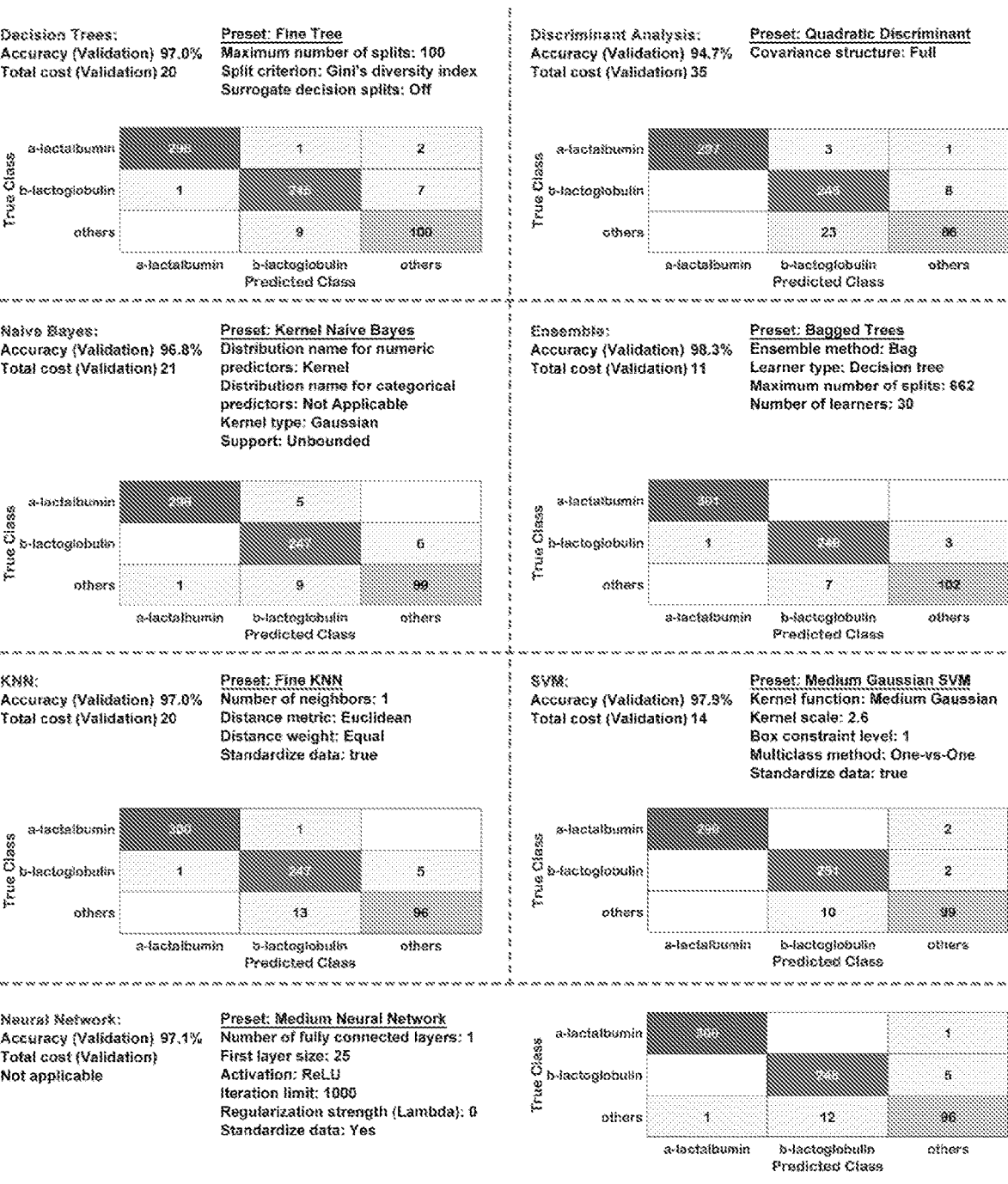

FIG. 100 shows information of machine learning evaluated with the whey protein. The parameter settings of the model with the best verification accuracy and the lowest cost in each classifier are demonstrated. The corresponding verification confusion matrix are also summarized. All models were trained using the Classification Learner toolbox in MATLAB with the training dataset containing the feature matrix of α-lactalbumin, β-lactoglobulin and the "others" events. The accuracies were derived from the 10-fold cross-validation results.

Figure 101:
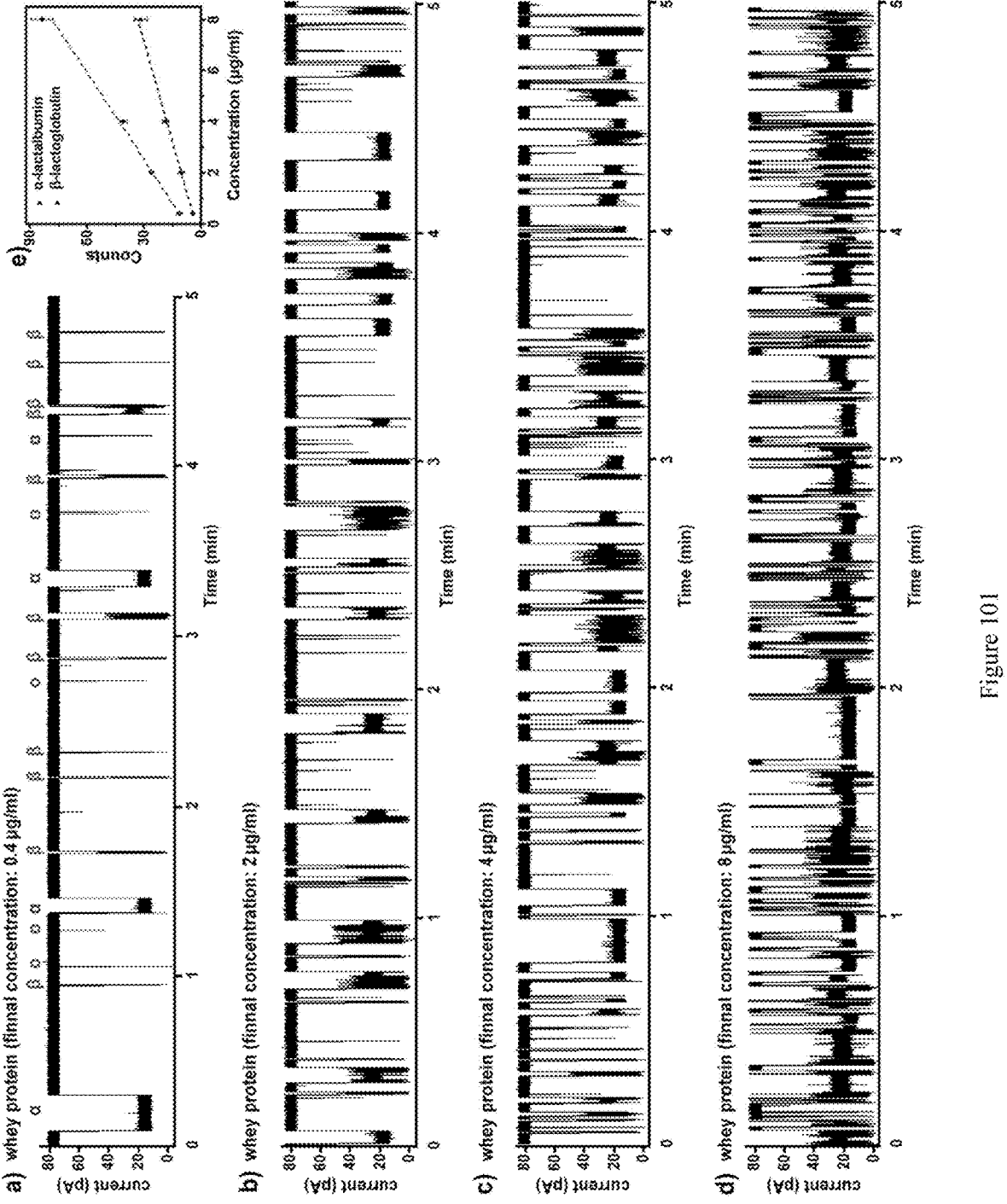

FIG. 101 shows the concentration dependence of whey protein during nanopore measurements. All measurements were carried out as described in Example 8 Methods 1. Briefly, the measurements were carried out in the buffers of 1.5 M KCl/1.0 M CaCl$_2$ (pH=7.0) and a transmembrane potential of +30 mV was continually applied. (a-d) Representative traces containing nanopore events caused by whey proteins with a final concentration of 0.4 μg/ml (a), 2 μg/ml (b), 4 μg/ml (c) and 8 μg/ml (d). By tentatively defining the limit of detection (LOD) to be the concentration required to detect 10 effective trapping events within 5 minutes, the LOD of MspA for whey protein is ~0.4 μg/ml. (e) Plot of α-lactalbumin and β-lactoglobulin trapping events versus the final concentrations of whey protein in cis during a 5 min measurement. Error bars in e represent standard deviations between three independent measurements, each with a 5 min measurement duration. For both α-lactalbumin and β-lactoglobulin, the counts of trapping events were linearly correlated with the final concentration of whey protein powder (with an R-square of 0.996 or 0.987, respectively).

Figure 102:
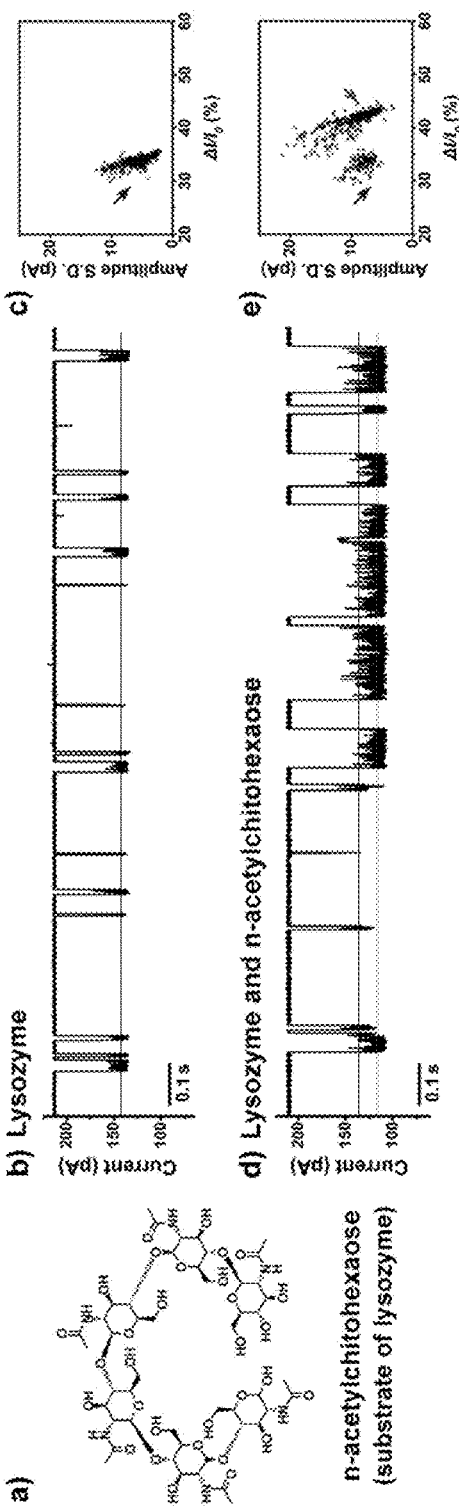

FIG. 102 shows stochastic sensing of lysozyme-substrate complex with MspA electroosmotic trap. All measurements were carried out with the buffer combination of 1.5 M KCl/1.0 M CaCl$_2$ (pH=5.5) and a continuously applied transmembrane potential of +100 mV (a) Structural formula of the n-acetylchitohexaose, which is the substrate of lysozyme. (b) Representative trace containing nanopore events caused by lysozyme trapping. The final concentration of lysozyme is 0.21 μM. (c) The corresponding event scatter plots of the percentage blockage ($\Delta I/I_0$) versus the standard deviations of blocking current (Amplitude S.D.). The scatter plots were generated from results of 5 min continuously recorded traces (n=450). The mean percentage blockage ($\overline{\Delta I/I_0}$) was 34.3%. (d) Representative traces showing state changing of lysozyme when the final concentration of n-acetylchitohexaose in cis was 0.24 μM. The changing of event types was observed, caused by structural changes of lysozyme induced by substrate binding. (e) The corresponding event scatter plots of the percentage blockage ($\overline{\Delta I/I_0}$) versus the standard deviations of blocking current (Amplitude S.D.). The scatter plots were generated from results of 5 min continuously recorded traces (n=557). A new population of events were observed with a $\overline{\Delta I/t_0}$ of 42.5%.

DETAILED DESCRIPTION OF THE INVENTION

It should be understood that this invention is not limited to particular embodiments described. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are to disclose and describe the methods and/or materials in connection with which the publications are cited.

Where a range of values is provided, it is understood that each intervening value, to the tenth of the unit of the lower limit, and the intervening range between the upper and lower limit of that range, is encompassed within the invention, unless the context clearly dictates otherwise. Where the stated range includes one or both of the limits, ranges excluding either or both of the limits included limits are also included in the invention.

It must be noted that as used herein and in the appended claims, the singular forms "a," "an," and "the" include plural referents unless the context clearly dictates otherwise. Thus, for example, reference to "an analyte" includes one analyte and a plurality of different analytes and reference to "the molecule" includes reference to one or more molecules. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "comprise", "include", "contain" and variations of these terms, such as comprising, comprises and comprised, are not intended to exclude further additions, components, integers or steps. These terms also encompass the meaning of "consist of" or "consisting of".

the term "about" refers to a range equal to the particular value plus or minus twenty percent (+20%).

The term "and/or" refers to any one, any few or all of the elements connected by the term.

It should be understood that the method of the present invention may be performed in vivo, in vitro, or ex vivo. The method of the present invention may be not for the purpose of disease treatment, and/or not for the purpose of disease diagnosis.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

*Mycobacterium smegmatis* porin A (MspA) is a conically shaped biological nanopore composed of rigid β-barrel structures[28]. Previous reports indicate that the pore in an octameric form possesses an incredible stability and consistency against extreme conditions[29]. Its narrow constriction, measuring ~1.2 nm in diameter is advantageous in applications of nanopore sequencing[30] or nanopore force spectroscopy[31]. On the other side, the inventors found that its large vestibule, which measures ~4.8 nm in diameter, would permit transient accommodation of a large analyte in its native form by nanopore trapping. Surprisingly, this geometric advantage has however been ignored since its original report.

Figure 1:
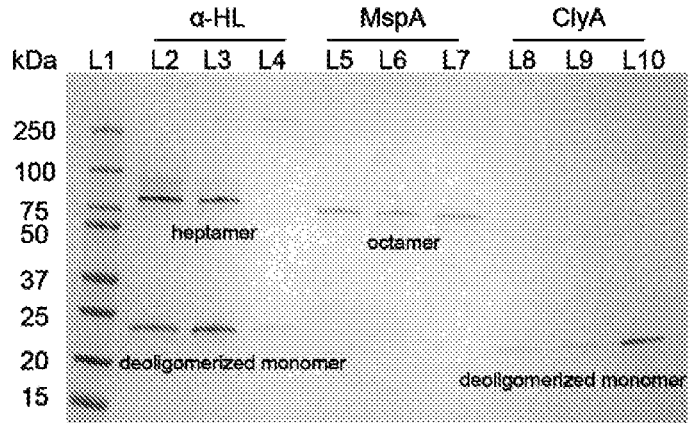
FIG. 1 shows stability comparison between different protein nanopores. L1: protein marker (precision plus protein standards, BIO-RAD, USA); L2: freshly prepared WT α-HL heptamer; L3: WT α-HL heptamer treated at 80° C. for 15 minutes; L4: WT α-HL heptamer stored at −80° C. for 3 months; L5: freshly prepared M2 MspA; L6: M2 MspA treated at 80° C. for 15 minutes; L7: M2 MspA stored at −80° C. for 3 months; L8: freshly prepared ClyA-RR; L9: ClyA-RR treated at 80° C. for 15 minutes; L10: ClyA-RR stored at −80° C. for 3 months. The M2 MspA demonstrated the best stability among all three nanopores by showing an unaltered octameric assembly form; A fraction of the freshly prepared WT a-HL heptamer showed deoligomerization state when heated or stored for 3 months; ClyA-RR showed complete deoligomerization under the condition of SDS-PAGE.
Figure 2:
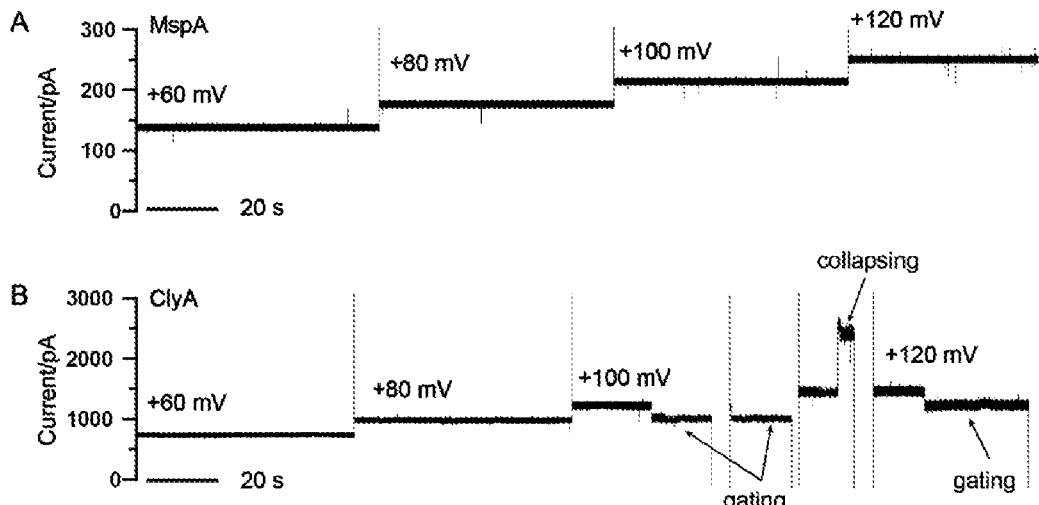
FIG. 2 shows comparison of high voltage performance between M2 MspA and ClyA-RR. Continuous long-term measurements with MspA at a high applied potential show stable open pore current. Based on previous reported literatures, the M2 MspA can sustain long term measurements at an applied potential up to +200 mV. On the other hand, the performance of ClyA-RR is much worse. Appearance of spontaneous gating or pore collapsing were frequently observed when the applied potential is more than +100 mV. Electrophysiology measurements were performed as described in Methods. An electrolyte buffer of 1.5 M KCl (cis)/1 M $CaCl_2$ (trans) as applied.

We here propose a new sensing mode with MspA, termed nanopore trapping/translocation, with which direct discrimination between differently structured low molecular weight (LMW) RNAs such as miRNA, overhanged siRNA, blunt siRNA, tRNA or 5s rRNA is reported. The RNA structure is profiled in its folded form during trapping. Translocation is not strictly needed and no denaturant or sample ligation is required. Complementary to existing developments of large channel proteins, advantages such as the efficiency of pore preparation, the ease of spontaneous pore insertion, the high consistency of pore assembly, the extremely long storage time and a high spatial resolution are all gained (FIGS. 1 and 2).

*Mycobacterium smegmatis* porin A (MspA) is a conically shaped biological nanopore with a ~4.8 nm diameter opening and a ~1.2 nm constriction. The β-barrel constriction has a desirable mechanical rigidity,[159] which serves to maintain a consistent pore assembly stable in extreme pH, temperature or detergent environments. More importantly, this constriction is critical to minimizing the measurement noises caused by structural fluctuations of the pore.[160] Acknowledging the high spatial resolution offered by its conical geometry, MspA was the first type of nanopore used in nanopore sequencing[161] and applications of nanopore tweezers adapting a similar scheme.[162] Its large channel conductance and low measurement noise have also enabled studies of single molecule chemistry within the pore lumen.[163,164] Design of these applications has benefitted from its rigid and narrow constriction, but the use of its large vestibule has unfortunately been quite overlooked since its original report.

In this work, we describe a previously unreported sensing mode called MspA nanopore trapping, in which large analytes such as proteins, may be lodged in the pore vestibule from where they can report sensing information. The narrow pore constriction does not permit direct passage of the protein through the pore but stochastic sensing of individual analytes can be achieved by probing spontaneous trapping and subsequent escape from the pore, which results in stochastic events during single channel recordings. Characteristic trapping events, which may reflect the overall size, charge, polarity and conformational changes of the protein can be analyzed to study the kinetics of conformational changes or ligand binding of a protein with a high resolution. To the best of our knowledge, direct sensing of proteins by MspA has not been reported previously. Advantages of MspA in this sensing scenario include an improved sensing resolution resulted from a sharp and rigid pore structure, ease of pore preparations and structural stability against extreme measurement or storage conditions.

Calmodulin (CaM), a calcium-binding 17 kDa messenger protein, was examined as a proof of concept. In eukaryotes, wild-type CaM (wtCaM) serves as a critical link in the signal transduction pathway between $Ca^{2+}$ and target proteins. Previous investigations performed by small-angle X-ray scattering (SAXS) and 3D/4D heteronuclear NMR spectroscopy have provided an accurate structure of CaM,[165, 166] and revealed that the signal transduction pathway is achieved by two step allosterism of wtCaM. The $Ca^{2+}$-free CaM (apo-wtCaM) first coordinates with $Ca^{2+}$ leading to the $Ca^{2+}$-bound form of CaM (Ca-wtCaM) and an overall structural change from a loose and flexible shape to a rigid dumbbell-shape (FIGS. 38*a* and 39*a*). Subsequently, Ca-wtCaM and the binding domain of the target protein, M13 peptide for example) form a functional protein complex (M13-Ca-wtCaM) driven by hydrophobic interactions. Then the N- and C-lobes of Ca-wtCaM collapse together to grip the M13 peptide (FIGS. 38*a* and 39*f*). All this allosteric behavior was well resolved by the MspA nanopore trapping, indicating an improved sensing resolution compared with previous attempts using solid-state nanopores[167] or surface plasmon resonance microscopy.[168] Notably, no protein unfolding or chemical labeling was required by this strategy.

In summary, the inventors found that a blockade current pattern during the presence of an analyte in the vestibule of MspA is sufficient to characterize an analyte or the interaction between the analyte and an agent. Measurement of the blockade current during the translocation of the analyte through the constriction zone of MspA is not necessary, but it can also be combined with the blockade current of the analyte in the vestibule to provide a current pattern for characterizing the analyte or the interaction between the analyte and an agent. This finding is particularly meaningful for detecting the conformation of molecules, as well as those events or features related to the conformation (for example, events or features that can cause changes in the conformation of the molecule).

Nanopore

The term "nanopore", as used herein, generally refers to a pore, channel or passage which has a very small diameter on the order of nanometers and extends through a membrane. A nanopore may have a characteristic width or diameter on the order of 0.1 nanometers (nm) to about 1000 nm. Some nanopores are proteins. MspA is an example of a protein nanopore.

The term "MspA", as used herein, generally refers to *Mycobacterium smegmatis* porin A. Sequence of wild type MspA are known by the person skilled in the art. For example, sequences of wild type MspA can be found in GenBank on https://www.ncbi.nlm.nih.gov/. In some embodiments, the wild-type MspA may have the following amino acid sequence:

```
                                    (SEQ ID NO: 1)
GLDNELSLVDGQDRTLTVQQWDTFLNGVFPLDRNRLTREWFHSGRAKYI

VAGPGADEFEGTLELGYQIGFPWSLGVGINFSYTTPNILIDDGDITAPP

FGLNSVITPNLFPGVSISADLGNGPGIQEVATFSVDVSGAEGGVAVSNA

HGTVTGAAGGVLLRPFARLIASTGDSVTTYGEPWNMN.
```

In some embodiments, the wild-type MspA may be consisted of SEQ ID NO: 1.

A homolog (such as ortholog or paralog) of MspA may also be used as the nanopore herein. The term "homolog", as defined herein, is a gene that has a similar structure and function with another gene. A homolog may have a sequence identity of at least 50%, 55%, 60%, 65%, 70%, 75%, 80%, 85%, 90%, 95%, 96%, 97%, 98%, or 99% compared to its counterpart. The term "homolog" is sometimes used to apply to the relationship between genes separated by the event of speciation (see "ortholog") or to the relationship between genes separated by the event of genetic duplication (see "paralog"). The term "ortholog" refers to genes in different species that evolved from a common evolutionary origin. The term "paralog" refers to genes related by duplication within a genome. Examples of paralog of MspA include MspB, MspC, and MspD. Examples of ortholog of MspA include MppA, PorM1, PorM2, PorM1, and Mmncs4296.

A variant of MspA or MspA homolog may also be used as the nanopore herein. A variant may have one or more additions, substitutions and/or deletions of amino acids compared to their wild-type ones, or may have a sequence identity of at least 70%, 75%, 80%, 85%, 90%, 95%, 96%, 97%, 98%, or 99% compared to the corresponding wild-type MspA or MspA homolog, and retains tunnel-forming capability.

The person skilled in the art readily understand how to determine the identity of two polypeptides. For example, the identity can be calculated after aligning the two sequences so that the identity is at its highest level. For example, to determine the "percent identity" of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences may be a function of the number of identical positions shared by the sequences (i.e., percent identity=number of identical positions/total number of positions (e.g., overlapping positions)× 100). In one embodiment, the two sequences are the same length. Sequence identity can be determined in a number of different manners and through a number of algorithms. To determine sequence identity, sequences can be aligned using various methods and computer programs (e.g., BLAST, T-COFFEE, MUSCLE, MAFFT, etc.), available over the world wide web at sites including ncbi.nlm.nili.gov/BI-LAST, ebi.ac.uk/Tools/msa/tcoffee/, ebi.ac.uk/Fools/msa/muscle/, mafft.chr.jp/alignment/software/. See, e.g., Altschul et al. (1990), J. Mol. Bioi. 215:403-40.

In some embodiments, a variant is one having a mutation (such as one or more additions, substitutions and/or deletions of amino acids in the constriction zone and/or the vestibule of a wild-type MspA or a wild-type MspA homolog. In some embodiments, a mutation may occur in the rim or the outside of the periplasmic loops of a wild-type MspA or a wild-type MspA homolog.

In some embodiments, a variant of MspA or a MspA homolog, may comprise at least one additional positively charged amino acid, at least one additional negatively charged amino acid, at least one less positively charged amino acid or at least one less negatively charged amino acid compared to a wild-type MspA or a wild-type MspA homolog in the vestibule and/or the constriction zone.

In some embodiments, one or more positively charged amino acid in the vestibule and/or the constriction zone of a wild-type MspA or a wild-type MspA homolog is replaced with a negatively charged amino acid, and each negatively charged amino acid is the same or different; or one or more negatively charged amino acid in the vestibule and/or the constriction zone of a wild-type MspA or a wild-type MspA homolog is replaced with a positively charged amino acid, and each positively charged amino acid is the same or different.

In some embodiments, the vestibule and/or the constriction zone of a variant of a MspA or a MspA homolog comprises a greater number of positively charged residues than a wild-type MspA or a wild-type MspA homolog, or the vestibule and/or the constriction zone comprises a greater number of negatively charged residues than a wild-type MspA or a wild-type MspA homolog; or at least one positively charged amino acid in the vestibule and/or the constriction zone of a wild-type MspA or a wild-type MspA homolog, is either deleted or replaced by a negatively charged amino acid; or at least one negatively charged amino acid in the vestibule and/or the constriction zone of a wild-type MspA or a wild-type MspA homolog is either deleted or replaced by a positively charged amino acid.

In some embodiments, a variant of Msp may comprise (i) mutations such that amino acid positions 90, 91, and 93 contain amino acids with a neutral charge and (ii) one or more mutations at the following amino acid positions: 88, 105, 108, 118, 126, 134, 138 or 139. In some embodiments, a variant MspA may comprise mutations of D90N/D91N/D93N or D93N/D91N/D90N/D118R/D134R/E139K compared to the wild-type MspA. D90N/D91N/D93N or D93N/D91N/D90N/D118R/D134R/E139K means that the mutant comprises simultaneously all of listed six mutations. In some embodiments, a variant of MspA may only has the mutations of D90N/D91N/D93N (M1 MspA) or D93N/D91N/D90N/D118R/D134R/E139K (M2 MspA) compared to the wild-type MspA. The number used herein identifies the location of site directed mutagenesis, where the first amino acid immediately after the start codon is defined as 1.

In the present invention, MspA, MspA homology or a variant thereof may be recombinant protein.

Preferably, MspA, MspA homology or a variant thereof used in the present invention does not gate spontaneously, even at 150 mV-200 mV or more. "To gate" or "gating" refers to the spontaneous change of electrical conductance through the tunnel of the protein that is usually temporary (e.g. lasting for as few as 1-10 milliseconds to up to a second). For some protein nanopore, the probability of gating increases with the application of higher voltages. Typically, the protein becomes less conductive during gating, and conductance may permanently stop (i.e., the tunnel may permanently shut) as a result, such that the process is irreversible. Optionally, gating refers to the conductance through the tunnel of a protein spontaneously changing to less than 75% of its open state current.

MspA, MspA homology or a variant thereof discussed herein may comprise a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel.

A "vestibule" refers to the cone-shaped portion of the interior of an MspA, MspA homology or a variant thereof whose diameter generally decreases from one end to the other along a central axis, where the narrowest portion of the vestibule is connected to the constriction zone.

When referring to a diameter of the vestibule, it is understood that because the vestibule is cone-like in shape, the diameter changes along the path of a central axis, where the diameter is larger at one end than the opposite end. The diameter may range from about 2 nm to about 6 nm. When referring to "diameter" herein, one may determine a diameter by measuring center-to-center distances or atomic surface-to-surface distances.

A "constriction zone" refers to the narrowest portion of the tunnel of an MspA, MspA homology or a variant thereof, in terms of diameter, that is connected to the vestibule.

As known by the person skilled in the art, a MspA nanopore can comprise two or more MspA monomers (e.g., eight monomers), which associate with each other and form a tunnel, wherein each monomer may be the same of different. MspA nanopore may be an octameric MspA. The MspA, MspA homology or a variant thereof, as used herein, should be capable of forming nanopore. Any one MspA monomer that formed the MspA porin may be selected from the group consisting of MspA, MspA homology and a variant thereof. In some embodiments, all monomers in a MspA nanopore are the same, such as the same variant of MspA monomers. In some embodiments, a MspA nanopore may contain one or more variants of MspA monomers. In some embodiments, all of the monomers in a MspA nanopore are the same or different variants of MspA monomers.

The preparation method of a MspA, MspA homology or a variant thereof is known by the person skilled in the art, for example, it could be prepared by prokaryote expression and easily purified by chromatography.

Unless otherwise stated, in the following detailed description of "Nanopore system", "Characterization of an analyte or the interaction between an analyte and an agent" and "Analytes and agents", "MspA" represents MspA. MspA homology or a variant thereof.

Nanopore System

A nanopore system typically comprises a nanopore disposed in a membrane that separates a first conductive liquid medium from a second conductive liquid medium. The tunnel of the nanopore is the only path for the first conductive liquid medium and the second conductive liquid medium to communicate. Generally, an analyte is added in at least one of the first conductive liquid medium and the second conductive liquid medium. The membrane can be an organic membrane, such as a lipid bilayer, or a synthetic membrane, such as a membrane formed of a polymeric material. The thickness of the membrane through which the nanopore extends can range from 1 nm to around 10 μm.

The preparation of a nanopore system is well known, for example, when a porin (such as MspA) is placed in any one of a first conductive liquid medium and a second conductive liquid medium separated by a membrane (such as a lipid bilayer), the protein can insert spontaneously into the membrane to form a nanopore.

When an electrical potential difference is applied between the first conductive liquid medium and the second conductive liquid medium (i.e., an electric field or a voltage is applied across the nanopore), an ionic current is generated through the tunnel of the nanopore, and the analyte may be electrophoretically driven into the nanopore from the conductive liquid medium and continue to electrophoretically move in a direction from one side of the nanopore to the other side. The electrical potential difference may be no less than 50 mV, no less than 100 mV, no less than 150 mV or no less than 200 mV; or range from about 50 mV to 200 mV, range from about 100 mV to 200 mV, range from about 150 mV to 200 mV. An analyte with positive charge electrophoretically moves to the side with lower potential. An analyte with negative charge electrophoretically moves to the side with higher potential. The direction of movement of the analyte can be controlled by adjusting the electric field. In some cases, the charge of the analyte depends on the pH of the medium, for example, when the analyte is a protein, the direction of movement of the analyte can also be controlled by adjusting the pH of the conductive liquid medium. The analyte may also be driven by a non-electrophoretic mean. In some embodiments, the electrical potential on the side of the constriction zone of MspA is higher than the electrical potential on the side of the vestibule of MspA. In some embodiments, the analyte is electrophoretically driven into the vestibule of MspA from the conductive liquid medium and continue to electrophoretically move in a direction from the vestibule of the nanopore to the constriction zone.

In some embodiments, the electrical potential difference between the first conductive liquid medium and the second conductive liquid medium varies or remains constant. Process and apparatus for applying an electric field to a nanopore are known to the person skilled in the art. For example, a pair of electrodes may be used to applying an electric field to a nanopore. As will be understood, the voltage range that can be used can depend on the type of nanopore system and the analyte being used.

The entry of the analyte into the nanopore (such as in the vestibule or the constriction zone) causes a blockage of to the ionic current, which is measurable, for example, by measuring the current after the analyte enters the nanopore and comparing it with the open pore current.

In general, a "blockage of the ionic current" may also be called a "blockade current", which is evidenced by a change in ionic current that is clearly distinguishable from noise fluctuations and is usually associated with the presence of an analyte molecule within the nanopore. The strength of the blockade, or change in current, will depend on a characteristic of the analyte. More particularly, "blockage" may refer to an interval where the ionic current drops to a level which is about 5-100% lower than the unblocked current level, remains there for a period of time, and returns spontaneously to the unblocked level. For example, the blockade current level may be about, at least about, or at most about 5%, 10%, 15%, 20%, 25%, 30%, 35%, 40%, 45%, 50%, 55%, 60%, 65%, 70%, 75%, 80%, 85%, 90%, 95%, or 100% lower than the unblocked current level. A blockage may be called a blockade event or an event.

Measurement of the current through a nanopore are well known in the art and may be performed by way of optical signal or electric current signal. For example, one or more measurement electrodes could be used to measure the current through the nanopore. These can be, for example, a patch-clamp amplifier or a data acquisition device.

A "liquid medium" includes aqueous, organic-aqueous, and organic-only liquid media. Organic media include, e.g., methanol, ethanol, dimethylsulfoxide, and mixtures thereof. Liquids employable in methods described herein are well-known in the art. Descriptions and examples of such media, including conductive liquid media, are provided in U.S. Pat. No. 7,189,503, for example, which is incorporated herein by reference in its entirety. Salts, detergents, or buffers may be added to such media. Such agents may be employed to alter pH or ionic strength of the liquid medium. Since it is not necessary for the method of the present invention to translocate the analyte through the nanopore, the liquid medium does not need to include a velocity-altering agent, such as glycerol or various polymers (e.g., polyvinylpyrrolidone, polyethylene glycol, polyvinyl alcohol, cellulose polymers) and mixtures thereof, to increases or decreases the velocity of an analyte. For example, in this invention, the first conductive liquid medium and the second conductive liquid medium may independently be buffer solution comprising an alkali metal ion, such as KCl. The buffering agent may be HEPES or Tris, etc. The pH of the first conductive liquid medium and/or the second conductive liquid medium may be 1.0-13.0, preferably 6.0-8.0, preferably 7.0-7.5, which may depend on the desired charge properties of the analyte. In some embodiments, the concentration of KCl is 1.5 M KCl.

In some embodiments, the nanopore system includes a symmetric buffer combination or an asymmetric buffer combination. A symmetric buffer combination means that the first conductive liquid medium and the second conductive liquid medium are the same. An asymmetric buffer combination means that the first conductive liquid medium and the second conductive liquid medium are different. An asymmetric buffer combination may facilitate the entry of the analyte into the nanopore. In the asymmetric buffer combination, one of the first conductive liquid medium and the second conductive liquid medium comprises monovalent cation, preferably an alkali metal ion, and more preferably selected from $K^+$, $Na^+$ and $Li^+$, and the other comprises divalent cation, preferably alkaline earth metal ion, preferably selected from $Ca^{2+}$, $Mn^{2+}$, $Mg^{2+}$ and $Ba^{2+}$. Preferably, the liquid medium that comprises monovalent cation does not comprise divalent cation.

Although not intending to be bound by theory, it is believed that the benefit of the asymmetric buffer combination should result from an increased electroosmotic flow induced by coordination interactions between divalent cation (such as alkaline earth metal ion, for example, $Ca^{2+}$, $Mn^{2+}$, $Mg^{2+}$ and $Ba^{2+}$) and amino acid residues in the pore lumen.

The asymmetric buffer is particularly useful for the simultaneous analysis or sequential analysis of a variety of different analytes. These analytes may have different charges and move in different directions under the action of electrophoretic force. However, in the asymmetric buffer, due to the effect of electroosmotic flow, the analytes having different charge can all move in one direction, making it possible to analyze them simultaneously or sequentially.

In some embodiments, the conductive liquid medium on the side of the vestibule of MspA comprises monovalent cation, and the conductive liquid medium on the side of the constriction zone of MspA comprises divalent cation. In some embodiments, the electrical potential on the side of the constriction zone of MspA is higher than the electrical potential on the side of the vestibule of MspA, and the direction of the electroosmotic flow is from the vestibule of MspA to the constriction zone.

Characterization of an Analyte or the Interaction Between an Analyte and an Agent For analytes with a certain conformation, such as analytes with secondary structure, tertiary structure, or three-dimensional structure, they generally cannot translocate through the constriction zone of MspA while maintaining their conformation due to the size. In a conventional MspA nanopore detection method, such analytes need to be unfolded or unzipped by additional means to become a linear single-chain to translocate through the nanopore.

The inventors found that as long as the analyte enters the vestibule of MspA, even if it does not translocate through the constriction zone of the nanopore, it can produce blockage information sufficient to distinguish different analytes. Since the vestibule of MspA is large enough, the analyte can enter the vestibule in its original conformation. Therefore, the current pattern containing the ionic current measured during the analyte is in the vestibule of MspA can be used to distinguish analytes with different conformation. The method of the present invention requires no prior chemical treatment or amplification of the analyte. The analyte does not need to be denatured (such as unfolded or unzipped) or connected to a molecular motor.

A current pattern can be provided by measuring the ionic current through a nanopore for a period of time, during which the analyte can enter and stay in the vestibule of MspA and/or continue to be unfolded or unzipped and move through the constriction zone. "A period of time", as used herein, is long enough so that the current pattern contains at least one complete event.

Some analytes, such as proteins or nucleic acid duplex with blunt end, are difficult to be unfolded in an electric field. They enter the vestibule of MspA under the action of electrophoretic force and/or electroosmotic flow and move along the direction from the vestibule to the constriction zone, but are blocked outside the constriction zone due to their size, thereby being trapped (or lodged) in the vestibule. In this case, the greater the electric potential difference between the first conductive liquid medium and the second conductive liquid medium, the deeper the analyte enters into the nanopore, it can even reach the junction between the vestibule and the constriction pore, and is lodged there. At this time, the amplitude of the blockage is the largest, the blockade signal is the strongest and the resolution is also the highest. Therefore, the resolution can be improved by increasing the potential difference, which may be equal or greater than 50 mV, equal or greater than 100 mV; equal or greater than 150 mV or equal or greater than 200 mV. The ionic current measured during the analyte is present in the vestibule may provide information about the original conformation of the analyte, which may be related to multiple aspects of the analyte, such as identity, sequence, types, interaction with an agent, etc., or any combination thereof.

After the measurement is completed, a reverse voltage can be applied to drive the analyte to move in a reverse direction (i.e., in a direction from the constriction zone to the vestibule) and exit the nanopore. Then, the voltage direction is changed again, and the next measurement can be performed. In the next measurement, different analytes or different interactions can be measured. Therefore, the method of the present invention can repeatedly use the same nanopore system for multiple detections.

Some other analytes, such as a nucleic acid with an overhanged end (such as tRNA, sRNA, or nucleic acid duplex with an overhanged end), although cannot translocate through the constriction zone of MspA in its original conformation, may be unfolded or unzipped under the action of the electric field to form a linear single-chain, which can translocate through the constriction zone of MspA. In this case, a current pattern that only contains the ionic current measured during the analyte is in the vestibule of MspA, or a current pattern that contains the ionic current measured during the analyte is in the vestibule of MspA and the ionic current measured during the unfolded or unzipped analyte translocates through the constriction zone can be used to characterize the analyte or the interaction between the analyte and an agent. The ionic current measured during the analyte is present in the vestibule may provide different information from those the ionic current measured during the unfolded or unzipped analyte is translocating through the constriction zone, for example, the ionic current measured during the analyte is present in the vestibule may provide information about the original conformation of the analyte, which may be associated with multiple aspects of the analyte, such as identity, sequence, types, interaction with an agent, etc., or any combination thereof.

A current pattern that contains at least the ionic current measured during the analyte is in the vestibule of MspA can be used to characterize the analyte itself and the interaction between the analyte and an agent. As can be understood, the current pattern that can be used to characterize the analyte itself and the interaction between the analyte and an agent may be either a current pattern that only contains the ionic current measured during the analyte is in the vestibule of MspA, or a current pattern that contains the ionic current measured during the analyte is in the vestibule of MspA and the ionic current measured during other stage (such as during the unfolded or unzipped analyte translocate through the constriction zone). The required current pattern (such as a current pattern that only contains the ionic current measured during the analyte is in the vestibule of MspA) can be extracted from a current record over a period of time, for example, according the characteristics of the current trace, e.g., blockage amplitude, etc. The person skilled in the art know how to distinguish the ionic current measured at different stage (such as during the analyte is in the vestibule of MspA or during the analyte translocate through the constriction zone of MspA). For example, the blockage amplitude of the ionic current trace during the analyte is present in the vestibule is generally shallower (which means a higher current level) than the blockage amplitude of the ionic current trace during the unfolded or unzipped analyte translocates through the constriction zone.

When the analyte itself is to be characterized, the analyte can be added in any one of the first conductive liquid medium and the second conductive liquid medium, preferably in the conductive liquid medium on the side of the vestibule of MspA, such that the analyte can enter the vestibule of MspA from the conductive liquid medium under the action of electrophoretic force and/or electroosmotic flow. When the analyte itself is to be characterized, preferably, the current is measured in absence of any agent that is capable of interacting with the analyte.

When the interaction between an analyte and an agent is to be characterized, the interaction may be the binding or dissociation of the analyte and the agent. The analyte can be any molecule with a conformation, including nucleic acid, protein, polysaccharides, polymer, enzyme, etc. The agent can be any substance that can interact, such as bind to, the analyte. Examples of the agent include ion, small molecule, ligand, receptor, substrate for an enzyme, etc. Preferably, the size of the agent allows it to pass freely through the constriction zone of MspA.

When the interaction between an analyte and an agent is to be characterized, both the analyte and the agent are added in any one of the first conductive liquid medium and the second conductive liquid medium, such that the analyte can enter the vestibule of MspA from the conductive liquid medium under the action of electrophoretic force and/or electroosmotic flow and can contact the agent. Preferably, the analyte is added in the conductive liquid medium on the side of the vestibule of MspA, such that the analyte can enter the vestibule of MspA from the conductive liquid medium under the action of electrophoretic force and/or electroosmotic flow. The agent can be added in the conductive liquid medium on the same side with the analyte, or can be added in the conductive liquid medium on the opposite side of the analyte, or can be added in the conductive liquid medium on both sides. For example, the analyte is added in the first conductive liquid medium, and the agent is added in the first conductive liquid medium, the second conductive liquid medium or both. The analyte and the agent can be added in the conductive liquid medium simultaneously or sequentially. The analyte can be brought into contact with the agent in the conductive liquid medium first, and then an electric field can be applied to drive the analyte into the vestibule of MspA, or the analyte can be first driven into the vestibule of MspA, and then the agent is added to contact the analyte.

A current pattern and a current trace, as used herein, may be used interchangeably, refer to the ionic current over time. A current pattern may contain one or more types of blockade event, and may contain one or more individual blockade events of the same type. Characteristics about distribution, frequency, amplitude, etc. of the blockade events can be learned from the current pattern.

"Event", as used herein, refers to a blockage of the nanopore by an analyte (i.e., an interval where the ionic current drops to a level which is about 5-100% lower than the unblocked current level, remains there for a period of time, and returns spontaneously to the unblocked level), and also refers to a current change caused by the blockage. The person skilled in the art know how to determine the occurrence of an event.

A variety of characteristic parameters can be obtained from the current pattern. The characteristic parameters include, but not limit to, features of individual events, such as first blockade amplitude (first $I_b$, which is also called first current level position), second blockade amplitude (second $I_b$, which is also called second current level position), dwell time ($t_{off}$), noise current level, minimum current, maximum current, median current, mean current, standard deviation, kurtosis and skewness of individual events. The characteristic parameters may further include events frequency, which is the frequency that the events of the same type occurs. The characteristic parameters may further include other features, such as blockage ratio ($\Delta I/I_0$, wherein $\Delta I=I_0-I_0$, or % $I_b$, which is defines as $(I_0-I_b)/I_0$), capture frequency ($k_{on}$, as defined by the equation $1/\tau_{on}=k_{on}\cdot c$, serves to evaluate the ability of nanopore trapping when different analytes were applied); inter-event duration ($t_{on}$), blockade current distributions and open pore current ($I_0$). One or more of these characteristic parameters can be used to characterize an analyte or the interaction between an analyte and an agent. In some embodiments, blockade amplitude (such as the first blockade amplitude and the second blockade amplitude) can be used to characterize an analyte or the interaction between an analyte and an agent, such as the identity of the analyte and/or the identity of the agent. In some embodiments, events frequency can be used to characterize an analyte or the interaction between an analyte and an agent, such as the quantity (or content) of the analyte, wherein the higher the events frequency is, the higher the analyte content is.

The characterization of an analyte, an agent or the interaction between an analyte and an agent may include associating the current pattern with at least one characteristic of the analyte, the agent the interaction between the analyte and an agent, for example, based on the features of the current pattern (such as the characteristic parameters mentioned above). Therefore, at least one characteristic of the analyte, the agent or the interaction between the analyte and an agent can be determined based on the current pattern. Generally, said characteristics or said interaction between the analyte and an agent confers the analyte a specific conformation, which corresponds to a specific current pattern through the nanopore. In other words, analytes or agents that differ in said characteristics, or different combination of the analytes and the agents will have different conformations, which correspond to different current patterns through the nanopore, such that said different analytes or agents or the different combination of the analytes and the agents can be distinguished by their respective current pattern.

The characteristics of the analyte or the agent may be any characteristic related to the conformation of the analyte or the agent, including, but not limited to, presence or absence of the analyte or the agent, the identity of the analyte or the agent, the sequence of the analyte or the agent, the mutations (such as number, position, or the identity of mutated nucleotide acids or mutated amino acids) in the analyte or the agent, the conformation of the analyte or the agent, the secondary structure, tertiary structure or local structure (such as the end structure of a nucleic acid, which may be overhanged or blunt) of the analyte or the agent, the content of the analyte or the agent, the overall size of the analyte or the agent, the charge of the analyte or the agent, the polarity of the analyte or the agent. "Identity of the analyte or the agent" refers to the distinguishing character of the analyte or the agent. Identity of the analyte or the agent may be the distinguishing character of a group of substances, which are the same regarding the distinguishing character and can be distinguished from other group of substances by the conformation. Identity may be or the distinguishing character of an individual substance. For example, the identity of an analyte or the agent may refer to that the analyte is a nucleic acid, a protein, a polysaccharide, a polymer or an enzyme. The identity of a RNA analyte may refer to that the RNA analyte is tRNA, siRNA, 5S rRNA, 16S rRNA, 18S rRNA, or 23S rRNA. The identity of a protein analyte or agent may refer to the protein is a specific protein, which can be distinguished from other specific proteins by the conformation.

"Associating the current pattern with at least one characteristic of an analyte, an agent or the interaction between the analyte and an agent" may be achieved in many ways, which may be known to the person skilled in the art. For example, at least one characteristic of an analyte, an agent or the interaction between the analyte and an agent can be determined by the features of a tested current pattern, or by comparing a tested current pattern with a reference current pattern or by a machine learning.

A tested current pattern, as used herein, refers to the current pattern obtained by using the tested analyte and/or the tested agent. Tested analyte and tested agent refer to the analyte to be characterized or the analyte and the agent involved in the interaction to be characterized.

A reference current pattern refers the current pattern used as a reference to determine at least one characteristic of the analyte or the interaction between the analyte and an agent. According to the purpose of detection, different reference current pattern can be used. For example, the reference current pattern can be a current pattern obtained by using a known analyte and/or a known agent under the same conditions with the tested current pattern. The known analyte and the known agent are called reference analyte and reference agent, respectively. It can be determined whether the tested analyte is the same with or different from the reference analyte, whether the tested agent is the same with or different from the reference agent, and how the difference is by the comparison. It can also be determined that whether the interaction between the tested analyte and the tested agent is the same with or different from the interaction between the reference analyte and the reference agent, and how the difference is. In the cases that the tested analyte is the same with the reference analyte, it can be determined whether the tested agent is the same with or different from the reference agent, and how the difference is. In the cases that the tested agent is the same with the reference agent, it can be determined whether the tested analyte is the same with or different from the reference analyte, and how the difference is.

A reference pattern may contain one or more types of blockade event, and may contain one or more individual blockade events of the same type. When comparing the tested current pattern and the reference current pattern, it is possible to compare one blockade event in the tested current pattern and one blockade event in the reference current pattern, or to compare multiple blockade events in the tested current pattern and multiple blockade events in the reference current pattern, and to determine whether the tested current pattern and the reference current pattern are the same or different. When comparing the tested current pattern and the reference current pattern, one or more of the above characteristic parameters obtained from the tested current pattern with those obtained from a reference current pattern. The skilled person knows how to compare the tested current pattern with the reference current pattern and how to determine whether they are the same or different.

The comparison can reflect whether there is a difference between the reference analyte and the tested analyte and/or a difference between the reference agent and the tested agent that cause a change of the conformation of the analyte. The comparison can also reflect whether the difference between the reference analyte and the tested analyte and/or the difference between the reference agent and the tested agent can cause a change of the conformation of the analyte. In some embodiments, to characterize the interaction between an analyte and an agent, a reference current pattern is obtained by measuring an ionic current through the protein nanopore in absence of the agent.

"Associating the current pattern with at least one characteristic of the analyte or the interaction between the analyte and an agent" may be achieved by using machine learning algorithm. In some embodiments, the step performed by using machine learning algorithm comprises: segmenting the tested current pattern into separate, unclassified events; extracting event features from the events; inputting the event features into a classifier model; predicting identity of each of the events based on the event features of each of the events in the classifier model; and outputting a result of prediction from the classifier model. The characteristics of the analyte or the interaction of the analyte and the agent can be determine by the identity of each of the events.

In some embodiments, the classifier model is trained by: segmenting the current pattern of known events to generate discrete nanopore events as training events which have known identities; extracting event features from the training events; and building the classifier model based on the event features of the training events and the known identities of the training events.

In some embodiments, the step of building the classifier model based on the event features of the training events and the known identities of the training events further comprises: inputting the event features of the training events into the classifier model; predicting the identity of each of the training events in the classifier model; and adjusting parameters of the classifier model based on the known identities of the training events so that the result of prediction is consistent with the known identities of the training events.

In some embodiments, the step of adjusting parameters of the classifier model further comprises fine-tuning parameters of the classifier model based on a validation dataset derived from the training events.

In some embodiments, the classifier model is selected and built from one of the following classifiers: Classification And Regression Tree (CART), Xgboost, Random Forest, KNN, and Gradient Boost.

Event features may be any feature that can be learned from the current pattern of an event. Preferably, the event features are specific for the event. The event features may include a variety of characteristic parameters that can be obtained from the current pattern of an event, preferably, the event features may include one or more selected from the characteristic parameters as mentioned above. For example, the event features may include one or more or all of first blockade amplitude (first $I_b$, which is also called first current level position), second blockade amplitude (second $I_b$, which is also called second current level position), dwell time ($t_{off}$), noise current level, minimum current, maximum current, median current, mean current, standard deviation, kurtosis and skewness of individual events.

"Identity of event", as used herein, refers to the distinctive character of the event, which may comprise the information of the analyte and/or the agent.

The method of the present invention can be used to determine a variety of characteristics of an analyte and/or the interaction between a variety of analytes and a variety of agents, and thus can be used in a variety of applications. The method of the present invention can be used not only to characterize a single analyte, but also to characterize multiple different analytes or multiple different interaction at the same time. Multiple different analytes and/or multiple different agents can be added to the conductive liquid medium together, and the current pattern provided by recording the ionic current in a period of time can be associated with the characteristics of each the multiple different analytes, with the interaction between each of the multiple different analytes and each of the multiple different agents. In some embodiments, multiple different analytes and one agent can be added to the conductive liquid medium together, and the current pattern provided by recording the ionic current in a period of time can be associated with the interaction between each of the multiple different analytes and the one agent. In some embodiments, one analyte and multiple different agents can be added to the conductive liquid medium together, and the current pattern provided by recording the ionic current in a period of time can be associated with the interaction between each of the multiple different agents and the one analyte.

In different applications, according to different purposes, different analytes, different agents, different reference analytes and/or and reference agents can be selected. When a machine learning algorithm is used, in different applications, different event features can be selected to train the classifier model.

The inventor found that the conformation of different types of RNA can be distinguished by the vestibule of MspA. Therefore, in some embodiments, for example, the method can be used to determine whether an analyte belongs or does not belong to a specific RNA type, such as tRNA, siRNA, rRNA (e.g., 5S rRNA, 16S rRNA, 18S rRNA, 23S rRNA). The tested current pattern may be obtained from at least the ionic current measured during the analyte is inside the vestibule of MspA, preferably without adding any agent capable of interacting with the analyte and changing the conformation of the analyte. The reference current pattern may be obtained by using one or more specific RNA type as a reference analyte. When the tested current pattern is the same with the reference current pattern, it is determined that the analyte belongs to the specific RNA type of the reference analyte. When the tested current pattern is different from the reference current pattern, it can be determined that the analyte does not belong to the specific RNA type of the reference analyte.

The inventor found that the conformation of the nucleic acid duplex with an overhanged end the nucleic acid duplex with the same duplex sequence or duplex length and blunt end can be distinguished by the vestibule of MspA. Therefore, in some embodiments, for example, the method is used to determine whether a nucleic acid duplex has an overhanged end or a blunt end, wherein the nucleic acid duplex may be a duplex consisting of two RNA sequences, a duplex consisting of two DNA sequences, or a hybrid duplex consisting of any two of sequences of DNA, RNA and other nucleic acid analogues. The nucleic acid duplex may be a siRNA. The tested current pattern may be obtained from at least the ionic current measured during the analyte is inside the vestibule of MspA, preferably without adding any agent capable of interacting with the analyte and changing the conformation of the analyte. The reference current pattern may be obtained by using a nucleic acid duplex having an overhanged end or a blunt end as a reference analyte. Preferably, the reference analyte has the same duplex sequence or duplex length with the tested analyte. When the tested current pattern is the same with the reference current pattern, it is determined that the analyte has the same type of end with the reference analyte.

In some embodiments, for example, the method can be used to identify multiple different analytes in one measurement, for example, to identify multiple different proteins or to identify the types of multiple different RNAs, for example, in a low-molecular weight (LMW) RNA profiling. The tested current pattern may be obtained by adding the multiple different analytes to the first or second conductive liquid medium, and recording the ionic current through nanopore for a period of time (such as 20 s). The identities of the analytes are determined by comparing the tested current pattern with multiple reference current patterns, respectively, or by using a machine learning algorithm.

In some embodiments, the method can be used to detect the analyte in a sample. It is not necessary to purify the analyte from the sample. The sample may be added directly to the first conductive liquid medium and the second conductive liquid medium.

In some embodiments, the method can be used to detect whether an analyte of interest is present in a sample. The tested current pattern may be obtained by adding the sample to the first or second conductive liquid medium, and recording the ionic current through nanopore for a period of time. The reference current pattern may be obtained by using the analyte of interest as a reference analyte, and the reference current pattern comprises at least the ionic current measured during the reference analyte is inside the vestibule of MspA. The appearance of the events which is the same with the events caused by the reference analyte in the reference current pattern indicates the presence of the analyte of interest in the sample. The absence of the events which is the same with the events caused by the reference analyte in the reference current pattern indicates the absence of the analyte of interest in the sample. In some embodiments, the method can be used to detect the content of an analyte of interest in a sample. The tested current pattern may be obtained by adding the sample to the first or second conductive liquid medium, and recording the ionic current through nanopore for a period of time. The reference current pattern may be obtained by using the analyte of interest with a specific content as a reference analyte and the reference current pattern comprises at least the ionic current measured during the reference analyte is inside the vestibule of MspA. The comparison of the events frequency between the tested current pattern and the reference current pattern indicates the content of the analyte of interest in the sample. Higher events frequency indicates higher content and lower events frequency indicates lower content. The content of the analyte of interest in a sample may also be quantified, for example, by the methods known in the art.

In some embodiments, a target molecule, for example, those do not have a conformation or are too small in size so that they can easily pass through the constriction zone of MspA without unzipping or unfolding, can combine with an assistant molecule to form a tested complex. The target molecule may combine with other molecule in different ways such as covalent bonds, hydrogen bonds, van der Waals forces, etc. so that the tested complex meets the analyte standards of the present invention, i.e., having a conformation, which allows the analyte to be accommodated in the vestibule of MspA, but prevents the analyte from entering and translocate through the constriction zone of MspA. The use of such a complex as the tested analyte in the method of the present invention allows for the characterization of the target molecule. For example, the use of such a complex as the tested analyte in the method of the present invention allows for the determination of one or more characteristics of the target molecule. The one or more characteristics confer the tested complex a specific conformation that can be detected by the vestibule of MspA. For example, by using a reference complex formed by the combination of a reference molecule and the same assistant molecule as the reference analyte, the difference between the target molecule and the reference molecule can be determine and the target molecule can be characterized. The difference between the target molecule and the reference molecule leads to the difference between the tested complex and the reference complex, which can be distinguished by the vestibule of MspA. The target molecule may be a peptide, a single-stranded nucleic acid (e.g., DNA or RNA, such as miRNA). The one or more characteristics of the target molecule may comprise sequence, etc.

As an example, in the characterization of a miRNA, the tested analyte may be a duplex formed by the hybridization of a miRNA and a nucleic acid probe, wherein the nucleic acid probe may be DNA, RNA or other nucleic acid analogues. It can be determined whether the sequence of the miRNA to be tested is completely complementary to or mismatched with the probe sequence, which can further determine whether the sequence of the miRNA to be tested is the expected sequence. The tested current pattern may be obtained from at least the ionic current measured during the analyte is inside the vestibule of MspA, preferably without adding any agent capable of interacting with the analyte and changing the conformation of the analyte. The reference current pattern may be obtained by using duplex consisting of the probe and a reference miRNA which is completely complementary to the probe. When the tested current pattern is the same with the reference current pattern, it is determined that the miRNA in the analyte is completely complementary to the probe. When the tested current pattern is different from the reference current pattern, it can be determined that the miRNA in the tested analyte is not completely complementary to the probe, i.e., there is a mismatch between the miRNA and the probe. According to the characteristics of the tested current pattern, it is even possible to determine the number and position of mismatched bases between the miRNA and the probe.

In some embodiments, for example, the method can be used to determine whether a mutation of a protein cause its conformation to change. The analyte may be a mutated protein, and the tested current pattern may be obtained from at least the ionic current measured during the mutated protein is inside the vestibule of MspA, preferably without adding any agent capable of interacting with the analyte and changing the conformation of the analyte. The reference current pattern may be obtained by using a parental protein as a reference analyte. When the tested current pattern is different from the reference current pattern, it can be determined that the mutation of the protein cause a conformation change.

The inventors found that the interaction between an analyte and an agent may cause the change of the conformation of the analyte, which may be detected by the vestibule of MspA. Therefore, in some embodiments, for example, the method can be used to determine the interaction between analyte and an agent (such as the presence of the interaction). The analyte can be any molecule with a conformation, including nucleic acid, protein, polysaccharides, polymer, enzyme, etc. The agent can be any substance that can interact, such as bind to, the analyte. Examples of the agent include ion, small molecule, ligand, receptor, substrate for an enzyme, etc. Preferably, the size of the agent allows it to pass freely through the constriction zone of MspA. Preferably, the interaction between an analyte and an agent is capable of causing the change of the conformation of the analyte In some embodiments, for example, the method can be used to determine whether the tested agent can interact with a known analyte. The tested current pattern can be obtained from at least the ionic current measured during the known analyte is inside the vestibule of MspA in presence of the tested agent. The reference current pattern may be obtained from at least the ionic current measured during the known analyte is inside the vestibule of MspA in absence of an agent capable of interacting with the known analyte. In some embodiments, when the tested current pattern has a change compared with the reference current pattern, it can be determined that the tested agent can interact with said known analyte.

The method can also be used to determine whether the tested analyte can interact with a known agent. The tested current pattern may be obtained from at least the ionic current measured during the tested analyte is inside the vestibule of MspA in presence of the known agent. The reference current pattern may be obtained from at least the ionic current measured during the tested analyte is inside the vestibule of MspA in absence of an agent capable of interacting with the tested analyte. In some embodiments, when the tested current pattern has a change compared with the reference current pattern, it can be determined that the tested analyte can interact with said known agent.

The method can also be used to determine whether a sample comprises an agent capable of interacting with the analyte. The tested current pattern may be obtained from at least the ionic current measured during the analyte is inside the vestibule of MspA in presence of the sample. The reference current pattern may be obtained from at least the ionic current measured during the analyte is inside the vestibule of MspA in absence of an agent capable of interacting with the analyte. In some embodiments, when the tested current pattern has a change compared with the reference current pattern, it can be determined that the sample comprises an agent capable of interacting with the analyte. In some embodiments, the reference current pattern can be obtained from at least the ionic current measured during the analyte is inside the vestibule of MspA in presence of a specific agent capable of interacting with the analyte, and when the tested current pattern is the same with the reference current pattern, it can be determined that the sample comprises said specific agent.

The method can also be used to characterize an agent capable of interacting with the analyte. The tested current pattern may be obtained from at least the ionic current measured during the analyte is inside the vestibule of MspA in presence of the agent capable of interacting with the analyte, i.e., the ionic current measured during the complex of the analyte and the agent is inside the vestibule of MspA. The reference current pattern may be obtained from at least the ionic current measured during the analyte is inside the vestibule of MspA in absence of an agent capable of interacting with the analyte. In some embodiments, when the tested current pattern has a change compared with the reference current pattern, the agent capable of interacting with the analyte can be characterized. In some embodiments, the reference current pattern can be obtained from at least the ionic current measured during the analyte is inside the vestibule of MspA in presence of a specific agent capable of interacting with the analyte, and when the tested current pattern is the same with the reference current pattern, it can be determined that the agent to be characterized is said specific agent and the concentration of the agent to be characterized may also be determined.

In some embodiments, the analyte may be a protein, such as an enzyme. The agent to be characterized is capable of interacting with the protein. Examples of the agent include, but are not limited to, a cofactor, a ligand or a receptor of the protein, or a substrate of an enzyme. The agent includes, but is not limited to ion, small molecule compound, nucleic acid, protein, peptide, polysaccharides, polymer. In some embodiments, the analyte is lysozyme. In some embodiments, the agent capable of interacting with the analyte may be polysaccharides substrate of lysozyme, such as peptidoglycan, chitosan, chitin, etc., for exam n acetylchitohexaose. Therefore, the method of the present may be used to characterize polysaccharides through the interaction between the polysaccharides and lysozyme.

The method can also be used to determine whether the mutation site of a protein mutant is the site where the parental protein interacts with a specific agent. The tested current pattern may be obtained from at least the ionic current measured during the protein mutant is inside the vestibule of MspA in presence of the agent. The reference current pattern may be obtained from at least the ionic current measured during the parental protein is inside the vestibule of MspA in presence of the agent. When the tested current pattern has a change compared with the reference current pattern, it can be determined that the mutation site of a protein mutant is the site where the parental protein interacts with the specific agent.

The method can also be used to detect or distinguish between wild-type and mutant of a protein or a nucleic acid, different mutants of a protein or a nucleic acid, different states of a protein (for example, binding to or not binding to a cofactor, receptor, ligand or a substrate (e.g., for an analyte such as enzyme)), etc., as long as what will be distinguished have different conformations.

Analytes and Agents

The analyte used herein should be a molecule that is smaller than the vestibule of MspA and bigger than the constriction zone of MspA in size. The size of the analyte is determined by its conformation. Therefore, the analyte used herein has a conformation, which allows the analyte to be accommodated in the vestibule of MspA, but prevents the analyte from entering and translocate through the constriction zone of MspA. That is to say, when the analyte is in its conformation, it can be accommodated in the vestibule of MspA, but cannot translocate through the constriction zone of MspA.

The analyte can be charged or neutral, and can be positively or negatively charged, for example, in a buffer, such as in the first conductive liquid medium and the second conductive liquid medium. The analyte preferably can be dissolved in the buffer, or can be moved under the action of an electric field or electroosmotic flow. The conformation may be a secondary structure, a tertiary structure, or a three-dimensional structure. The conformation may be the natural conformation of the analyte, that is, the conformation when it functions. The conformation may be the conformation when the analyte is in a buffer, such as in the first conductive liquid medium and the second conductive liquid medium. In some embodiments, the analyte has its natural conformation when it is in a buffer, such as in the first conductive liquid medium and/or the second conductive liquid medium.

When the components of the analyte change, or when a certain agent interacts with the analyte, it may cause the conformation of the analyte to change, which can be detected by the method of the present invention, thereby characterizing the analyte or the interaction between the analyte and the agent.

The analyte can be any molecule with a conformation, including nucleic acid, protein, peptide, polysaccharides, polymer, enzyme, etc., or a complex of any two or more of them. The analyte may also be a complex of nucleic acid, protein, peptide, polysaccharides, polymer, enzyme, etc. and an agent capable of interacting with them, such as their cofactor, ligand, receptor, substrate, etc.

The nucleic acid may be a LMW RNA (Low molecular weight RNA, typically <200 nt, such as a tRNA, a siRNA, a rRNA (e.g., 5S rRNA, 16S rRNA, 18S rRNA, 23S rRNA), a miRNA), a aptamer, a ribozyme, a nucleic acid duplex or a RNA with specific structure (such as kissing loop, three-way junction, pseudoknot, kink-turn or G-quadruplex). The nucleic acid duplex may have an overhanged end or a blunt end. The nucleic acid duplex may be a duplex consisting of two RNA sequences, a duplex consisting of two DNA sequences, or a hybrid duplex consisting of any two of sequences of DNA, RNA and other nucleic acid analogues. The nucleic acid duplex may be consisted of a miRNA and a nucleic acid probe, and the nucleic acid probe is a RNA, a DNA or a nucleic acid analogue.

"Nucleic acid analogues", as used herein, refer to are compounds which are analogous (structurally similar) to naturally occurring RNA and DNA. Nucleic acids are chains of nucleotides, which are composed of three parts: a phosphate backbone, a pentose sugar, either ribose or deoxyribose, and one of four nucleobases. An analogue may have any of these altered. Nucleic acid analogues may be distinguished from naturally occurring DNA or RNA by changes to the backbone of the molecule. Nucleic acid analogues include, but not limit to, arabino nucleic acids (ANA), bridged nucleic acid (BNA), cyclohexenyl nucleic acid (CeNA), 2'-fluoroarabino nucleic acids (FANA), glycol nucleic acid (GNA), hexose nucleic acid (HNA), locked nucleic acid (LNA), morpholino, peptide nucleic acid (PNA), threose nucleic acid (TNA).

"Protein", as used herein, may include an individual protein, a subunit of a protein, a mixture of different kinds of proteins, and a protein complex. "Protein complex", as used herein, may refer to a complex formed by interaction between two or more individual proteins or subunits thereof. Examples of protein include calmodulin, lysozyme, myoglobin, ACTR/NCBD complex, whey protein, α-lactalbumin and β-lactoglobulin.

The protein or peptide which is used as an analyte may have a secondary structure, a tertiary structure, or a quaternary structure formed by folding an amino acid sequence. The secondary structure may include, for example, α-helix, β-sheet, β-turn, etc. The tertiary structure may include a three-dimensional structure formed by hydrogen bonds, ionic bonds, hydrophobic interactions, disulfide bonds, etc. on the basis of the secondary structure of the amino acid sequence. The quaternary structure may include, for example, a structure formed of two or more subunits.

The protein or peptide which is used as an analyte may have different isoelectric point (pI), such as an isoelectric point (pI) of about 7.0, a protein with pI less than about 7.0, and a protein with pI of about 7.0. An isoelectric point (pI) of about 7.0 may be in the range of about 6.5 to about 7.5. pI less than about 7.0 includes pI less than about 6.5, less than about 6.0, less than about 5.5, less than about 5.0, less than about 4.5, less than about 4.0, etc. pI greater than 7.0 includes pI greater than about 7.5, greater than about 8.0, greater than about 8.5, greater than about 9.0, greater than about 9.5, greater than about 10.0, etc.

The analyte may comprise two or more different analytes. For example, the analyte comprises different LMW RNA or different proteins. In some embodiments, the different proteins or peptides may be independently selected from the group consisting of neutral protein, positively charged protein and negatively charged protein. In some embodiments, the different proteins or peptides may be independently selected from the group consisting of a protein with pI of about 7.0, a protein with pI less than about 7.0, and a protein with pI greater than about 7.0. In some embodiments, the analyte comprises all of neutral protein, positively charged protein and negatively charged protein. In some embodiments, the analyte comprises two or three of neutral protein, positively charged protein and negatively charged protein. In some embodiments, the analyte comprises two or three of a protein with an isoelectric point (pI) of about 7.0, a protein with a pI less than about 7.0, and a protein with a pI greater than about 7.0.

The analyte can be an analyte that is capable of interacting with (such as binding to) an agent. Examples of the agent that can interact with the analyte herein include ion, small molecule, ligand, receptor, cofactor, substrate for an enzyme, etc. Preferably, the size of the agent allows it to pass freely through the constriction zone of MspA. The agent preferably can be dissolved in the buffer, or can be moved under the action of an electric field or electroosmotic flow.

"Small molecule", as used herein, refer to a low molecular weight organic compound or peptide, e.g., <900 daltons, or with a size on the order of 1 nm.

In some embodiments, the analyte or the agent can be comprised in a sample. The sample may be a blood, a serum, a plasma, cerebrospinal fluid, a body fluid derived from a subject, or a sample from a tissue or organ of the subject. The subject may be an animal or a plant, wherein the animal may be a mammal, including human. The sample can also be a sample derived from the environment, such as from water or soil, etc. The analyte can be a biomarker, such as a disease biomarker.

The sample may also be a food, a beverage, a healthy product which comprises the analyte, and the analyte may be a nutritional ingredient or a harmful ingredient in the food, the beverage or the healthy product. The sample may also be a medicament which comprises the analyte as an active ingredient or a harmful ingredient. In some embodiments, the sample may be milk (such as liquid milk or milk powder) or protein powder, and the method of the present invention may be used to detect the concentration of some proteins in the sample. For example, the method of the present invention may be used to detect the concentration of whey protein, especially α-lactalbumin and/or β-lactoglobulin in milk or protein powder, which can be used to evaluate the quality of milk or protein powder. This allows people to abandon the traditional method of evaluating the protein content in milk or protein powder by detecting nitrogen, and directly determine the protein content in milk or protein powder, so that no misjudgment will occur.

The analyte or the agent may not be purified from the sample. The sample may be directly added to the first conductive liquid medium and/or the second conductive liquid medium. For samples in non-liquid form, the sample can be directly added to the first conductive liquid medium and/or the second conductive liquid medium to dissolve and then measured, or the sample can be formulated into a solution or suspension first, and then added to the first conductive liquid medium and/or the second conductive liquid medium.

In some embodiments, the analyte is a complex formed by the combination of a target molecule and an assistant molecule. The target molecule may combine with the assistant molecule in different ways such as covalent bonds, hydrogen bonds, van der Waals forces, etc. so that complex meets the analyte standards of the present invention, i.e., having a conformation, which allows the analyte to be accommodated in the vestibule of MspA, but prevents the analyte from entering and translocate through the constriction zone of MspA. The use of such an analyte in the present method may facilitate characterization of the target molecule. In some embodiments, the target molecule is miRNA.

EXAMPLES

Example 1: Structural-Profiling of Low Molecular Weight (LMW) RNAs by Nanopore Trapping/Translocation Using *Mycobacterium smegmatis* Porin A (MsPA)

1. Single Molecule Sensing of miRNA

Figure 3:
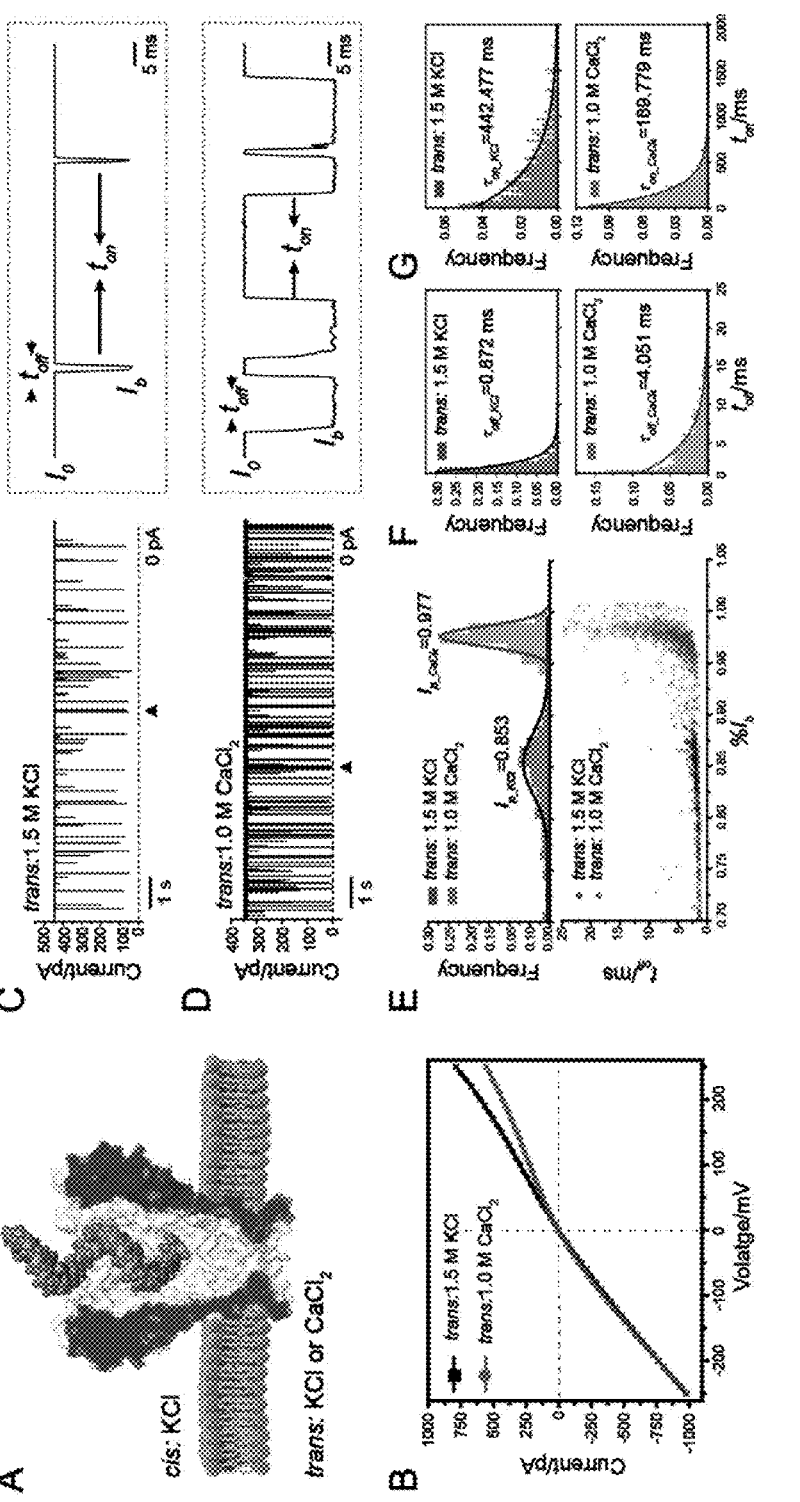
FIG. 3 shows retarded translocation of hsa-miR-21 through MspA. A. A schematic diagram of hsa-miR-21 translocation through MspA. A single MspA is inserted in a lipid membrane separating the cis and the trans chambers. The cis chamber was filled with 1.5 M KCl buffer and the trans chamber with a 1.5 M KCl or a 1 M $CaCl_2$) buffer. Hsa-miR-21 was added to cis with a final concentration of 200 nM. A transmembrane potential of +150 mV was continuously applied. B. Current-voltage (I-V) curves of MspA. Different combinations of electrolyte buffers were applied and no analytes were added. C. Left: A representative trace containing successive hsa-miR-21 translocations. The measurement was performed with a 1.5 M KCl buffer in both cis and trans. Dashed box: a zoomed-in view of the section marked with a triangle on the trace. The open pore current ($I_o$), blockage current ($I_b$), dwell time ($t_{off}$) and inter-event duration ($t_{on}$) are marked. D. Left: A representative trace containing successive hsa-miR-21 translocations. The measurement was performed with a 1.5 M KCl buffer in cis and a 1 M $CaCl_2$ buffer in trans. Dashed box: a zoomed-in view of the section marked with a triangle on the trace. In this condition, translocation events appear more frequently and are systematically retarded when compared with those in C. E. Bottom: Scatter plot of % $I_b$ versus $t_{off}$ for hsa-miR-21 translocations. % $I_b$ is defined as $(I_o-I_b)/I_o$. Top: The corresponding histogram of % $I_b$. % $I_b$ is larger and more uniformly distributed when a 1 M $CaCl_2$) buffer in trans was applied. F. The event histogram of $t_{off}$ for hsa-miR-21 translocations. G. The event histogram of $t_{on}$ for hsa-miR-21 translocations. The histogram in F and G were single exponential fitted according to the equation $y=a*exp(-x/r)$. The mean dwell time ($\tau_{off}$) or the mean inter-event interval ($\tau_{on}$) was respectively derived from the fitting results. Events with a dwell time <1 ms were ignored during the statistics.

Electrophysiology measurements were performed as described in Methods using the M2 MspA mutant (D93N/D91N/D90N/D118R/D134R/E139K)[32] (FIG. 3A). If not otherwise stated, this mutant is referred to as MspA throughout this paper. Following the recently developed nanopore sensing strategy[33], in which the presence of a calcium flux around the pore vicinity extends the dwell time of nucleic acid translocation, a 1.5 M KCl buffer (1.5 M KCl, 10 mM HEPES, pH 7.0) was placed in cis and a 1 M $CaCl_2$ buffer (1 M $CaCl_2$, 10 mM HEPES, pH 7.0) was placed in trans. According to the current-voltage characterization, the placement of a 1 M $CaCl_2$ buffer instead of a 1.5 M KCl buffer in trans reduces the open pore current only slightly when a positive potential is applied (FIG. 3B).

Figure 4:
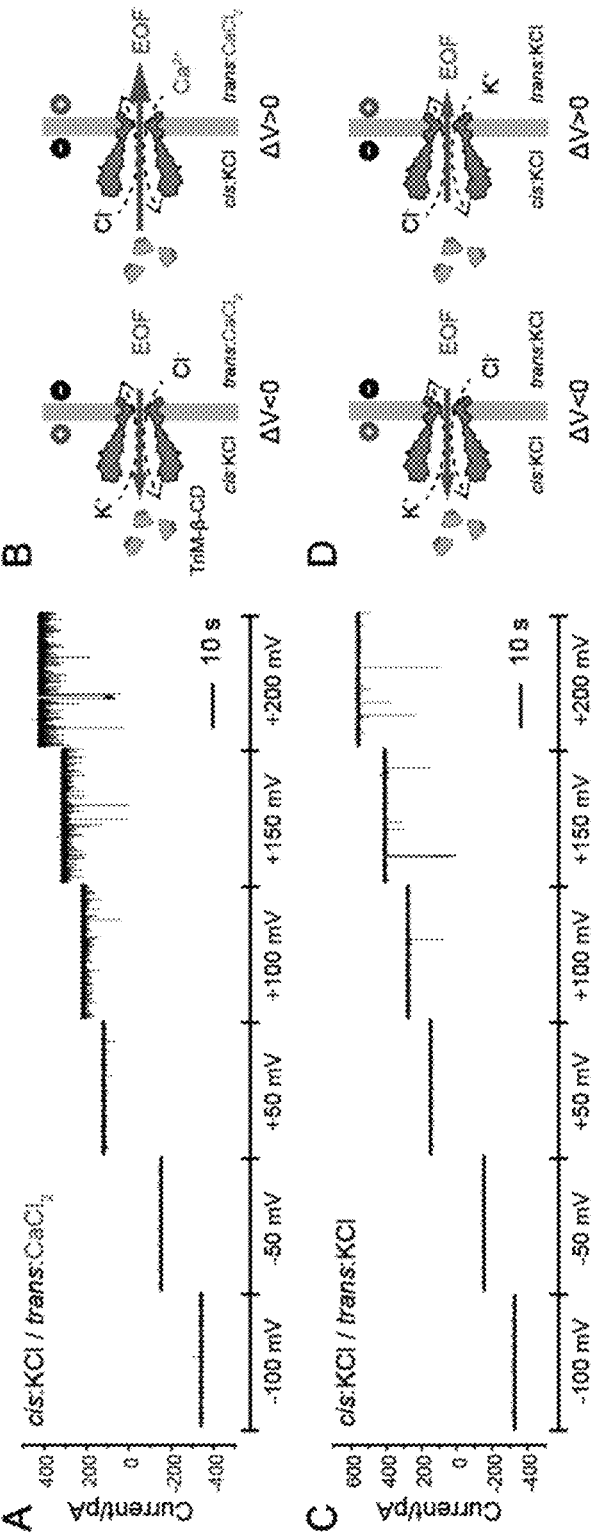
FIG. 4 shows experimental evidence of EOF in MspA. Similarly to previous studies[92, 93], EOF in MspA was determined by observing the voltage-dependence of events generated by neutral analytes. Trimethyl-β-cyclodextrin (TriM-β-CD) was applied as the analyte. A. Voltage dependence of TriM-β-CD sensing using MspA when a 1.5 M KCl buffer and a 1 M $CaCl_2$ buffer were separately added to cis and trans. The rate of event appearance increased at a higher applied potential. No events were observed at negative potentials. It implies that an EOF from cis to trans exists in MspA when a potential was applied. B. Cartoon diagrams of the EOF flow in MspA at negative (left) and positive (right) potentials. The direction of EOF was indicated with the red arrow. C. Voltage dependence of TriM-β-CD sensing using MspA in a symmetric 1.5 M KCl buffer. The rate of event appearance was lower than that demonstrated in A. However, slightly more events were observed at a higher potential, indicating the existence of a weak EOF. D. Cartoon diagrams of the EOF flow in MspA at negative (left) and positive (right) potentials. The direction of EOF was indicated with the red arrow. The measurements in (A, C) were performed as described in Methods. The applied potential was indicated in the x axis of (A, C). TriM-β-CD was added to cis with a final concentration of 2 mM.
Figure 5:
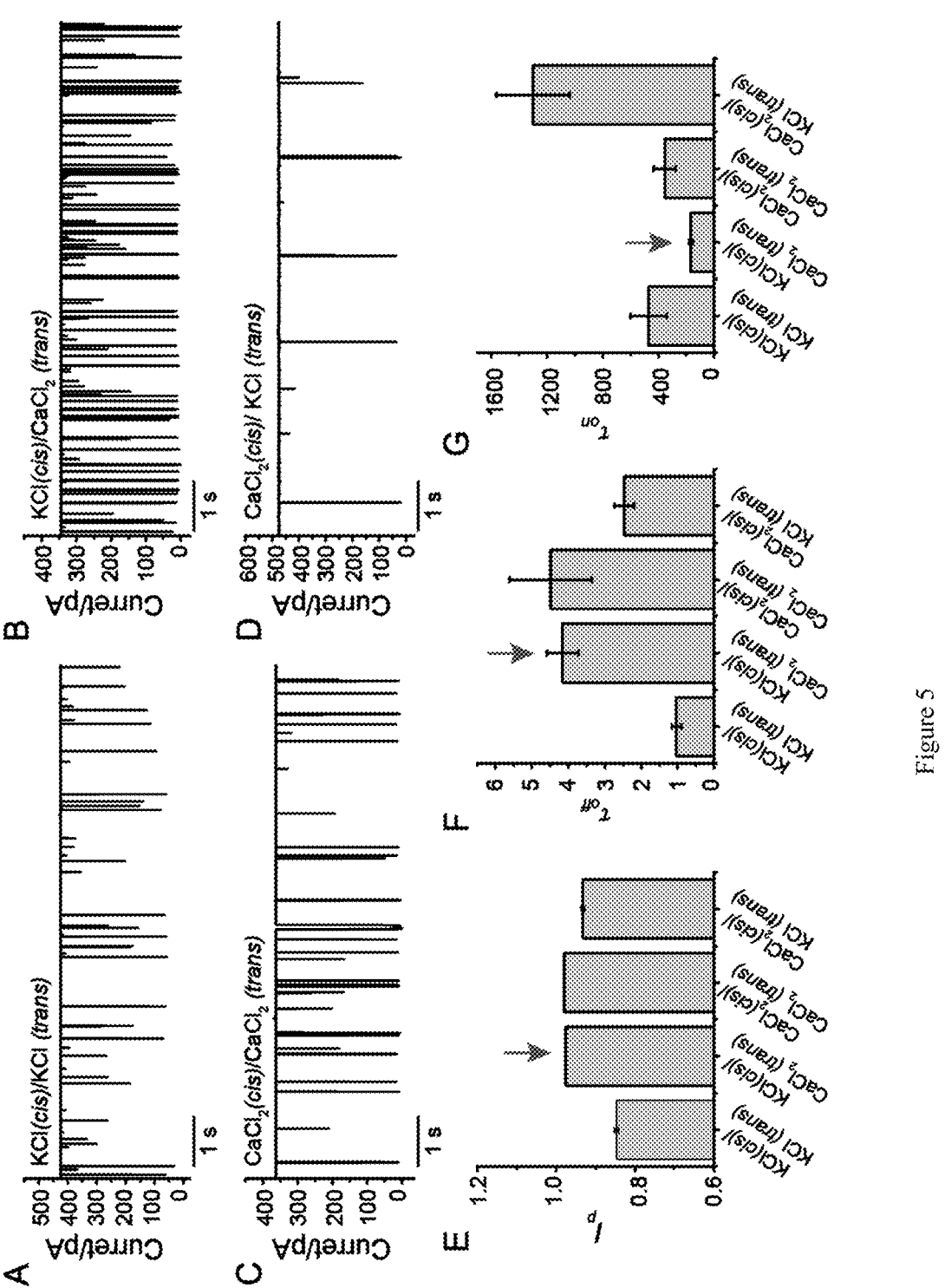
FIG. 5 shows miRNA sensing with varied salt combinations. A-D. Representative traces of miRNA sensing performed with a buffer of 1.5 M KCl (cis)/1.5 M KCl (trans) (A), 1.5 M KCl (cis)/1 M $CaCl_2$ (trans) (B), 1 M $CaCl_2$ (cis)/1 M $CaCl_2$ (trans) (C) or 1.5 M $CaCl_2$ (cis)/1.5 M KCl (trans) (D). E. $I_p$ of miRNA events with varied salt combinations. F. $\tau_{off}$ of miRNA events with varied salt combinations. G. $\tau_{on}$ of miRNA events with varied combinations. The red arrows indicate the asymmetric KCl/$CaCl_2$ buffer condition we used in our manuscript. Three independent measurements were conducted for each condition to form the statistics. Has-miR-21 was added to cis with a final concentration of 200 nM. A voltage of +150 mV was continuously applied during the measurements.
Figure 6:
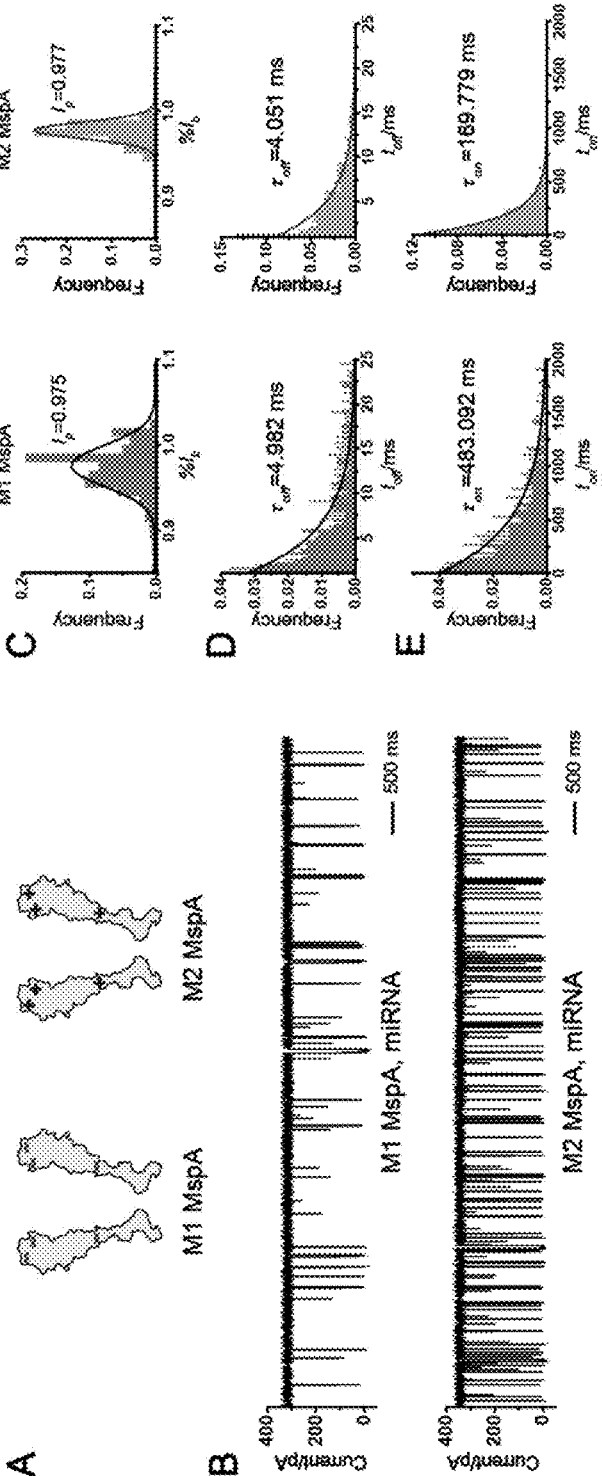
FIG. 6 shows miRNA sensing with M1 or M2 MspA. A. The internal charge distribution of MspA mutants (the M1 or M2 MspA). B. Representative current traces of miRNA translocations through an M1 or M2 MspA. C. Histogram of miRNA translocation events performed with M1 or M2 MspA. D. Histogram of $t_{off}$ of miRNA translocation events performed with M1 or M2 MspA. E. Histogram of $t_{on}$ of miRNA translocation events performed with M1 or M2 MspA. Due to the presence of positively charged amino acids in the pore lumen, the M2 MspA shows a higher capture rate of RNA molecules. Electrophysiology measurements were performed in 1.5 M KCl (cis)/1 M $CaCl_2$ (trans). MiRNA was added to cis side with a final concentration of 200 nM. A voltage of +150 mV was continuously applied during the measurements.

Hsa-miR-21, which is one of the first identified mammalian microRNAs (miRNA) and has been well investigated as multiple cancer biomarkers[34], was custom synthesized and treated as a model miRNA to test the method (Table 1). Experimentally, after the addition of hsa-miR-21 with a 200 nM final concentration to cis and with a +150 mV constantly applied potential, successive resistive pulses immediately appeared in both experiments. The open pore current ($I_o$), the blockage amplitude ($I_b$), the dwell time ($t_{off}$) and the inter-event interval ($t_{on}$) are defined in FIGS. 3C and 3D. The percentage blockade % $I_b$ is determined from $(I_o - I_b)/I_o$. With the buffer combination of 1.5 M KCl (cis)/1.5 M KCl (trans), translocation events of hsa-miR-21 appeared as extremely short-residing spikes as demonstrated in FIG. 3C. However, with the combination of 1.5 M KCl (cis)/1 M $CaCl_2$ (trans) while keeping all other conditions identical, the rate of event appearance was significantly increased. The event dwell time was dramatically extended and the blockage amplitude ($I_b$) became more uniformly distributed (FIG. 3D). This difference is more quantitatively demonstrated in the event scatter plot of % $I_b$ vs $t_{on}$ and the corresponding histogram of % $I_b$, from which the mean blockage amplitude $I_p$ was determined from the Gaussian fitting results (FIG. 3E, Table 2). Histograms of $t_{off}$ and $t_{on}$ for both conditions were demonstrated in FIGS. 3F and 3G. The histograms were singly exponentially fitted, from the results of which the mean dwell time ($\tau_{off}$) and the mean inter-event interval ($\tau_{on}$) were derived. The results shown in FIGS. 3C-3G clearly demonstrate that with all other conditions identical, a change of electrolyte buffer in trans to $CaCl_2$ resulted in a dramatic increase in the rate of event appearance and event dwell time. The higher rate of event appearance should result from an increased electroosmotic flow induced by coordination interactions between $Ca^{2+}$ and amino acid residues in the pore lumen (FIG. 4). $Ca^{2+}$ is known to stabilize RNA structure via efficient electrostatic charge screening or coordination binding, which have contributed to the extended dwell time. We have also performed hsa-miR-21 sensing with other electrolyte buffer combinations (FIG. 5) and different MspA mutants (FIG. 6). These results further confirm that an asymmetric buffer combination and the choice of M2 MspA are optimal for RNA structural profiling.

TABLE 1

Nucleic acid abbreviations and sequences.

| abbreviations | sequences (5'-3') |
|---|---|
| hsa-miR-21 | UAGCUUAUCAGACUGAUGUUGA |
| siFoxA1-a | CUUACGCUGAGUACUUCGAAA |
| siFoxA1-b | UCGAAGUACUCAGCGUAAGUG |
| luciferase siRNA-a | AGCAAUAGUUCACGCUGAAAG |
| luciferase siRNA-b | CUUUCAGCGUGAACUAUUGCU |

Footnote:
siFoxA1 was prepared by the hybridization of siFoxA1-a and siFoxA1-b. Luciferase siRNA was prepared by the hybridization of luciferase siRNA-a and luciferase siRNA-b.

TABLE 2

Statistics for hsa-miR-21 sensing in different buffers. All measurements were performed as described in Methods. Hsa-miR-21 was added to cis with a final concentration of 200 nM. $I_p$ was derived from Gaussian fitting results. $\tau_{off}$ and $\tau_{on}$ were derived from single exponential fitting results. All statistical results were from 5-min continuous recordings for each condition. $\overline{I_p}$, $\overline{\tau_{off}}$ and $\overline{\tau_{on}}$ were mean values of $I_p$, $\tau_{off}$ and $\tau_{on}$ from three independent measurements, respectively.

| cis | trans | $\overline{I_p}$ | $\overline{\tau_{off}}$/ms | $\overline{\tau_{on}}$/ms |
|---|---|---|---|---|
| 1.5M KCl | 1.5M KCl | 0.847 ± 0.006 | 1.02 ± 0.14 | 470 ± 120 |
| 1.5M KCl | 1.0M $CaCl_2$ | 0.976 ± 0.001 | 4.2 ± 0.4 | 165 ± 12 |
| 1.0M $CaCl_2$ | 1.0M $CaCl_2$ | 0.980 ± 0.000 | 4.5 ± 1.1 | 350 ± 80 |
| 1.0M $CaCl_2$ | 1.5M KCl | 0.933 ± 0.005 | 2.5 ± 0.3 | 1300 ± 300 |

2. Single Molecule Sensing of siRNA

Figure 9:
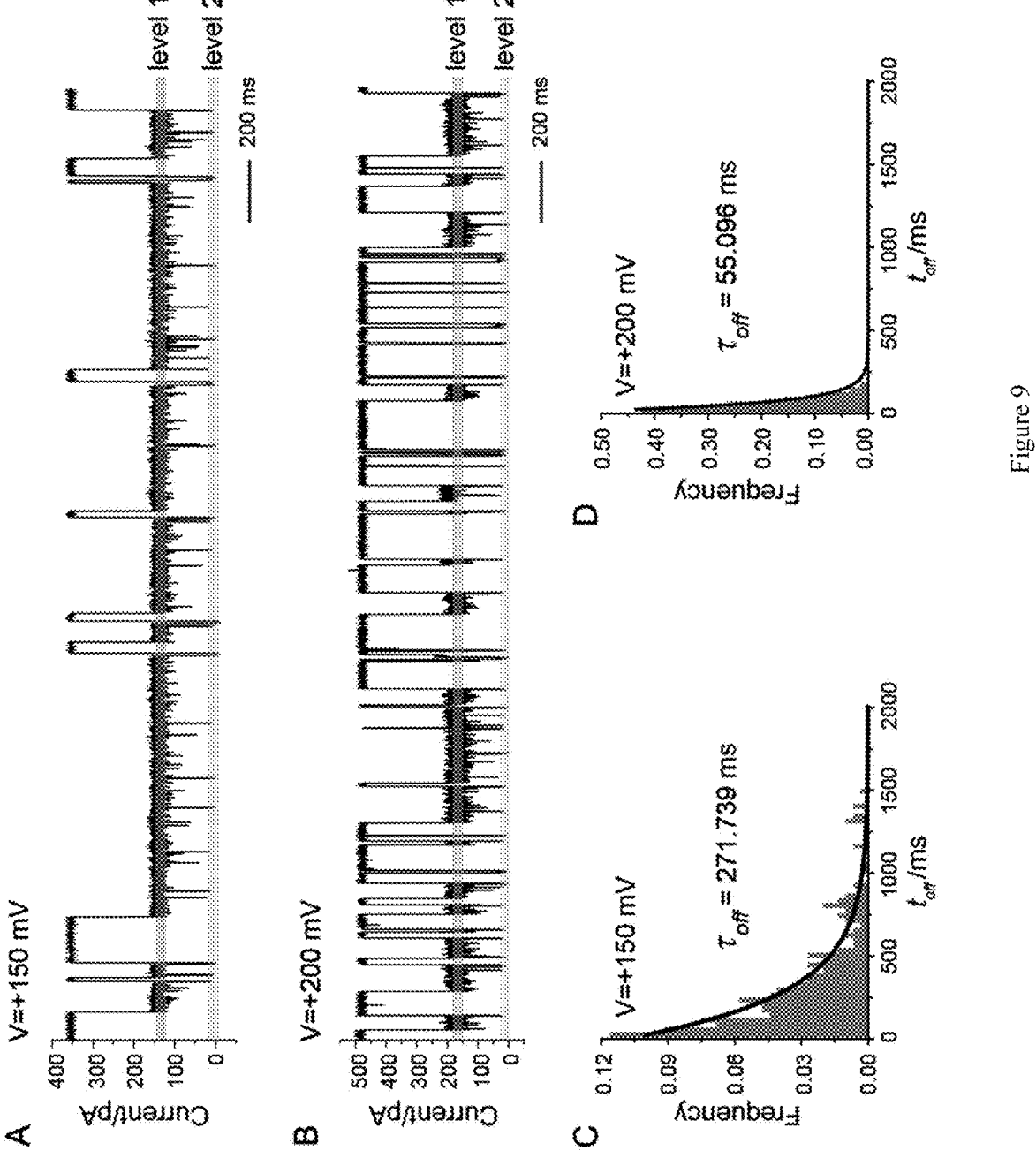
FIG. 9 shows overhanged siRNA translocation events at different voltages. A. A representative trace of overhanged siRNA translocation acquired at +150 mV. B. A representative trace of overhanged siRNA translocation acquired at +200 mV. With a strong electrophoretic force applied, events caused by overhanged siRNA appears with a significantly reduced dwell time of level 1, indicating that the analyte has translocated through the pore. C. The event histogram of $t_{off}$ of level 1 at +150 mV D. The event histogram of $t_{off}$ of level 1 at +200 mV. Nanopore measurements were performed as described in Methods. Hybridized overhanged siFoxA1 (Materials, Table 1) was added in cis with a final concentration of 200 nM.

Small interfering RNA (siRNA), measuring 20-25 bp in length, appears as a RNA duplex with 2-nt 3'-overhangs or blunt ends and plays a central role in gene silencing[35]. This duplex of siRNA is conformationally more confined than that of dsDNA and is primarily in the A form[36]. The duplex of siRNA has a cross sectional diameter of ~2.4 nm[37], larger than that of the MspA constriction, indicating that a direct translocation of siRNA through MspA is geometrically restricted (FIG. 7A). To the best of our knowledge, previous attempts of siRNA translocation through an MspA have not been reported.

siFoxA1, which inhibits the expression of Forkhead protein FoxA1, is a 19-bp siRNA duplex with overhanging nucleotides on each end[38] (Table 1, FIG. 7B). After the addition of siFoxA1 to cis with a final concentration of 200 nM, successive appearance of two-step blockade events was immediately observed during nanopore measurements (FIG. 8). The first blockage level, measuring 0.600±0.006 (n=3) in $\overline{I_p}$ and a mean dwell time of a few hundred milliseconds, may represent the state when the siFoxA1 was accommodated in the pore vestibule. Immediately subsequent to this, the second blockage level, measuring 0.932±0.004 (n=3) in $\overline{I_p}$ and with a much shorter dwell time of a few milliseconds, may represent the state when the siFoxA1 was electrophoretically unfolded, allowing for a linearized, single stranded portion of the analyte reaching the pore constriction and eventually generating a full translocation (FIG. 8, FIG. 7C, D). By raising the applied potential to +200 mV, the dwell time of level 1 was significantly shortened (FIG. 9). This is expected because an enhanced electrophoretic force would reduce the dwell time of siFoxA1 in its native folded state, further supporting the suggested model of translocation. Though the siRNA eventually translocates through the pore, the most characteristic event feature $\overline{I_p}$, measuring 0.600±0.006 (n=3) was obtained during the trapping stage.

Figure 10:
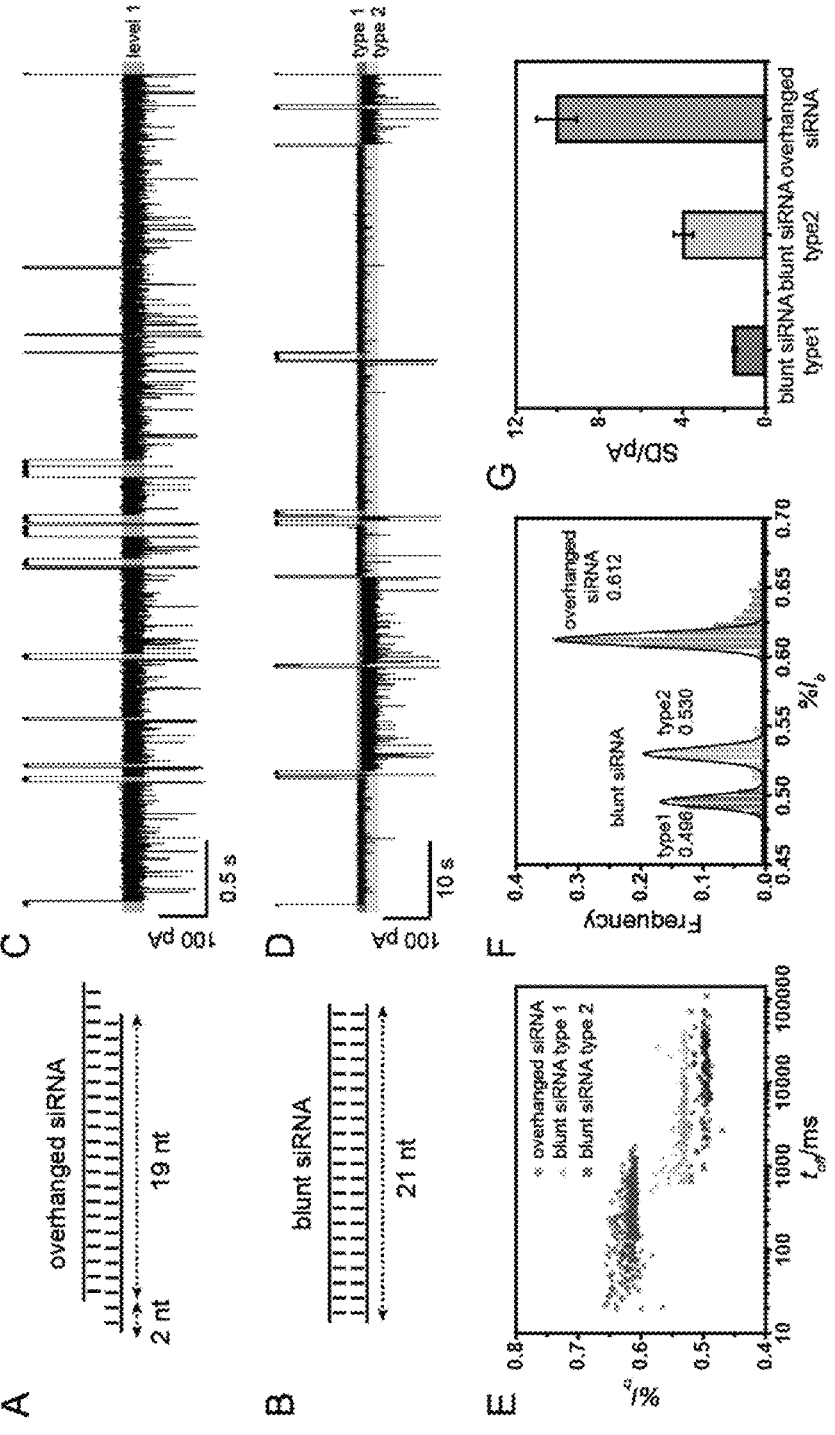
FIG. 10 shows discrimination of overhanged and blunt siRNA with MspA. A-B. The secondary structures of overhanged and blunt siRNA. C. Representative trace of overhanged siRNA sensing with MspA. Characteristic events appear as a two-step blockade. D. Representative trace of blunt siRNA sensing with MspA. Two types of signals with different blockade amplitudes are observed. E. A scatter plot of $t_{off}$ versus % $I_b$ for two RNA samples (the scatter plots from top to bottom correspond to overhanged siRNA, blunt siRNA type 1 and blunt siRNA type 2, respectively). Events from two types of RNAs are clearly distinguishable. F. The corresponding event histogram of % $I_b$ of two RNA samples. Black lines are Gaussian fittings to the data. G. Standard deviation of characteristic levels (marked in C and D) for two RNA samples. 20 events of each types were analyzed to form the statistics. Electrophysiology measurements were performed in 1.5 M KCl (cis)/1 M CaCl$_2$ (trans). RNA was added to cis side with a final concentration of 200 nM. A voltage of +150 mV was applied during the measurements.
Figure 11:
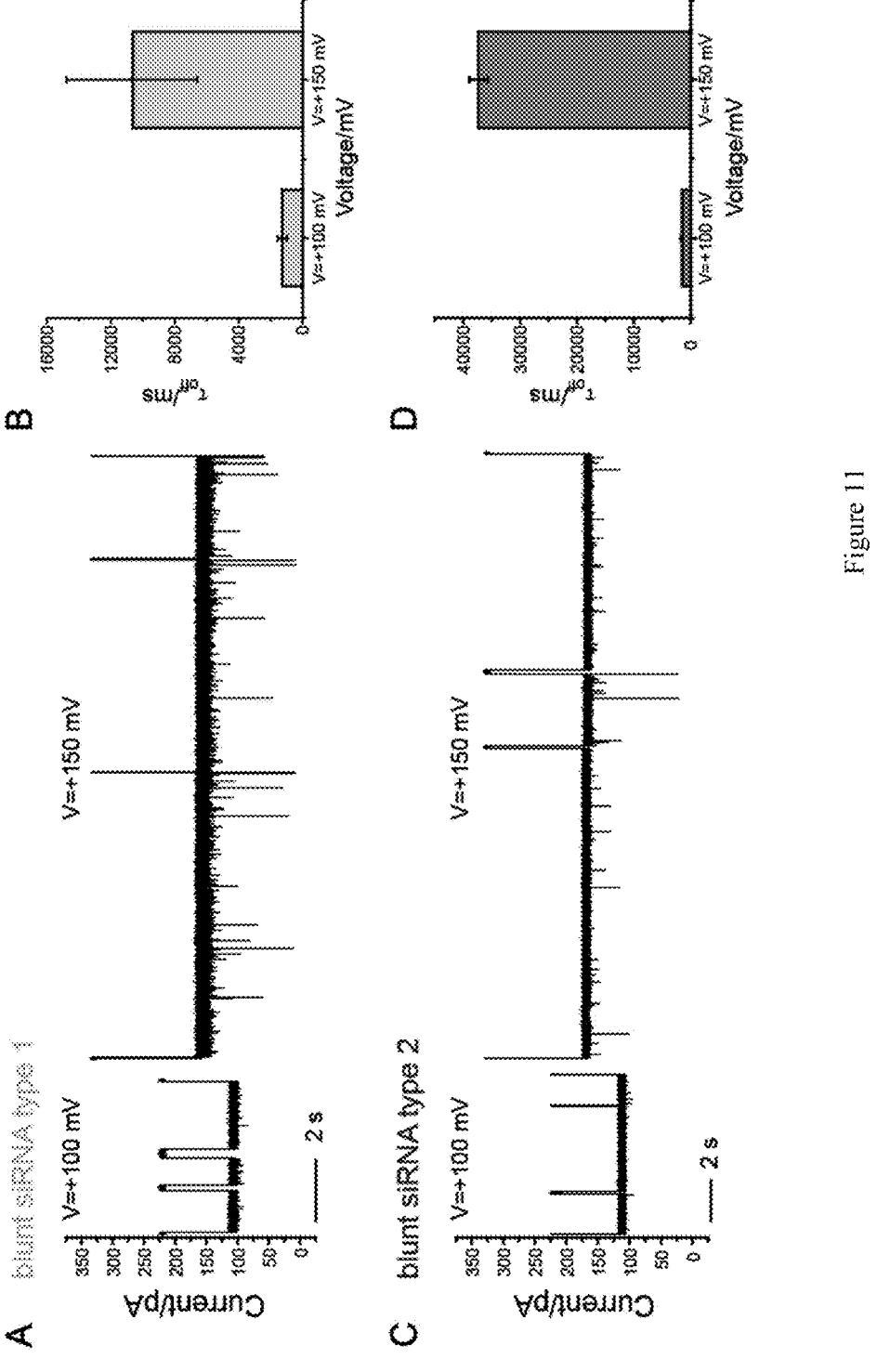
FIG. 11 shows blunt siRNA translocation events at different voltages. A. Representative type 1 events at +100 mV and +150 mV. The event dwell time is extended when the applied potential is increased. B. $\tau_{off}$ of type 1 events at different voltages. C. Representative type 2 events at +100 mV and +150 mV. The dwell time increases when the applied potential is increased. D. $\tau_{off}$ of type 2 events at different voltages. The reported events result from nanopore trapping instead of translocation. All measurements were carried out as described in Methods. Blunt siRNA was added to cis with a final concentration of 200 nM. Three independent measurements were performed for each condition to form the statistics (B, D).

Luciferase siRNA[39], a 21-bp duplex and an inefficient silencing structure[40], was employed as a model blunt siRNA (Table 1, FIG. 7B). With the addition of luciferase siRNA to cis with a final concentration of 200 nM, two types of event, termed type 1 and type 2, were immediately observed (FIG. 10, FIG. 7C, D), which are clearly distinguished from those produced by siFoxA1. Specifically, the type 1 event demonstrates a mean blockage amplitude ($\overline{I_p}$) of 0.490±0.010 (n=3, Table 3). The type 2 event demonstrate a blockade with a mean blockage amplitude ($\overline{I_p}$) of 0.533±0.004 (n=3, Table 3). Because the blunt ends are hard to be unzipped to reach the pore constriction (FIG. 11), the events generally demonstrate shallower, longer residing and less noisy a blockage level than those generated by siFoxA1 (FIG. 10). The two types of events may thus result from blunt siRNA trapped by MspA in an opposite direction. Considering that the overall length and structure are similar, this comparison demonstrates that nanopore trapping/translocation by MspA can efficiently resolve minor structural differences between RNAs.

TABLE 3

I_p of RNA sensing by MspA. All measurements were performed
as described in Methods. I_p was derived from Gaussian fitting
results. $\overline{I_p}$ was the mean value of I_p from
three independent measurements.

| types of RNA | $\overline{I_p}$ |
| --- | --- |
| miRNA | 0.976 ± 0.001 |
| overhanged siRNA | 0.600 ± 0.006 |
| blunt siRNA | 0.490 ± 0.010 (type 1)/0.533 ± 0.004 (type 2) |
| tRNA | 0.567 ± 0.004 (type 1)/0.453 ± 0.002 (type 2) |
| 5S rRNA | 0.356 ± 0.003 (type 1)/0.566 ± 0.017 (type 2)/ 0.737 ± 0.005(type 3) |

3. Single Molecule Sensing of tRNA

Transfer RNA (tRNA) is another intensively studied and a well-known model in RNA structural biology. Its secondary structure is composed of four domains: the acceptor stem, the D-arm, the T-arm and the anticodon loop (FIG. 12). In a three-dimensional space, these domains fold into an L-shaped tertiary structure, in which the anticodon loop and the acceptor stem respectively form the two ends of the L-shaped geometry (FIG. 12). Judging from a visual inspection of its tertiary structure, tRNA, in its native form cannot directly translocate through MspA. However, it nevertheless fits into the pore vestibule and may have multiple orientations when entering the pore, suggesting that it might generate a set of translocation characteristics when probed by MspA (FIG. 7A).

Purification of a specific type of tRNA is difficult due to the biochemical similarity of different types of tRNAs[41]. Reported tRNA isolation is extremely labor intensive, involving ionic exchange chromatography, solvent extraction, countercurrent extraction, chromatography on benzyl-DEAE-cellulose and reverse phase chromatography[41]. However, phenylalanine specific tRNA, abbreviated here as tRNA[phe], is unique because it can be simply obtained with high purity by elution from a benzylated DEAE-cellulose column with a gradient of NaCl[42]. Brewer's yeast tRNA[phe], which was extracted as described above[42], is commercially provided by Sigma-Aldrich and was employed as a representative tRNA in follow-up studies.

Figure 13:
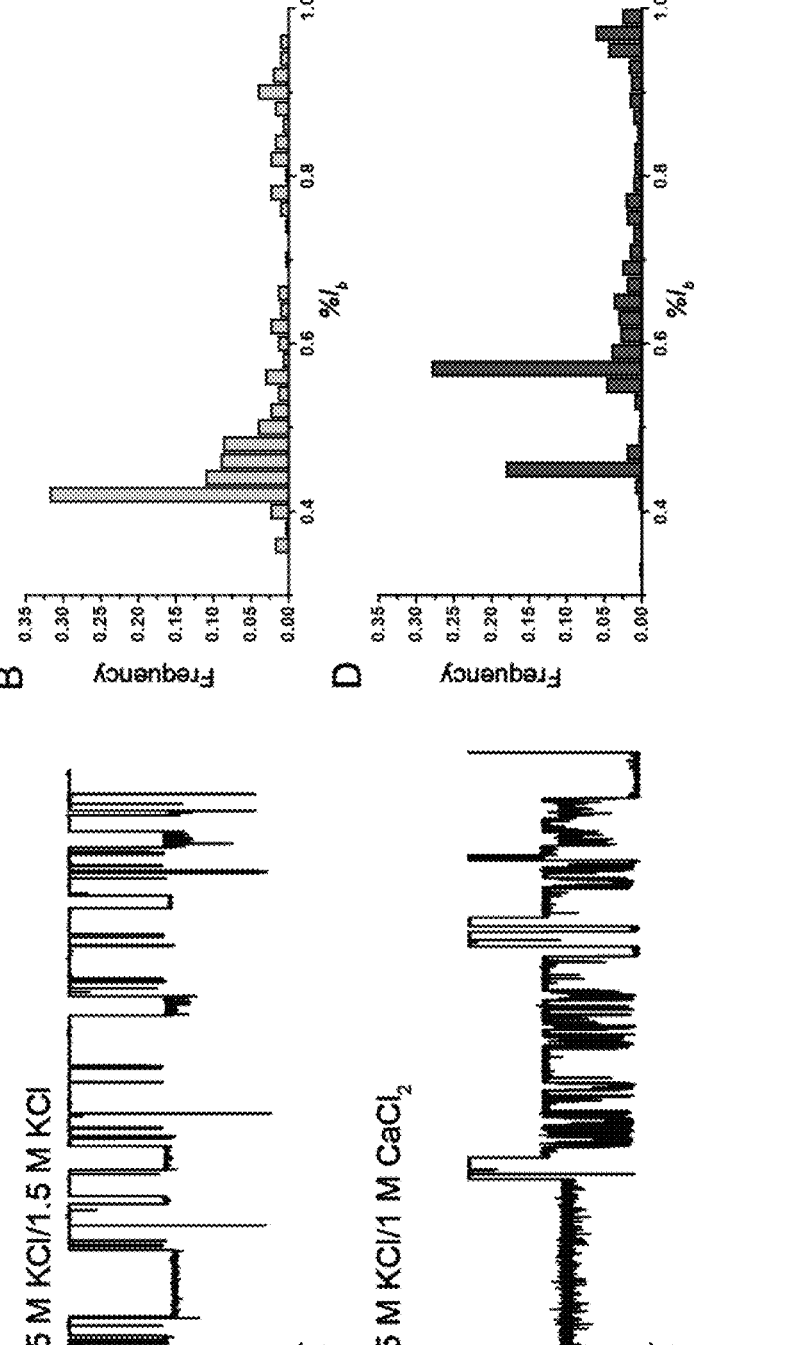
FIG. 13 shows tRNA$^{phe}$ sensing with different buffers. Nanopore measurements were performed as described in Methods. The electrolyte buffer in trans is either a 1.5 M KCl buffer (1.5 M KCl, 10 mM HEPES, pH 7.0) or a 1 M CaCl$_2$ buffer (1 M CaCl$_2$, 10 mM HEPES, pH 7.0). tRNA$^{phe}$ was added to cis with a 200 nM final concentration. A. A representative trace containing successive tRNA$^{phe}$ translocation events. A 1.5 M KCl buffer was employed in both cis and trans. The majority of translocation events has only one step and does not appear uniformly. B. The event histogram of % $I_b$ from a time extended measurement as described in A. In this condition, % $I_b$ is widely distributed. C. A representative trace containing successive tRNA$^{phe}$ translocation events. A 1.5 M KCl buffer in cis and a 1 M CaCl$_2$ buffer in trans was employed. The dwell time of tRNA events were significantly extended and the characteristic tRNA translocation events (FIG. 7B) were frequently observed. D. The event histogram of % $I_b$ of event level 1 (FIG. 7B) from a time extended measurement as described in C. From the histogram, characteristic two populations of events were clearly observable. Based on previously reported literatures[94-96] and our results, we speculate that the presence of Ca$^{2+}$ is two-fold, to retard the translocation the analyte and to maintain the structural of the tRNAs. Though not tested in this work, other divalent ions such as Mg$^{2+}$ may have similar effects stabilizing tRNA structures.

During a nanopore measurement (Methods), Brewer's yeast tRNA[phe] was added to cis with a final concentration of 200 nM. Successive long residing and fluctuating translocation events were subsequently observed, among which two types of events, tentatively termed tRNA type 1 or type 2 events, demonstrate a high reproducibility in their event characteristics (FIG. 12, FIG. 7C, D). When the measurements were carried out with 1.5 M KCl (cis)/1.5 M KCl (trans), tRNA[phe] translocation results in events with non-uniform characteristics. Previously observed type 1 and type 2 events have completely disappeared (FIG. 13). This suggests that the presence of the calcium flux may have helped to stabilize tRNA tertiary structures during nanopore sensing (FIG. 13)[43]. Specifically, the tRNA type 1 event demonstrates a single-step blockade with a mean blockage amplitude ($\overline{I_p}$) of 0.567±0.004 (n=3, Table 3). The tRNA type 2 event contains a well-defined upper blockage level (level 1) with an $\overline{I_p}$ of 0.453±0.002 (n=3, Table 3). Besides, the event contains persistent transitions to deeper blockage levels and eventually ends with an extremely deep pore blockage (level 2) measuring 0.997±0.010 in $\overline{I_p}$ (n=3, Table 3) before being restored to the open pore level. The shallow blockage amplitude (I_p) in type 1 or level 1 of type 2 suggests that the tRNA was in the form of partial translocation, leaving a large remaining space in the pore vestibule unoccupied and resulting in a large residual current. The highly distinguishable differences in I_p between these two types of events may result from two distinct tRNA trapping orientations. According to its tertiary structure, either the anticodon loop or the acceptor stem of tRNA may face the pore constriction during translocation.

Figure 14:
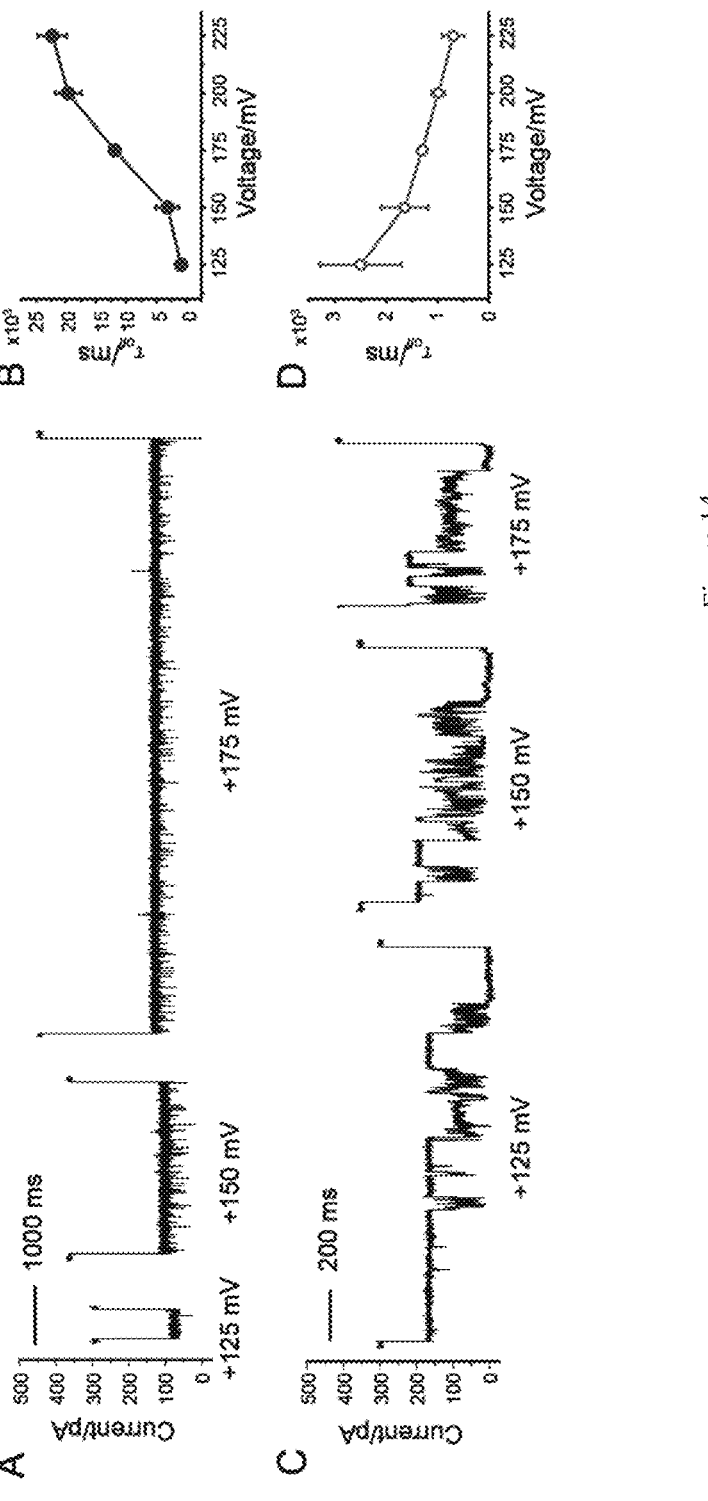
FIG. 14 shows tRNA$^{phe}$ translocation events at different voltages. A. Representative type 1 events at +125 mV, +150 mV and +175 mV. The event dwell time is extended when the applied potential is increased. B. $\tau_{off}$ of type 1 events at different voltages. C. Representative type 2 events at +125 mV, +150 mV and +175 mV. The dwell time decreases when the applied potential is increased. D. $\tau_{off}$ of type 2 events at different voltages. All measurements were carried out as described in Methods. tRNA$^{phe}$ was added to cis with a final concentration of 200 nM. Three independent measurements were performed for each condition to form the statistics (B, D).

To further explore this phenomenon, nanopore measurements with tRNA[phe] were carried out with applied voltages varying between +125 and +225 mV. Both tRNA type 1 or type 2 events were still observed. In general, the residence times of all type 1 events were systematically extended when the applied voltage was increased (FIG. 14, Table 4), indicating that a type 1 event actually represents trapping of the tRNA without an eventual passage through the pore. In this case, a higher electrophoretic force would keep the trapped tRNA more tightly in the pore vestibule before escaping back to the cis chamber, resulting in a systematically extended dwell time for the event. Without any observation of further pore blockages in any type 1 event, a full translocation with this orientation seems to be impossible. This suggests that the anticodon loop of the tRNA tertiary structure, which forms a covalently closed molecular circle, is facing the pore constriction during translocation (FIG. 12). The overall dwell time of type 2 events however behaves in the opposite sense (FIG. 14, Table 4), indicating that the type 2 event actually represents a kind of translocation during which the tRNA was unfolded, leading eventually to a full translocation. This hypothesis is reinforced by the observation of persistent attempts of the tRNA to reach a further pore blockage level, as observed from the fluctuations below the level 1 blockage state. The acceptor stem, which has a phosphorylated 5' end and an overhanging 3' end which contains a CAA tail for amino acid attachments, may facilitate electrophoretically driven unfolding of the tRNA structure, when facing the pore constriction (FIG. 12). These findings have reinforced the speculation that two tRNA$^{phe}$ translocation orientations were observed. The spatially asymmetric tRNA results in distinguishing of tRNA$^{phe}$ translocation orientations, generating two tracks of sensing information for tRNA structural profiling.

TABLE 4

$\tau_{off}$ of tRNA$^{phe}$ measured at different voltages. All measurements were performed as described in Methods. tRNA$^{phe}$ was added to the cis chamber with a final concentration of 200 nM. $\tau_{off}$ was derived from single exponential fitting results. $\overline{\tau_{off}}$ was the mean value of $\tau_{off}$ from three independent measurements.

| voltage/mV | $\overline{\tau_{off}}$ of type 1/ms | $\overline{\tau_{off}}$ of type 2/ms |
|---|---|---|
| 125 | 900 ± 800 | 82500 ± 800 |
| 150 | 3000 ± 2000 | 1600 ± 500 |
| 175 | 11900 ± 500 | 1290 ± 90 |
| 200 | 20000 ± 2000 | 980 ± 130 |
| 225 | 22000 ± 2000 | 700 ± 200 |

4. Single Channel Recording of 5S rRNA 5S ribosomal RNA (5S rRNA) is an integral component of the ribosome. Its small size (approximately 120 nt), conserved structure and association with ribosomal proteins made it an ideal model RNA for studies of RNA structure[44] and RNA-protein interactions[45]. The secondary structure of 5S rRNA is composed of five helices (denoted I-V in roman numerals), four loops (B-E), and one hinge (A), which form a Y-shaped tertiary structure[46]. The loop C, loop E and helix I are located at the three ends of the "Y" shape[46]. The structure shows a higher complexity than that of tRNA and might generate different event characteristics when probed by MspA.

Figure 15:
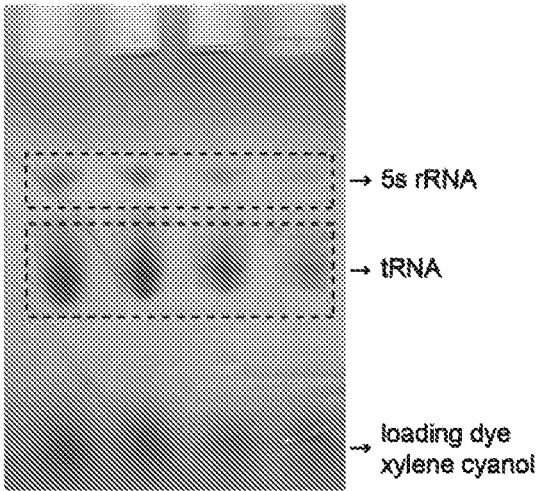
FIG. 15 shows E. coli 5S rRNA prepared by recovering RNA fragments from urea-PAGE gel electrophoresis. E. coli low molecular weight (LMW) RNA (<200 nt) extracted by the small RNA extraction reagent from Takara (Example 2 Methods), was loaded onto a 12% urea-PAGE gel. Gel electrophoresis was continuously run for 100 min with a +180 V applied potential. The gel was visualized with a portable UV lamp (254 nm). Three bands were clearly observable and were respectively recognized as 5S rRNA, tRNA and xylene cyanol, according to the published literature[97]. The region corresponding to 5S rRNA was separately excised. The excised gel fragments were treated with the ZR small-RNA™ PAGE Recovery Kit (ZYMO Research, USA) to recover the RNA (Example 2 Methods).
Figure 16:
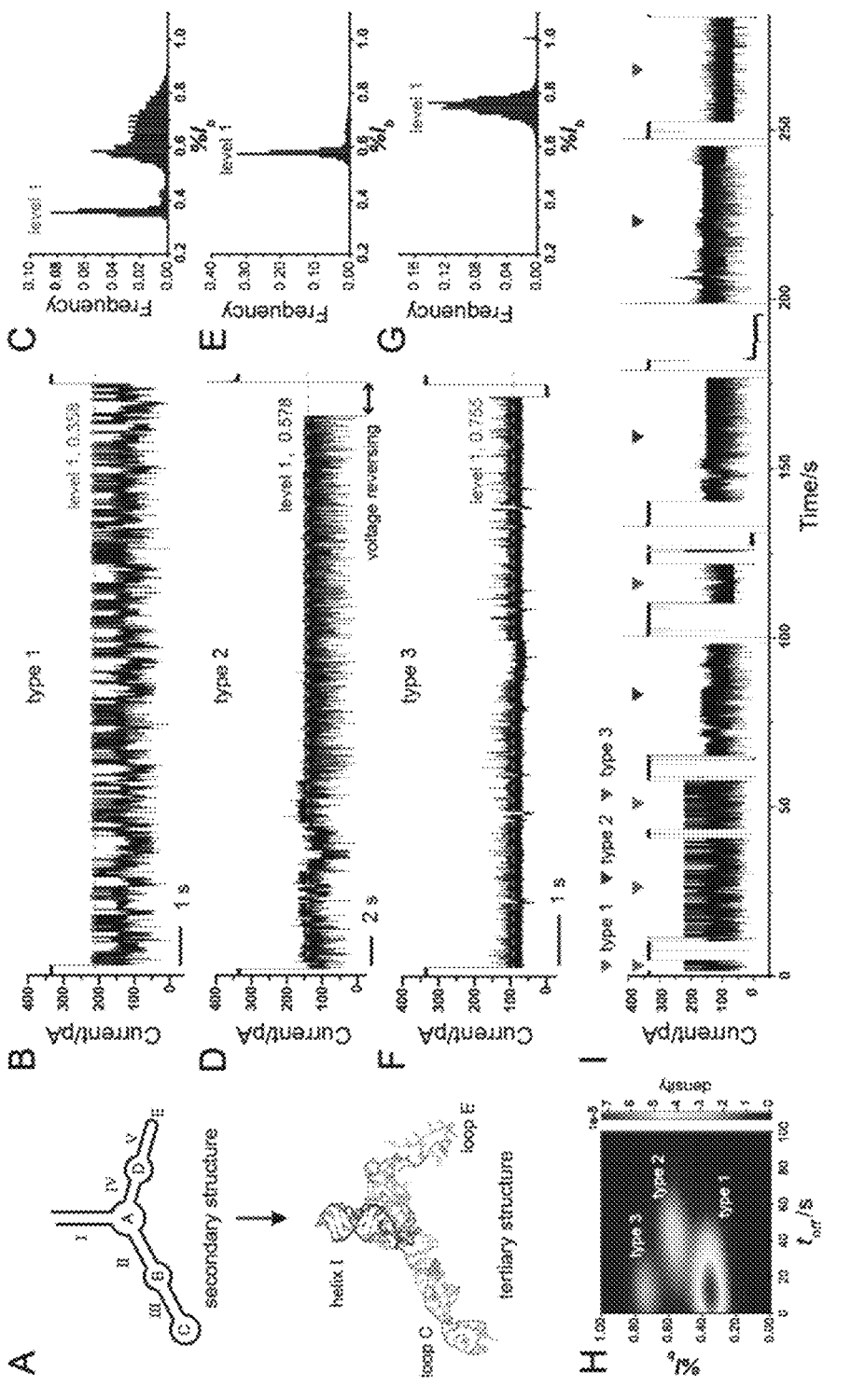
FIG. 16 shows translocation of E. coli 5S rRNA. A. The structure of E. coli 5S rRNA (PDB: 1C2X). The secondary structure of E. coli 5S rRNA (top) is composed of five helices (denoted I-V in roman numerals), four loops (B-E), and one hinge (A), which form together a Y-like tertiary structure (bottom). The loop C, loop E and helix I are located at the three ends of the "Y" shape. B. A representative 5S rRNA type 1 event. The type 1 event appears as reciprocating current oscillations below a constant blockade with a % $I_b$ of about 0.358 (level 1). C. Corresponding all-point histogram of the type 1 event. D. A representative 5S rRNA type 2 event. The type 2 event starts with random current fluctuations. Then it becomes a single-step blockade (level 1, % $I_b$=0.578) with many downward burrs. The type 2 events will block the pore until a reversed voltage is applied. E. Corresponding all-point histogram of the type 2 event. F. A representative 5S rRNA type 3 event. The type 3 event has two blockage levels. The characteristic blockade level measures about 0.775 (level 1). G. Corresponding all-point histogram of the type 3 event. H. A heat map of t$_{off}$ versus % $I_b$. % $I_b$ refers to the blockade amplitude of the level 1 of the three types. The hot map was generated by custom Python codes. I. A representative trace containing successive 5S rRNA translocation events. The three types of sensing events of 5S rRNA are clearly recognized from the trace, which are marked with red, blue and green bars respectively. Nanopore measurements were performed as described in Methods. 5S rRNA (Materials, Table 1) was added in cis with a final concentration of 10 nM.
Figure 17:
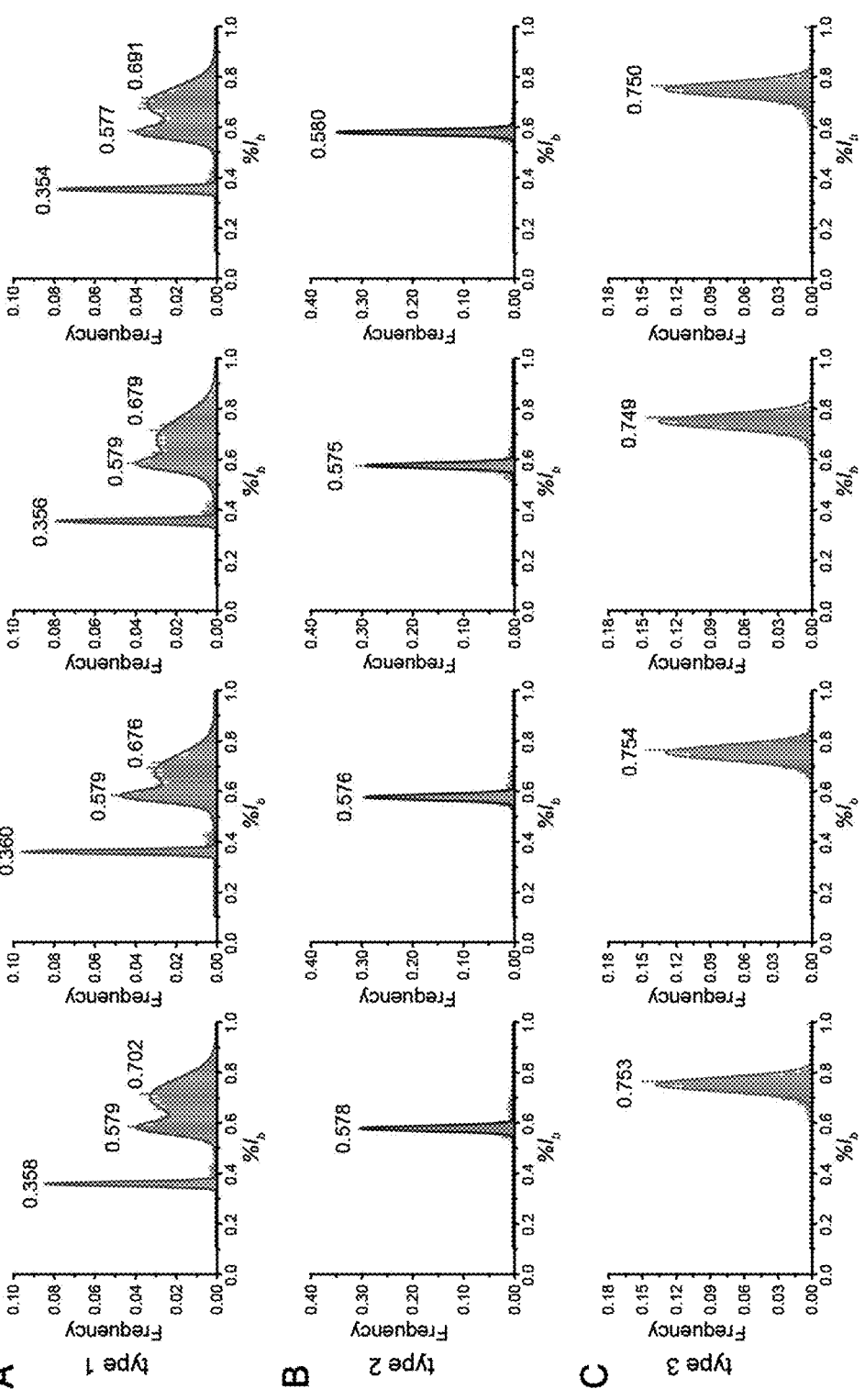
FIG. 17 shows the event features of three types of 5S rRNA signals. All-point histograms from representative 5S rRNA type 1 events (A), type 2 events (B) and type 3 events (C) are demonstrated. Distinct patterns were seen in the histograms from different event types. However, the pattern is highly conserved when events of the same type were evaluated. Specifically, all-point histograms of each type 1 event all demonstrate 3 characteristic peaks. Histograms of each type 2 event all demonstrate a single narrower peak with the peak % at ~0.58. Histograms of each type 3 events all demonstrate a single wider peak with the peak % $I_b$ at ~0.75.

5S rRNA extracted from *E. coli* (FIG. 7B, FIG. 15) was employed as a model analyte, which was added to cis with a final concentration of 10 nM. Three types of characteristic events were observed which might be corresponding to the three terminals of 5S rRNA entering the pore, respectively (FIG. 16). Specifically, the type 1 event appears as current oscillations below a characteristic blockage level with a mean blockage amplitude (1) of 0.356±0.003 (n=3, Table 3). The type 2 event starts with random current fluctuations. Then it becomes a single-step blockage (level 1, $\overline{I_p}$=0.566±0.017, n=3) with many negative going spikes. The type 3 event demonstrates a two-step blockage and the mean blockage amplitude ($\overline{I_p}$) of the first step is 0.737±0.005 (n=3, Table 3). Different event types were well distinguished from each other based on results of their all-point histograms (FIG. 17). Among the three types of events, the type 1 event demonstrates the most unique event shape and the highest appearance probability, which was considered the most characteristic event type of 5S rRNA (FIG. 18). By performing a voltage dependence assay, it was discovered that the type 1 event is a combination of trapping and translocation. A higher applied voltage would eventually drive the 5S rRNA structure to unfold and translocate through the pore (FIG. 19). Thus, the type 1 event is most likely to be the result of the helix I-down pose instead of any loop-down poses. The type 2 events, which never demonstrate any sign of successful translocation through the pore, should result from trapping of the structure with a loop-down pose (FIG. 16). Whereas, the type 3 events, which are relatively short residing and much less frequent in appearance, always appear as translocation through the pore (FIG. 16). Thus, the type 3 events should result from translocation of unfolded or fragmented 5S rRNA considering that the large size of 5S rRNA won't easily permit its translocation through the pore. Rich sensing information generated by MspA trapping/ translocation have provided a clear reference in recognition of 5S rRNA in single molecule. However, structural profiling of 5S rRNA by nanopore has not yet been previously reported, to the best of our knowledge.

5. Single Molecule RNA Structural Profiling

Hsa-miR-21, siFoxA1, luciferase siRNA, tRNA$^{phe}$ and 5S rRNA demonstrate an increased complexity in their overall structures. These differences in structure were all discriminable by the same pore MspA, utilizing the large opening of the pore vestibule and an overall conical pore geometry (FIGS. 7A, 7B and FIG. 20). The event scatter plots of % $I_b$ vs $t_{off}$ of different RNA types are shown in FIG. 7E (Table 3). For 5S rRNA, the type 1 event, which is the most representative event type of 5S rRNA, is demonstrated. For multi-step blockade events, the blockade amplitude of the first step was counted. Event characteristics generated by different analyte form highly distinguishable populations of distribution in the scatter plot. A corresponding event amplitude histogram is also demonstrated in FIG. 7F, in which 5S rRNA results in the shallowest blockade, followed by tRNA$^{phe}$, luciferase siRNA, siFoxA1 and hsa-miR-21. This is expected as RNAs with a larger tertiary structure have more difficulty accessing the pore constriction.

Simultaneous sensing of siFoxA1, luciferase siRNA, tRNA$^{phe}$ and 5S rRNA using MspA were also demonstrated (FIG. 7G). Different RNA types can be clearly recognized based on their distinct blockade characteristics. These results indicate that MspA, which has a conical shape, effectively distinguishes between a wide variety of RNA types for structural profiling. Although not demonstrated, other classical RNA structures, including kissing loop[47], three-way junction[48], pseudoknot[49], kink-turn[50] and G-quadruplex[51] are in principle detectable by the same strategy and distinct event features are expected. Subsequent feature extraction and analysis can be labor-intensive or may be biased by human supervision. Events resulted from RNA structures with a higher order of complexity may also require multiple parameters in the description of their characteristics. A highly intelligent and user-friendly computer algorithm is urgently needed to cope with these challenges.

6. Machine Learning Assisted RNA Identification

Machine learning is a branch of artificial intelligence research, whose aim is to build computerized algorithms which learn from input data without focusing on the programing. This concept demonstrates a generality suitable for analyzing nanopore sensing data, as previously reported[13, 52-54 55]. Event characteristics of siRNA, tRNA and 5S rRNA demonstrate a high consistency when probed by MspA, and such data are well suited for the construction of a machine learning algorithm aiming to automatically recognize different RNA structures. To begin with, raw time traces containing nanopore sensing events were first automatically segmented to generate discrete nanopore events (FIG. 21). To form model training sets, model events including 118 overhanged siRNA (siFoxA1) events, 176 blunt siRNA (luciferase siRNA) type 1 events, 161 blunt siRNA (luciferase siRNA) type 2 events, 143 tRNA (tRNA$^{phe}$) type 1 events, 155 tRNA (tRNA$^{phe}$) type 2 events, 133 5S rRNA (E. coli 5S rRNA) events and 134 "others" events were used. All these training events have known identities since they were generated during measurements involving a sole, known analyte. Here, events defined as "others" were abnormal nanopore events mainly caused by nanopore clogging or spontaneous gating (FIG. 22). These events were also included in the training dataset serving as interfering events, reinforcing the robustness of the training. The type 1 or type 2 events were separately labeled according to their highly discriminable %$^1$, values (FIG. 7C, Table 3).

The training process is composed of feature extraction and model building (FIG. 23A). During feature extraction, level 1 position (pos_level 1), level 2 position (pos_level 2), noise, dwell time (length), minimum (min), maximum (max), median (med), mean, standard deviation (std) kurtosis (kurt) and skewness (skew) of individual events were respectively extracted, forming a feature matrix for each event (FIG. 23A). The method of feature extraction is detailed in FIG. 24. Then the training datasets were split into the training subsets for model training and the validation subsets for model testing. The training set was further randomly split by the 10-fold cross validation into a training subset for model training and a validation subset for model parameter fine-tuning and model validation. The training process was performed 10 times during which the training dataset was randomly partitioned and performance bias is avoided. To build the model, five different classifiers, including Classification And Regression Tree (CART), Xgboost, Random Forest, KNN and Gradient Boost were estimated. Due to a large variation of event length between event types, Deep-Learning was not selected for model building. Hyper-parameters such as "n_setimators" from RandomFoest, "k value" from KNN were fine-tune by the validation subset. Each model accuracy score is computed by averaging the accuracy score of all model training. Among all five classifiers, the Random Forest model has scored the highest and became the optimum choice of model builder. The trained models were tested by the testing dataset. The phase of model testing outputs the classification accuracy, feature importance, confusion matrix and learning curve. The classification accuracy is computed by the quotient of correctly classified samples and total samples.

The feature importance was generated during model testing which demonstrates the relative importance of all nine features in event recognition (FIG. 23B). The confusion matrix results of model testing are demonstrated in FIG. 23C, from which the accuracy of overhanged siRNA, blunt siRNA type 1 and siRNA type 2, tRNA type 1 and type 2, 5S rRNA are 0.9694, 0.9630, 0.9206, 0.9600, 0.9079, and 0.9118, respectively. To estimate the efficiency of the model, the accuracy was estimated with a varying amount of input data during model testing to form a learning curve, which suggested that an overall judgement accuracy of 85% can be achieved with an input of only 148 training events, randomly selected from the whole training sets (FIG. 23D).

The model was employed to predict events with unknown identities (FIG. 23E). Nanopore measurements were carried out with a sequential addition of overhanged siRNA, blunt siRNA, tRNA and 5S rRNA. A twenty-minute trace was recorded for each condition. The recorded data forms the predicting datasets, which were subsequently identified by the previously trained model (Video S1). As shown in the histogram of event recognition (FIG. 23F, FIG. 25), an obvious rise in the proportion of the corresponding RNA event emerges after each addition. This efficiently assists automatic nanopore sensing of different RNA structures, and is especially advantageous in RNA identification from mixed samples.

Video S1. Simultaneous sensing of siRNA, tRNA and 5S rRNA. Electrophysiology measurements were performed as described in Methods. A 1.5 M KCl buffer (1.5 M KCl, 10 mM HEPES, pH 7.0) was placed in cis and a 1 M CaCl$_2$ buffer (1 M CaCl$_2$, 10 mM HEPES, pH 7.0) was placed in trans. Overhanged siRNA (SiFoxA1, 25 nM), blunt siRNA (luciferase siRNA, 10 nM), tRNA (tRNA$^{phe}$, 400 nM) and 5S rRNA (30 nM) were simultaneously added to cis. Characteristic events of siRNA, tRNA and 5S rRNA were clearly observed from the trace. Assisted by the machine learning algorithm, each event was automatically identified and labelled with letters of O (overhanged siRNA), B1 (blunt siRNA type 1), B1 (blunt siRNA type 2), T1 (tRNA type 1), T2 (tRNA type 2) or R (5S rRNA type 1) respectively.

7. Molecular Dynamics (MD) Study of tRNA Trapping/Translocation

Among all tested analyte, tRNA demonstrates two highly characteristic types of events. Experimentally, these two event types respectively demonstrate trapping (type 1) and translocation (type 2) of tRNA when probed by MspA (FIG. 12). Since the overall structure of tRNA is multi-branched, the origin of the two event types likely results from different orientations of tRNA entering the pore. To reveal how it determines the blockade amplitude and the kinetics of tRNA during nanopore sensing, all-atom MD simulations were performed (Example 2 Methods). The simulations were initiated by placing a tRNA with different start orientations immediately above the pore vestibule without any direct contact with the pore. The conformations demonstrating these orientations, which were respectively referred to as the stem-down, the loop-down or the arm-down orientation, were equilibrated and demonstrated in FIG. 26A-C. To further characterize the translocation process of tRNA, we probed the z-coordinate of the leading nucleotide (green sphere in FIG. 26A-C) during a 100-ns simulation. Here, Z=0 corresponds to the narrowest region of MspA (FIG. 26A-C), which is the center of mass of the Ca atoms of the N90 in all the eight subunits. Thus, a result of Z<0 demonstrates that the leading nucleotide has successfully translocated through the pore. Experimentally, trapping/translocation of tRNA lasts ~seconds when probed by MspA, which is far beyond the accessible timescale of conventional MD simulations. In a previous work$^{56}$, the whole vestibule of MspA was removed to speed up the calculation so that a ~μs timescale in a single trajectory of the all-atom simulations was achieved. However, the vestibule of MspA is critical to accommodate large RNA structures and a ~μs timescale is still much shorter than that took for nanopore trapping/translocation. Alternatively, to observe the full process of nanopore trapping/translocation within a feasible simulation timescale, a higher voltage was applied to speed up the process. However, the corresponding ionic current is derived by switching the applied voltage to +150 mV. To avoid the formation of electroporation, the positions of lipid molecules were restrained. The simulations were identically carried out for all three different orientations of tRNA entering the pore for a qualitative comparison.

FIG. 26D-F shows representative trajectories from seven independent simulations when respectively simulated with three different conformations. The results show that tRNA with the stem-down conformation can translocate through the pore constriction much more easily than the others. In all simulations with the stem-down pose, the leading nucleotide has successfully translocated through the MspA porin within 100 ns. Whereas in the simulations with the other two tRNA poses, no successful translocation events were observed within the simulation timescale. Further simulations suggest that the successful translocation with the stem-down conformation is coupled with the unfolding of tRNA (FIG. 27, Video S2). At the early stage of the simulation, tRNA involves dramatic deformation without disrupting the base-pair hydrogen bonds (H-bond) as indicated by the increase of the root mean square deviation (RMSD) and the relatively stable values of the H-bond (FIG. 27). Due to the deformation, tRNA can reach a deeper position of MspA, which is followed by the tRNA unfolding and the successful translocation of the leading nucleotide through the pore constriction, as shown by the drop of the reaction coordinate Z, the decrease of the H-bond, and the increase of the RMSD (FIG. 27). The translocation processes with the other two conformations are also provided in Video S3 and S4.

The different analyte-pore interactions caused by different conformations of tRNA lead to distinctive ionic currents. To quantitatively compare the resulting ionic current for the different conformational states of the system, the external electric field was switched to 0.09 V/10 nm, which corresponds to a voltage bias of ~+150 mV as used in the experiments. Following a previous study[57], the instantaneous ionic current was calculated based on the coordinates of the ions. Since the instantaneous ionic current has large fluctuations, we first calculated the cumulative currents. Then the ionic currents were derived from the slope of the cumulative currents by linear fitting. In addition to the above mentioned three simulation systems, we also performed ion current simulations for the systems without tRNA (open pore) and with the tRNA translocating through the pore (Z<0). As shown in FIGS. 26G and 26H, the simulations of the open pore state of MspA shows the highest ion current. After tRNA was trapped into the pore vestibule, the ionic currents abruptly decreased, leading to a current blockade event. Compared to the stem-down conformations, the loop-down reports a higher current, consistent with the experiment observation that level 1 of type 2 event is always higher than that of the type 1 event. The current almost vanishes when the tRNA is translocating through the pore constriction, which well describes the state of level 2 of a tRNA type 2 event. These results were similarly observed when the voltage was further up-regulated (FIG. 28). To summarize, above results by MD simulations have well explained the possible origin of two tRNA event types, especially the type 2 event which corresponds to tRNA translocation driven by voltage driven unfolding. The type 1 event, which is a trapping event (FIG. 14), is likely resulted from the loop-down orientation instead of the arm-down orientation. The arm-down orientation demonstrates an extremely shallow trapping depth from the simulation, which is less likely to happen than the loop-down orientation when experimentally measured. MD simulation was also similarly carried out for 5S rRNA (FIG. 29, Video S5), which has demonstrated details of molecular translocation of a much larger RNA structure. Voltage driven unfolding was also observed in the simulation initiated from a helix I down trapping orientation.

Video S2-4. Animations of tRNA translocation generated by MD simulation. MD simulations were performed as described in Example 2 Methods. An external electric field of 4.0 V/10 nm was continuously applied along the direction perpendicular to the membrane plane. The simulations lasted for 100 ns with a time step of 2 fs per frame. In each animation, the tRNA enters the pore with the stem down (Video S2), the loop down (Video S3) or the arm down (Video S4) conformation.

Video S5. Animation of 5S rRNA translocation generated by MD simulation. MD simulations were performed as described in Example 2 Methods. An external electric field of 4.0 V/10 nm was continuously applied along the direction perpendicular to the membrane plane. The simulations lasted for 100 ns with a time step of 2 fs per frame. 5S rRNA enters the pore with the helix I down conformation.

8. Event Feature Conservation for tRNAs from Different Sources

Previous crystallographic studies indicate that with the exception of particular mammalian mitochondrial tRNAs, tRNAs of a widely divergent phylogenetic origin demonstrate a highly conserved L-shaped tertiary conformation[58]. With this knowledge in mind, the structure-induced nanopore events of brewer's yeast tRNA$^{phe}$ might be generally applied to a much wider variety of tRNAs from different sources. To explore this speculation, we performed nanopore sensing of the total tRNAs from brewer's yeast and from *E. coli*, both supplied by Sigma-Aldrich.

Gel electrophoresis was performed for both tRNA samples, from which the yeast total tRNAs have the desired purity but the *E. coli* total tRNAs contain noticeable contaminations, including 5S rRNA and other higher molecular weight RNAs[59] (FIG. 30). To avoid interference from contaminants, *E. coli* tRNA was purified by RNA recovery from a polyacrylamide gel prior to nanopore measurements (FIG. 31).

During nanopore measurements (Methods), yeast tRNA or purified *E. coli* tRNA were respectively added to cis at a 20 ng/μl or 2 ng/μl final concentration. Representative traces were separately demonstrated in FIGS. 32A and 32B. Characteristic tRNA type 1 and type 2 events, as previously defined when brewer's yeast tRNA$^{phe}$ was studied, were clearly observed from both traces. FIG. 32C shows the event histogram of blockade characteristics of type 1 (level 1) and type 2 (level 1 and level 2) events induced by yeast tRNA$^{phe}$, yeast tRNA or *E. coli* tRNA. Generally, tRNA events from different sources or species demonstrate a high similarity in event statistics when probed by MspA. Statistical analysis from three independent experiments also showed that the I$_p$ of the three characteristic levels of yeast tRNA and *E. coli* tRNA translocation events is close to that from yeast tRNA$^{phe}$ (FIG. 32D, Table 5). The proportions of characteristic tRNA events from yeast tRNA and *E. coli* tRNA are also similar (FIG. 32E, Table 6). These results reveal that tRNA characteristic events are highly conserved for tRNAs from different sources or species. Though the same conclusion has been previously drawn from crystallographic results[60-64], this is the first demonstration of tRNA structural conservation from single molecule observation, and acquired with natural samples in an aqueous buffer environment instead of samples in a static, crystallized form. In addition, the blockade current distributions of type 1 level 1 and type 2 level 2 appear slightly wider than that of yeast tRNA$^{phe}$, possibly indicating that different tRNAs may show further distinguishable characteristics, though the general shape of event appears to be similar. The unique event characteristics along with the single molecule resolution of the nanopore enables direct tRNA recognition from complex biological samples, such as a crude extract from the cell lysate in which a significant amount of interfering analyte is present.

TABLE 5

$I_p$ of tRNA events from different biological sources. All measurements were performed as described in Methods. tRNA$^{phe}$ was added to cis with a final concentration of 200 nM. Yeast total tRNA was added to cis with a final concentration of 20 ng/μL. E. coli total tRNA (unpurified) was added to cis with a final concentration of 20 ng/μL. E. coli total tRNA (purified) was added to cis with a final concentration of 2 ng/μL. $I_p$ was derived from Gaussian fitting results. $\overline{I_p}$ was the mean value of $I_p$ from three independent measurements.

| biological samples | $\overline{I_p}$_type 1 level 1 | $\overline{I_p}$_type 2 level 1 | $\overline{I_p}$_type 2 level 2 |
|---|---|---|---|
| tRNA$^{phe}$ | 0.567 ± 0.004 | 0.453 ± 0.002 | 0.970 ± 0.003 |
| Yeast total tRNA | 0.549 ± 0.009 | 0.451 ± 0.002 | 0.979 ± 0.012 |
| E. coli total tRNA (purified) | 0.55 ± 0.02 | 0.478 ± 0.004 | 0.986 ± 0.002 |

TABLE 6

Proportion of tRNA signals determined with machine learning algorithms. All measurements were performed as described in Methods. Different analytes were respectively added to cis. Three independent measurements were performed for each condition to produce the statistics.

| biological samples | proportion of tRNA signals | proportion of type 1 signals | proportion of type 2 signals |
|---|---|---|---|
| tRNA$^{phe}$ | 0.71 ± 0.05 | 0.41 ± 0.05 | 0.30 ± 0.04 |
| Yeast tRNA | 0.380 ± 0.013 | 0.21 ± 0.04 | 0.17 ± 0.03 |
| E. coli tRNA (purified) | 0.402 ± 0.009 | 0.206 ± 0.016 | 0.196 ± 0.007 |
| E. coli LMW RNA | 0.48 ± 0.11 | 0.24 ± 0.09 | 0.23 ± 0.06 |

9. Direct tRNA Identification from E. coli Extracts

To verify its feasibility, cultured E. coli (BL21) DE3 was lysed. All low molecular weight (LMW) RNA (<200 nt) was extracted by the small RNA extraction reagent from Takara, named RNAiso for Small RNA. The extraction procedure is schematically illustrated in FIG. 33A and detailed in Example 2 Methods. The kit efficiently extracts all low molecular weight RNAs in the lysate, including tRNA, 5S rRNA, miRNA and siRNA[65]. Other than tRNA, the other RNAs may serve as interfering RNAs with which to test the robustness of the machine learning algorithm.

Prior to nanopore measurements, the extracted sample was first characterized by 12% denaturing urea polyacrylamide gel electrophoresis (Urea-PAGE) analysis (FIG. 33B). According to published reports[61], the band with a molecular weight equivalent to ~80 nt corresponds to the tRNAs[65]. Nanopore sensing of LMW RNA was performed with 40 ng/μL LMW RNA in cis. A representative trace of a 70 s duration is shown in FIG. 33C. According to the custom machine learning algorithm, the characteristic type 1 and type 2 events were automatically identified, and are marked with triangles in FIG. 33C. Statistics show that the identified tRNA events have made up 48% of all detected translocation events (FIGS. 33D-33E, Table 6). This is expected considering the possible interferences from 5S rRNA, miRNA or siRNA, simultaneously present in the lysate.

As a negative control, high molecular weight (HMW) RNAs (>200 nt) of E. coli (BL21) DE3 were extracted using MiniBEST Universal RNA Extraction Kit (Takara). This kit preferentially extracts all RNAs with a molecular weight >200 nucleotides (nt) according to the manufacturer's protocol[66]. Detailed extraction procedures are described in Example 2 Methods. Experimentally, from 1% agarose gel electrophoresis results, the sharp bands respectively correspond to the 23S Ribosome RNA (rRNA) (2904 nt) and the 16S rRNA (1542 nt) which is a good indication that the HMW RNA extraction was successful (FIG. 34). 5S rRNA (120 nt) and tRNA (70-90 nt) which cannot be efficiently extracted by the Takara kit, were not clearly visible in the gel.

Nanopore sensing of the HMW RNA extraction was performed with a 50 ng/μL final concentration of HMW RNA in cis. A representative 10 min trace is shown in FIG. 35, from which extremely long blockade events ranging from 1-60 s appear successively in the trace. These events may result from either 23S rRNAs or 16S rRNAs and show less defined event characteristics. However, they are clearly distinguishable from all tRNA events. Only 3.7% tRNA type 1 and no type 2 events were observed (FIG. 35). Previous trials with tRNA containing samples all demonstrate both type 1 and type 2 events (FIG. 7C) of which the type 2 is more characteristic in the identification of tRNA. In this case, without a simultaneous appearance of the tRNA type 2 event, the observation likely results from a minority of the events from HMW RNAs appearing similar to the tRNA type 1 event.

10. Conclusions:

In summary, this paper presents a nanopore sensing strategy which directly distinguishes between RNA native structures utilizing the large vestibule of an MspA nanopore. Representative RNA analytes, including miRNA, siRNA, tRNA or rRNA, generate rich sensing information during translocation which reports their identities unambiguously. We admit that RNA structural profiling by nanopore trapping/translocation may get complicated when extremely structurally similar RNAs were simultaneously evaluated. However, compared with existing RNA detection methods based on hybridization[67,68] or reverse transcription[69, 70], it requires no prior chemical treatment or amplification and a single molecule resolution is achieved. It thus serves as an alternative method for fast estimation of the expression level of a particular RNA, and is suitable for assessment of RNA integrity, stress-induced tRNA differential expression[71] or tRNA cleavage derived fragments[72]. Acknowledging an overall rigidity and conical geometry of the pore, trapping by MspA also reports highly consistent and distinguishable event characteristics. To cope automatically and quantitatively with sensing events, a custom machine learning algorithm has been developed (FIG. 23A). Though machine learning has only been previously applied in few practices of nanopore sensing[13, 53, 54], tools from artificial intelligence are gaining a growing importance in the field, in preparation of the new era to be led by high throughput sensing[73]. With the above sensing strategy, tRNA which possesses an L shaped tertiary structure, reports highly unique sensing characteristics. This unique feature also shows a high conservation between samples from different species (FIG. 32A) or sources (FIG. 32B).

Our results confirm that the vestibule of MspA can serve as a large constriction, complementary to the development of large pores such as ClyA[23], Phi29 DNA connector[24], FraC[25], PlyA/PlyB[26] or DNA nanopores[74], however the exceptional structural stability of MspA is advantageous for sample storage, long-term measurement and a low noise of measurement. Thought not yet disclosed in this study, the strategy of nanopore trapping has as well been successfully used to sense proteins or their allosteric transitions caused by small molecule bindings, which is to be published separately. Following the same principle, future applications of the technique may also include direct sensing of ribozymes, aptamers or their interactions with small molecules.

11. Methods

Nanopore measurements: The measurement device is composed of two custom poly-formaldehyde chambers separated by a ~20 μm-thick Teflon film drilled with an aperture (~100 m in diameter). Prior to the measurement, the aperture was first treated with 0.5% (v/v) hexadecane (dissolved in pentane) and set for pentane evaporation. Afterwards, 500 μL electrolyte buffers were respectively added to both chambers. A pair of custom Ag/AgCl electrodes, electrically connected to the patch clamp amplifier, were respectively placed in both chambers, in contact with the buffers. Conventionally, the chamber which is electrically grounded was defined as the cis chamber, while the opposing chamber was defined as the trans chamber. 100 μL pentane solution of DPhPC (5 mg/mL) was added to both chambers. A lipid bilayer was formed by pipetting the electrolyte buffer in either chamber up and down several times. Upon successful formation of the lipid bilayer, the acquired current immediately drops to 0 pA, indicating that the aperture connecting both chambers has been completely sealed. MspA was added to the cis chamber to initiate spontaneous pore insertion. Upon a single nanopore insertion, the buffer in the cis chamber was manually exchanged to avoid further pore insertions.

To avoid external electromagnetic and vibration noises during the measurements, the device was shielded in a custom Faraday cage (34 cm by 23 cm by 15 cm) mounted on a floating optical table (Jiangxi Liansheng Technology). All electrophysiology measurements were performed with an Axonpatch 200B patch clamp amplifier paired with a Digidata 1550B digitizer (Molecular Devices). All single channel recordings were sampled at 25 kHz and low-pass filtered with a 1 kHz cutoff frequency. The acquired traces were further digitally filtered with a 500 Hz low-pass Bessel filter (eight-pole) using Clampfit 10.7 (Molecular Devices).

Unless otherwise stated, all nanopore measurements in this paper were performed with a 1.5 M KCl buffer (1.5 M KCl, 10 mM HEPES, pH 7.0) in cis and a 1 M CaCl$_2$ buffer (1 M CaCl$_2$, 10 mM HEPES, pH 7.0) in trans and a +150 mV potential was continuously applied.

Data analysis: RNA translocation events were recognized with the "single channel research" option in Clampfit 10.7. The machine learning algorithm was custom programmed by Python. Subsequent analyses including histogram plotting and curve fitting were performed in Origin 9.1 (Origin Lab).

12. Data and Code Availability Statement

The machine learning based executable software "RNA-Classification" and its code have been deposited at https://drive.google.com/file/d/17JoqS2JUY-QOY4e5Ib0HE4PsexYtEIKq/view?usp=sharing. The workflow of this software is provided in FIG. 36. A set of demo events were accompanied for code validation. All data presented in this work can be provided by the corresponding authors upon reasonable requests.

13. Acknowledgments

This project was funded by National Natural Science Foundation of China (Grant No. 31972917, No. 91753108, No. 21675083), Programs for high-level entrepreneurial and innovative talents introduction of Jiangsu Province (individual and group program). Natural Science Foundation of Jiangsu Province (Grant No. BK20200009), Excellent Research Program of Nanjing University (Grant No. ZYJH004), State Key Laboratory of Analytical Chemistry for Life Science (Grant No. 5431ZZXM1902), Technology innovation fund program of Nanjing University and the HPC center of Nanjing University.

Example 2: Materials and Methods for Example 1

1. Materials

Hexadecane, pentane, ethylenediamine tetraacetic acid (EDTA), Triton X-100, Genapol X-80, calcium chloride (CaCl$_2$), tRNA$^{phe}$ from brewer's yeast, total tRNA from brewer's yeast and total tRNA from *E. coli* were from purchased from Sigma-Aldrich. Dioxane-free isopropyl-β-D-thiogalactopyranoside (IPTG), kanamycin sulfate, imidazole, N,N,N',N'-tetramethyl-ethylenediamine (TEMED) and tris (hydroxymethyl) aminomethane (Tris) were from Solarbio. DNA Marker DL2000, RNA Marker RL1000, RNA Marker RL6000, RNAiso for Small RNA, MiniBEST Universal RNA Extraction Kit and RNase-free water were from Takara. ZR small-RNA™ PAGE Recovery Kit was from ZYMO research. Low Range ssRNA Ladder was from New England Biolabs. SYBR gold nucleic acid gel stain was from Invitrogen. Potassium chloride (KCl) was from Aladdin. 4-(2-hydroxyethyl)-1-piperazineethanesulfonic acid (HEPES) was from Shanghai Yuanye Biotechnology. 1,2-diphytanoyl-sn-glycero-3-phosphocholine (DPhPC) was from Avanti Polar Lipids. *E. coli* strain BL21 (DE3) was from Biomed. Luria-Bertani (LB) agar and LB broth were from Hopebio. Chloroform was from Labol. Isopropanol and urea were from GHTECH. 75% ethanol (prepared with DEPC treated water) was from KeyGeN. 40% Acrylamide/methylene diacrylamide solution was from Sangon. High-performance liquid chromatography-purified hsa-miR-21, siFoxA1 and luciferase siRNA were hybridized by Sangon and delivered as a double stranded form (Table 1).

1.5 M KCl buffer (1.5 M KCl, 10 mM HEPES, pH 7.0) and 1 M CaCl$_2$ buffer (1 M CaCl$_2$, 10 mM HEPES, pH 7.0) were prepared and membrane-filtered (0.2 m cellulose acetate; Nalgene) prior to use. RNA was dissolved in RNase-free water before use. The M1 MspA (D90N/D91N/D93N) and M2 MspA (D90N/D91N/D93N/D118R/D134R/E139K) were expressed with *E. coli* BL21 (DE3) and purified by nickel affinity chromatography as described previously[1]. The plasmid DNAs encoding M1 or M2 MspA were custom synthesized by Genescript (New Jersey) and have been shared via https.//www.molecularcloud.org/s/shuo-huang. The access codes are MC_0101207 (M1 MspA) and MC_0101191 (M2 MspA). The majority of results were acquired with the M2 MspA. For simplicity, M2 MspA is referred to as MspA throughout the text, if not otherwise stated.

2. Methods

Molecular Dynamics (MD) Simulations

All molecular dynamics simulations were conducted by GROMACS 2019[76] with the CHARMM36m force field[77] and TIP3P water model[78]. The setup of the simulation system was prepared by using the CHARMM-GUI web server[79]. The atomic coordinates of MspA[80] and tRNA[81] were taken from the Protein Data Bank (PDB) with the entries 1UUN and 1EVV, respectively. Following the experimental setup, the mutations R96A, D93N, D91N, D90N, D118R, D134R and E139K were introduced to simulate the composition of an M2 MspA. A 1-palmitoyl-2-oleoyl-glycero-3-phosphocholine (POPC) lipid bilayer with the size of 12×12 nm$^2$ was added. The resulting system was then solvated in a rectangular water box with periodic boundary condition. To simplify the simulations, the system was established in a symmetric KCl buffer electrolyte system. $K^+$ and $Cl^-$ ions were added at random positions to give a salt concentration of 1.5 M and to neutralize the simulation system. The final system is consisted of ~225000 atoms. The long-range electrostatic interactions were calculated using the smooth particle-mesh Ewald method[82]. The cutoff distance for the calculations of the short-range part of the electrostatic interactions and the van der Waals interactions were set to 1.2 nm. The covalent bonds involving hydrogen atoms were restrained with the LINCS algorithm[83].

To simulate tRNA translocation, each system was firstly minimized for 1000 steps and then equilibrated at 298 K for 0.25 ns under NVT ensemble using Berendsen weak-coupling thermostat[84]. The heated systems were further equilibrated under NPT ensemble at 298 K and 1 atm for another 1.75 ns, with the Berendsen semi-isotropic barostat[84], leading to a box size of ~11.6 nm×11.6 nm×16.5 nm. The simulations of translocation were initiated from the final structures of the above equilibrating simulations with NVT ensemble. An external electric field of 2.0 V/10 nm was applied along the direction perpendicular to the membrane plane for 0.5 ns, then the external electric field was switched to 4.0 V/10 nm. The production simulations lasted for 100 ns with a time step of 2 fs. During the simulations, harmonic positional restraints were applied to the C atoms of MspA with a spring constant of 500 kJ/mol/nm². Experimentally, translocation of tRNA typically lasts ~second, which is far beyond the accessible timescale of conventional all-atom MD simulations. In order to observe a full translocation process within a feasible simulation timescale, the external electric field of 4.0 V/10 nm used in the translocation simulations corresponds to a much higher voltage bias than that is applied in experiment. As discussed in previously reported literatures[85, 86], high electric fields often result in the formation of electroporation of the lipid bilayer even in short MD simulations, which can lead to ion leakages. Consequently, different simulation strategies were used to avoid the formation of electroporation of the lipid bilayer, such as adding positional restraints[87], using puling force with steered MD to drive the translocation[86], or using more sophisticated Grid-steered MD[89]. Here we applied positional restraints to avoid the formation of electroporation, in which all the heavy atoms of the lipid molecules were restrained to the positions in the structures obtained from the minimization step by a harmonic potential with a spring constant of 1000 kJ/mol/nm².

To characterize the simulated tRNA translocation process, we used three reaction coordinates, including the number of base-pair hydrogen bonds (H-bond), the root mean square deviation (RMSD) from the native structure, and the z-coordinate of the tRNA (Z). The H-bond represents the number of hydrogen bonds between the nucleotide pairs which form base pairs in the native structure. Therefore, decrease of the H-bond corresponds to the disruption of the tRNA base pairing. The RMSD characterizes the overall structure change of the tRNA, which is not only sensitive to the structural unfolding, but is also sensitive to the overall deformation of the molecules. Therefore, the H-bond and RMSD can be applied to describe different conformational properties of the tRNA during translocation. The reaction coordinate Z is defined by the z-coordinate of the leading nucleotide during the translocation (green sphere in FIGS. 26A-C). The nucleotides A76, G34 or U55 were respectively assigned as the leading nucleotides for simulations with the stem-down, the loop-down and the arm-down orientations. Z=0 corresponds to the z position of the narrowest spot in the MspA pore (FIGS. 26A-C), which was defined by the center of mass of the C, atoms of the N90 of all eight subunits. Z<0 means that the leading nucleotide has successfully translocated through the pore.

To simulate the ionic current, starting from the equilibrated structures with the above mentioned three different tRNA orientations, the systems were firstly relaxed for 20 ns under an external electric field of 1.0 V/10 nm, so that the tRNA makes sufficient contacts with the entrance of the MspA. The production simulations started from the relaxed structures under an external electric field of 0.09 V/10 nm, which corresponds to a voltage bias of ~+150 mV, similar to that used in the experiments. The production simulations lasted for 100 ns. We also repeated the simulations at higher electric fields, including 0.2 V/10 nm and 0.6 V/10 nm. As the lipid bilayer can keep stable under these electric fields within the simulation timescale, the positional restraints were applied only to the C atoms of the MspA and the lipid molecules are free to move. Following a previous study[90], the instantaneous ionic current was calculated based on the coordinates of the ions. Since the instantaneous ionic current has large fluctuations, we calculated the cumulative currents. The ionic currents were derived from the slope of the cumulative currents by linear fitting. In addition to the above mentioned three simulation systems, we also performed ionic current simulations for the systems without the presence of any tRNA and the state when the tRNA is translocating through the pore (Z<0). The initial structure of the system with the tRNA translocating through the pore was extracted from the above translocation simulations. The software PyMOL was used for the structural visualization[91].

Similar simulations were performed for translocation of 5srRNA (FIG. 29). The POPC lipid bilayer has the size of 13×13 nm². The atomic coordinates of 5srRNA were taken from the PDB with the entry 1C2X. The final system for the translocation of the 5srRNA is consisted of ~270000 atoms with the box size of ~12.5 nm×12.5 nm×17.0 nm.

RNA Recovery from Polyacrylamide Gels 30 g commercial *E. coli* total tRNA (Sigma-Aldrich) was loaded into a 12% denaturing urea polyacrylamide gel. Gel electrophoresis was continuously run for 100 min with a +180 V applied potential. The gel was illuminated with a portable UV lamp (254 nm). The gel fragments respectively containing 5S rRNA or tRNA were excised for further recovery. RNA recovery was performed using ZR small-RNA™ PAGE Recovery Kit (ZYMO research). According to the manual, crushed RNA fragment was transferred into a Zymo-Spin™ IV Column. 400 µL RNA Recovery Buffer was add to the column and incubated at 65° C. for 15 min. The column was quickly frozen in a −80° C. freezer for 5 minutes and incubated at 65° C. for 5 min. The column was then centrifuged at 1500×g for 30 sec. The filtrate was transferred to a Zymo-Spin™ IIICG Column and centrifuged at 1500×g for 30 sec. The filtrate was added with 2 volumes of RNA MAX Buffer and thoroughly mixed. The mixture was then transferred to a Zymo-Spin™ IC Column and centrifuged at 12000×g for 30 sec and the supernatant was discarded. The column was added with 400 µL RNA Prep Buffer and centrifuged at 12000×g for 1 min and the filtrate was discarded. The column was added with 800 µL RNA Wash Buffer and centrifuged at 12000×g for 1 min then the filtrate was discarded. The column was added with 400 µL RNA Wash Buffer and centrifuged at 12000×g for 1 min and the filtrate was discarded. The column was centrifuged at 12000×g for 2 min to ensure complete removal of the wash buffer. The column was added with 30 µL RNase-free water. After standing for 1 min, the column was centrifuged at 10000×g for 1 min to elute the RNA. The eluted RNA concentration was determined by nanodrop (Thermo, USA)

and the sample was further characterized using 12% denaturing urea polyacrylamide gel electrophoresis. Finally, the recovered RNA was stored at −80° C. for subsequent electrophysiology measurements. All tips and tubes used were RNase-free.

Low Molecular Weight (LMW) RNA Extraction from *E. coli*

*E. coli* strain BL21 (DE3) was cultured in LB broth and shaken overnight (230×rpm) at 16° C. The cells were pelleted by centrifugation at 12000×g for 20 min at 4° C. and washed with 1×PBS to remove residual LB broth. The deposition was collected and lysed in 1 mL RNAiso for Small RNA (Takara). After vigorous vortexing, the lysis solution was placed at room temperature (rt) for 5 min. To extract LMW RNA, the lysis solution was added with 200 μL chloroform and fully emulsified through vortexing. After standing for 5 min, the mixture was centrifuged at 12000×g for 15 min at 4° C. When carefully removed from the centrifuge, the mixture was divided into three layers: the colorless supernatant containing LMW RNA, the white middle layer containing protein and the colored lower layer containing the organic solvent. The supernatant was transferred to a new centrifugal tube and added with 600 μL isopropanol. After thorough mixing, it was set for 10 min at 15~ 30° C. The mixture was centrifuged at 12000×g for 10 min at 4° C. to collect the pellet. The pellet was washed with 1 mL 75% ethanol and centrifuged at 12000×g for 5 min at 4° C. and the supernatant was discarded. The pellet, which is the LMW RNA, was dried at room temperature for 30 min. 25 μL of RNase-free water was then added to dissolve the LMW RNA. The concentration of the sample was determined by nanodrop. This LMW RNA sample was further characterized using 12% denaturing urea polyacrylamide gel electrophoresis. Finally, LMW RNA was stored at −80° C. for subsequent electrophysiology measurements. All tips and tubes used are RNase-free.

High Molecular Weight (HMW) RNA Extraction from *E. coli*

High molecular weight (HMW) RNA (>200 nt) of *E. coli* (BL21) DE3 was extracted using MiniBEST Universal RNA Extraction Kit. *E. coli* strain BL21 (DE3) was cultured in LB broth and shaken overnight (230 rpm) at 16° C. The cells were pelleted by centrifugation at 13800×g for 20 min at 4° C. and washed with 1×PBS water to remove residual LB broth. 350 μL lysis Buffer RL was added to the collected cells. The lysate was transferred to a gDNA Eraser Spin Column and centrifuged at 13800×g for 1 min at 20° C. to remove the gDNA. The filtrate was added with isopycnic 70% ethanol and mixed thoroughly. The mixture was transferred to RNA Spin Column and centrifuged at 13800×g for 1 min at 20° C. The RNA Spin Column was added with 500 μL Buffer RWA and centrifuged at 13800×g for 30 sec at 20° C. The filtrate was discarded. The RNA Spin Column was added with 600 μL buffer RWB and centrifuged at 13800×g for 3 min at 20° C. The RNA Spin Column was placed onto 1.5 mL RNase Free Collection Tube and added with 30-200 μL RNase free water. After 5 min, HMW RNA was eluted by centrifugation at 13800×g for 2 min at 20° C. The concentration was measurement using nanodrop and the desired fraction was determined using 1% agarose gel electrophoresis. Finally, HMW RNA was stored at −80° C. for subsequent electrophysiology measurements. Tips and tubes used were RNase-free.

Example 3: miRNA Sensing

MicroRNAs (miRNAs) are small RNA molecules, with their role in gene silencing and translational repression by binding to target mRNAs, and miRNAs influence essentially all developmental process and diseases. Therefore, how to quickly detect the types, mutations, and modifications of miRNAs is extremely important. As shown in FIG. 37, we designed a DNA probe with a known sequence, which could form a double-stranded structure with target miRNA family. Then we can use the wide vestibule of the MspA to detect the hybrid DNA-miRNA complex. Since the two ends of the double-stranded structure can partially enter into MspA, two characteristic blockade currents are observed (FIG. 37D). In this case, single base mismatch among miRNA family could be well distinguished with MspA due to their tiny duplex structural difference (FIG. 37E). In summary, nanopore trapping technology can quickly achieve ultra-high resolution miRNA detection.

Example 4: Allosteric Switching of Calmodulin in a *Mycobacterium Smegmatis* Porin A (MspA) Nanopore-Trap 1. Allosterism of wtCaM Upon $Ca^{2+}$ and Target Peptide Binding.

The wtCaM and its D129G mutant were prepared for the measurements as described in Example 5-Methods 1 and FIGS. 40-41. The M13 peptide from the skeletal muscle myosin light chain kinase (residues 577-602) was obtained by enzymolysis of the corresponding fusion protein (Example 5-Methods 2, FIG. 42). All protein analytes were used directly in all downstream nanopore measurements without further purification. Electrophysiology measurements were carried out in a 1.5 M KCl, 10 mM HEPES (pH=7.0) buffer environment using M2 MspA (D90N/D91N/D93N/D118R/D134R/E139K) (Example 5-Methods 3 and 4). If not otherwise stated, M2 MspA is referred to here as MspA. With a single MspA inserted in the membrane, different conformers of CaM were added to the cis side of the pore. An acidic protein, CaM was electrophoretically driven into the pore and when a continuous positive potential was applied was lodged in the vestibule from where it reports trapping events (FIG. 38b).

Nanopore measurements were first carried out by adding $Ca^{2+}$-free wild-type CaM (apo-wtCaM) to cis to a final concentration of 0.6 μM. With a +60 mV applied potential, continuous short resident resistive pulses were observed (FIG. 43a). These events were however not observed in the absence of analyte. The rate of event appearance is proportional to the final concentration of the added apo-wtCaM, indicating that the events certainly result from the addition of wtCaM. Following the measurement described in FIG. 43a, $CaCl_2$ was further added to cis to a final concentration of 4 mM. The coordination between $Ca^{2+}$ and apo-wtCaM results in immediate formation of the $Ca^{2+}$-bound form of wtCaM (Ca-wtCaM). The events observed subsequently were changed in consequence, to appear as much longer resident and deeper blocking events with clearly observable noise on top of the blockage level (FIG. 43b). Nanopore measurement of the M13 peptide-bound form of Ca-wtCaM (M13-Ca-wtCaM) was achieved by further addition of M13 peptide to cis. The final concentration of M13 was increased from 0 to 0.8 μM, generating a new type of sensing events, different from apo-wtCaM or Ca-wtCaM (FIGS. 43c, 44). A set of measurements with a combination of analytes confirmed that this new type of event was not generated by translocation of M13 peptide as the sole analyte (FIG. 45a). Measurements with a mixture of apo-wtCaM and M13 peptide without the presence of $Ca^{2+}$ also failed to report this event (FIG. 45c). These results confirm that the new event type was generated by M13-Ca-wtCaM and the presence of $Ca^{2+}$ is critical in the formation of this structure, consistent with the mechanism presented in FIG. 38*a*. Representative events of apo-wtCaM, Ca-wtCaM and M13-Ca-wtCaM are shown in FIG. 43*d*, in which the characteristics of all three event types can be distinguished.

To describe these events quantitatively for an in-depth analysis, event parameters such as the open-pore current ($I_0$), the blocked pore current ($I_b$), the blocking amplitude ($\Delta I$), the blocking ratio ($\Delta I/I_0$), the event dwell time ($t_{off}$) and the inter-event intervals ($t_{on}$) are defined in FIG. 46. Scatter plots of events caused by apo-wtCaM (874 events), Ca-wtCaM (571 events) or M13-Ca-wtCaM (608 events) are depicted in FIG. 43*e*, in which three completely separated populations of event points were observed.

Based on three independent measurements for each condition (N=3, Table 6), trapping events of apo-wtCaM are $51.9\pm1.1\%$ in the blocking ratio ($\Delta I/I_0$) and $5.1\pm0.3$ ms in the mean event dwell time ($\tau_{off}$). Events of Ca-wtCaM report a $\Delta I/I_0$ of $93.0\pm0.7\%$ and a $\tau_{off}$ of $3.7\pm0.6$ s (N=3) (Table 6) and events of M13-Ca-wtCaM report a $\Delta I/I_0$ of $83.9\pm0.3\%$ and a $\tau_{off}$ of $0.18\pm0.19$ s (N=3) (Table 6). Events of Ca-wtCaM report the largest level fluctuations when compared with those of apo-wtCaM and M13-Ca-wtCaM, indicating that these structures respectively report different fluctuations when confined in the pore vestibule (FIG. 43*f*). The reciprocal of the mean inter-event interval ($\overline{1/\tau_{on}}$) was proportional to the concentration of wtCaM (c) conformers in cis (FIG. 47). The capture frequency (k), defined by the equation $1/\tau_{on}=k_{on}\cdot c$, was derived as the slope of the linear fitting results in plots of $1/\tau_{on}$ vs. c (FIG. 47). As summarized in Table 7, $\overline{k_{on}}$ of apo-wtCaM is $0.89$ $M^{-1}$ $s^{-1}$, which is higher than that of Ca-wtCaM ($0.29$ $M^{-1}$ $s^{-1}$) or M13-Ca-wtCaM ($0.5$ $M^{-1}$ $s^{-1}$). The difference in $\overline{k_{on}}$ might be related to the decrease in electrophoretic force caused by the electrical neutralization of wtCaM by $Ca^{2+}$ and M13 peptide binding.[169]

To fully understand the thermodynamics of the sensing processes, we further calculated the Helmholtz free energy (F) of CaM-MspA interactions which represents the entropy cost to maintain a CaM conformer in MspA.[170] $F_{Ca-wtCaM}$ was calculated to be $-0.71$ kcal/mol, $F_{apo-wtCaM}$ was $-2.18$ kcal/mol and $F_{M13-ca-wtCaM}$ was $-1.73$ kcal/mol (Example 5 Methods 5). Regarding the structural change of CaM before and after $Ca^{2+}$ or M13 binding, the formation of the central helix of CaM upon $Ca^{2+}$ binding reduces the structural flexibility of Ca-wtCaM, greatly decreasing the entropic costs of being trapped by MspA. The results of molecular dynamics (MD) simulations showed that the order of root-mean-square deviation (RMSD) of the three conformers after being trapped could be correlated with that of the reciprocal of the event duration times from experimental measurements (apo-wtCaM>M13-Ca-wtCaM>Ca-wtCaM, FIG. 48). This confirms that the conformational flexibility of three conformers may play a critical role in the event dwell time.

A voltage gradient measurement was also performed (FIG. 49). Generally, by applying a larger potential, the $\tau_{off}$ of apo-wtCaM, Ca-wtCaM and M13-Ca-wtCaM events were all further extended, further confirming that the observed events were from trapping instead of from translocation. At an applied potential above +80 mV, a two-step event type was observed for apo-wtCaM. This indicates that the trapping events observed at +60 mV results from a loosely trapped state. The overall structure of apo-wtCaM can be further stretched to reach a deeper spot of MspA when a higher potential was applied (FIG. 49, Table 8).

TABLE 6

Statistics of blocking events. All measurements were carried out as described in Example 5 Methods 1 with M2 MspA. A +60 mV voltage was continuously applied during the measurements. Apo-wtCaM, Ca-wtCaM, apo-CaM-D129G and M13-Ca-wtCaM were applied as the analyte. All statistical results were derived from results of three independent experiments (N = 3).

| THE | INDEPENDE | | CURRENT | MEAN DWELL |
|---|---|---|---|---|
| APO- | 1 | | 52.61 | 5.44 ms |
| WTCAM | 2 | | 50.72 | 4.86 ms |
| | 3 | | 52.49 | 4.88 ms |
| | mean | | 51.9 ± 1.1 | 5.1 ± 0.3 ms |
| CA- | 1 | | 92.71 | 3.93 s |
| WTCAM | 2 | | 93.76 | 3.03 s |
| | 3 | | 92.41 | 4.06 s |
| | mean | | 93.0 ± 0.7 | 3.7 ± 0.6 s |
| APO-CAM- | 1 | type 1 | 64.07 | 0.16 s |
| D129G | | type 2 | 81.08 | 0.15 s |
| | 2 | type 1 | 65.09 | 0.20 s |
| | | type 2 | 78.93 | 0.25 s |
| | 3 | type 1 | 64.30 | 0.20 s |
| | | type 2 | 79.90 | 0.19 s |
| | mean | type 1 | 64.5 ± 0.5 | 0.18 ± 0.19 s |
| | | type 2 | 80.0 ± 1.1 | 0.20 ± 0.05 s |
| M13-CA- | 1 | | 84.23 | 0.15 s |
| WTCAM | 2 | | 83.68 | 0.12 s |
| | 3 | | 83.77 | 0.12 s |
| | mean | | 83.9 ± 0.3 | 0.13    0.02 s |

TABLE 7

Mean capture frequency ($\overline{k_{on}}$) of Ca-wtCaM, apo-wtCaM, apo-CaM-D129G or M13-Ca-wtCaM. The capture frequency ($k_{on}$) is defined as described in the equation $1/\tau_{on} = k_{on}\cdot c$, in which $\tau_{on}$ was the mean interevent intervals and c was the concentration of the protein analytes in the cis solution. $\overline{1/\tau_{on}}$ were the mean values derived from results of three independent experiments (N = 3). The reciprocal of the inter-event intervals ($1/\tau_{on}$) was plotted against the final concentration of the analyte and the mean capture frequency ($\overline{k_{on}}$) was derived as the slope of the fitting results (FIG. 47). The $\overline{k_{on}}$ values between different analyte follows the order of apo-wtCaM > M13-Ca-wtCaM ≈ apo-CaM D129G > Ca-wtCaM.

| THE ANALYTE | CONCENTRATIO | $\overline{1/\tau_{on}}$ ($S^{-1}$) | $\overline{k_{on}}$ ($MM^{-1}S^{-1}$) |
|---|---|---|---|
| APO-WTCAM | 0.3 | 0.32 ± 0.05 | 0.89 |
| | 0.6 | 0.57 ± 0.04 | |
| | 0.9 | 0.86 ± 0.10 | |
| | 1.2 | 1.2 ± 0.2 | |
| CA-WTCAM | 0.6 | 0.09 ± 0.01 | 0.29 |
| | 0.9 | 0.18 ± 0.02 | |
| | 1.2 | 0.25 ± 0.04 | |
| | 1.5 | 0.38 ± 0.06 | |
| APO-CAM- | 0.6 | 0.19 ± 0.09 | 0.51 |
| D129G | 1.2 | 0.37 ± 0.15 | |
| | 1.8 | 0.80 ± 0.17 | |
| | 2.4 | 1.2 ± 0.2 | |
| M13-CA- | 0.2 | 0.07 ± 0.01 | 0.52 |
| WTCAM | 0.4 | 0.19 ± 0.02 | |
| | 0.6 | 0.31 ± 0.02 | |
| | 0.8 | 0.37    0.01 | |

TABLE 8

Mean blockade ratio $(\overline{\Delta I/I_0})$ and mean dwell time $(\overline{\tau_{off}})$ measured at different voltages. All statistical results were derived from three independent experiments (N = 3).

| THE ANALYTE | VOLTA | CURRENT BLOCKADE RATIO | | MEAN |
|---|---|---|---|---|
| APO-WTCAM | +60 | Step 1 | 51.2 ± 0.4 | 5.57 ± 0.16 ms |
| | +70 | Step 1 | 51.43 ± 0.15 | 16.1 ± 0.8 ms [a] |
| | +80 | Step 1 | 51.85 ± 0.16 | 57 ± 8 ms [a] |
| | | Step 2 | 87.0 ± 0.3 | |
| | +90 | Step 1 | 51.6 ± 0.2 | 150 ± 29 ms [a] |
| | | Step 2 | 86.4 ± 0.6 | |
| CA-WTCAM | +60 | | 91.7 ± 0.6 | 2.48 ± 0.15 s |
| | +65 | | 92.37 ± 0.18 | 3.4 ± 0.3 s |
| | +70 | | 91.6 ± 0.5 | 5.0 ± 0.8 s |
| | +75 | | 91.04 ± 0.18 | 6.0 ± 0.5 s |
| M13-CA-WTCAM | +60 | | 82.9 ± 0.3 | 0.1 ± 0.2 s |
| | +70 | | 82.8 ± 0.4 | 0.49 ± 0.10 s |
| | +80 | | 82.6 ± 0.3 | 1.8 ± 0.4 s |
| | +90 | | 82.74 ± 0.12 | 6.1 ± 0.9 s |

[a] The mean dwell times were counted as the total duration of steps 1 and 2.

2. Probing the CaM Variant with a Single Mutation, D129G

Recently, some CaM mutants were found to be associated with life-threatening arrhythmia syndromes.[171] These CaM variants showed structural deviations causing interference with the function of cardiac ion channels such as the voltage-gated $Ca^{21}$ channel CaV1.2[172]. Here, a MspA nanopore-trap was applied to study a disease related mutant CaM-D129G, which gives rise to a long QT syndrome (LQTS) phenotype.[171,173]

According to the structures predicted by MD simulations, the D129G mutation could induce structural deviation of an EF-hand in the C-lobe of apo-wtCaM (FIG. 50a), possibly detectable by nanopore trapping. Experimentally, apo-CaM-D129G was added to cis to a final concentration of 0.6 µM and a +60 mV continuous potential was applied. Resistive pulse events were observed, but were not observed in the absence of apo-CaM-D129G (FIG. 51a), confirming that the events were certainly related to trapping of apo-CaM-D129G. The trapping events of apo-CaM-D129G report a shallow (type 1) and a deep (type 2) type of blockage, the shallow event type contributing to the majority of all events. The mean $\Delta I/I_0$ values were derived from the Gaussian fitting results of 678 events from each independent measurement (N=3) and these two event types respectively report $\Delta I/I_0$ of 64.5±0.5% and 80.0±1.1% (N=3, FIG. 51b, Table 7), which are fully resolvable from each other. The observation of two types of events from apo-CaM-D129G were however never observed from apo-wtCaM, indicating that a single mutation of CaM has resulted in an unfavored but detectable trapping conformation during the nanopore measurements. The mean inter-event intervals $(\overline{\tau_{on}})$ were plotted against the concentrations of apo-CaM-D129G and linearly fitted (FIG. 47). The derived mean capture efficiency $(\overline{k_{on}})$ of apo-CaM-D129G was 0.51 $\mu M^{-1} \cdot s^{-1}$ (N=3, Table 7), which is lower than that of apo-wtCaM (0.89 $\mu M^{-1} \cdot s^{-1}$). To demonstrate the event discrimination, simultaneous sensing of apo-wtCaM and apo-CaM-D129G was conducted (FIG. 50b). Though having only a single mutation, the variants can be visually distinguished, indicating a refined resolution of nanopore trapping to discriminate between proteins differing by a single amino acid mutation. Quantitatively, the scatter plot of $\Delta I/I_0$ vs. $t_{off}$ was demonstrated with the corresponding histograms (n=1440 events, FIG. 50c) and 2 major and 1 minor distribution of events were observed. The minor event distribution, which results from the type 2 event of apo-CaM-D129G, was demonstrated by the green fitting curve in the histogram. The $\tau_{off}$ of apo-CaM-D129G (0.18±0.19 s, N=3) was much longer than that of apo-wtCaM (5.1±0.3 ms, N=3), indicating that the D129G mutant suits the confined space of the nanopore-trap better than apo-wtCaM does.

A recent study suggested that the mutant D129G lost its ability to bind $Ca^{2+}$ as a result of the separation of EF-hands within the C-lobe,[174] consistent with results of the MD simulations conducted in this study (FIG. 50d). To investigate this experimentally, with 0.6 µM CaM-D129G and 4 mM $Ca^{2+}$ added to cis, nanopore measurements report a new type of event with a deeper blockage depth, similar to that of Ca-wtCaM. This new event type is also never observed in the absence of added $Ca^{2+}$, confirming that the event emanates from the $Ca^{2+}$ bound form of CaM-D129G (Ca-CaM-D129G). However, in identical measurement conditions, the rate of appearance of Ca-CaM-D129G events (FIG. 50e) in a continuous 20 min measurement is much lower than that of Ca-wtCaM (FIG. 50f). For a quantitative comparison, only 13% of the events were from the $Ca^{2+}$ bound form in the trial with CaM D129G. However, 97% of the events were from the $Ca^{2+}$ bound form when identically performed with wtCaM (FIG. 50g), providing the first single molecule evidence that the D129G mutant has significantly reduced its affinity to $Ca^{2+}$. These findings also suggest that binding of $Ca^{2+}$ to each EF domain of CaM is cooperative. The loss of $Ca^{2+}$ binding in EF-hand 4 has significantly affected the overall $Ca^{2+}$-binding affinity of CaM. Though events of Ca-CaM D129G and Ca-wtCaM share a similar blockage depth, they can still be effectively distinguished from different fluctuations of the blockage level (FIG. 50h-50i, FIG. 52, 54), which further supports the resolution of MspA nanopore trapping in the recognition of minor structural variations resulting from a single mutation.

3. Monitor the Binding Capacity of Apo-wtCaM to Divalent Ions

Although $Ca^{2+}$ is the most investigated factor triggering the conformational change of wtCaM and the consequent signal transduction, other evidence has shown that other ions can also activate wtCaM.[175] In 1983, Crowell et al. proved that different ions also can bind to wtCaM[176] and Vogel et al. observed similar phenomena by NMR analysis.[175] With a much improved resolution to a single molecule, binding of several divalent ions ($Mg^{2+}/Ca^{2+}/Sr^{2+}/Ba^{2+}/Pb^{2+}$) to wtCaM was studied by MspA nanopore trapping in this work. Limited by the poor solubility of $Pb^{2+}$ in an aqueous KCl solution, the concentration applied for all divalent ions was set at 2 mM. FIGS. 55a-55e show the degree of allosterism of apo-wtCaM (0.6 µM) when mixed with $Mg^{2+}/Ca^{2+}/Sr^{2+}/Ba^{2+}/Pb^{2+}$, respectively.

The histogram results of $\Delta I/I_0$ in FIG. 43e demonstrate only two types of events of wtCaM either unoccupied or fully occupied with $Ca^{2+}$, respectively reporting a $\overline{\Delta I/I_0}$ of 51.2% and 91.7% (Table 8). Measurements at a 2 mM $Ca^{2+}$ concentration however report 3 distributions of $\Delta I/I_0$ (56.8±1.1%, 75.0±2.1% and 90.4±0.2%, N=3, FIG. 53a, Table 8) indicating that 3 states of wtCaM coexist in the presence of 2 mM $Ca^{2+}$. This is expected since a single wtCaM contains 4 EF-hand domains all of which can bind $Ca^{2+}$. A lower concentration of $Ca^{2+}$ thus generates transient structures of which not all four EF-hand domains were fully occupied with $Ca^{2+}$ and were detected by the nanopore trap. This transient state was also observed when other divalent ions were bound to the CaM. Despite the type of the bound ions, to be distinguished from the transient states, the state when all four EF-hand domains were occupied was referred to as holo-wtCaM. Generally, events with a $\Delta I/I_0$ higher than 85% (FIGS. 55a-55e, red area, i.e., the lowest area) were considered the holo-wtCaM state and events with a $\Delta I/I_0$ less than 60% (FIGS. 55a-55e, green area, i.e., the highest area and absent in FIG. 55e) were considered to be the apo-wtCaM state. Events with a $\Delta I/I_0$ between 60% and 85% (FIGS. 55a-55e, blue area, i.e., the middle area and absent in FIGS. 55b and 55c) were considered to be transient states. For $Ca^{2+}$, the ratio of event types was summarized on the right of FIG. 55a, in which 54% of the events were from holo-wtCaM, indicating that $Ca^{2+}$ has a strong binding affinity to wtCaM.

Measurements with $Mg^{2+}$ or $Ba^{2+}$ however failed to report a clear distribution of the events corresponding to transient states. The proportion of the holo-wtCaM events were also extremely low, measuring only 4.0% or 4.4% (N=3, FIGS. 55b and 55c, FIGS. 53b and 53c and Table 9), respectively indicating that both $Mg^{2+}$ and $Ba^{2+}$ have a poor binding capacity to wtCaM. For $Sr^{2+}$, the ratio of holo-wtCaM events is 14.0±2.4% (N=3, FIG. 55d, FIG. 53d and Table 9) and the events of transient states are detectable, indicating a slightly better binding capacity to wtCaM than that of $Mg^{2+}$ or $Ba^{2+}$. $Pb^{2+}$ shows a strong binding to wtCaM with a ratio of holo-wtCaM of 62.0±3.1% (N=3, FIG. 55e, FIG. 53e and Table 9) and no transient states were observed, suggesting that the overall binding capacity of $Pb^{2+}$ to wtCaM is even stronger than that of $Ca^{2+}$. Since no single molecule study of this type has been reported previously, we tentatively suggest use of the ratio of holo-wtCaM events to evaluate the binding capacity of different divalent ions to wtCaM, in which the order $Pb^{2+}>Ca^{2+}>Sr^{2+}>Mg^{2+}\approx Ba^{2+}$ is summarized, consistent with conclusions drawn from macroscopic measurements.[176]

Despite of the types of the bound ions, all holo-wtCaM events have highly characteristic level fluctuations. When confined in an MspA nanopore trap, these fluctuations reflect minor structural differences of holo-wtCaM when bound with different ion types, which might be related to dynamic coordination and dissociation of divalent ions. The corresponding all-point histograms patterns generated from these fluctuations are highly conservative when ions of the same type were bound to wtCaM (FIGS. S14-S18). The patterns are also fully distinguishable from each other when different ions were applied (FIGS. 55f-55j, FIGS. 54-59), again confirming a high sensing resolution of MspA nanopore trapping in the discrimination of minor structural differences of proteins when coordinated with different divalent ions.

nation and activation in Ca-binding proteins, acknowledging the fact that $Tb^{3+}$ and $Ca^{2+}$ share a similar ionic radii and a preference for binding charged oxygen groups.[178,179] However, previous investigations have demonstrated that $Tb^{3+}$-bound wtCaM tend to become dysfunctional when the environment concentration of $Tb^{3+}$ ($[Tb^{3+}]$) was dramatically increased,[180] although the property of Ca-wtCaM is not affected by high $Ca^{2+}$ concentrations. It was theoretically speculated that significant structural disorder and pseudo-bridging metal coordination may form in $Tb^{3+}$ bound wtCaM (FIG. 60a).[181] However, to the best of our knowledge, relevant single molecule observations were never reported.

Experimentally, apo-wtCaM (0.3 µM) is fully activated by 5 µM $Tb^{3+}$, forming the activated state induced by $Tb^{3+}$ binding (Tb-wtCaM) and detectable by MspA nanopore trapping (FIG. 60b-c). However, when $[Tb^{3+}]$ was further increased to 150 PM, a new type of event, which is more transient and overlaid with small positive spikes, was continuously observed (FIG. 60d). The events of Tb-wtCaM gradually disappeared (FIG. 60d and FIG. 61), indicating that the structure of Tb-wtCaM may have experienced a transition to a different state. Further titration of $[Tb^{3+}]$ to 500 µM results in complete disappearance of all events, probably due to aggregation of wtCaM (FIG. 60e). The new type of event, which may be from a transition state prior to complete aggregation of CaM, was thus named the pre-aggregated state. Representative events of these three types are demonstrated with more details in FIG. 60f.

The reciprocal of inter-event intervals ($1/\tau_{on}$) of Tb-wtCaM capture was applied to evaluate the $Tb^{3+}$-induced structural change of wtCaM in the presence of different concentrations of $Tb^{3+}$ (FIG. 60g). The most Tb-wtCaM events were observed when $[Tb^{3+}]$ was slightly below 10 µM. In contrast, wtCaM could be fully activated by 0.6 mM $Ca^{2+}$. The $1/\tau_{on}$ remained relatively constant upon further increase of the $Ca^{2+}$ concentration, indicating that a higher concentration of $Ca^{2+}$ will not cause further structural changing or aggregation of CaM (FIG. 60h). $Tb^{3+}$ reports a lower response concentration than that of $Ca^{2+}$ (FIGS. 60g-60h), and consequently, the binding capacity of $Tb^{3+}$ to wtCaM is stronger than that of $Ca^{2+}$. This difference may be due to the extra positive charge of $Tb^{3+}$ compared to $Ca^{2+}$. Native-PAGE gel electrophoresis was also applied to char-

TABLE 9

The mean blocking ratios ($\overline{\Delta I/I_0}$) and percentage of various types of blocking events in total events (Proportion) corresponding to the blockade amplitude histogram from different divalent ions-binding wtCaM in FIG. 53. All statistical results were derived from three independent experiments (N = 3).

| | Apo-wtCaM | | Transient States | | Holo-wtCaM | |
|---|---|---|---|---|---|---|
| | $\overline{\Delta I/I_0}$ (%) | Proportion (%) | $\overline{\Delta I/I_0}$ (%) | Proportion (%) | $\overline{\Delta I/I_0}$ (%) | Proportion (%) |
| $Mg^{2+}$ | 52.6 ± 0.4 | 96.0 ± 1.7 | — | — | 88.8 ± 1.1 | 4.0 ± 1.7 |
| $Ca^{2+}$ | 56.8 ± 1.1 | 21.2 ± 3.1 | 75.0 ± 2.1 | 24.8 ± 2.7 | 90.4 ± 0.2 | 54.1 ± 4.8 |
| $Sr^{2+}$ | 54.0 ± 0.5 | 73.1 ± 1.4 | 75.7 ± 1.5 | 12.6 ± 0.4 | 90.22 ± 0.16 | 14.0 ± 2.4 |
| $Ba^{2+}$ | 51.6 ± 0.6 | 95.6 ± 2.9 | — | — | 86.9 ± 1.0 | 4.4 ± 2.9 |
| $Pb^{2+}$ | — | — | 77.91 ± 0.13 | 38.0 ± 3.1 | 90.6 ± 0.7 | 62.0 ± 3.1 |

4. Probing $Tb^{3+}$-Bound wtCaM

Many lanthanide ions were involved in the study of CaM, which acknowledges their characteristic fluorescent properties[177]. For example, $Tb^{3+}$ is an excellent luminescent analog of $Ca^{2+}$ and has been used in the study of ion coordiacterize these processes in ensembles (FIG. 62). By reporting bands of a much higher molecular weight than that of apo-wtCaM, our hypothesis that a high concentration of $Tb^{3+}$ would induce aggregation of CaM was confirmed and observation of the intermediate pre-aggregated state was enabled by the high resolution of MspA, which had however never been reported previously.

5. Advantages of MspA as a Nanopore-Trap

MspA nanopore trapping has successfully demonstrated single molecule discrimination in a variety of conformers of CaM. An immediate question is how this sensing scheme is performing when a different nanopore is applied and how future optimization should be carried out. Although we cannot compare all reported nanopores in this study, another two types of nanopores including wildtype α-hemolysin (α-HL WT) and Cytolysin A-RR (ClyA-RR) were used for a comparison (FIG. 63). Though composed entirely of protein, MspA demonstrates an exceptional stability against extreme conditions of a temperature up to 85° C. and a storage time of more than 3 months (FIG. 64). This property may be easily overlooked, but it is highly desirable when applied as a component of a commercial sensing device, since the consistency of the measurement performance is critical. This property also helps to reduce the difficulty and the cost of repetitive pore preparation when a long-term storage is required (FIG. 64). The advantage of structural stability is more obvious when compared with nanopores composed of alpha-helices such as Cytolysin A (ClyA)[149] which was reported to have a short storage time of every fresh preparation. Another advantage that may partially result from the structural stability of MspA is the lack of spontaneous gating when measured at a high applied potential (FIG. 65).

α-HL also is thermally stable and has a capacity for long-term storage. However, thermal treatment of α-HL at of other allosteric states of CaM and the wider opening of MspA allows allocation of a much wider variety of protein analyte structures. The blocking events acquired by α-HL have a shorter dwell times and the standard deviation of the blocking signal is lower, indicating a more restrained space when a wtCaM was trapped. The loss of detailed information of the structural fluctuations has also limited α-HL to discriminate binding of CaM with different divalent ions similar to MspA (FIG. 55).

ClyA however has a much wider vestibule than both α-HL and MspA and may be more suitable for trapping protein analytes (FIG. 63c). ClyA-RR, a charge optimized mutant of ClyA was used for this comparison. However, single channel recording with ClyA at a high applied potential would generate too frequent spontaneous gating, interfering with our measurements (FIG. 68). Measurements at +60 mV or lower failed to report any appearance of events, possibly due to a lack of sufficient driving force of CaM to enter the pore (FIG. 69). During most scenarios of nanopore sensing, a higher applied potential is generally preferred as it improves the sensing resolution by generating a larger event amplitude and generally enhances the rate of appearance of events when the effect of electrophoresis or electroosmosis is involved. A higher applied potential may result however in limitations such as the introduction of noise or frequent spontaneous gating, which is more frequently observed in large protein nanopores.[152,157] The stability against detergent and long-term storage of ClyA was also unsatisfactory based on our evaluation (FIG. 64).

TABLE 10

The minimal capture potentials and stability of different nanopores. [a]

| NANOPORE | | M2 MSPA | α-HL WT | CLYA-RR |
|---|---|---|---|---|
| MINIMAL CAPTURE POTENTIAL [B] (MV) | apo-wtCaM | +45 | N/A | N/A |
| | Ca-wtCaM | +40 | +130 | N/A |
| NANOPORE STABILITY [C] | | 1. No spontaneous gating [d] 2. Remain assembled after heating or long-term storage | 1. No spontaneous gating [d] 2. Partial deoligomerized after heating or long-term storage | 1. Spontaneous gating above +70 mV 2. Completly depolymerized in SDS-PAGE |

[a] All measurements were performed as described in Example 5 Methods 4 but different voltages were applied. [wtCaM] = 0.9 μM.
[B] The lowest applied potential when trapping events could be observed. The results were extracted from FIG. 66, 67 and 69.
[C] The conclusions are summarized from the results in FIG. 64, 65, 66 and 68.
[d] No spontaneous gating was observed during electrophysiological measurements in this work.

85° C. or with storage for 3 months results in noticeable disassembly of the pore structure, which is a slightly worse performance than that of MspA (FIG. 64). Geometrically, the pore vestibule of α-HL is narrower than that of MspA, meaning that some allosteric structure of CaM may not be trapped by the pore (FIG. 63b and FIGS. 66b, 66c). To experimentally evaluate this possibility, α-HL WT was applied to sense wtCaM. A minimal capture potential of +130 mV was required to trap Ca-wtCaM (Table 10 and FIG. 66) and trapping of apo-wtCaM was never observed, even with a significantly large applied potential. However, trapping of either form of wtCaM was achieved with MspA when a minimum applied potential of +45 mV was applied (FIG. 67). This is expected because the allosteric structure of Ca-wtCaM is more rigid and rod-like, and can more easily reach a deeper spot of the pore. However, the inability to observe apo-wtCaM has limited α-HL WT to investigations 6. Conclusions We have used the large vestibule of MspA in an investigation of single molecules of proteins, and different event types caused by allosteric transitions of wtCaM and a disease related mutant have been resolved. The binding capacities of wtCaM with different divalent ions such as $Mg^{2+}$, $Sr^{2+}$, $Ba^{2+}$ and $Pb^{2+}$ were evaluated, reporting a result consistent with previous conclusions drawn by NMR or fluorescence studies.[175,176] Direct discrimination of CaM when bound with different ions was also achieved by analyzing current fluctuations of the trapping level, indicating a high resolution offered by the conical and rigid structure of MspA. To the best of our knowledge, this is the first demonstration of single molecule protein sensing using MspA. We have observed different states of $Tb^{3+}$-induced aggregation of wtCaM in a continuous real-time measurement. A pre-aggregated state of $Tb^{3+}$ bound to wtCaM was recognized but has not been reported previously. This concentration-dependent aggregation processes reveals the scope of application of $Tb^{3+}$ when used as a luminescent $Ca^{2+}$ analog[179,180] in studies of $Ca^{2+}$ binding proteins. The demonstrated advantages such as a high sensing resolution, a stable sensing background without spontaneous gating, a low measurement noise, a mechanical stability, a consistent pore assembly and the ease of pore preparation and engineering have suggested that MspA may be an ideal choice of nanopore in protein sensing, complementary to existing approaches of nanopore protein sensing using solid state nanopores,[130,133] A-HL,[129,145] OmpG[144], FhuA,[143] ClyA,[134,154] FraC[152] or PlyAB.[151]

7. Data and Code Availability Statement

All data presented in this work can be provided by the corresponding authors upon reasonable requests.

8. Acknowledgments

The authors acknowledge Prof Hagan Bayley (University of Oxford), Prof. Giovanni Maglia (University of Groningen), Prof. Zijian Guo (Nanjing University) and Prof Congqing Zhu (Nanjing University) for inspiring discussions and useful suggestions on manuscript submission. This project was funded by National Natural Science Foundation of China (Grant No. 31972917, No. 91753108, No. 21675083), Programs for high-level entrepreneurial and innovative talents introduction of Jiangsu Province (individual and group program). Natural Science Foundation of Jiangsu Province (Grant No. BK20200009), Excellent Research Program of Nanjing University (Grant No. ZYJH004), State Key Laboratory of Analytical Chemistry for Life Science (Grant No. 5431ZZXM1902), Technology innovation fund program of Nanjing University.

Example 5: Materials and Methods for Example 4

1. Materials

Hexadecane, pentane, ethylenediamine tetraacetic acid (EDTA) and Genapol X-80 were purchased from Sigma-Aldrich. Dioxane-free isopropyl-β-D-thiogalactopyranoside (IPTG), kanamycin sulfate, ampicillin sodium salt, tris (hydroxymethyl)aminomethane (Tris) and imidazole were from Solarbio. PreScission Protease and PBS (phosphate-buffered saline) was from Beyotime. Pre-stained protein standards and 4-20% SDS-polyacrylamide precast gel was from Bio-Rad and color-coded pre-stained low range protein marker was from Cell Signaling. Instant Blue staining solution for protein gels was from Expedeon. Potassium chloride (KCl), calcium chloride ($CaCl_2$), sodium chloride (NaCl), magnesium chloride ($MgCl_2$), strontium chloride ($SrCl_2$), barium chloride ($BaCl_2$), lead chloride ($PbCl_2$), terbium chloride ($TbCl_3$) and potassium hydroxide (KOH) were from Aladdin. 4-(2-hydroxyethyl)-1-piperazineethanesulfonic acid (HEPES) was from Shanghai Yuanye Biotechnology. Ethylenediaminetetraacetic acid disodium salt (EDTA) was from Sigma-Aldrich. 1,2-diphytanoyl-sn-glycero-3-phosphocholine (DPhPC) was from Avanti Polar Lipids. E. coli BL21 (DE3) was from TransGen Biotech. Luria-Bertani (LB) agar and LB broth were from Hopebio. The potassium chloride buffer (1.5M KCl, 10 mM HEPES, pH 7.0) was prepared with Milli-Q water and membrane (0.2 m, Whatman) and filtered prior to use. Metal chlorides were dissolved in Milli-Q water as a stock solution for subsequent measurements. The stock solution of $PbCl_2$ was prepared with a 100 mM concentration. All other stock solutions were prepared with a 1M concentration.

2. Methods

The Preparation of Calmodulin (CaM)

The genes coding for CaM, including the wildtype calmodulin (wtCaM) and the CaM-D129G mutant, were respectively synthesized and cloned into separate pET-20b (+) plasmids by Genescript. The overproduction and purification of these two types of CaM were carried out identically in separate batches. Briefly, the corresponding plasmid was first transformed into E. coli BL21 (DE3), which were cultivated on LB agar plates with 100 μg/ml Ampicillin at 37° C. overnight. Then, the cells were transferred into a 300 mL LB medium and shaken at 170 rpm until reaching $OD_{600}$=0.6. The medium was added with 1 mM IPTG and shaken for 2 h at 37° C. to induce protein overexpression. The cells were harvested, resuspended in the extraction buffer A1 (50 mM Tris-HCl, pH 8.0) and sonicate lysed. The lysate was centrifuged at 15,871 g for 30 min at 4° C. The supernatant, which contained the CaM, was collected and applied on a Hi-Trap™ (GE Healthcare) anion exchange column for purification. The column was sequentially eluted with 2.5%, 5%, 10%, 15% and 25% concentration of the elution buffer B1 (50 mM Tris-HCl, 2 M NaCl, pH 7.0). All eluted fractions were collected for further characterizations. CaM is a typical acidic protein (isoelectric point=4.3, MW: 16.8 kDa), which has a stronger binding capacity to the anion exchange resin than other proteins in the lysates. It was thus expected to be eluted by 25% elution buffer B1. FIGS. 40 and 41 demonstrate the UV absorbance spectra acquired during elution and the 4-20% SDS-PAGE characterization results of the purified CaM and CaM-D129G. The purified wtCaM and CaM-D129G were either used immediately or stored at −80° C. for long term storage.

The Preparation of M13 Peptide

The M13 peptide was obtained by protease treatment of the GST-M13 fusion protein. The gene coding for the M13 peptide (with a terminator at the end of the sequence) was custom synthesized and cloned into a pGEX-6p-1 plasmid (a bacterial vector for expressing GST fusion proteins with a PreScission protease site) by Genescript. After being transformed with the plasmid, the E. coli BL21 (DE3) cells were cultivated on an LB agar plate with 100 g/ml Ampicillin at 37° C. overnight. A single colony was transferred into a 300 ml LB medium. The medium was shaken at 170 rpm at 37° C. until $OD_{600}$=0.8. The overproduction was induced by the addition of 1 mM IPTG and the cultures were incubated at 28° C. for a further 5 h. The cells were harvested, resuspended in a 20 mL extraction buffer A2 (PBS: 135 mM NaCl, 4.7 mM KCl, 10 mM $Na_2HPO_4$, 2 mM $NaH_2PO_4$, pH 7.4) and lysed by sonication. Afterwards, the solution was centrifuged at 15,871 g for 30 min at 4° C. to collect the supernatant. The supernatant was applied to a GSTrap™ (GE Healthcare) column. Then the column was washed with a PBS buffer. Afterwards, the buffer in the column was changed to the PreScission cleavage buffer (50 mM Tris-HCl, 150 mM NaCl, 1 mM EDTA, 1 mM dithiothreitol, pH 7.0). The PreScission Protease mix (with a GST-tag in the N-terminal) was loaded to the column and incubated at 4° C. for 8 h. The M13 peptide, which is the desired protein, was eluted with a 15 ml PreScission cleavage buffer and the GST moiety of the fusion protein and the PreScission Protease remained on the column. The column was eventually washed with the elution buffer B2 (50 mM Tris-HCl 10 mM glutathione, pH 8.0) to remove the bound GST moiety of the fusion protein and the PreScission Protease so that the column was re-initiated for future use. All eluates were characterized by 4-20% SDS-PAGE (FIG. 42).

Nanopore Preparations.

The majority of measurements in this work were performed with an MspA mutant, previously named as M2 MspA (D90N/D91N/D93N/D118R/D134R/E139K)[182]. For simplicity, M2 MspA is referred to as MspA all through this manuscript, if not otherwise stated. Other biological nanopores, including wild-type α-HL (WT α-HL) and ClyA-RR (D64R/C87A/L99Q/E103G/S110R/F166Y/1203V/C285S/–K294R/H307Y) were also used in this work. All the aforementioned nanopores were expressed with E. Coli BL21 (DE3) and purified using nickel affinity chromatography, as described previously.[183,184] All plasmid DNAs encoding these nanopores were shared in the Molecular Cloud repository (https://www.molecularcloud.org/s/shuo-huang).

Nanopore Measurements and Data Analysis

Nanopore measurements were performed as described previously.[185] The measurement device is composed of two custom polyformaldehyde chambers separated by a ~20 μm-thick Teflon film with a drilled aperture (~100 m in diameter). Before the measurement, the aperture was first treated with 0.5% (v/v) hexadecane in pentane and set for pentane evaporation. Afterward, 500 μL electrolyte buffers were added to both chambers, respectively. The buffered solution used for all electrical recordings is composed of 1.5 M KCl and 10 mM HEPES at pH 7.0. Two custom made Ag/AgCl electrodes, electrically connected to the patch-clamp amplifier, were placed in the chambers, in contact with the buffers. Conventionally, the electrically grounded chamber was defined as the cis chamber, while the opposing chamber was defined as the trans chamber. After adding 100 μL pentane solution of DPhPC (5 mg/mL) to both chambers, a lipid bilayer was formed by pipetting the electrolyte buffer in either chamber up and down several times. Upon bilayer formation, the acquired current immediately drops to 0 pA indicating that the aperture connecting both chambers has been sealed. MspA was added to the cis chamber to initiate spontaneous pore insertion. Upon a single nanopore insertion, the buffer in the cis chamber was manually exchanged to avoid further pore insertions.

To avoid interferences of external electromagnetic and vibration noises, the device was shielded in a custom Faraday cage (34 cm by 23 cm by 15 cm) mounted on a floating optical table (Jiangxi Liansheng Technology). All electrophysiology measurements were performed with an Axonpatch 200B patch-clamp amplifier paired with a Digidata 1550B digitizer (Molecular Devices). Unless otherwise stated, the voltage applied during all measurements is +60 mV. All measurements were carried out at room temperature (rt) (25° C.). All single-channel recordings were sampled at 25 kHz and low-pass filtered with a corner frequency of 1 kHz.

Calmodulin (CaM) trapping events were detected by the "single channel research" function in Clampfit 10.7. Subsequent analyses, including histogram plotting, scatter plotting and curve fitting, were performed by Origin 9.2 (Origin Lab).

Molecular Dynamics (MD) Simulations

All molecular dynamics simulations were conducted by Amber20 with the Amber ff14SB force field. The crystal structure of the MspA nanopore was adapted from the Protein Data Bank (PDB) file (1UUN, containing an A96R mutation) by the mutation module of PyMOL (R96A, D93N, D91N, D90N, D118R, D134R and E139K). The initial structures of Ca-wtCaM, apo-wtCaM or M13-Ca-wtCaM were derived from the PDB files 3CLN, 1CFC or 2BBN, respectively. The D129G mutation of CaM was introduced by the mutation module of PyMOL based on the crystal structures of wtCaM for further equilibration. The docking of wtCaM conformers to an MspA was generated by SwarmDock server to set the initial relative positions of Ca-wtCaM and MspA.[186] The preprocessing stage of SwarmDock involves repairing disordered loops, modelling missing atoms and posttranslational modifications and minimizing the input structures using the CHARMM molecular mechanics package.[187] A 1-palmitoyl-2-oleoyl-glycero-3-phosphocholine (POPC) lipid bilayer and 1.5 M KCl were added by CHARMM-GUI server.[188] The tleap module provided by Amber20 was used to fill in the missing hydrogen atoms in the composite system and the system was neutralized by adding K+ ions. The systems of the MspA-wtCaM complexes were immersed in a 113 Å×113 Å×113 Å periodic TIP3P cubic water box. The tleap program was used to generate the topology files needed for MD simulation.

To simulate wtCaM-trapping in an MspA, the trapped apo-wtCaM, Ca-wtCaM or M13-Ca-wtCaM conformers with MspA were firstly minimized for 10,000 steps with a 2.0 fs time step. Then the heating process was conducted with Langevin dynamics at 300 K and 1.0 atm for 5 ns. In the production simulations, the SHAKE algorithm was applied to all hydrogen-containing bonds to allow a 2.0 fs time step. Particle Mesh Ewald was utilized for electrostatics and the van der Waals interactions with a real-space cutoff of 12 Å was applied. Also, the position restraint with a force constant of 5 kcal/mol/Å$^2$ was applied to the MspA nanopore to restrain the pore shape. The free energy of the protein-pore interaction F to overcome the entropic costs of squeezing a CaM into a narrow pore were estimated by the equation:

$$F = k_B T \ln \left( T_t / T_{total} \right) \qquad \text{(Eq. 1)}^{189}$$

where $T_t$ is the measurable characteristic temporal parameters, $T_{total}$ is the total recording time and $T_t/T_{total}$ is the measured residence probability (Pr) of the protein within the pore. Accordingly, weak constant force pulling simulations (0.012-0.060 kcal/mol/A) were performed continuously along the direction perpendicular to the membrane plane to mimic the constant flow in the experiments according to the F from experiments. Each production simulation lasted for 100 ns.

To compare the trapping capacity of MspA to different wtCaM conformers, the root-mean-square deviations (RMSD) from the initial structures were summarized for the quantitative comparison of conformational fluctuation (FIG. 48). PyMOL and VMD were used to visualize the equilibrated structure and for trajectory visualization.

Movie S1. Stochastic sensing of apo-wtCaM. The electrophysiology recording (Example 5 Methods) was carried out with an M2 MspA. Apo-wtCaM was added to cis at a final concentration of 0.6 μM. At a +60 mV continuously applied potential, highly consistent resistive pulses caused by apo-wtCaM trapping were observed. For demonstration, the movie is replayed with a ⅕ speed of data acquisition.

Movie S2. Stochastic sensing of Ca-wtCaM. The electrophysiology recording (Example 5 Methods) was carried out with an M2 MspA. Apo-wtCaM and CaCl₂) was added to cis with a final concentration of 0.6 μM and 4 mM for each component. Spontaneous binding between apo-wtCaM and Ca²⁺ forms Ca-wtCaM. At a +60 mV continuously applied potential, consistent resistive pulses caused by Ca-wtCaM trapping were observed. For demonstration, the movie was replayed with a ⅕ speed of data acquisition.

Movie S3. Stochastic sensing of M13-Ca-wtCaM. The electrophysiology recording (Example 5 Methods) was carried out with an M2 MspA. Ca-wtCaM and M13 peptide was added to cis with a final concentration of 0.6 µM and 1.0 µM for each component. Spontaneous biding between a Ca-wtCaM and an M13 peptide forms the complex M13-Ca-wtCaM. At a +60 mV continuously applied potential, consistent resistive pulses caused by M13-Ca-wtCaM trapping were observed. For demonstration, the movie was replayed with a ⅕ speed of data acquisition.

Movie S4. Stochastic sensing of Pb-wtCaM. The electrophysiology recording (Example 5 Methods) was carried out with an M2 MspA. Apo-wtCaM and $PbCl_2$ was added to cis with a final concentration of 0.6 µM and 2 mM. Spontaneous binding between apo-wtCaM and $Pb^{2+}$ forms Pb-wtCaM. For demonstration, the movie was replayed with a ⅕ speed of data acquisition.

Movies S5-S7. Simulated trajectories of CaM trapping. MD simulations were performed as described in Example 3 Methods. An octameric M2 MspA was applied as the nanopore trap (a grey goblet shaped porin). An apo-wtCaM (Movie S5), a Ca-wtCaM (Movie S6) or a M13-Ca-wtCaM (Movie S7) was respectively applied as the analyte to be trapped. According to results in FIG. 48d, trapping of either type of CaM conformers has reached the steady state. Specifically, trapping of apo-wtCaM demonstrates the highest structural fluctuations (Movie S5). Ca-wtCaM lodges much deeper in the lumen of MspA. Consequently, trapping of Ca-wtCaM reports the lowest structural fluctuations (Movie S6). Due to its ellipsoidal structure, only a fraction of M13-Ca-wtCaM can lodge in the MspA lumen, reporting moderate structural fluctuations (Movie S6). All structures were drawn by NewCartoon and VDW (van der Waals). For ease of demonstration, all CaM structures were blue colored (Movie S5-S7). All calcium ions were yellow colored (Movie S5-S6). The M13 peptide was orange colored (Movie S7). All demonstrated movies were generated by 100 ns simulation. For ease of demonstration, all three movies were replayed in a 33 s duration.

Example 6: General Protein Sensing

As shown in FIG. 70-76, proteins with different charges at pH 7.0 could be trapped efficiently by the optimized MspA nanopore-trap in the presence of calcium flux. Firstly, lysozyme served as the typical basic protein analyte to demonstrate the optimization effect of calcium flux on the efficiency of protein analysis (FIGS. 70 and 71). By combining 1.5 M KCl (cis)/1 M $CaCl_2$ (trans) while keeping all other conditions identical, the capture frequency ($1/\tau_{on}$) and event dwell time ($\tau_{off}$) were significantly increased than the those of the 1.5 M KCl (cis)/1.5 M KCl (trans) group. This result may due to the additional electro-osmotic flow (EOF) from cis to trans under +100 mV, when the lumen of MspA were positively electrified after coupling with $Ca^{21}$. Secondly, myoglobin and heme-free myoglobin (apo-myoglobin), the relatively neutral proteins, could also be distinguished with the optimized MspA nanopore-trap as the fluctuation range of blocking current (quantified with Amplitude S.D.) of apo-myoglobin was significantly larger than that of myoglobin (FIGS. 72 and 73). Thirdly, the intrinsically unstructured protein domains (IUP) ACTR and NCBD could bind to each other and fold into a binary well-folded complex, and the distinct conformational changes upon this process were characterized (FIG. 74). Under the same experimental condition, the MspA nanopore-trap exhibited powerful discerning capacity that all the protein analytes with different charge, size and structure mentioned above were discriminable by at +100 mV in the presence of calcium flux (FIG. 75). The blocking efficiency ($\Delta I/I_0$) and the event dwell time ($t_{off}$) could be the main distinguishing criterions. Finally, α-lactalbumin, an acidic protein, has been proved to be more easily captured by MspA nanopore traps with calcium flux (FIG. 76). The applied voltage could even be reduced to +20 mV or lower, which may be due to its negative charge at pH 7.0.

Example 7: Machine Learning Assisted
Simultaneous Structural Profiling of Differently
Charged Proteins in a *Mycobacterium Smegmatis*
Porin a (MspA) Electroosmotic Trap Nanopore is emerging as a means of single molecule protein sensing. However, proteins demonstrate different charge properties, which complicates the design of a sensor that can achieve simultaneous sensing of differently charged proteins. In this example, we introduce an asymmetric electrolyte buffer combined with the *Mycobacterium smegmatis* porin A (MspA) nanopore to form an electroosmotic flow (EOF) trap. Apo and holo-myoglobin, which differ in only a single heme, can be fully distinguished with the superior resolution provided by MspA. Direct discrimination of lysozyme, apo/holo-myoglobin and the ACTR/NCBD protein complex, which are basic, neutral and acidic proteins respectively, was simultaneously achieved by the MspA EOF trap. To automate event classification, multiple event features were extracted to build a machine learning model, with which a 99.9% accuracy is achieved. The demonstrated method was also applied to identify single molecules of α-lactalbumin and β-lactoglobulin directly from the whey protein powder. This protein sensing strategy is useful in direct recognition of a protein from a mixture, suggesting its prospective use in rapid and sensitive detection of biomarkers or real-time protein structural analysis.

We applied the asymmetric electrolyte combination to the MspA nanopore-trap for protein structural profiling. The accumulated multivalent cations bound tightly to the negatively charged pore lumen were expected to switch the effective surface charge and to trigger the generation of EOF in nanopores. With an iso-osmotic asymmetric electrolyte buffer combination (cis: 1.5 M KCl/trans: 1 M $CaCl_2$), the capture efficiencies of proteins with different charges were significantly improved and the duration of single protein trapping was significantly extended, providing rich information for protein recognition, assisted by a machine learning algorithm.

Results and Discussion

MspA nanopore-trap in the presence of calcium flux. All electrophysiology measurements were performed using an M2 MspA mutant (D90N/D91N/D93N/D118R/D134R/E139K, Example 8-Methods 2) (FIG. 77a). For simplicity, the M2 MspA is referred to as MspA throughout this example. The electrically grounded chamber was defined as the cis chamber and the opposing chamber was defined as the trans chamber. Unless otherwise stated, all measurements were carried out in asymmetric electrolytes: 1.5 M KCl buffer (1.5 M KCl, 10 mM HEPES, pH 7.0) in cis and a 1.0 M $CaCl_2$ buffer (1.0 M $CaCl_2$, 10 mM HEPES, pH 7.0) in trans. After insertion of a single MspA into the membrane, the protein analytes were added to the cis chamber (Example 8-Methods 1).

Lysozyme, an antimicrobial enzyme that forms part of the innate immune system of animals, was employed as a representative basic protein with an isoelectric point (pI) of 11.[228] To demonstrate the effect of an asymmetric electrolyte combination, the sensing performance was evaluated with a symmetric electrolyte combination of 1.5 M KCl (cis)/1.5 M KCl (trans) and an asymmetric electrolyte combination of 1.5 M KCl (cis)/1.0 M CaCl₂ (trans). With a +100 mV potential continuously applied and an addition of lysozyme to a final concentration of 0.42 μM, sequential appearance of resistive pules was observed in both measurement conditions (FIGS. 77b and 77e). For a quantitative comparison, event parameters such as the open-pore current ($I_0$), blocked pore current ($I_b$), blocking amplitude ($\Delta I$), blocking ratio ($\Delta I/I_0$), event dwell time ($t_{off}$) and inter-event intervals ($t_{on}$) are defined in FIGS. 77b and 77e. Histograms of $t_{off}$ and $t_{on}$ for both conditions were generated. The mean event dwell time ($\tau_{off}$) (FIGS. 77c, 77f) and the mean inter-event intervals ($\tau_{on}$) (FIGS. 77d, 77g) were derived respectively from results of single exponential fitting. The results reveal that, by varying the electrolyte solutions while keeping all other conditions identical, the mean event dwell time ($\tau^{off}$) was significantly extended to 47.3±3.5 ms, N=3 (Table 11) when measured with an asymmetric electrolyte combination. This is significantly longer than that acquired with the symmetric electrolyte combination (5.4±0.2 ms, N=3, Table 11). Meanwhile, a significant increase in the rate of even appearance was also observed with the asymmetric electrolyte combination. In this case, $\tau_{on}$ was consequently reduced by a factor of 12, from 460.7±51.2 ms to 38.0±11.0 ms, N=3 (Table 11). The combination of asymmetric electrolytes (1.5 M KCl (cis)/1 M CaCl₂ (trans)) improved the efficiency of nanopore trapping and the event residence time was extended, providing more information of event characteristics during data acquisition.

Recent studies indicated that the use of polyvalent cations such as $Mg^{2+}$ and $La^{3+}$ in the electrophysiology measurements could produce localized charge inversion in a nanopore,[229-232] because the accumulated multivalent ions can change the nanopore surface charge profile. The surface charge profile in the pore lumen is relevant to the generation of the EOF, a potential driving force distinct from the electrophoretic force to trap an analyte in the nanopore.[209-212] Consequently, the asymmetric electrolyte combination may optimize the protein sensing capacity of MspA. To eliminate the interference of the electrophoretic force, trimethyl-β-cyclodextrin (trimethyl-3-CD), an electrically neutral molecule[233-234] was applied as a test analyte to probe the EOF generation in MspA (FIGS. 77h-77i). The voltage dependence of trimethyl-β-CD sensing using MspA was demonstrated in different combinations of electrolyte buffers. The frequency of event appearance increased in both testing conditions when the applied voltage was increased from −150 mV to +150 mV, confirming that an EOF from cis to trans exists when positive voltages are applied. This phenomenon was greatly enhanced in the presence of CaCl₂ in trans (FIG. 77i), indicating that a stronger EOF was generated. However, when both electrolyte chambers were filled with CaCl₂, the rate of event appearance is significantly reduced for both trimethyl-β-CD and lysozyme being treated as the analyte (FIG. 83). Though the divalent cations would coordinate tightly with the negatively charged amino acids such as D32, E39, D56, E57, E59, E63 and E127 in the MspA lumen, leading to the generation of EOF[235] (FIG. 84), the placement of CaCl₂ in cis may trigger $Ca^2$ binding to the analyte in cis prior to its entrance into the pore. This is not favorable because the added positive charge on the analyte may induce EPF oppositive to the direction to the pore, which results in a significant drop of the detection rate. It thus confirms that an assymetric buffer condition is advantageous.

Results of lysozyme trapping were as well analyzed (FIG. 85). A mean blocking ratio ($\overline{\Delta I/I_0}$) of 34.4±0.15 (N=3, 2580 events, Table 12) was obtained. As shown in FIG. 85d and Table 13, the trapping events appeared more frequently as the final concentration of lysozyme was increased. Meanwhile, both $1/\tau_{on}$ and $\tau_{off}$ of lysozyme were extended and then shortened when the applied voltage was increased from +60 mV to +120 mV (Table 14, FIGS. 85e-85f, 833a). Since the lysozyme is positively charged in the test buffer environment, the electrophoretic force (EPF) is opposite to the direction of EOF. When the applied voltage was lower than +80 mV, the EOF may serve as the more dominant driving force than the EPF.[235] When the voltage was higher than +100 mV, the influence of EPF was increased, resulting in a shorter escape time and a lower trapping efficiency of lysozyme.

Discrimination of apo-myoglobin and holo-myoglobin. Myoglobin, an electrically neutral protein found in the human bloodstream after skeletal muscle injury or renal insufficiency, is a sensitive disease marker.[236-237] Subtle differences in the structure and charge properties between the heme-free (apo-) and heme-bound (holo-) forms of myoglobin make it a suitable model protein for structural methodology studies (FIG. 78a).[238] Accordingly, myoglobin was applied to evaluate the sensing resolution of the MspA trap.

Nanopore measurements were carried out by adding apo-myoglobin to cis with a final concentration of 0.14 μM. Under a +100 mV applied potential, continuous current blockage was observed (FIGS. 78c and 78c). The blockage events observed with apo-myoglobin showed unique noise fluctuations on top of the blockage level, and in some cases of blockage, a further blockage level was generated (step 2). The extended blockage might be caused by further stretching of apo-myoglobin to reach a deeper position in the pore lumen, but to avoid interference from step 2, event features of both steps are discussed separately (FIG. 78b). As the concentration of apo-myoglobin is increased, the mean inter-event intervals ($\overline{\tau_{on}}$) are gradually shortened, indicating that the events certainly resulted from the addition of apo-myoglobin (FIG. 86g). Results of three independent measurements for each condition were recorded and used to support an in-depth analysis (N=3, Tables 11 and 12). The mean event dwell time ($\overline{\tau_{off}}$) of trapping events of apo-myoglobin was 531.0±27.5 ms. The blockage levels with observable noise (step 1) have a mean blocking ratio of 51.3±0.2% and the standard deviation of the blocking current (Amplitude S.D.) is 13.6±0.2 pA, while the further blockage level (step 2) observed has a mean blocking ratio of 89.1±0.3% (FIG. 86e).

A cofactor of myoglobin heme was further added to cis to coordinate with the apo-myoglobin. When the final concentration of heme was increased from 0 to 0.15 μM, a different type of sensing events began to appear (FIGS. 78c-78f). With 0.15 μM of heme in cis, the state of the myoglobin was completely changed (FIG. 78f). The amplitude S.D of the new type of trapping events was 6.0±0.2 pA, and the mean blocking ratio ($\Delta I/I_0$) was 47.6±0.3% (Table 12). No detectable events were observed however when heme was added to cis as the sole analyte with a final concentration of 0.2 μM, which confirms that this new type of event was not generated by translocation of heme (FIG. 87). A set of measurements with a standard holo-myoglobin sample showed that this new event type corresponds to holo-myoglobin, as the addition of standard holo-myoglobin sample in cis with a final concentration of 0.26 μM would produce events with the same characteristics (FIG. 86*d*). The above single molecule results suggest a close to 100% conversion from apo- to holo-myoglobin. This is also verified in the corresponding UV-Vis absorption spectroscopy assay (FIG. 88) and the same conclusion is drawn. The mean event dwell time ($\overline{\tau_{off}}$; 588.1±43.2 ms), the mean blocking ratio ($\overline{\Delta I/I_0}$, 47.4±0.2%, Table 12) and Amplitude S.D. (5.8±0.1 pA, Table 12) of holo-myoglobin standard trapping events are consistent with that of the events in FIG. 78*f*. Both the $\overline{\Delta I/I_0}$ and Amplitude S.D of apo-myoglobin are higher than those of holo-myoglobin, which confirms that the structure of apo-myoglobin is looser in the absence of heme, and has more interconvertible sub-states when in the lumen of MspA.[239] Furthermore, simultaneous sensing of holo- and apo-myoglobin standards was performed in a mixture. All event characteristics in FIGS. 78*d*-78*e* during the sequential titration of heme to apo-myoglobin could be reproduced in the simultaneous sensing of the standards mixture (FIGS. 89*b*, 89*c*) and showed the same distribution in the scatter plot (FIG. 89*d*). Both forms of myoglobin can be visually distinguished in the original current trace or in the filtered current trace with a 50 Hz high-pass Bessel filter (8-pole) by Clampfit (FIG. 89*b*), indicating a refined resolution of MspA to recognize protein conformational change caused by cofactor binding or dissociation.

By applying a larger potential, the $\tau_{off}$ and $1/\tau_{off}$ values of the holo-myoglobin events were increased (FIGS. 90*a*-90*b*, 95*b*-95*c* and Table 14), confirming that the observed events were from trapping rather than translocation. However, the $\tau_{off}$ of apo-myoglobin was only systematically extended when the voltage was increased to +100 mV and no further extension was observed at higher voltages (FIGS. 90*c*, 90*d* and Table 14). We speculate that the EPF was more dominant on apo-myoglobin than holo-myoglobin when the applied voltage was higher than +100 mV because apo-myoglobin has a higher isoelectric point (pI=8.5)[228] than holo-myoglobin (pI=7.3)[240]. In addition, with all other conditions identical, changing the electrolyte in trans to 1.5 M KCl also resulted in a dramatic reduction of the frequency of blocking events and a diminished escape time for both apo- and holo-myoglobin ($\tau_{on(apo)}$=3640.4633.6 ms; $\tau_{on(holo)}$=1319.2±321.1 ms; $\tau_{off(apo)}$=7.3±1.3 ms; $\tau_{off(holo)}$=3.7±0.4 ms) (FIGS. 91, Table 11).

Single-molecule trapping of the ACTR/NCBD complex. The p160 steroid receptor coactivator (ACTR, theoretical pI=4.1, Example 8-Method 3) and the nuclear coactivator binding domain of CREB-binding protein (NCBD, theoretical pI=11.1, Example 8-Method 3) were then adopted as representative intrinsic disordered proteins (IDP) to be probed by the nanopore trap. The mutual-induced folding process of these IDPs is activated only by mixing[241], causing formation of the ACTR/NCBD complex (theoretical pI=5.75, Example 8-Method 3) (FIGS. 79*a* and 79*b*). It is expected that these bound and unbound protein states would result in current variations caused by conformational differences between the disordered protein domains and their bound complex.

ACTR and NCBD were obtained by enzymolysis of corresponding GST fusion proteins (Example 8-Methods 3, FIGS. 92 and 93). As shown in FIGS. 79*c* and 79*d*, after independent addition of ACTR or NCBD at a final concentration of 1.28 μM, spike-like short-resident translocation events were respectively reported. Both analytes were clearly differentiated by the nanopore, as the translocation of ACTR and NCBD demonstrated mean blocking ratios ($\overline{\Delta I/I_0}$) of 24.6±0.5% and 62.6±0.5%, respectively (N=3, FIGS. 94*a*, 94*b* and Table 12). Furthermore, as the concentration of protein analytes was increased, the mean inter-event intervals ($\tau_{on}$) of both ACTR and NCBD were gradually shortened, indicating that the events did result from the addition of protein analytes (FIGS. 94*e* and 94*f*).

After mixing ACTR and NCBD in an equimolar ratio for 5 min, the mixture was added to cis. The folded ACTR/NCBD complex was formed and during subsequent nanopore measurements exhibited a new type of single conformational state, different from that of either ACTR or NCBD (FIG. 79*e*). The blockage events of ACTR/NCBD complex appeared as residence events ($\tau_{off}$=160.2±0.9 ms, N=3, FIG. 79*h* and Table 11) longer than those of either ACTR ($\overline{\tau_{off}}$=0.1±0.01 ms, N=3, FIG. 94*c* and Table 11) or NCBD ($\tau_{off}$=1.2 0.1 ms, N=3, FIG. 94*d* and Table 11). Furthermore, there was a clear fluctuating noise in the blockage level of ACTR/NCBD complex (FIG. 79*f*), with an Amplitude S.D. of 25.0±0.6 pA (N=3, Table 12). It is speculated that the current fluctuation might result from dynamic structural self-adjustment of the ACTR/NCBD complex when trapped in the pore lumen. The blockage amplitude ($I_b$) showed a more uniform distribution than that of the two intrinsic disordered proteins (IDP) according to the results of fitting the $\Delta I/I_0$ histograms (FIG. 79*g*), which proved that a well-folded protein structure was formed. As the final concentration of the ACTR/NCBD complex was increased, the value of $\overline{1/T_{on}}$ increased in parallel (FIG. 79*i*), showing that the blocking events were from the ACTR/NCBD complex in the MspA nanopore trap. Moreover, as expected from the consideration of charged properties, when the voltage was increased, the negatively charged ACTR/NCBD complex in cis was subjected to stronger EOF and EPF, resulting in an increase in the capture frequency ($\overline{1/\tau_{on}}$) (FIG. 95*d*). Similar experiments were carried out in a symmetrical electrolyte buffer environment (1.5 M KCl), but the capture efficiency and analysis duration of the ACTR/NCBD complex were much reduced (FIG. 96), indicating that the asymmetric electrolyte combination assists the trapping of negatively charged proteins. Though the EOF and EPF acting on the ACTR/NCBD are in the same direction whereas the EOF and EPF acting on the lysozyme are opposing each other, trapping of ACTR/NCBD demonstrates a shorter $\tau_{on}$ (FIG. 79*h*) than that of lysozyme (FIG. 77*f*). This phenomenon seems to be counterintuitive. It however suggests that the event dwell time may as well influenced by the overall structural of the protein analyte or the interaction between the pore and the analyte.

Artificial intelligence assisted profiling of differently charged proteins. Assisted by the asymmetric electrolyte buffer combination, lysozyme (pI=11), holo-myoglobin (pI=7.3), apo-myoglobin (pI=8.5) and ACTR/NCBD complex (theoretical pI=5.75) which have different charge and structural properties, were all detectable in the same measurement buffer condition (FIGS. 80*a*, 80*b*). Consistent and unique blockage features were reported by different protein types, suggesting the feasibility of simultaneous distinguishment between these protein analytes using the same nanopore. Experimentally, with a single pore inserted, the protein analytes were sequentially added to cis in the order of lysozyme (0.16 μM), holo-myoglobin (0.35 μM), ACTR/NCBD complex (1.28 μM) and apo-myoglobin (0.18 μM) (FIGS. 80*c*, 80*e*, 80*g*, 80*i*). The $\Delta I/I_0$ of blockage events gradually appeared with four distinct distributions (33.9, 47.4, 51.5 and 68.8%, FIG. 80*d*, 80*f*, 80*h*, 80*j*). These distributions correspond to trapping of lysozyme, holo-myoglobin, apo-myoglobin or ACTR/NCBD complex, respectively, according to statistical results previously acquired from independent measurements (Table 12). Size exclusion here is not the only factor that affects the degree of current blockage since the blocking ratio and the molecular weight and sizes of the four protein analytes are not linearly related. The event scatter plots of $\Delta I/I_o$ vs $t_{off}$ or Amplitude S.D. corresponding to the continuously recorded trace of the simultaneous sensing are shown in FIG. 80*j* (n=542). Event characteristics generated by different proteins formed four distinct populations of distribution in the scatter plot.

We established an artificial intelligence (AI) algorithm which assists automated protein recognition (Example 8-Methods 1). The strategy was to train AI to "learn" from the training data to build an optimum classification model to classify unknown nanopore events, similarly to those applied in previous nanopore researches.[227, 242-244] This strategy is particularly useful when events caused by different analytes are only distinguishable by simultaneously analyzing multiple event features. To train the model, several training data sets were assembled. Nanopore events were first extracted from raw time current traces (FIG. 97) and then seven features of the blocking current including mean value (mean), kurtosis (kurt), skewness (skew), dwell time (time), central value of distribution (peak) and noise (FWHM) were automatically extracted using MATLAB to form a feature matrix (FIG. 97). The feature matrices of lysozyme (n=785 events), holo-myoglobin (holoMB, n=763), ACTR/NCBD complex (ACTR_NCBD, n=673) and apo-myoglobin (apoMB, n=701) have known identities since they were generated during measurements with a single, known analyte. This feature matrix then forms a training dataset (FIG. 81*a*).

Model training was performed using the Classification Learner toolbox of MATLAB. A set of classifiers including decision trees, discriminant analysis, support vector machines (SVM), K nearest neighbors (KNN), naive Bayes, ensemble, and neural network classifiers were estimated (FIG. 81*a*). A 10-fold cross-validation, which randomly splits the dataset into a training subset for model training and a validation subset for model parameter fine-tuning and model validation against performance bias, was performed for each model to report the cross-validation accuracies (FIG. 98). Generally, all the models demonstrated satisfactory validation accuracies, and the bagged trees model of ensemble classifier demonstrated the highest score. As shown in the confusion matrix (FIG. 81*b*), the ensemble classifier using the bagged trees model performed well in each class. For lysozyme and holo-myoglobin, the proportion of correctly classified observations per true class (TPR) were 100%. Only 2 of the 673 ACTR/NCBD blocking events and 673 apo-myoglobin blocking events were misclassified (TPR=99.9%). The parallel coordinate plots of features from the bagged trees model showed that all 7 features play a role in event classification. In particular, the features of 'mean' and 'peak' have contributed the most by demonstrating clear event separations in the plot (FIG. 81*c*). To evaluate the efficiency of the training, model training was performed using a varying amount of training data and the cross-validation accuracies were reported. The results were plotted as a learning curve (FIG. 81*d*), according to which, an overall prediction accuracy of 0.990 is achieved with an input of only 180 training events, randomly selected from all 2922 events in the entire training dataset. The comparison between the training data accuracy and the cross-validation accuracy (FIG. 81*d*) also approves that no overfitting is happening in the model and a sampling number of 860 is sufficient to reach a 99.8% accuracy score.

The trained model was then exported to predict events with unknown identities, as demonstrated in FIG. 80. The features of events during sequential addition of lysozyme, holo-myoglobin, ACTR/NCBD complex and apo-myoglobin were extracted to form the predictive datasets, which were subsequently identified by the previously trained bagged trees model (FIG. 81*e*). The proportions of each type of protein are summarized in FIG. 81*f*, clearly demonstrating that whenever a protein analyte is newly added, the prediction results will report the appearance of corresponding events.

Machine Learning Assisted Whey Protein Identification.

The MspA EOF trap and the machine learning algorithm was further applied to the identification of protein ingredients in commercial whey protein powder. Whey protein accounts for about 18%-20% of all milk protein. It is widely used as a protein supplement to improve athletic performance. The major protein components of whey protein include α-lactalbumin and β-lactoglobulin along with a minor amount of other proteins and peptides.[247]

Experimentally, α-lactalbumin or β-lactoglobulin were first respectively analyzed as the sole analyte during each measurement with a +30 mV continually applied potential. The corresponding nanopore events were collected to form the training dataset (FIG. 6*a*). Briefly, trapping of α-lactalbumin showed two types of events with different blocking ratios and a low Amplitude S.D. (FIG. 82*b*-82*d*). In contrast, trapping of β-lactoglobulin resulted in blockage level fluctuations in the form of alternating conversions between high and low noise states (FIG. 82*e*-82*g*). Afterwards, commercially available whey protein powder with a 99% purity (Swisee™) was added to cis with a final concentration of 25 μg/ml and nanopore measurements were performed identically to that performed with α-lactalbumin or β-lactoglobulin. 1000 nanopore events were collected, from which 109 events were recognized as "others" as they were never observed in measurements with α-lactalbumin or β-lactoglobulin as the only analyte. These "others" events were mainly from other low abundant whey proteins detected by MspA and were applied as a part of the training dataset (FIG. 82*a*).

Seven event features were extracted from events of α-lactalbumin standards (n=301 events), β-lactoglobulin standards (n=253 events) and "others" (n=109 events) to form the training dataset (FIG. 99*a*). The training process was performed in the same workflow as described in FIG. 5. A set of classifiers were evaluated (FIG. 100), among which the bagged tree model has the highest validation accuracy (98.3%) and the lowest total cost (11). The confusion matrix shows that the TPR of α-lactalbumin, β-lactoglobulin and "others" are 100%, 98.4% and 93.6%, respectively (FIG. 99*b*). All event features play a role in event classification to describe the unique blockage event of each analyte according to the parallel coordinate plots (FIG. 99*c*). Also, a learning curve generated by 10-fold cross-validation (FIG. 99*d*) shows no overfitting because the classification model trained with more than 375 training samples has the same predictive ability for the training and the predicting dataset.

The bagged tree model was then employed to identify the ingredients in whey protein (FIG. 82*h*). From the single channel recording trace, the events corresponding to α-lactalbumin, β-lactoglobulin and "others" were automatically classified (FIG. 82*i*, n=333 events). Statistics show that 51.4% of all acquired events were recognized as β-lactoglobulin events and 39.6% were recognized as α-lactalbumin events (FIG. 82*j*). Moreover, the counts of $\alpha$-lactalbumin and $\beta$-lactoglobulin blocking events and the concentration of added whey protein show a linear correlation with an R-square of 0.996 or 0.987, respectively (FIG. 101). It's worth noting that whey protein with a final concentration of only 0.4 µg/ml could produce more than 10 effective trapping events within 5 min (FIG. 101*a*), suggesting a sensitivity of the MspA EOF trap.

CONCLUSIONS

An electroosmotic trap based on *Mycobacterium smegmatis* porin A (MspA) has been demonstrated. The application of an asymmetric buffer combination is critical in the generation of an EOF, which improves the efficiency of protein trapping by a factor of 7-18 and can extend the event dwell time by a factor of up to 159 (holo-myoglobin) (Table 11).

Our results demonstrate a balance between EOF and EPF in the pore lumen, which is qualitatively consistent with that predicted by a recently published theoretical model[235]. However to quantitatively describe the results of acquired with the specific pore and analyte, an all atom molecular dynamics simulation may be required.

Acknowledging the conical lumen geometry which enables a high resolution of sensing, MspA clearly discriminates between apo- and holo-myoglobin[239]. The structural difference between the intrinsically disordered proteins (ACTR and NCBD) and their bimolecular complex was also clearly identified. Generally, the MspA EOF trap demonstrates a structural consistency down to an atomic precition, which is not yet achieved by any solid state nanopores. This is important to guarantee the measurement consistency between different batches of pores. Compared with other biological nanopores such as ClyA[248], FraC[209] and PlyAB[213], an advantage of MspA is that it has a much enhanced assembly stability and structural rigidity, which is free of spontaneous gating and provides a low noise and highly consistent measurement performance. The conical lumen geometry of MspA also provides an advantage to simultaneously deal with a wider size range of protein analytes.

The EOF trap also demonstrates simultaneous sensing of representative acidic proteins such as the ACTR/NCBD complex, basic proteins (lysozyme) and neutral proteins (apo- and holo-myoglobin). This is the first time that proteins with an obvious difference in charge properties have been analyzed simultaneously. Previously reported nanopore traps such as ClyA[219] and FraC[209] have proved to be more suitable for the analysis of positively charged proteins. The unfavorable signal from negatively charged proteins usually needs to be eliminated by lowering the pH of the test buffer or introducing a charged dipole to the protein analyte. However, proteins with pI=5.75, 7.3, 8.5 or 11 can be simultaneously captured by a MspA nanopore-trap in a buffer condition at pH=7.0 and the protein identities can be recognized reliably. These results indicate that the combination of 1.5 M KCl in cis and 1 M $CaCl_2$ in trans could optimize the MspA trapping for protein structure profiling. By performing realtime observation of a single trapped protein, valuable information such as the kinetics of ligand/protein interaction or conformational change of the protein may be obtained with a high resolution, useful in fundamental research of protein science.

A machine learning based protein classifier has also been developed to automate data analysis. The classification algorithm is based on simultaneous consideration of multiple event features. It is thus advantageous to discriminate between events that are however difficult to be distinguished solely based on the blockage amplitude. An impressive 99.9% validation accuracy was also reported in the distinguishment between lysozyme, ACTR/NCBD complex, holo-myoglobin and apo-myoglobin. The MspA EOF trap and the machine learning classifier has also been applied to identify $\alpha$-lactalbumin and $\beta$-lactoglobulin directly from whey protein powder, suggesting that the developed method and the classifier algorithm is generic to a wide variety of protein types as an analytical tool. The automatic algorithm also saves human labor and avoids errors caused by subjective human judgments.

Data Availability Statement

All data presented in this work can be provided by the corresponding authors upon reasonable requests.

Acknowledgment

This project was funded by National Natural Science Foundation of China (Grant No. 31972917, No. 91753108, No. 21675083), Supported by the Fundamental Research Funds for the Central Universities (Grant No. 020514380257, No. 020514380261), Programs for high-level entrepreneurial and innovative talents introduction of Jiangsu Province (individual and group program), Natural Science Foundation of Jiangsu Province (Grant No. BK20200009), Excellent Research Program of Nanjing University (Grant No. ZYJH004), Shanghai Municipal Science and Technology Major Project, State Key Laboratory of Analytical Chemistry for Life Science (Grant No. 5431ZZXM1902), Technology innovation fund program of Nanjing University, China Postdoctoral Science Foundation (Grant No. 2021M691508).

Example 8: Materials and Methods for Example 7

Materials

Hexadecane, pentane, ethylenediamine tetraacetic acid (EDTA), glutathione (GSH), apo-myoglobin (from equine skeletal muscle), lysozyme (from chicken egg white), $\alpha$-lactalbumin (from bovine milk) and Genapol X-80 were purchased from Sigma-Aldrich. $\beta$-lactoglobulin (from bovine milk) was purchased from RHAWN. Whey protein powder was purchased from Swisse™. Ferroheme was purchased from CSNpharm. Dioxane-free isopropyl-$\beta$-D-thiogalactopyranoside (IPTG), kanamycin sulfate, ampicillin sodium salt, tris (hydroxymethyl)aminomethane (Tris) and imidazole were from Solarbio. PreScission Protease and PBS (phosphate-buffered saline) were from Beyotime. Pre-stained protein standards and 4-20% SDS-polyacrylamide precast gel was from Bio-Rad. Instant Blue staining solution was from Expedeon. Potassium chloride (KCl), calcium chloride ($CaCl_2$), sodium chloride (NaCl) and magnesium chloride ($MgCl_2$) were from Aladdin. 4-(2-hydroxyethyl)-1-piperazineethanesulfonic acid (HEPES) and holo-myoglobin (from equine skeletal muscle) were from Shanghai Yuanye Biotechnology. Ethylenediaminetetraacetic acid disodium salt (EDTA) was from Sigma-Aldrich. 1,2-diphytanoyl-sn-glycero-3-phosphocholine (DPhPC) was from Avanti Polar Lipids. *E. coli* BL21 (DE3) was from TransGen Biotech. Luria-Bertani (LB) agar and LB broth were from Hopebio. The potassium chloride buffer (1.5M KCl, 10 mM HEPES, pH 7.0) was prepared with Milli-Q water and membrane (0.2 m, Whatman) filtered prior to use. The stock solution of lysozyme, holo-myoglobin and apo-myoglobin were prepared with a 1 mg/mL concentration for subsequent measurements. The stock solution of α-lactalbumin, β-lactoglobulin and whey protein were prepared with a concentration of 2.5 mg/mL for subsequent measurements.

Methods

1. Nanopore Measurements and Data Analysis

All nanopore measurements were performed as described previously.[249] Briefly, the measurement device is composed of two custom polyformaldehyde chambers separated by a ~20 μm-thick Teflon film with a drilled aperture (~100 μm in diameter). Before the measurement, the aperture was first treated with 0.5% (v/v) hexadecane in pentane and allowed to stand for pentane evaporation. Conventionally, the electrically grounded chamber was defined as the cis chamber, while the opposing chamber was defined as the trans chamber. Afterwards, 500 μL electrolyte buffers were respectively added to both chambers. Unless otherwise stated, all nanopore measurements in this paper were performed with a 1.5 M KCl buffer (1.5 M KCl, 10 mM HEPES, pH 7.0) in cis and a 1.0 M CaCl₂ buffer (1.0 M CaCl₂, 10 mM HEPES, pH 7.0) in trans. Two custom-made Ag/AgCl electrodes, electrically connected to the patch-clamp amplifier, were placed in both chambers, in contact with the buffers to form a closed circuit. After adding 100 μL pentane solution of DPhPC (5 mg/mL) to both chambers, a lipid bilayer was formed by pipetting the electrolyte buffer in either chamber up and down several times. Upon bilayer formation, the acquired current immediately drops to 0 pA indicating that the aperture has been sealed by the formed lipid bilayer. MspA was then added to the cis chamber to initiate spontaneous pore insertion. Upon a single nanopore insertion, the buffer in the cis chamber was manually exchanged to avoid further pore insertions.

To avoid interferences from external electromagnetic and vibration noises, the device was shielded in a custom Faraday cage (34 cm by 23 cm by 15 cm) mounted on a floating optical table (Jiangxi Liansheng Technology). All electrophysiology results were acquired with an Axonpatch 200B patch-clamp amplifier paired with a Digidata 1550B digitizer (Molecular Devices). Unless otherwise stated, the voltage applied during all measurements was +100 mV and all measurements were carried out at room temperature (rt) (25° C.). All single-channel recordings were sampled at 25 kHz and low-pass filtered with a corner frequency of 1 kHz.

All protein trapping events were detected by the "single channel research" function in Clampfit 10.7. The Axon abf files are imported into MATLAB using a 'abfload' algorithm (Harald Hentschke (2021). abfload (https://www.mathworks.com/matlabcentral/fileexchange/6190-abfload), MATLAB Central File Exchange. Retrieved Sep. 1, 2021) to read the features of blocking current. The machine learning model training process were performed using the Classifi-cation Learner toolbox of MATLAB. The prediction process was performed using a custom algorithm in MATLAB. Subsequent analyses, including histogram plotting, scatter plot generation and curve fitting were performed by Origin 9.2 (Origin Lab).

2. Nanopore Preparations.

All measurements in this work were performed with an MspA mutant named M2 MspA (D90N/D91N/D93N/D118R/D134R/E139K). For simplicity, M2 MspA is referred to as MspA all through this manuscript, if not otherwise stated. The monomeric MspA was expressed with E. Co/i BL21 (DE3) and purified using nickel affinity chromatography.[250] The plasmid DNA coding for M2 MspA was shared in the Molecular Cloud repository (https://www.noleculalogorg/s/shuo-huang, access code: MC_0101191).

3. The Preparation of ACTR and NCBD Peptides

The ACTR and NCBD peptides were both prepared by protease treatment of the GST-peptide fusion protein. The gene coding for the ACTR or NCBD peptide (with a terminator at the end of the sequence) was custom-synthesized and cloned into a pGEX-6p-1 plasmid (a bacterial vector for expressing GST fusion proteins with a PreScission protease site) by Genescript. After being transformed with the plasmid, the *E. coli* BL21 (DE3) cells were cultivated on an LB agar plate with 100 μg/ml Ampicillin at 37° C. for 10 h. A single colony was transferred into a 300 mL LB medium with 100 μg/ml Ampicillin. The medium was shaken at 170 rpm at 37° C. until $OD_{600}=0.8$. Overproduction was induced by the addition of 1 mM IPTG and the cultures were incubated at 28° C. for another 5 h. The cells were harvested, resuspended in a 20 mL extraction buffer A1 (135 mM NaCl, 4.7 mM KCl, 10 mM Na₂HPO₄, 2 mM NaH₂PO₄, pH 7.4) and lysed by sonication. Afterwards, the solution was centrifuged at 15,871 g for 30 min at 4° C. to collect the supernatant. The supernatant was applied to a GSTrap™ (GE Healthcare) column. Then the column was washed with PBS buffer. Subsequently, the buffer in the column was changed to the PreScission cleavage buffer (50 mM Tris-HCl, 150 mM NaCl, 1 mM EDTA, 1 mM dithiothreitol, pH=7.0). The PreScission Protease mix with a GST-tag in the N-terminal was loaded to the column and incubated at 4° C. for 8 h. The ACTR peptide (or NCBD peptide), which is the target protein, was eluted with a 15 mL PreScission cleavage buffer while the GST moiety of the fusion protein and the PreScission Protease remained on the column. The column was eventually washed with elution buffer B1 (50 mM Tris-HCl 10 mM glutathione, pH 8.0) to remove the bound GST moiety of the fusion protein and the PreScission Protease so that the column was re-initiated for future use. All eluates were characterized by 4-20% SDS-PAGE (FIGS. 92 and 93).

The isoelectric points (pI) of ACTR, NCBD and their complex have never been reported. Their theoretical pI values, as referenced in this article, were calculated by Expasy, (https://web.expasy.org/protparam/) based on their amino acid sequence.

TABLE 11

Mean dwell time ($\tau_{off}$) and mean interevent duration ($\tau_{on}$) of the protein trapping
with different electrolyte combinations. All measurements were carried out as described
in Example 8 Methods 1 with M2 MspA. A +100 mV voltage was continuously applied
during the measurements. Lysozyme, holo-myoglobin, apo-myoglobin, ACTR peptide,
NCBD peptide and ACTR/NCBD complex were applied as the analytes. All statistical
results were derived from results of three independent measurements (N = 3).

| THE ANALYTE | ELECTROLYTE CIS/TRANS | INDEPENDENT MEASUREMENTS | MEAN DWELL TIME ($\tau_{off}$, MS) | MEAN INTEREVENT DURATION TIME ($\tau_{on}$, MS) |
|---|---|---|---|---|
| LYSOZYME | 1.5M KCl/1.0M CaCl$_2$ | 1 | 50.8 | 27.5 |
| | | 2 | 47.5 | 49.4 |
| | | 3 | 43.7 | 37.3 |
| | | mean ± std | 47.3 ± 3.5 | 38.0 ± 11.0 |
| | 1.5M KCl/1.5M KCl | 1 | 5.4 | 492.6 |
| | | 2 | 5.6 | 487.8 |
| | | 3 | 5.3 | 401.6 |
| | | mean ± std | 5.4 ± 0.2 | 460.7 ± 51.2 |
| HOLO-MYOGLOBIN | 1.5M KCl/1.0M CaCl$_2$ | 1 | 598.8 | 248.1 |
| | | 2 | 625.0 | 186.9 |
| | | 3 | 540.5 | 152.0 |
| | | mean ± std | 588.1 ± 43.2 | 195.7 ± 48.7 |
| | 1.5M KCl/1.5M KCl | 1 | 3.8 | 1470.6 |
| | | 2 | 4.1 | 1111.1 |
| | | 3 | 3.2 | 1694.9 |
| | | mean ± std | 3.7 ± 0.4 | 1319.2 ± 321.1 |
| APO-MYOGLOBIN | 1.5M KCl/1.0M CaCl$_2$ | 1 | 552.5 | 389.1 |
| | | 2 | 500.0 | 371.7 |
| | | 3 | 540.5 | 334.4 |
| | | mean ± std | 531.0 ± 27.5 | 365.1 ± 27.9 |
| | 1.5M KCl/1.5M KCl | 1 | 8.7 | 3125.0 |
| | | 2 | 7.1 | 4347.8 |
| | | 3 | 6.0 | 3448.3 |
| | | mean ± std | 7.3 ± 1.3 | 3640.4 ± 633.6 |
| ACTR/NCBD COMPLEX | 1.5M KCl/1.0M CaCl$_2$ | 1 | 15.5 | 194.9 |
| | | 2 | 15.8 | 166.7 |
| | | 3 | 17.3 | 129.2 |
| | | mean ± std | 16.2 ± 0.9 | 163.6 ± 33.0 |
| | 1.5M KCl/1.5M KCl | 1 | 7.1 | 3448.3 |
| | | 2 | 6.8 | 2857.1 |
| | | 3 | 7.2 | 2613.6 |
| | | mean ± std | 7.0 ± 0.2 | 2979.0 ± 421.8 |
| ACTR PEPTIDE | 1.5M KCl/1.0M CaCl$_2$ | 1 | 0.1 | 246.3 |
| | | 2 | 0.1 | 363.6 |
| | | 3 | 0.1 | 333.3 |
| | | mean ± std | 0.1 ± 0.01 | 314.4 ± 60.9 |
| NCBD PEPTIDE | 1.5M KCl/1.0M CaCl$_2$ | 1 | 1.0 | 322.6 |
| | | 2 | 1.2 | 352.1 |
| | | 3 | 1.3 | 234.2 |
| | | mean ± std | 1.2 ± 0.1 | 303.0 ± 61.35 |

TABLE 12

Mean current blockade ratio ($\overline{\Delta I/I_0}$, %) and amplitude
S.D. (pA) of protein trapping events. All measurements were
carried out as described in Example 8 Methods 1. A buffer combination
of 1.5M KCl (cis)/1.0M CaCl$_2$ (trans), pH = 7.0 was applied.
A +100 mV voltage was continuously applied during the measurements.
All statistical results were derived from results of three
independent measurements (N = 3).

| THE ANALYTE | INDEPENDENT MEASURE-MENTS | CURRENT BLOCKADE RATIO ($\overline{\Delta I/I_0}$, %) | AMPLITUDE S.D. (PA) |
|---|---|---|---|
| LYSOZYME | 1 | 34.4 | 7.1 |
| | 2 | 34.6 | 6.6 |
| | 3 | 34.3 | 6.6 |
| | mean | 34.4 ± 0.15 | 6.8 ± 0.3 |
| HOLO-MYOGLOBIN (STANDARD) | 1 | 47.6 | 5.8 |
| | 2 | 47.4 | 5.7 |
| | 3 | 47.2 | 5.8 |
| | mean | 47.4 ± 0.2 | 5.8 ± 0.1 |
| HOLO-MYOGLOBIN (APO- | 1 | 47.5 | 5.9 |
| | 2 | 47.9 | 6.2 |
| | 3 | 47.4 | 6.0 |

TABLE 12-continued

Mean current blockade ratio ($\overline{\Delta I/I_0}$, %) and amplitude
S.D. (pA) of protein trapping events. All measurements were
carried out as described in Example 8 Methods 1. A buffer combination
of 1.5M KCl (cis)/1.0M CaCl$_2$ (trans), pH = 7.0 was applied.
A +100 mV voltage was continuously applied during the measurements.
All statistical results were derived from results of three
independent measurements (N = 3).

| THE ANALYTE | INDEPENDENT MEASURE-MENTS | | CURRENT BLOCKADE RATIO ($\overline{\Delta I/I_0}$, %) | AMPLITUDE S.D. (PA) |
|---|---|---|---|---|
| MYOGLOBIN | mean | | 47.6 ± 0.3 | 6.0 ± 0.2 |
| APO-MYOGLOBIN | 1 | Step 1 | 51.5 | 13.5 |
| | | Step 2 | 89.4 | |
| | 2 | Step 1 | 51.3 | 13.5 |
| | | Step 2 | 88.8 | |
| | 3 | Step 1 | 51.1 | 13.9 |
| | | Step 2 | 89.1 | |
| | mean | Step 1 | 51.3 ± 0.2 | 13.6 ± 0.2 |
| | | Step 2 | 89.1 ± 0.3 | |

TABLE 12-continued

Mean current blockade ratio ($\overline{\Delta I/I_0}$, %) and amplitude

S.D. (pA) of protein trapping events. All measurements were carried out as described in Example 8 Methods 1. A buffer combination of 1.5M KCl (cis)/1.0M CaCl$_2$ (trans), pH = 7.0 was applied.

A +100 mV voltage was continuously applied during the measurements.

All statistical results were derived from results of three independent measurements (N = 3).

| THE ANALYTE | INDEPENDENT MEASURE-MENTS | CURRENT BLOCKADE RATIO ($\overline{\Delta I/I_0}$, %) | AMPLITUDE S.D. (PA) |
|---|---|---|---|
| ACTR/NCBD | 1 | 68.9 | 24.3 |
| COMPLEX | 2 | 69.7 | 25.2 |
| | 3 | 68.8 | 25.4 |
| | mean | 69.1 ± 0.5 | 25.0 ± 0.6 |
| ACTR | 1 | 24.9 | N.A. [a] |
| PEPTIDE | 2 | 25.0 | N.A. [a] |
| | 3 | 24.1 | N.A. [a] |
| | mean | 24.6 ± 0.5 | N.A. [a] |
| NCBD | 1 | 62.1 | N.A. [a] |
| PEPTIDE | 2 | 62.3 | N.A. [a] |
| | 3 | 63.5 | N.A. [a] |
| | mean | 62.6 ± 0.5 | N.A. [a] |

[a] N.A.: $\tau_{off}$ of spike-shaped blocking events were too short to obtain credible amplitude S.D.

TABLE 13

Correlation analysis between $\overline{1/\tau_{on}}$ and concentrations of
the protein analytes. All measurements were carried out
as described in Example 8 Methods 1. A buffer combination
of 1.5M KCl (cis)/1.0M CaCl$_2$ (trans), pH = 7.0 was
applied. A +100 mV voltage was continuously applied
during the measurements. The value of $\overline{1/\tau_{on}}$ was
positively correlated with the concentration of the
protein analytes. All statistical results were derived
from results of three independent measurements (N = 3).

| THE ANALYTE | CONCENTRATION (MM) | $\overline{1/\tau_{on}}$ (MS$^{-1}$) |
|---|---|---|
| LYSOZYME | 0.21 | $(6.4 \pm 2.6) \times 10^{-3}$ |
| | 0.42 | $(2.8 \pm 0.8) \times 10^{-2}$ |
| | 0.63 | $(4.2 \pm 1.2) \times 10^{-2}$ |
| | 0.83 | $(5.5 \pm 0.7) \times 10^{-2}$ |
| HOLO-MYOGLOBIN | 0.09 | $(1.5 \pm 0.5) \times 10^{-3}$ |
| | 0.17 | $(3.8 \pm 1.0) \times 10^{-3}$ |
| | 0.26 | $(6.0 \pm 1.2) \times 10^{-3}$ |
| | 0.35 | $(1.1 \pm 0.1) \times 10^{-2}$ |
| APO-MYOGLOBIN | 0.04 | $(4.4 \pm 0.5) \times 10^{-4}$ |
| | 0.07 | $(9.9 \pm 0.9) \times 10^{-3}$ |
| | 0.11 | $(2.1 \pm 0.2) \times 10^{-3}$ |
| | 0.14 | $(2.8 \pm 0.2) \times 10^{-3}$ |
| ACTR/NCBD | 0.32 | $(7.1 \pm 1.4) \times 10^{-4}$ |
| COMPLEX | 0.64 | $(1.8 \pm 0.2) \times 10^{-3}$ |
| | 0.96 | $(4.3 \pm 0.5) \times 10^{-3}$ |
| | 1.28 | $(6.3 \pm 1.3) \times 10^{-3}$ |
| ACTR PEPTIDE | 0.32 | $(1.4 \pm 0.3) \times 10^{-3}$ |
| | 0.64 | $(3.3 \pm 0.7) \times 10^{-3}$ |
| | 0.96 | $(6.6 \pm 0.8) \times 10^{-3}$ |
| | 1.28 | $(9.3 \pm 1.5) \times 10^{-3}$ |
| NCBD PEPTIDE | 0.32 | $(5.5 \pm 4.8) \times 10^{-4}$ |
| | 0.64 | $(3.4 \pm 0.8) \times 10^{-3}$ |
| | 0.96 | $(4.8 \pm 0.5) \times 10^{-3}$ |
| | 1.28 | $(7.3 \pm 0.7) \times 10^{-3}$ |

TABLE 14

Mean dwell time ($\overline{\tau_{off}}$) and $\overline{1/\tau_{on}}$ measured
at different voltages. All measurements were carried out as described in
Example 8 Methods 1. A buffer combination of 1.5M KCl (cis)/1.0M
CaCl$_2$ (trans), pH = 7.0 was applied. All statistical results
were derived from results of three independent measurements (N = 3).

| THE ANALYTE | VOLTAGE (MV) | $\overline{\tau_{off}}$ (MS) | $\overline{1/\tau_{on}}$ (MS$^{-1}$) |
|---|---|---|---|
| LYSOZYME | +60 | 35.5 ± 0.9 | $(1.0 \pm 0.2) \times 10^{-2}$ |
| | +80 | 47.8 ± 6.7 | $(1.4 \pm 0.4) \times 10^{-2}$ |
| | +100 | 47.3 ± 3.5 | $(1.8 \pm 0.2) \times 10^{-2}$ |
| | +120 | 38.8 ± 8.9 | $(1.8 \pm 0.3) \times 10^{-2}$ |
| HOLO-MYOGLOBIN | +60 | 53.3 ± 7.2 | $(1.9 \pm 0.6) \times 10^{-3}$ |
| | +80 | 210.4 ± 15.5 | $(3.3 \pm 0.8) \times 10^{-3}$ |
| | +100 | 588.1 ± 43.2 | $(5.3 \pm 1.3) \times 10^{-3}$ |
| | +120 | 1121.6 ± 60.1 | $(9.0 \pm 1.5) \times 10^{-3}$ |
| APO-MYOGLOBIN | +60 | 99.3 ± 20.2 | $(1.0 \pm 0.3) \times 10^{-3}$ |
| | +80 | 317.5 ± 18.3 | $(2.0 \pm 0.5) \times 10^{-3}$ |
| | +100 | 531.0 ± 27.5 | $(2.8 \pm 0.3) \times 10^{-3}$ |
| | +120 | 522.0 ± 15.0 | $(4.5 \pm 0.6) \times 10^{-3}$ |
| ACTR/NCBD | +60 | 22.9 ± 3.1 | $(3.2 \pm 0.6) \times 10^{-3}$ |
| COMPLEX | +80 | 18.8 ± 1.9 | $(4.3 \pm 0.5) \times 10^{-3}$ |
| | +100 | 16.2 ± 0.9 | $(6.3 \pm 1.3) \times 10^{-3}$ |
| | +120 | 8.8 ± 0.5 | $(7.6 \pm 1.4) \times 10^{-3}$ |

Movie S8. Stochastic sensing of apo-myoglobin and holo-myoglobin. The electrophysiology recording was carried out as described in Example 8 Methods 1. The measurements were carried out in a buffer of 1.5 M KCl/1.0 M CaCl$_2$ (pH=7.0). Apo-myoglobin and holo-myoglobin were added to cis with a final concentration of 0.18 μM and 0.35 μM, respectively. A transmembrane potential of +100 mV was continuously applied, during which highly consistent resistive pulses caused by apo- or holo-myoglobin trapping were observed. Event identification was carried out by machine learning prediction. The identified events were labelled as AM (apo-myoglobin) and HM (holo-myoglobin), respectively. For the demonstration, the movie is played back with 0.5× speed of the actual data acquisition.

Movie S9. Stochastic sensing of lysozyme, apo-myoglobin, holo-myoglobin and ACTR/NCBD complex. The electrophysiology recording was carried out as described in Example 8 Methods 1. The measurements were carried out in the buffer of 1.5 M KCl/1.0 M CaCl$_2$ (pH=7.0). Lysozyme, apo-myoglobin, holo-myoglobin and ACTR/NCBD were added to the cis chamber with a final concentration of 0.16, 0.18, 0.35 and 1.28 μM, respectively. A transmembrane potential of +100 mV was continuously applied, during which highly consistent resistive pulses caused by different proteins are observed. Event identification was carried out by machine learning prediction (FIG. 81e). The identified events were labelled as L (lysozyme), AM (apo-myoglobin), HM (holo-myoglobin) and AN (ACTR/NCBD complex), respectively. For the demonstration, the movie is played back with a 0.5× speed of the actual data acquisition.

Movie S10. Stochastic sensing of whey proteins. The electrophysiology recording was carried out as described in Example 8 Methods 1. The measurements were carried out in the buffer of 1.5 M KCl/1.0 M CaCl$_2$ (pH=7.0). Whey protein was added to cis with a final concentration of 25 μg/ml. A transmembrane potential of +30 mV was continually applied, during which highly consistent resistive pulses caused by different components were observed. Event identification was carried out by machine learning (FIG. 82a). The identified events were labelled as α (α-lactalbumin), β

(β-lactoglobulin), and o (others), respectively. For the demonstration, the movie is played back with a 2× speed of the actual data acquisition.

Example 9: Stochastic Sensing of Lysozyme-Substrate Complex with MsPA Electroosmotic Trap The structure changes of lysozyme after binding with n-acetylchitohexaose (substrate of lysozyme) could been clearly distinguished with the MspA electroosmotic trap under this asymmetric electrolyte buffer condition (FIG. 102).

REFERENCE

1. Mortimer, S. A., Kidwell, M. A. & Doudna, J. A. Insights into RNA structure and function from genome-wide studies. Nat. Rev. Genet. 15, 469-479 (2014).
2. Batey, R. T., Rambo, R. P. & Doudna, J. A. Tertiary motifs in RNA structure and folding. Angewandte Chemie-International Edition 38, 2327-2343 (1999).
3. Zhuang, X. W. et al. A single-molecule study of RNA catalysis and folding. Science 288, 2048-2051 (2000).
4. Lee, J. T. Epigenetic Regulation by Long Noncoding RNAs. Science 338, 1435-1439 (2012).
5. Keel, A. Y., Rambo, R. P., Batey, R. T. & Kieft, J. S. A general strategy to solve the phase problem in RNA crystallography. Structure 15, 761-772 (2007).
6. Lukavsky, P. J., Kim, I., Otto, G. A. & Puglisi, J. D. Structure of HCVIRES domain II determined by NMR. Nature Structural Biology 10, 1033-1038 (2003).
7. Varani, G., Aboulela, F. & Allain, F. H. T. NMR investigation of RNA structure. Progress in Nuclear Magnetic Resonance Spectroscopy 29, 51-127 (1996).
8. Zhang, H. & Keane, S. C. Advances that facilitate the study of large RNA structure and dynamics by nuclear magnetic resonance spectroscopy. Wiley Interdisciplinary Reviews-Rna 10, e1541 (2019).
9. Zhang, K. et al. Structure of the 30 kDa HIV-1 RNA Dimerization Signal by a Hybrid Cryo-EM, NMR, and Molecular Dynamics Approach. Structure 26, 490-498 (2018).
10. Zhang, K. et al. Cryo-EM structure of a 40 kDa SAM-IV riboswitch RNA at 3.7 angstrom resolution. Nature Communications 10, 5511 (2019).
11. Zhao, R. & Rueda, D. RNA folding dynamics by single-molecule fluorescence resonance energy transfer. Methods 49, 112-117 (2009).
12. Williams, M. C. & Rouzina, I. Force spectroscopy of single DNA and RNA molecules. Current Opinion in Structural Biology 12, 330-336 (2002).
13. Henley, R. Y. et al. Electrophoretic Deformation of Individual Transfer RNA Molecules Reveals Their Identity. Nano Letters 16, 138-144 (2016).
14. Rozevsky, Y. et al. Quantification of mRNA expression using single-molecule nanopore sensing. ACS nano 14, 13964-13974 (2020).
15. Shasha, C. et al. Nanopore-Based Conformational Analysis of a Viral RNA Drug Target. ACS Nano 8, 6425-6430 (2014).
16. Wanunu, M. et al. Nanopore analysis of individual RNA/antibiotic complexes. ACS Nano 5, 9345-9353 (2011).
17. Skinner, G. M., van den Hout, M., Broekmans, O., Dekker, C. & Dekker, N. H. Distinguishing single-and double-stranded nucleic acid molecules using solid-state nanopores. Nano Letters 9, 2953-2960 (2009).
18. Ying, Y.-L., Cao, C. & Long, Y.-T. Single molecule analysis by biological nanopore sensors. Analyst 139, 3826-3835 (2014).
19. Cao, C. et al. Discrimination of oligonucleotides of different lengths with a wild-type aerolysin nanopore. Nature Nanotechnology 11, 713-718 (2016).
20. Thakur, A. K. & Movileanu, L. Real-time measurement of protein-protein interactions at single-molecule resolution using a biological nanopore. Nature biotechnology 37, 96-101 (2019).
21. Ouldali, H. et al. Electrical recognition of the twenty proteinogenic amino acids using an aerolysin nanopore. Nature Biotechnology 38, 176-181 (2020).
22. Zhang, X. et al. Nanopore electric snapshots of an RNA tertiary folding pathway. Nature Communications 8, 1458 (2017).
23. Lu, B. et al. Protein Motion and Configurations in a Form-Fitting Nanopore: Avidin in ClyA. Biophysical Journal 115, 801-808 (2018).
24. Jing, P., Haque, F., Vonderheide, A. P., Montemagno, C. & Guo, P. Robust properties of membrane-embedded connector channel of bacterial virus phi29 DNA packaging motor. Molecular Biosystems 6, 1844-1852 (2010).
25. Tanaka, K., Caaveiro, J. M. M., Morante, K., Manuel Gonzalez-Manas, J. & Tsumoto, K. Structural basis for self-assembly of a cytolytic pore lined by protein and lipid. Nature Communications 6, 6337 (2015).
26. Huang, G. et al. Electro-Osmotic Vortices Promote the Capture of Folded Proteins by PlyAB Nanopores. Nano Letters 20, 3819-3827 (2020).
27. Soskine, M., Biesemans, A., De Maeyer, M. & Maglia, G. Tuning the Size and Properties of ClyA Nanopores Assisted by Directed Evolution. J Am Chem Soc 135, 13456-13463 (2013).
28. Faller, M., Niederweis, M. & Schulz, G. E. The structure of a mycobacterial outer-membrane channel. Science 303, 1189-1192 (2004).
29. Heinz, C., Engelhardt, H. & Niederweis, M. The core of the tetrameric mycobacterial porin MspA is an extremely stable beta-sheet domain. Journal of Biological Chemistry 278, 8678-8685 (2003).
30. Manrao, E. A. et al. Reading DNA at single-nucleotide resolution with a mutant MspA nanopore and phi29 DNA polymerase. Nature Biotechnology 30, 349-353 (2012).
31. Craig, J. M. et al. Determining the effects of DNA sequence on Hel308 helicase translocation along single-stranded DNA using nanopore tweezers. Nucleic Acids Research 47, 2506-2513 (2019).
32. Butler, T. Z., Pavlenok, M., Derrington, I. M., Niederweis, M. & Gundlach, J. H. Single-molecule DNA detection with an engineered MspA protein nanopore. Proceedings of the National Academy of Sciences of the United States of America 105, 20647-20652 (2008).
33. Wang, S. et al. Retarded Translocation of Nucleic Acids through alpha-Hemolysin Nanopore in the Presence of a Calcium Flux. ACS Applied Materials & Interfaces 12, 26926-26935 (2020).
34. Chan, J. A., Krichevsky, A. M. & Kosik, K. S. MicroRNA-21 is an antiapoptotic factor in human glioblastoma cells. Cancer Research 65, 6029-6033 (2005).
35. Elbashir, S. M. et al. Duplexes of 21-nucleotide RNAs mediate RNA interference in cultured mammalian cells. Nature 411, 494-498 (2001).
36. Pan, Y. P. & MacKerell, A. D. Altered structural fluctuations in duplex RNA versus DNA: a conformational switch involving base pair opening. Nucleic Acids Research 31, 7131-7140 (2003).

37. Perera, R. T. et al. Unzipping of A-Form DNA-RNA, A-Form DNA-PNA, and B-Form DNA-DNA in the alpha-Hemolysin Nanopore. Biophysical Journal 110, 306-314 (2016).

38. Carroll, J. S. et al. Chromosome-wide mapping of estrogen receptor binding reveals long-range regulation requiring the forkhead protein FoxA1. Cell 122, 33-43 (2005).

39. Sano, M. et al. Effect of asymmetric terminal structures of short RNA duplexes on the RNA interference activity and strand selection. Nucleic Acids Research 36, 5812-5821 (2008).

40. Ghosh, P. et al. Comparing 2-nt 3' overhangs against blunt-ended siRNAs: a systems biology based study. BMC genomics 10, S17 (2009).

41. Sponer, J. et al. RNA Structural Dynamics As Captured by Molecular Simulations: A Comprehensive Overview. Chemical Reviews 118, 4177-4338 (2018).

42. Wimmer, E., Maxwell, I. H. & Tener, G. M. A Simple Method for Isolating Highly Purified Yeast Phenylalanine Transfer Ribonucleic Acid. Biochemistry-Us 7, 2623-2628 (1968).

43. Yatime, L. et al. Structural basis for the targeting of complement anaphylatoxin C5a using a mixed L-RNA/L-DNA aptamer. Nature Communications 6, 6481 (2015).

44. Correll, C. C., *Freeborn*, B., Moore, P. B. & Steitz, T. A. Metals, motifs, and recognition in the crystal structure of a 5S rRNA domain. Cell 91, 705-712 (1997).

45. Steitz, J. A. et al. A 5S rRNA/L5 complex is a precursor to ribosome assembly in mammalian cells. The Journal of cell biology 106, 545-556 (1988).

46. Mueller, F. et al. The 3D arrangement of the 23 S and 5 S rRNA in the *Escherichia coli* 50 S ribosomal subunit based on a cryo-electron microscopic reconstruction at 7.5 Å resolution. Journal of molecular biology 298, 35-59 (2000).

47. Friebe, P., Boudet, J., Simorre, J. P. & Bartenschlager, R. Kissing-loop interaction in the 3' end of the hepatitis C virus genome essential for RNA replication. Journal of Virology 79, 380-392 (2005).

48. Shu, D., Shu, Y., Haque, F., Abdelmawla, S. & Guo, P. Thermodynamically stable RNA three-way junction for constructing multifunctional nanoparticles for delivery of therapeutics. Nature Nanotechnology 6, 658-667 (2011).

49. Namy, O., Moran, S. J., Stuart, D. I., Gilbert, R. J. C. & Brierley, I. A mechanical explanation of RNA pseudoknot function in programmed ribosomal frameshifting. Nature 441, 244-247 (2006).

50. Klein, D. J., Schmeing, T. M., Moore, P. B. & Steitz, T. A. The kink-turn: a new RNA secondary structure motif. Embo Journal 20, 4214-4221 (2001).

51. Kumari, S., Bugaut, A., Huppert, J. L. & Balasubramanian, S. An RNA G-quadruplex in the 5' UTR of the NRAS proto-oncogene modulates translation. Nature Chemical Biology 3, 218-221 (2007).

52. Schreiber, J. et al. Error rates for nanopore discrimination among cytosine, methylcytosine, and hydroxymethylcytosine along individual DNA strands. Proceedings of the National Academy of Sciences of the United States of America 110, 18910-18915 (2013).

53. Smith, A. M., Abu-Shumays, R., Akeson, M. & Bernick, D. L. Capture, Unfolding, and Detection of Individual tRNA Molecules Using a Nanopore Device. Frontiers in bioengineering and biotechnology 3, 91 (2015).

54. Misiunas, K., Ermann, N. & Keyser, U. F. QuipuNet: Convolutional Neural Network for Single-Molecule Nanopore Sensing. Nano Letters 18, 4040-4045 (2018).

55. Cardozo, N. et al. Multiplexed direct detection of barcoded protein reporters on a nanopore array. bioRxiv, 837542 (2019).

56. Bhattacharya, S. et al. Molecular Dynamics Study of MspA Arginine Mutants Predicts Slow DNA Translocations and Ion Current Blockades Indicative of DNA Sequence. ACS Nano 6, 6960-6968 (2012).

57. Aksimentiev, A., Heng, J. B., Timp, G. & Schulten, K. Microscopic kinetics of DNA translocation through synthetic nanopores. Biophysical journal 87, 2086-2097 (2004).

58. Leehey, M. A., Squassoni, C. A., Friederich, M. W., Mills, J. B. & Hagerman, P. J. A noncanonical tertiary conformation of a human mitochondrial transfer RNA. Biochemistry-Us 34, 16235-16239 (1995).

59. Farnsworth, R. W., Keating, J., McAuley, M. & Smith, R. Optimization of a Protocol for *Escherichia coli* RNA Extraction and Visualization. Journal of Experimental Microbiology and Immunology 5, 87-94 (2004).

60. Hingerty, B., Brown, R. S. & Jack, A. Further refinement of structure of yeast transfer-RNA phe. Journal of Molecular Biology 124, 523-534 (1978).

61. Sussman, J. L., Holbrook, S. R., Warrant, R. W., Church, G. M. & Kim, S. H. Crystal structure of yeast phenylalanine transfer RNA. I. Crystallographic refinement. Journal of Molecular Biology 123, 607-630 (1978).

62. Schevitz, R. W., Podjarny, A. D., Krishnamachari, N., Hughes, J. J. & Sigler, P. B. Crystal-structure of a eukaryotic initiator transfer-RNA. Nature 278, 188-190 (1979).

63. Woo, N. H., Roe, B. A. & Rich, A. 3-dimensional structure of *Escherichia-coli* initiator transfer RNA-f (met). Nature 286, 346-351 (1980).

64. Westhof, E., Dumas, P. & Moras, D. Crystallographic refinement of yeast aspartic-acid transfer-RNA. Journal of Molecular Biology 184, 119-145 (1985).

65. Huang, Q., Mao, Z., Li, S., Hu, J. & Zhu, Y. A non-radioactive method for small RNA detection by northern blotting. Rice 7, 26 (2014).

66. Guo, C. et al. Silica nanoparticles induce oxidative stress, inflammation, and endothelial dysfunction in vitro via activation of the MAPK/Nrf2 pathway and nuclear factor-kappa B signaling. International Journal of Nanomedicine 10, 1463-1477 (2015).

67. Grosshans, H., Hurt, E. & Simos, G. An aminoacylation-dependent nuclear tRNA export pathway in yeast. Genes & Development 14, 830-840 (2000).

68. Dittmar, K. A., Goodenbour, J. M. & Pan, T. Tissue-specific differences in human transfer RNA expression. Plos Genetics 2, 2107-2115 (2006).

69. Honda, S., Shigematsu, M., Morichika, K., Telonis, A. G. & Kirino, Y. Four-leaf clover qRT-PCR: A convenient method for selective quantification of mature tRNA. Rna Biology 12, 501-508 (2015).

70. Zheng, G. et al. Efficient and quantitative high-throughput tRNA sequencing. Nature Methods 12, 835-837 (2015).

71. Torrent, M., Chalancon, G., de Groot, N. S., Wuster, A. & Babu, M. M. Cells alter their tRNA abundance to selectively regulate protein synthesis during stress conditions. Science Signaling 11, eaat6409 (2018).

72. Fu, H. et al. Stress induces tRNA cleavage by angiogenin in mammalian cells. Febs Letters 583, 437-442 (2009).

73. Wang, Y. et al. Electrode-free nanopore sensing by DiffusiOptoPhysiology. Science Advances 5, eaar3309 (2019).

74. Krishnan, S. et al. Molecular transport through large-diameter DNA nanopores. Nature Communications 7, 12787 (2016).

75. Wang, Y. et al. Osmosis-Driven Motion-Type Modulation of Biological Nanopores for Parallel Optical Nucleic Acid Sensing. ACS applied materials & interfaces 10, 7788-7797 (2018).

76. Abraham, M. J. et al. GROMACS: High performance molecular simulations through multi-level parallelism from laptops to supercomputers. SoftwareX 1, 19-25 (2015).

77. Huang, J. et al. CHARMM36m: an improved force field for folded and intrinsically disordered proteins. Nature methods 14, 71-73 (2017).

78. Jorgensen, W. L., Chandrasekhar, J., Madura, J. D., Impey, R. W. & Klein, M. L. Comparison of simple potential functions for simulating liquid water. The Journal of chemical physics 79, 926-935 (1983).

79. Jo, S., Kim, T., Iyer, V. G. & Im, W. CHARMM-GUI: a web-based graphical user interface for CHARMM. Journal of computational chemistry 29, 1859-1865 (2008).

80. Faller, M., Niederweis, M. & Schulz, G. E. The structure of a mycobacterial outer-membrane channel. Science 303, 1189-1192 (2004).

81. Jovine, L., Djordjevic, S. & Rhodes, D. The crystal structure of yeast phenylalanine tRNA at 2.0 Å resolution: cleavage by Mg2+ in 15-year old crystals. Journal of molecular biology 301, 401-414 (2000).

82. Hess, B., Bekker, H., Berendsen, H. J. & Fraaije, J. G. LINCS: a linear constraint solver for molecular simulations. Journal of computational chemistry 18, 1463-1472 (1997).

83. Darden, T., York, D. & Pedersen, L. Particle mesh Ewald: An N log (N) method for Ewald sums in large systems. The Journal of chemical physics 98, 10089-10092 (1993).

84. Berendsen, H. J., Postma, J. v., van Gunsteren, W. F., DiNola, A. & Haak, J. R. Molecular dynamics with coupling to an external bath. The Journal of chemical physics 81, 3684-3690 (1984).

85. Tarek, M. Membrane electroporation: a molecular dynamics simulation. Biophysical journal 88, 4045-4053 (2005).

86. Aksimentiev, A. Deciphering ionic current signatures of DNA transport through a nanopore. Nanoscale 2, 468-483 (2010).

87. Bjelkmar, P., Niemelä, P. S., Vattulainen, I. & Lindahl, E. Conformational changes and slow dynamics through microsecond polarized atomistic molecular simulation of an integral Kv1. 2 ion channel. PLoS Comput Biol 5, e1000289 (2009).

88. Isralewitz, B., Izrailev, S. & Schulten, K. Binding pathway of retinal to bacterio-opsin: a prediction by molecular dynamics simulations. Biophysical journal 73, 2972 (1997).

89. Wells, D. B., Abramkina, V. & Aksimentiev, A. Exploring transmembrane transport through α-hemolysin with grid-steered molecular dynamics. The Journal of chemical physics 127, 09B619 (2007).

90. Aksimentiev, A., Heng, J. B., Timp, G. & Schulten, K. Microscopic kinetics of DNA translocation through synthetic nanopores. Biophysical journal 87, 2086-2097 (2004).

91. DeLano, W. L. Pymol: An open-source molecular graphics tool. CCP4 Newsletter on protein crystallography 40, 82-92 (2002).

92. Boukhet, M. et al. Probing driving forces in aerolysin and α-hemolysin biological nanopores: electrophoresis versus electroosmosis. Nanoscale 8, 18352-18359 (2016).

93. Piguet, F. et al. Electroosmosis through α-hemolysin that depends on alkali cation type. The journal of physical chemistry letters 5, 4362-4367 (2014).

94. Wimmer, E., Maxwell, I. H. & Tener, G. M. A Simple Method for Isolating Highly Purified Yeast Phenylalanine Transfer Ribonucleic Acid. Biochemistry-Us 7, 2623-2628 (1968).

95. Celander, D. W. & Cech, T. R. Visualizing the higher order folding of a catalytic RNA molecule. Science 251, 401-407 (1991).

96. Cate, J. H., Hanna, R. L. & Doudna, J. A. A magnesium ion core at the heart of a ribozyme domain. Nature structural biology 4, 553-558 (1997).

97. Farnsworth, R. W., Keating, J., McAuley, M. & Smith, R. Optimization of a Protocol for Escherichia coli RNA Extraction and Visualization. Journal of Experimental Microbiology and Immunology 5, 87-94 (2004).

98. Guo, C. et al. Silica nanoparticles induce oxidative stress, inflammation, and endothelial dysfunction in vitro via activation of the MAPK/Nrf2 pathway and nuclear factor-kappa B signaling. International Journal of Nanomedicine 10, 1463-1477 (2015).

99. Di Cello, F., Xie, Y., Paul-Satyaseela, M. & Kim, K. S. Approaches bacterial RNA isolation and purification for microarray analysis of Escherichia coli K1 interaction with human brain microvascular endothelial cells. Journal of Clinical Microbiology 43, 4197-4199 (2005).

100. Summer, H., Gramer, R. & Droge, P. Denaturing urea polyacrylamide gel electrophoresis (Urea PAGE). Journal of visualized experiments, e1485 (2009).

101. Simanshu, D. K., Nissley, D. V. & McCormick, F. RAS Proteins and Their Regulators in Human Disease. Cell 170, 17-33 (2017).

102. Kim, E. et al. A single-molecule dissection of ligand binding to a protein with intrinsic dynamics. Nature Chemical Biology 9, 313-318 (2013).

103. de Boer, M. et al. Conformational and dynamic plasticity in substrate-binding proteins underlies selective transport in ABC importers. eLife 8, e44652 (2019).

104. Boehr, D. D., Nussinov, R. & Wright, P. E. The role of dynamic conformational ensembles in biomolecular recognition. Nature Chemical Biology 5, 789-796 (2009).

105. Papaleo, E. et al. The Role of Protein Loops and Linkers in Conformational Dynamics and Allostery. Chemical Reviews 116, 6391-6423 (2016).

106. Orellana, L. Large-Scale Conformational Changes and Protein Function: Breaking the in silico Barrier. Frontiers in molecular biosciences 6, 117-117 (2019).

107. Park, S. J., Borin, B. N., Martinez-Yamout, M. A. & Dyson, H. J. The client protein p53 adopts a molten globule-like state in the presence of Hsp90. Nature Structural & Molecular Biology 18, 537-541 (2011).

108. Shim, S.-H., Strasfeld, D. B., Ling, Y. L. & Zanni, M. T. Automated 2D IR spectroscopy using a mid-IR pulse shaper and application of this technology to the human islet amyloid polypeptide. Proceedings of the National Academy of Sciences 104, 14197-14202 (2007).

109. Bertini, I. et al. Accurate Solution Structures of Proteins from X-ray Data and a Minimal Set of NMR Data: Calmodulin-Peptide Complexes As Examples. Journal of the American Chemical Society 131, 5134-5144 (2009).

110. Sedlak, S. M., Schendel, L. C., Gaub, H. E. & Bernardi, R. C. Streptavidin/biotin: Tethering geometry defines unbinding mechanics. Science Advances 6, eaay5999 (2020).

111. Krieg, M. et al. Atomic force microscopy-based mechanobiology. Nature Reviews Physics 1, 41-57 (2019).

112. Rivas-Pardo, J. A., Alegre-Cebollada, J., Ramirez-Sarmiento, C. A., Fernandez, J. M. & Guix6, V. Identifying Sequential Substrate Binding at the Single-Molecule Level by Enzyme Mechanical Stabilization. ACS Nano 9, 3996-4005 (2015).

113. Inkpen, M. S. & Albrecht, T. Probing Electron Transport in Proteins at Room Temperature with Single-Molecule Precision. ACS Nano 6, 13-16 (2012).

114. Margittai, M. et al. Single-molecule fluorescence resonance energy transfer reveals a dynamic equilibrium between closed and open conformations of syntaxin 1. Proceedings of the National Academy of Sciences 100, 15516-15521 (2003).

115. Lerner, E. et al. Toward dynamic structural biology: Two decades of single-molecule Förster resonance energy transfer. Science 359, eaan1133 (2018).

116. Yoo, D. et al. Low-Power Optical Trapping of Nanoparticles and Proteins with Resonant Coaxial Nanoaperture Using 10 nm Gap. Nano Letters 18, 3637-3642 (2018).

117. Pang, Y. & Gordon, R. Optical Trapping of a Single Protein. Nano Letters 12, 402-406 (2012).

118. Hong, C., Yang, S. & Ndukaife, J. C. Stand-off trapping and manipulation of sub-10 nm objects and biomolecules using opto-thermo-electrohydrodynamic tweezers. Nature Nanotechnology (2020).

119. Tapia-Rojo, R., Alonso-Caballero, A. & Fernandez, J. M. Direct observation of a coil-to-helix contraction triggered by vinculin binding to talin. Science Advances 6, eaaz4707 (2020).

120. Eckels, E. C., Tapia-Rojo, R., Rivas-Pardo, J. A. & Fernandez, J. M. The Work of Titin Protein Folding as a Major Driver in Muscle Contraction. Annual Review of Physiology 80, 327-351 (2018).

121. Popa, I. et al. A HaloTag Anchored Ruler for Week-Long Studies of Protein Dynamics. Journal of the American Chemical Society 138, 10546-10553 (2016).

122. Frsnzl, M. et al. Thermophoretic trap for single amyloid fibril and protein aggregation studies. Nature Methods 16, 611-614 (2019).

123. Ruggeri, F. et al. Single-molecule electrometry. Nature Nanotechnology 12, 488-495 (2017).

124. Talaga, D. S. & Li, J. Single-Molecule Protein Unfolding in Solid State Nanopores. Journal of the American Chemical Society 131, 9287-9297 (2009).

125. Stefureac, R. I. & Lee, J. S. Nanopore Analysis of the Folding of Zinc Fingers. Small 4, 1646-1650 (2008).

126. Nivala, J., Marks, D. B. & Akeson, M. Unfoldase-mediated protein translocation through an α-hemolysin nanopore. Nature Biotechnology 31, 247-250 (2013).

127. Pastoriza-Gallego, M. et al. Dynamics of Unfolded Protein Transport through an Aerolysin Pore. Journal of the American Chemical Society 133, 2923-2931 (2011).

128. Hu, Z.-L., Huo, M.-Z., Ying, Y.-L. & Long, Y.-T. Biological Nanopore Approach for Single-Molecule Protein Sequencing. Angewandte Chemie International Edition n/a.

129. Wang, H.-Y., Ying, Y.-L., Li, Y., Kraatz, H.-B. & Long, Y.-T. Nanopore Analysis of 03-Amyloid Peptide Aggregation Transition Induced by Small Molecules. Analytical Chemistry 83, 1746-1752 (2011).

130. Yusko, E. C. et al. Real-time shape approximation and fingerprinting of single proteins using a nanopore. Nature Nanotechnology 12, 360-367 (2017).

131. Fologea, D., Ledden, B., McNabb, D. S. & Li, J. Electrical characterization of protein molecules by a solid-state nanopore. Applied Physics Letters 91, 053901 (2007).

132. Sha, J. et al. Identification of Spherical and Nonspherical Proteins by a Solid-State Nanopore. Analytical Chemistry 90, 13826-13831 (2018).

133. Houghtaling, J. et al. Estimation of Shape, Volume, and Dipole Moment of Individual Proteins Freely Transiting a Synthetic Nanopore. ACS Nano 13, 5231-5242 (2019).

134. Galenkamp, N. S., Biesemans, A. & Maglia, G. Directional conformer exchange in dihydrofolate reductase revealed by single-molecule nanopore recordings. Nature Chemistry (2020).

135. Hu, R. et al. Differential Enzyme Flexibility Probed Using Solid-State Nanopores. ACS Nano 12, 4494-4502 (2018).

136. Plesa, C. et al. Fast Translocation of Proteins through Solid State Nanopores. Nano Letters 13, 658-663 (2013).

137. Varongchayakul, N., Song, J., Meller, A. & Grinstaff, M. W. Single-molecule protein sensing in a nanopore: a tutorial. Chemical Society Reviews 47, 8512-8524 (2018).

138. Diederichs, T. et al. Synthetic protein-conductive membrane nanopores built with DNA. Nature Communications 10, 5018 (2019).

139. Fragasso, A., Schmid, S. & Dekker, C. Comparing Current Noise in Biological and Solid-State Nanopores. ACS Nano 14, 1338-1349 (2020).

140. Varongchayakul, N., Huttner, D., Grinstaff, M. W. & Meller, A. Sensing Native Protein Solution Structures Using a Solid-state Nanopore: Unraveling the States of VEGF. Scientific Reports 8, 1017 (2018).

141. Han, A. et al. Sensing protein molecules using nanofabricated pores. Applied Physics Letters 88, 093901 (2006).

142. Schmid, S. & Dekker, C. Nanopores: a versatile tool to study protein dynamics. Essays in Biochemistry (2020).

143. Thakur, A. K. & Movileanu, L. Real-time measurement of protein-protein interactions at single-molecule resolution using a biological nanopore. Nature Biotechnology 37, 96-101 (2019).

144. Fahie, M., Chisholm, C. & Chen, M. Resolved Single-Molecule Detection of Individual Species within a Mixture of anti-Biotin Antibodies Using an Engineered Monomeric Nanopore. ACS Nano 9, 1089-1098 (2015).

145. Rotem, D., Jayasinghe, L., Salichou, M. & Bayley, H. Protein Detection by Nanopores Equipped with Aptamers. Journal of the American Chemical Society 134, 2781-2787 (2012).

146. Rodriguez-Larrea, D. & Bayley, H. Multistep protein unfolding during nanopore translocation. Nature Nanotechnology 8, 288-295 (2013).

147. Zhang, S. et al. Bottom-up fabrication of a multicomponent nanopore sensor that unfolds, processes and recognizes single proteins. bioRxiv, 2020.12.04.411884 (2020).

148. Wang, S., Haque, F., Rychahou, P. G., Evers, B. M. & Guo, P. Engineered Nanopore of Phi29 DNA-Packaging Motor for Real-Time Detection of Single Colon Cancer Specific Antibody in Serum. ACS Nano 7, 9814-9822 (2013).

149. Peng, W., de Souza Santos, M., Li, Y., Tomchick, D. R. & Orth, K. High-resolution cryo-EM structures of the *E. coli* hemolysin ClyA oligomers. PLOS ONE 14, e0213423 (2019).

150. Tanaka, K., Caaveiro, J. M. M., Morante, K., Gonzalez-Manas, J. M. & Tsumoto, K. Structural basis for self-assembly of a cytolytic pore lined by protein and lipid. Nature Communications 6, 6337 (2015).

151. Huang, G. et al. Electro-Osmotic Vortices Promote the Capture of Folded Proteins by PlyAB Nanopores. Nano Lett (2020).

152. Huang, G., Willems, K., Soskine, M., Wloka, C. & Maglia, G. Electro-osmotic capture and ionic discrimination of peptide and protein biomarkers with FraC nanopores. Nature Communications 8, 935 (2017).

153. Galenkamp, N. S., Soskine, M., Hermans, J., Wloka, C. & Maglia, G. Direct electrical quantification of glucose and asparagine from bodily fluids using nanopores. Nat Commun 9, 4085 (2018).

154. Zernia, S., van der Heide, N. J., Galenkamp, N. S., Gouridis, G. & Maglia, G. Current Blockades of Proteins inside Nanopores for Real-Time Metabolome Analysis. ACS Nano (2020).

155. Soskine, M., Biesemans, A. & Maglia, G. Single-Molecule Analyte Recognition with ClyA Nanopores Equipped with Internal Protein Adaptors. Journal of the American Chemical Society 137, 5793-5797 (2015).

156. Wloka, C. et al. Label-Free and Real-Time Detection of Protein Ubiquitination with a Biological Nanopore. ACS Nano 11, 4387-4394 (2017).

157. Soskine, M., Biesemans, A., De Maeyer, M. & Maglia, G. Tuning the size and properties of ClyA nanopores assisted by directed evolution. J Am Chem Soc 135, 13456-63 (2013).

158. Lu, B. et al. Protein Motion and Configurations in a Form-Fitting Nanopore: Avidin in ClyA. Biophysical Journal 115, 801-808 (2018).

159. Faller, M., Niederweis, M. & Schulz, G. E. The Structure of a Mycobacterial Outer-Membrane Channel. Science 303, 1189 (2004).

160. Heinz, C., Engelhardt, H. & Niederweis, M. The Core of the Tetrameric Mycobacterial Porin MspA Is an Extremely Stable β-Sheet Domain. Journal of Biological Chemistry 278, 8678-8685 (2003).

161. Manrao, E. A. et al. Reading DNA at single-nucleotide resolution with a mutant MspA nanopore and phi29 DNA polymerase. Nat Biotechnol 30, 349-53 (2012).

162. Craig, J. M. et al. Revealing dynamics of helicase translocation on single-stranded DNA using high-resolution nanopore tweezers. Proceedings of the National Academy of Sciences 114, 11932 (2017).

163. Wang, S. et al. Single molecule observation of hard-soft-acid-base (HSAB) interaction in engineered *Mycobacterium smegmatis* porin A (MspA) nanopores. Chemical Science 11, 879-887 (2020).

164. Cao, J. et al. Giant single molecule chemistry events observed from a tetrachloroaurate(III) embedded *Mycobacterium smegmatis* porin A nanopore. Nature Communications 10, 5668 (2019).

165. Zhang, M., Tanaka, T. & Ikura, M. Calcium-induced conformational transition revealed by the solution structure of apo calmodulin. Nature Structural Biology 2, 758-767 (1995).

166. Kursula, P. The many structural faces of calmodulin: a multitasking molecular jackknife. Amino Acids 46, 2295-304 (2014).

167. Waduge, P. et al. Nanopore-Based Measurements of Protein Size, Fluctuations, and Conformational Changes. ACS Nano 11, 5706-5716 (2017).

168. Ma, G. et al. Optical imaging of single-protein size, charge, mobility, and binding. Nature Communications 11, 4768 (2020).

169. Ikura, M. et al. Solution structure of a calmodulin-target peptide complex by multidimensional NMR. Science 256, 632-638 (1992).

170. Oukhaled, A., Bacri, L., Pastoriza-Gallego, M., Betton, J.-M. & Pelta, J. Sensing Proteins through Nanopores: Fundamental to Applications. ACS Chemical Biology 7, 1935-1949 (2012).

171. Crotti, L. et al. Calmodulin mutations and life-threatening cardiac arrhythmias: insights from the International Calmodulinopathy Registry. European heart journal 40, 2964-2975 (2019).

172. Pipilas, D. C. et al. Novel calmodulin mutations associated with congenital long QT syndrome affect calcium current in human cardiomyocytes. Heart Rhythm 13, 2012-2019 (2016).

173. Wren, L. M. et al. Genetic Mosaicism in Calmodulinopathy. Circulation: Genomic and Precision Medicine 12, e002581 (2019).

174. Wang, K. et al. Arrhythmia mutations in calmodulin can disrupt cooperativity of $Ca^{2+}$ binding and cause misfolding. The Journal of Physiology 598, 1169-1186 (2020).

175. Ouyang, H. & Vogel, H. J. Metal ion binding to calmodulin: NMR and fluorescence studies. Biometals 11, 213-222 (1998).

176. Habermann, E., Crowell, K. & Janicki, P. Lead and Other Metals can Substitute for Ca 2+ in Caimodulin. Archives of Toxicology 54, 61 (1983).

177. Hemmils, I. & Laitala, V. Progress in Lanthanides as Luminescent Probes. Journal of Fluorescence 15, 529-542 (2005).

178. Martin, B. & Richardson, F. S. Lanthanides as probes for calcium in biological systems. Quarterly Reviews of Biophysics 12, 181-209 (1979).

179. Brittain, H. G., Richardson, F. S. & Martin, R. B. Terbium(III) emission as a probe of calcium(II) binding sites in proteins. Journal of the American Chemical Society 98, 8255-8260 (1976).

180. Wallace, R. W., Tallant, E. A., Dockter, M. E. & Cheung, W. Y. Calcium binding domains of calmodulin. Sequence of fill as determined with terbium luminescence. Journal of Biological Chemistry 257, 1845-1854 (1982).

181. Edington, S. C. et al. Coordination to lanthanide ions distorts binding site conformation in calmodulin. Proceedings of the National Academy of Sciences 115, E3126 (2018).

182. Butler, T. Z., Pavlenok, M., Derrington, I. M., Niederweis, M. & Gundlach, J. H. Single-molecule DNA detection with an engineered MspA protein nanopore. Proceedings of the National Academy of Sciences 105, 20647-20652 (2008).

183. Yan, S. et al. Direct sequencing of 2'-deoxy-2'-fluoro-arabinonucleic acid (FANA) using nanopore-induced phase-shift sequencing (NIPSS). Chemical Science 10, 3110-3117 (2019).

184. Wang, Y. et al. Electrode-free nanopore sensing by DiffusiOptoPhysiology. Science Advances 5, eaar3309 (2019).

185. Wang, Y. et al. Osmosis-Driven Motion-Type Modulation of Biological Nanopores for Parallel Optical Nucleic Acid Sensing. ACS Applied Materials & Interfaces 10, 7788-7797 (2018).

186. Torchala, M., Moal, I. H., Chaleil, R. A. G., Fernandez-Recio, J. & Bates, P. A. SwarmDock: a server for flexible protein-protein docking. Bioinformatics 29, 807-809 (2013).

187. Torchala, M. & Bates, P. A. Predicting the Structure of Protein-Protein Complexes Using the SwarmDock Web Server. in Protein Structure Prediction (ed. Kihara, D.) 181-197 (Springer New York, New York, NY, 2014).

188. Jo, S., Kim, T., Iyer, V. G. & Im, W. CHARMM-GUI: A web-based graphical user interface for CHARMM. Journal of Computational Chemistry 29, 1859-1865 (2008).

189. Oukhaled, A., Bacri, L., Pastoriza-Gallego, M., Betton, J.-M. & Pelta, J. Sensing Proteins through Nanopores: Fundamental to Applications. ACS Chemical Biology 7, 1935-1949 (2012).

190. Zhang, M., Tanaka, T. & Ikura, M. Calcium-induced conformational transition revealed by the solution structure of apo calmodulin. Nature Structural Biology 2, 758-767 (1995).

191. Ikura, M. et al. Solution structure of a calmodulin-target peptide complex by multidimensional NMR. Science 256, 632-638 (1992).

192. Soskine, M., Biesemans, A., De Maeyer, M. & Maglia, G. Tuning the size and properties of ClyA nanopores assisted by directed evolution. Journal of the American Chemical Society 135, 13456-63 (2013).

193. Wang, W.-Q.; Jensen, O. N.; Møller, I. M.; Hebelstrup, K. H.; Rogowska-Wrzesinska, A., Evaluation of sample preparation methods for mass spectrometry-based proteomic analysis of barley leaves. Plant Methods 2018, 14 (1), 72.

194. Timp, W.; Timp, G., Beyond mass spectrometry, the next step in proteomics. Sci. Adv. 2020, 6 (2), eaax8978.

195. Nakayasu, E. S.; Gritsenko, M.; Piehowski, P. D.; Gao, Y.; Orton, D. J.; Schepmoes, A. A.; Fillmore, T. L.; Frohnert, B. I.; Rewers, M.; Krischer, J. P.; Ansong, C.; Suchy-Dicey, A. M.; Evans-Molina, C.; Qian, W.-J.; Webb-Robertson, B.-J. M.; Metz, T. O., Tutorial: best practices and considerations for mass-spectrometry-based protein biomarker discovery and validation. Nat. Protoc. 2021, 16 (8), 3737-3760.

196. Hnasko, R.; Lin, A.; McGarvey, J. A.; Stanker, L. H., A rapid method to improve protein detection by indirect ELISA. Biochem. Biophys. Res. Commun. 2011, 410 (4), 726-731.

197. de Lannoy, C. V.; Filius, M.; van Wee, R.; Joo, C.; de Ridder, D., Evaluation of FRET X for single-molecule protein fingerprinting. iScience 2021, 24 (11), 103239.

198. Tripathi, P.; Benabbas, A.; Mehrafrooz, B.; Yamazaki, H.; Aksimentiev, A.; Champion, P. M.; Wanunu, M., Electrical unfolding of cytochrome c during translocation through a nanopore constriction. Proc. Natl. Acad. Sci. U.S.A. 2021, 118 (17), e2016262118.

199. Mitscha-Baude, G.; Stadlbauer, B.; Howorka, S.; Heitzinger, C., Protein Transport through Nanopores Illuminated by Long-Time-Scale Simulations. ACS Nano 2021, 15 (6), 9900-9912.

200. Gu, L.-Q.; Shim, J. W., Single molecule sensing by nanopores and nanopore devices. Analyst 2010, 135 (3), 441-451.

201. Alfaro, J. A.; Bohlsnder, P.; Dai, M.; Filius, M.; Howard, C. J.; van Kooten, X. F.; Ohayon, S.; Pomorski, A.; Schmid, S.; Aksimentiev, A.; Anslyn, E. V.; Bedran, G.; Cao, C.; Chinappi, M.; Coyaud, E.; Dekker, C.;

Dittmar, G.; Drachman, N.; Eelkema, R.; Goodlett, D.; Hentz, S.; Kalathiya, U.; Kelleher, N. L.; Kelly, R. T.; Kelman, Z.; Kim, S. H.; Kuster, B.; Rodriguez-Larrea, D.; Lindsay, S.; Maglia, G.; Marcotte, E. M.; Marino, J. P.; Masselon, C.; Mayer, M.; Samaras, P.; Sarthak, K.; Sepiashvili, L.; Stein, D.; Wanunu, M.; Wilhelm, M.; Yin, P.; Meller, A.; Joo, C., The emerging landscape of single-molecule protein sequencing technologies. Nat. Methods 2021, 18 (6), 604-617.

202. Cao, C.; Cirauqui, N.; Marcaida, M. J.; Buglakova, E.; Duperrex, A.; Radenovic, A.; Dal Peraro, M., Single-molecule sensing of peptides and nucleic acids by engineered aerolysin nanopores. Nat. Commun. 2019, 10 (1), 4918-4918.

203. Quick, J.; Loman, N. J.; Duraffour, S.; Simpson, J. T.; Severi, E.; Cowley, L.; Bore, J. A.; Koundouno, R.; Dudas, G.; Mikhail, A.; Ouédraogo, N.; Afrough, B.; Bah, A.; Baum, J. H. J.; Becker-Ziaja, B.; Boettcher, J. P.; Cabeza-Cabrerizo, M.; Camino-Sanchez, A.; Carter, L. L.; Doerrbecker, J.; Enkirch, T.; Dorival, I. G.; Hetzelt, N.; Hinzmann, J.; Holm, T.; Kafetzopoulou, L. E.; Koropogui, M.; Kosgey, A.; Kuisma, E.; Logue, C. H.; Mazzarelli, A.; Meisel, S.; Mertens, M.; Michel, J.; Ngabo, D.; Nitzsche, K.; Pallasch, E.; Patrono, L. V.; Portmann, J.; Repits, J. G.; Rickett, N. Y.; Sachse, A.; Singethan, K.; Vitoriano, I.; Yemanaberhan, R. L.; Zekeng, E. G.; Racine, T.; Bello, A.; Sall, A. A.; Faye, O.; Faye, O.; Magassouba, N. F.; Williams, C. V.; Amburgey, V.; Winona, L.; Davis, E.; Gerlach, J.; Washington, F.; Monteil, V.; Jourdain, M.; Bererd, M.; Camara, A.; Somlare, H.; Camara, A.; Gerard, M.; Bado, G.; Baillet, B.; Delaune, D.; Nebie, K. Y.; Diarra, A.; Savane, Y.; Pallawo, R. B.; Gutierrez, G. J.; Milhano, N.; Roger, I.; Williams, C. J.; Yattara, F.; Lewandowski, K.; Taylor, J.; Rachwal, P.; J. Turner, D.; Pollakis, G.; Hiscox, J. A.; Matthews, D. A.; Shea, M. K. O.; Johnston, A. M.; Wilson, D.; Hutley, E.; Smit, E.; Di Caro, A.; Wôlfel, R.; Stoecker, K.; Fleischmann, E.; Gabriel, M.; Weller, S. A.; Koivogui, L.; Diallo, B.; Keita, S.; Rambaut, A.; Formenty, P.; Gunther, S.; Carroll, M. W., Real-time, portable genome sequencing for Ebola surveillance. Nature 2016, 530 (7589), 228-232.

204. Plesa, C.; Kowalczyk, S. W.; Zinsmeester, R.; Grosberg, A. Y.; Rabin, Y.; Dekker, C., Fast Translocation of Proteins through Solid State Nanopores. Nano Lett. 2013, 13 (2), 658-663.

205. Cardozo, N.; Zhang, K.; Doroschak, K.; Nguyen, A.; Siddiqui, Z.; Bogard, N.; Strauss, K.; Ceze, L.; Nivala, J., Multiplexed direct detection of barcoded protein reporters on a nanopore array. Nat. Biotechnol. 2021, DOI: 10.1038/s41587-021-01002-6.

206. Palla, M.; Punthambaker, S.; Stranges, B.; Vigneault, F.; Nivala, J.; Wiegand, D.; Ayer, A.; Craig, T.; Gremyachinskiy, D.; Franklin, H.; Sun, S.; Pollard, J.; Trans, A.; Arnold, C.; Schwab, C.; McGaw, C.; Sarvabhowman, P.; Dalal, D.; Thai, E.; Amato, E.; Lederman, I.; Taing, M.; Kelley, S.; Qwan, A.; Fuller, C. W.; Roever, S.; Church, G. M., Multiplex Single-Molecule Kinetics of Nanopore-Coupled Polymerases. ACS Nano 2021, 15 (1), 489-502.

207. Nivala, J.; Mulroney, L.; Li, G.; Schreiber, J.; Akeson, M., Discrimination among Protein Variants Using an Unfoldase-Coupled Nanopore. ACS Nano 2014, 8 (12), 12365-12375.

208. Bell, N. A. W.; Keyser, U. F., Digitally encoded DNA nanostructures for multiplexed, single-molecule protein sensing with nanopores. Nat. Nanotechnol. 2016, 11 (7), 645-651.

209. Huang, G.; Willems, K.; Soskine, M.; Wloka, C.; Maglia, G., Electro-osmotic capture and ionic discrimination of peptide and protein biomarkers with FraC nanopores. Nat. Commun. 2017, 8 (1), 935.

210. Schmid, S.; Dekker, C., Nanopores: a versatile tool to study protein dynamics. Essays Biochem. 2021, 65 (1), 93-107.

211. Boukhet, M.; Piguet, F.; Ouldali, H.; Pastoriza-Gallego, M.; Pelta, J.; Oukhaled, A., Probing driving forces in aerolysin and alpha-hemolysin biological nanopores: electrophoresis versus electroosmosis. Nanoscale 2016, 8 (43), 18352-18359.

212. Bhamidimarri, S. P.; Prajapati, J. D.; van den Berg, B.; Winterhalter, M.; Kleinekathôfer, U., Role of Electroosmosis in the Permeation of Neutral Molecules: CymA and Cyclodextrin as an Example. Biophys. J. 2016, 110 (3), 600-611.

213. Huang, G.; Willems, K.; Bartelds, M.; van Dorpe, P.; Soskine, M.; Maglia, G., Electro-Osmotic Vortices Promote the Capture of Folded Proteins by PlyAB Nanopores. Nano Lett. 2020, 20 (5), 3819-3827.

214. Soskine, M.; Biesemans, A.; Maglia, G., Single-Molecule Analyte Recognition with ClyA Nanopores Equipped with Internal Protein Adaptors. J. Am. Chem. Soc. 2015, 137 (17), 5793-5797.

215. Li, X.; Lee, K. H.; Shorkey, S.; Chen, J.; Chen, M., Different Anomeric Sugar Bound States of MBP Resolved by a Cytolysin A Nanopore Tweezer. ACS Nano 2020, 14 (2), 1727-1737.

216. Van Meervelt, V.; Soskine, M.; Maglia, G., Detection of Two Isomeric Binding Configurations in a Protein-Aptamer Complex with a Biological Nanopore. ACS Nano 2014, 8 (12), 12826-12835.

217. Galenkamp, N. S.; Biesemans, A.; Maglia, G., Directional conformer exchange in dihydrofolate reductase revealed by single-molecule nanopore recordings. Nat. Chem. 2020, 12 (5), 481-488.

218. Galenkamp, N. S.; Soskine, M.; Hermans, J.; Wloka, C.; Maglia, G., Direct electrical quantification of glucose and asparagine from bodily fluids using nanopores. Nat. Commun. 2018, 9 (1), 4085.

219. Zernia, S.; van der Heide, N. J.; Galenkamp, N. S.; Gouridis, G.; Maglia, G., Current Blockades of Proteins inside Nanopores for Real-Time Metabolome Analysis. ACS Nano 2020, 14 (2), 2296-2307.

220. Restrepo-Pérez, L.; Wong, C. H.; Maglia, G.; Dekker, C.; Joo, C., Label-Free Detection of Post-translational Modifications with a Nanopore. Nano Lett. 2019, 19 (11), 7957-7964.

221. Lucas, F. L. R.; Piso, T. R. C.; van der Heide, N. J.; Galenkamp, N. S.; Hermans, J.; Wloka, C.; Maglia, G., Automated Electrical Quantification of Vitamin B1 in a Bodily Fluid using an Engineered Nanopore-Sensor. Angew. Chem. Int. Ed. 2021, 60 (42), 22849-22855.

222. Fragasso, A.; Schmid, S.; Dekker, C., Comparing Current Noise in Biological and Solid-State Nanopores. ACS Nano 2020, 14 (2), 1338-1349.

223. Soskine, M.; Biesemans, A.; De Maeyer, M.; Maglia, G., Tuning the size and properties of ClyA nanopores assisted by directed evolution. J. Am. Chem. Soc. 2013, 135 (36), 13456-13463.

224. Liu, Y.; Pan, T.; Wang, K.; Wang, Y.; Yan, S.; Wang, L.; Zhang, S.; Du, X.; Jia, W.; Zhang, P.; Chen, H.-Y.; Huang, S., Allosteric Switching of Calmodulin in a *Mycobacterium smegmatis* porin A (MspA) Nanopore-Trap. Angew. Chem. Int. Ed. 2021, 60 (44), 23863-23870.

225. Shorkey, S. A.; Du, J.; Pham, R.; Strieter, E. R.; Chen, M., Real-Time and Label-Free Measurement of Deubiquitinase Activity with a MspA Nanopore. ChemBioChem 2021, 22 (17), 2688-2692.

226. Wang, S.; Wang, Y.; Yan, S.; Du, X.; Zhang, P.; Chen, H.-Y.; Huang, S., Retarded Translocation of Nucleic Acids through α-Hemolysin Nanopore in the Presence of a Calcium Flux. ACS Appl. Mater. Interfaces 2020, 12 (24), 26926-26935.

227. Wang, Y.; Guan, X.; Zhang, S.; Liu, Y.; Wang, S.; Fan, P.; Du, X.; Yan, S.; Zhang, P.; Chen, H.-Y.; Li, W.; Zhang, D.; Huang, S., Structural-profiling of low molecular weight RNAs by nanopore trapping/translocation using *Mycobacterium smegmatis* porin A. Nat. Commun. 2021, 12 (1), 3368.

228. Postnikova, G. B.; Tselikova, S. V.; Shekhovtsova, E. A., Myoglobin and mitochondria: Oxymyoglobin interacts with mitochondrial membrane during deoxygenation. Biochemistry (Moscow) 2009, 74 (11), 1211.

229. Fologea, D.; Krueger, E.; Al Faori, R.; Lee, R.; Mazur, Y. I.; Henry, R.; Arnold, M.; Salamo, G. J., Multivalent ions control the transport through lysenin channels. Biophys. Chem. 2010, 152 (1), 40-45.

230. He, Y.; Gillespie, D.; Boda, D.; Vlassiouk, I.; Eisenberg, R. S.; Siwy, Z. S., Tuning Transport Properties of Nanofluidic Devices with Local Charge Inversion. J. Am. Chem. Soc. 2009, 131 (14), 5194-5202.

231. Ramirez, P.; Manzanares, J. A.; Cervera, J.; Gomez, V.; Ali, M.; Pause, I.; Ensinger, W.; Mafe, S., Nanopore charge inversion and current-voltage curves in mixtures of asymmetric electrolytes. J. Membr. Sci. 2018, 563, 633-642.

232. Alcaraz, A.; Nestorovich, E. M.; López, M. L.; Garciá-Giménez, E.; Bezrukov, S. M.; Aguilella, V. M., Diffusion, Exclusion, and Specific Binding in a Large Channel: A Study of OmpF Selectivity Inversion. Biophys. J. 2009, 96 (1), 56-66.

233. Piguet, F.; Discala, F.; Breton, M.-F.; Pelta, J.; Bacri, L.; Oukhaled, A., Electroosmosis through α-Hemolysin That Depends on Alkali Cation Type. J. Phys. Chem. Lett. 2014, 5 (24), 4362-4367.

234. Gu, L.-Q.; Cheley, S.; Bayley, H., Electroosmotic enhancement of the binding of a neutral molecule to a transmembrane pore. Proc. Natl. Acad. Sci. U.S.A. 2003, 100 (26), 15498-15503.

235. Chinappi, M.; Yamaji, M.; Kawano, R.; Cecconi, F., Analytical Model for Particle Capture in Nanopores Elucidates Competition among Electrophoresis, Electroosmosis, and Dielectrophoresis. ACS Nano 2020, 14 (11), 15816-15828.

236. Sekhon, N.; Peacock, W. F., Chapter 11—Biomarkers to Assist in the Evaluation of Chest Pain: A Practical Guide. In Biomarkers in Cardiovascular Disease, Nambi, V., Ed. Elsevier: 2019; pp 115-128.

237. Chung, M. J.; Brown, D. L., 9—Diagnosis of Acute Myocardial Infarction. In Cardiac Intensive Care (Third Edition), Brown, D. L., Ed. Elsevier: Philadelphia, 2019; pp 91-98.e3.

238. Cammarata, M. B.; Brodbelt, J. S., Structural characterization of holo- and apo-myoglobin in the gas phase by ultraviolet photodissociation mass spectrometry. Chem. Sci. 2015, 6 (2), 1324-1333.

239. Lin, L.; Pinker, R. J.; Forde, K.; Rose, G. D.; Kallenbach, N. R., Molten globular characteristics of the native state of apomyoglobin. Nat. Struct. Biol. 1994, 1 (7), 447-452.

240. Sankaranarayanan, K., Studies on pH-Controlled Transition of Myoglobin Capsules from Hollow to Multilayered Structures. Adsorpt. Sci. Technol. 2015, 33 (9), 759-768.

241. Ganguly, D.; Zhang, W.; Chen, J., Synergistic folding of two intrinsically disordered proteins: searching for conformational selection. Mol. Biosyst. 2012, 8 (1), 198-209.

242. Misiunas, K.; Ermann, N.; Keyser, U. F., QuipuNet: Convolutional Neural Network for Single-Molecule Nanopore Sensing. Nano Lett. 2018, 18 (6), 4040-4045.

243. Henley, R. Y.; Ashcroft, B. A.; Farrell, I.; Cooperman, B. S.; Lindsay, S. M.; Wanunu, M., Electrophoretic Deformation of Individual Transfer RNA Molecules Reveals Their Identity. Nano Lett. 2016, 16 (1), 138-144.

244. Barati Farimani, A.; Heiranian, M.; Aluru, N. R., Identification of amino acids with sensitive nanoporous MoS2: towards machine learning-based prediction. NPJ 2D Mater. Appl. 2018, 2 (1), 14.

245. Ohayon, S.; Girsault, A.; Nasser, M.; Shen-Orr, S.; Meller, A., Simulation of single-protein nanopore sensing shows feasibility for whole-proteome identification. PLoS Comput. Biol. 2019, 15 (5), e1007067.

246. Kolmogorov, M.; Kennedy, E.; Dong, Z.; Timp, G.; Pevzner, P. A., Single-molecule protein identification by sub-nanopore sensors. PLoS Comput. Biol. 2017, 13 (5), e1005356.

247. Goulding, D. A.; Fox, P. F.; O'Mahony, J. A., Chapter 2—Milk proteins: An overview. In Milk Proteins (Third Edition), Boland, M.; Singh, H., Eds. Academic Press: 2020; pp 21-98.

248. Willems, K.; Ruic, D.; Biesemans, A.; Galenkamp, N. S.; Van Dorpe, P.; Maglia, G., Engineering and Modeling the Electrophoretic Trapping of a Single Protein Inside a Nanopore. ACS Nano 2019, 13 (9), 9980-9992

249. Wang, Y.; Yan, S.; Zhang, P.; Zeng, Z.; Zhao, D.; Wang, J.; Chen, H.; Huang, S., Osmosis-Driven Motion-Type Modulation of Biological Nanopores for Parallel Optical Nucleic Acid Sensing. ACS Appl. Mater. Interfaces 2018, 10 (9), 7788-7797.

250. Yan, S.; Li, X.; Zhang, P.; Wang, Y.; Chen, H. Y.; Huang, S.; Yu, H., Direct sequencing of 2'-deoxy-2'-fluoroarabinonucleic acid (FANA) using nanopore-induced phase-shift sequencing (NIPSS). Chem. Sci. 2019, 10 (10), 3110-3117.

---

The invention claimed is:

1. A method of characterizing an analyte in a nanopore system, wherein the nanopore system comprises a protein nanopore disposed in a membrane that separates a first conductive liquid medium from a second conductive liquid medium, wherein the protein nanopore is MspA, MspA homolog or variant thereof, wherein the analyte has a conformation and the analyte with the conformation can be accommodated in the vestibule of the MspA, the MspA homolog or the variant thereof but cannot translocate through the MspA, the MspA homolog or the variant thereof, the method comprising:

i) applying an electrical potential difference between the first conductive liquid medium and the second conductive liquid medium to drive the analyte into the nanopore;

ii) measuring an ionic current through the protein nanopore to provide a tested current pattern that contains at least blockade ionic current caused by the analyte accommodated in the vestibule of the MspA, the MspA homolog or the variant thereof;

iii) associating the tested current pattern with at least one characteristic of the analyte.

2. The method of claim 1, wherein the analyte is selected from the group consisting of a nucleic acid, a protein, a peptide, a peptide complex, a polysaccharide, a polymer, an enzyme, and a complex of a nucleic acid, a protein, a peptide, a polysaccharide, a polymer, an enzyme and an agent capable of interacting with them.

3. The method of claim 2, wherein the nucleic acid is selected from the group consisting of a LMW RNA, a nucleic acid duplex, an aptamer, a ribozyme or a nucleic acid with a structure of kissing loop, three-way junction, pseudo-knot, kink-turn or G-quadruplex; wherein the LMW RNA comprises a siRNA with an overhanged or blunt end, a tRNA, a miRNA and/or a rRNA and wherein the nucleic acid duplex has an overhanged or blunt end.

4. The method of claim 3, wherein the nucleic acid duplex is consisted of a miRNA and a nucleic acid probe, and the nucleic acid probe is an RNA, a DNA or a nucleic acid analogue.

5. The method of claim 1, wherein the analyte comprises two or more different analytes and the characterization of these analytes is completed in one measurement.

6. The method of claim 1, wherein step iii) comprising associating the tested current pattern with at least one characteristic selected from the group consisting of the presence or the absence of the analyte, the identity of the analyte, the sequence of the analyte, the mutations in the analyte, the conformation of the analyte, the local structure of the analyte, the content of the analyte, the overall size of the analyte, the charge of the analyte, and the polarity.

7. The method of claim 1, wherein the analyte is a complex formed by the combination of a target molecule and an assistant molecule.

8. The method of claim 7, wherein step iii) comprises associating the tested current pattern with at least one characteristic of the target molecule.

9. The method of claim 1, wherein step iii) is performed by comparing the tested current pattern with a reference current pattern or by using a machine learning algorithm.

10. The method of claim 1, wherein the conductive liquid medium on the vestibular side of MspA, the MspA homolog or the variant thereof contains monovalent cation, and the conductive liquid medium on the constriction side of MspA, the MspA homolog or the variant thereof contains divalent cation.

11. The method of claim 10, wherein the monovalent cation is alkali metal ion, the divalent cation is alkaline earth metal ion.

12. The method of claim 11, wherein the divalent cation is selected from $Ca^{2+}$, $Mn^{2+}$, $Mg^{2+}$ and $Ba^{2+}$, and the monovalent cation is selected from $K^+$, $Na^+$ and $Li^+$.

13. A method for characterizing the interaction between an analyte and an agent or the agent capable of interacting with the analyte in a nanopore system, wherein the nanopore system comprises a protein nanopore disposed in a membrane that separates a first conductive liquid medium from a second conductive liquid medium, wherein the protein nanopore is MspA, MspA homolog or variant thereof, wherein the analyte has a conformation and the analyte with the conformation can be accommodated in the vestibule of the MspA, the MspA homolog or the variant thereof but cannot translocate through the MspA, the MspA homolog or the variant thereof, the method comprising:

i) contacting the analyte with the agent, and driving the analyte into the nanopore by an electrical potential difference between the first conductive liquid medium and the second conductive liquid medium;

ii) measuring an ionic current through the protein nanopore to provide a tested current pattern that contains at least ionic current measured during the analyte is in the vestibule of the MspA, the MspA homolog or the variant thereof;

iii) associated the current pattern with the interaction between the analyte and the agent or with the agent.

14. The method of claim 13, wherein the analyte is selected from the group consisting of a nucleic acid, a protein, a peptide, a polysaccharide, a polymer and an enzyme, or the analyte can interact with an ion, a small molecule, a ligand, a receptor or a substrate, and the agent is an ion, a small molecule, a ligand, a receptor or a substrate.

15. The method of claim 14, wherein the analyte is an aptamer, a ribozyme, a calmodulin, a lysozyme or a myoglobin.

16. The method of claim 13, wherein the agent is a polysaccharide, peptidoglycan, chitosan or chitin.

17. A method for detecting an analyte of interest in a sample in a nanopore system, wherein the nanopore system comprises a protein nanopore disposed in a membrane that separates a first conductive liquid medium from a second conductive liquid medium, wherein the protein nanopore is MspA, the MspA homolog or the variant thereof, wherein the analyte of interest has a conformation and the analyte of interest with the original conformation can be accommodated in the vestibule of MspA, the MspA homolog or the variant thereof but cannot translocate through MspA, the MspA homolog or the variant thereof, the method comprising:

i) adding the sample to the at least one of the first conductive liquid medium from a second conductive liquid medium and applying an electrical potential difference between the first conductive liquid medium and the second conductive liquid medium that is suitable for driving the analyte of interest into the nanopore;

ii) measuring an ionic current through the protein nanopore for a period of time to provide a tested current pattern;

iii) comparing the tested current pattern which comprises at least ionic current trace measured during the analyte of interest is in the vestibule of MspA, the MspA homolog or the variant thereof with a reference current pattern;

iv) determining the presence or the absence of the analyte of interest in the sample and/or the content of the analyte of interest in the sample by the comparison of iii).

18. The method of claim 17, wherein the analyte is whey protein, α-lactalbumin and/or β-lactoglobulin.

19. The method of claim 17, wherein the sample is milk or protein powder.

20. The method of claim 17, wherein the analyte of interest is selected from the group consisting of a nucleic acid, a protein, a polysaccharide, a polymer and an enzyme.

* * * * *

SEQUENCE LISTING

<160> NUMBER OF SEQ ID NOS: 6

<210> SEQ ID NO 1
<211> LENGTH: 184
<212> TYPE: PRT
<213> ORGANISM: Mycobacterium smegmatis

<400> SEQUENCE: 1

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
                100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Ala Glu Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
                180
```

<210> SEQ ID NO 2
<211> LENGTH: 22
<212> TYPE: RNA

-continued

```
<213> ORGANISM: Artificial Sequence
<220> FEATURE:
<223> OTHER INFORMATION: hsa-miR-21

<400> SEQUENCE: 2
uagcuuauca gacugauguu ga                                    22

<210> SEQ ID NO 3
<211> LENGTH: 21
<212> TYPE: RNA
<213> ORGANISM: Artificial Sequence
<220> FEATURE:
<223> OTHER INFORMATION: siFoxA1-a

<400> SEQUENCE: 3
cuuacgcuga guacuucgaa a                                     21

<210> SEQ ID NO 4
<211> LENGTH: 21
<212> TYPE: RNA
<213> ORGANISM: Artificial Sequence
<220> FEATURE:
<223> OTHER INFORMATION: siFoxA1-b

<400> SEQUENCE: 4
ucgaaguacu cagcguaagu g                                     21

<210> SEQ ID NO 5
<211> LENGTH: 21
<212> TYPE: RNA
<213> ORGANISM: Artificial Sequence
<220> FEATURE:
<223> OTHER INFORMATION: luciferase siRNA-a

<400> SEQUENCE: 5
agcaauaguu cacgcugaaa g                                     21

<210> SEQ ID NO 6
<211> LENGTH: 21
<212> TYPE: RNA
<213> ORGANISM: Artificial Sequence
<220> FEATURE:
<223> OTHER INFORMATION: luciferase siRNA-b

<400> SEQUENCE: 6
cuuucagcgu gaacuauugc u                                     21
```